(12) United States Patent
Kim et al.

(10) Patent No.: US 9,793,500 B2
(45) Date of Patent: Oct. 17, 2017

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Jongwoo Kim, Yongin (KR); Sooyon Kim, Yongin (KR); Youngkook Kim, Yongin (KR); Haejin Kim, Yongin (KR); Sanghyun Han, Yongin (KR); Seokhwan Hwang, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 428 days.

(21) Appl. No.: 14/614,607

(22) Filed: Feb. 5, 2015

(65) Prior Publication Data

US 2016/0005984 A1    Jan. 7, 2016

(30) Foreign Application Priority Data

Jul. 4, 2014  (KR) .................. 10-2014-0083894

(51) Int. Cl.
| | | |
|---|---|---|
| H01L 51/00 | (2006.01) | |
| C07C 211/61 | (2006.01) | |
| C07D 307/91 | (2006.01) | |
| C07F 7/08 | (2006.01) | |
| H01L 51/50 | (2006.01) | |

(52) U.S. Cl.
CPC ........ *H01L 51/0094* (2013.01); *C07C 211/61* (2013.01); *C07D 307/91* (2013.01); *C07F 7/0818* (2013.01); *H01L 51/006* (2013.01); *H01L 51/0052* (2013.01); *H01L 51/0055* (2013.01); *H01L 51/0061* (2013.01); *H01L 51/0073* (2013.01); *H01L 51/0074* (2013.01); *C07C 2603/18* (2017.05); *C07C 2603/26* (2017.05); *C07C 2603/52* (2017.05); *H01L 51/0058* (2013.01); *H01L 51/5012* (2013.01)

(58) Field of Classification Search
CPC ............. H01L 51/0094; H01L 51/0074; H01L 51/0052; H01L 51/0073; H01L 51/0055; H01L 51/0061; H01L 51/006; H01L 51/5012; H01L 51/0058; C07F 7/0818; C07D 307/91; C07C 211/61; C07C 2603/52; C07C 2603/18; C07C 2603/26
See application file for complete search history.

(56) References Cited

U.S. PATENT DOCUMENTS

| | | | |
|---|---|---|---|
| 7,053,255 | B2 | 5/2006 | Ikeda et al. |
| 7,233,019 | B2 | 6/2007 | Ionkin et al. |
| 2005/0156164 | A1 | 7/2005 | Sotoyama |
| 2010/0277061 | A1 | 11/2010 | Matsuura et al. |
| 2011/0006289 | A1 | 1/2011 | Mizuki et al. |

FOREIGN PATENT DOCUMENTS

| | | |
|---|---|---|
| KR | 10-2006-0006760 | 1/2006 |
| KR | 10-2010-0097182 | 9/2010 |
| KR | 10-1031463 | 4/2011 |
| KR | 10-2011-0103141 A | 9/2011 |
| KR | 10-2011-0104765 | 9/2011 |
| KR | 10-2011-0108574 a | 10/2011 |
| KR | 10-1142056 | 4/2012 |
| WO | WO-2010/038956 A2 | 4/2010 |
| WO | WO-2011/115378 A1 | 9/2011 |

*Primary Examiner* — Alexander Kollias
(74) *Attorney, Agent, or Firm* — Lee & Morse, P.C.

(57) ABSTRACT

A condensed cyclic compound is represented by Formula 1:

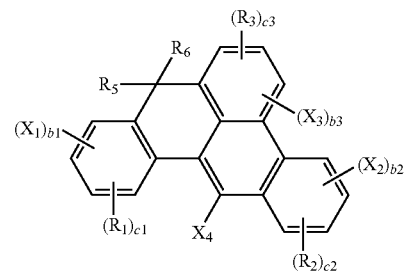

where $X_1$-$X_4$, $L_1$-$L_4$ $R_1$-$R_6$ and $Ar_1$-$Ar_8$ are as defined in the specification. An organic light-emitting device includes the condensed cyclic compound.

20 Claims, 1 Drawing Sheet

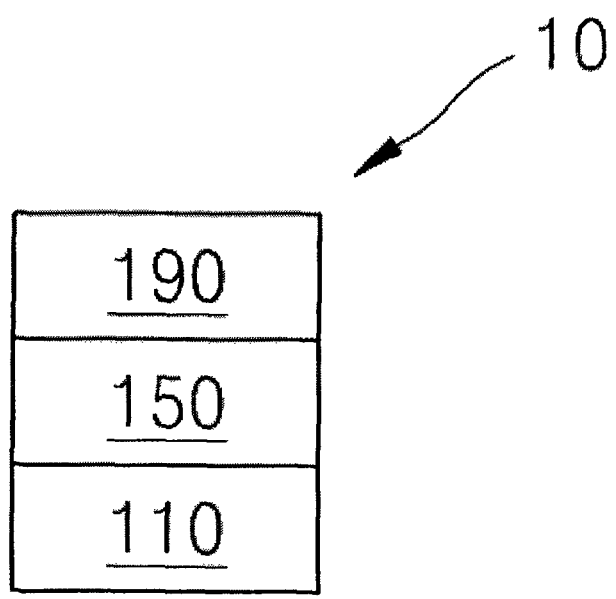

CONDENSED CYCLIC COMPOUND AND ORGANIC LIGHT-EMITTING DEVICE INCLUDING THE SAME

CROSS-REFERENCE TO RELATED APPLICATION

Korean Patent Application No. 10-2014-0083894, filed on Jul. 4, 2014, in the Korean Intellectual Property Office, and entitled: "Condensed Cyclic Compound and Organic Light-Emitting Device Including the Same," is incorporated by reference herein in its entirety.

BACKGROUND

1. Field

One or more embodiments relate to a condensed cyclic compound and an organic light-emitting device including the same.

2. Description of the Related Art

Organic light emitting devices are self-emission devices that have wide viewing angles, high contrast ratios, short response times, and excellent brightness, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, are recombined in the emission layer to produce excitons. These excitons change from an excited state to a ground state, thereby generating light.

SUMMARY

Embodiments are directed to a condensed cyclic compound represented by Formula 1 below:

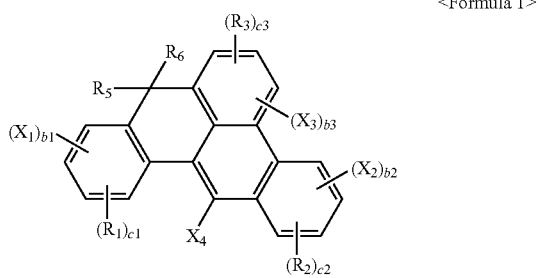

<Formula 1> wherein in Formula 1,
$X_1$ is $-[(L_1)_{a1}-N(Ar_1)(Ar_2)]$;
$X_2$ is $-[(L_2)_{a2}-N(Ar_3)(Ar_4)]$;
$X_3$ is $-[(L_3)_{a3}-N(Ar_5)(Ar_6)]$;
$X_4$ is $-[(L_4)_{a4}-N(Ar_7)(Ar_5)]$ or $R_4$;
$L_1$ to $L_4$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;

a1 to a4 are each independently selected from 0, 1, 2, and 3;

$Ar_1$ to $Ar_8$ are each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group;

b1 and b2 are each independently an integer selected from 0 to 4, b3 is an integer selected from 0 to 3, and i) when $X_4$ is $R_4$, b1+b2+b3≥2, and ii) when $X_4$ is $-[(L_4)_{a4}-N(Ar_7)(Ar_5)]$, b1+b2+b3≥1;

$R_1$ to $R_6$ are each independently selected form a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthiogroup, a substituted or unsubstituted $C_2$-$C_{60}$ heteroaryl group, a substituted or unsubstituted monovalent non-aromatic condensed polycyclic group, a substituted or unsubstituted monovalent non-aromatic condensed hetero polycyclic group, $-Si(Q_1)(Q_2)(Q_3)$, and $-B(Q_4)(Q_5)$;

c1 and c2 are each independently an integer selected from 0 to 4, and c3 is an integer selected from 0 to 3;

At least one of substituents of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$) and —N($Q_{36}$)($Q_{37}$);

wherein $Q_1$ to $Q_5$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

Embodiments are also directed to an organic light-emitting device includes: a first electrode; a second electrode facing the first electrode; and an organic layer between the first electrode and the second electrode, the organic layer including an emission layer. The organic layer includes at least one condensed cyclic compound as described above.

BRIEF DESCRIPTION OF THE DRAWING

Features will become apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

A condensed cyclic compound in some embodiments may be represented by Formula 1 below:

<Formula 1> wherein in Formula 1, $X_1$ is -[($L_1$)$_{a1}$-N(Ar$_1$)(Ar$_2$)];

$X_2$ is -[($L_2$)$_{a2}$-N(Ar$_3$)(Ar$_4$)];

$X_3$ is -[($L_3$)$_{a3}$-N(Ar$_5$)(Ar$_6$)];

$X_4$ is -[($L_4$)$_{a4}$-N(Ar$_7$)(Ar$_8$)] or $R_4$.

$L_1$ and $L_4$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, $L_1$ to $L_4$ in Formula 1 may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubycenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a phenylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

According to some embodiments, $L_1$ to $L_4$ may be each independently represented by at least one of Formulae 3-1 to 3-32 below:

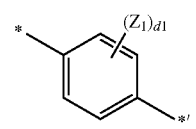

Formula 3-1


Formula 3-2

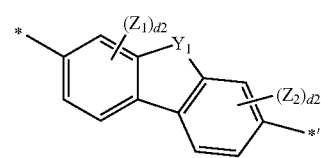

Formula 3-3

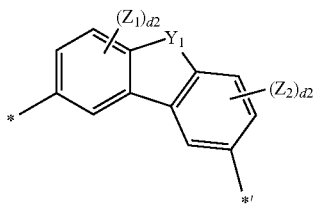
Formula 3-4
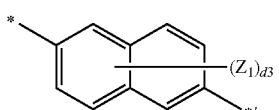
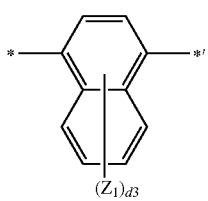
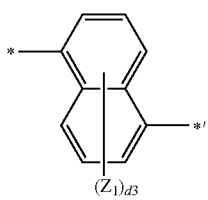
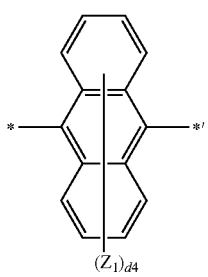
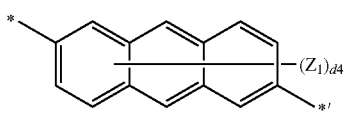
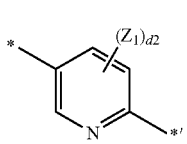
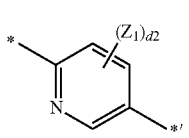
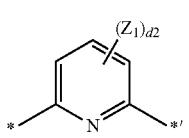
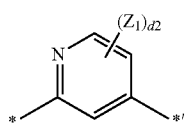
Formula 3-13
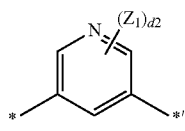
Formula 3-14
Formula 3-5
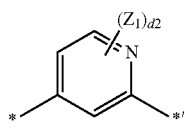
Formula 3-15
Formula 3-6
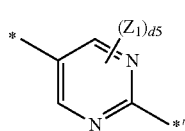
Formula 3-16
Formula 3-7
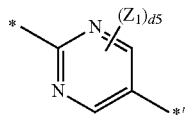
Formula 3-17
Formula 3-8
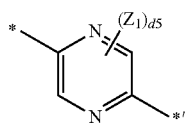
Formula 3-18
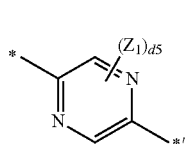
Formula 3-19
Formula 3-9
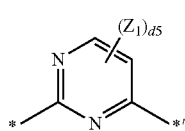
Formula 3-20
Formula 3-10
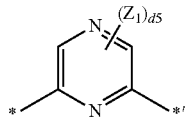
Formula 3-21
Formula 3-11
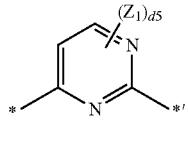
Formula 3-22
Formula 3-12
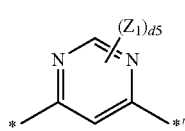
Formula 3-23

-continued

Formula 3-24
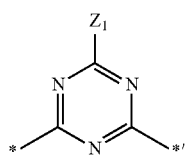

Formula 3-25
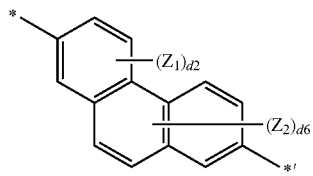

Formula 3-26
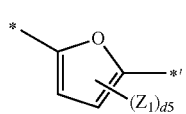

Formula 3-27
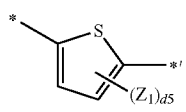

Formula 3-28
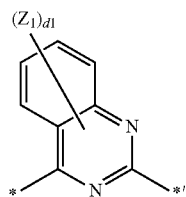

Formula 3-29
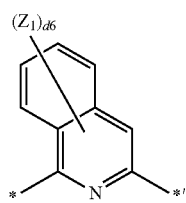

Formula 3-30
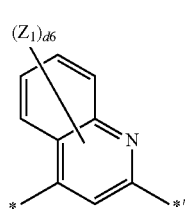

Formula 3-31
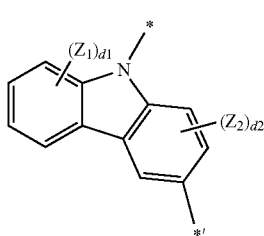

Formula 3-32
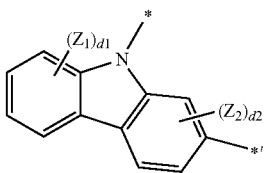

wherein in Formulae 3-1 to 3-32, $Y_1$ is O, S, C($Z_3$)($Z_4$), N($Z_5$), or Si($Z_6$)($Z_7$);

$Z_1$ to $Z_7$, each independently may be selected form a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 is an integer selected from 1 to 4, d2 is an integer selected from 1 to 3, d3 is an integer selected from 1 to 6, d4 is an integer selected from 1 to 8, d5 is 1 or 2, d6 is an integer selected from 1 to 5, and * and *' each indicates binding sites with an adjacent atom.

According to another embodiment, $L_1$ to $L_4$ may be each independently represented by one of Formulae 4-1 to 4-23 below:

Formula 4-1
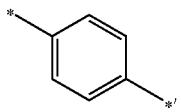

Formula 4-2
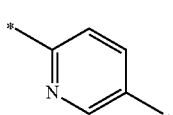

Formula 4-3
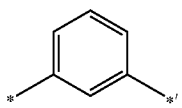

Formula 4-4
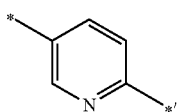

Formula 4-5
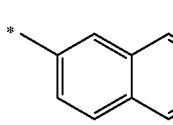

Formula 4-6
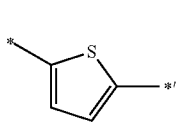

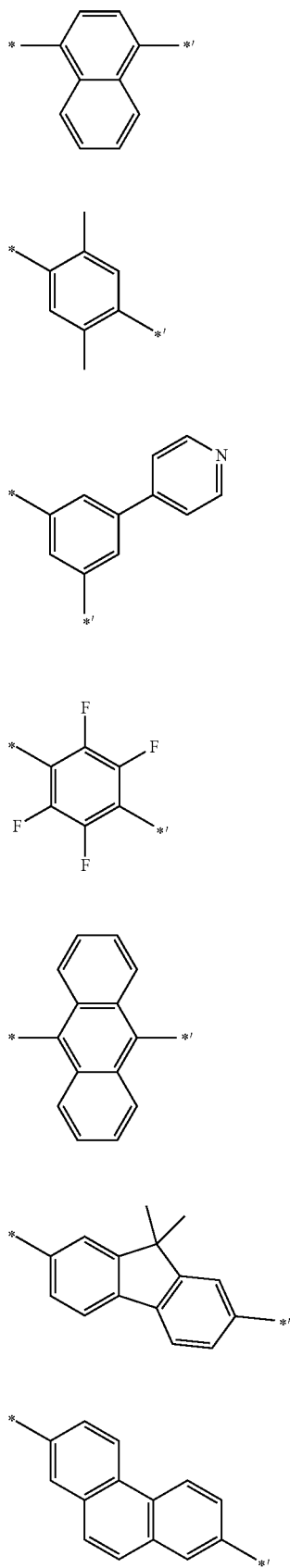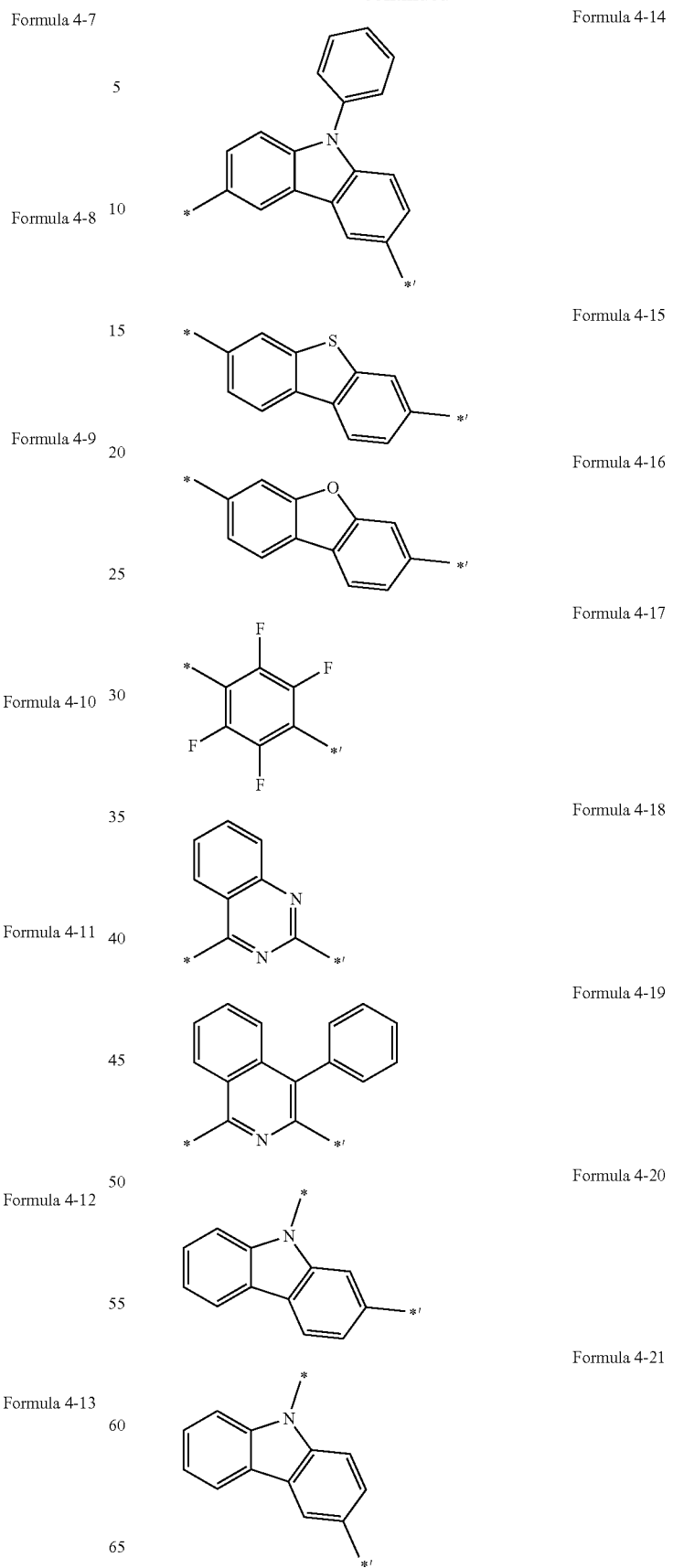

Formula 4-22

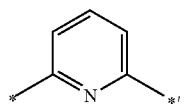

Formula 4-23

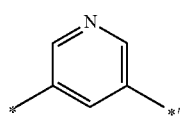

\* and \*' in Formulae 4-1 to 4-23 indicate a binding site with an adjacent atom.

a1 in Formula 1 indicates the number of $L_1$, a2 indicates the number of $L_2$, a3 indicates the number of $L_3$, and a4 indicates the number of $L_4$, and a1 to a4 may be each independently selected from 0, 1, 2, and 3.

For example, a1 to a4 may be each independently 0 or 1. When a1, a2, a3, or a4 is 0, $-(L_1)_{a1}$-, $-(L_2)_{a2}$-, $-(L_3)_{a3}$- or $-(L_4)_{a4}$- may be a single bond. When a1, a2, a3, or a4 is 2 or greater, a plurality of $L_1$s, a plurality of $L_2$s, a plurality of $L_3$s or a plurality of $L_4$s may be identical or different from each other, respectively.

$Ar_1$ to $Ar_8$ in Formula 1 are each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, $Ar_1$ to $Ar_8$ in Formula 1 may be each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$);

wherein $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

According to some embodiments, $Ar_1$ to $Ar_8$ in Formula 1 may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, a dibenzocarbazolyl group, and —Si($Q_{31}$)($Q_{32}$)($Q_{33}$);

wherein $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

According to some embodiments, $Ar_1$ to $Ar_8$ in Formula 1 may be each independently selected from Formulae 5-1 to 5-14 below.

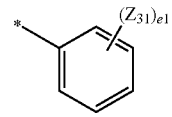

Formula 5-1

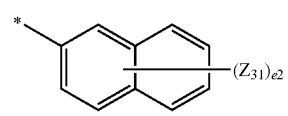

Formula 5-2

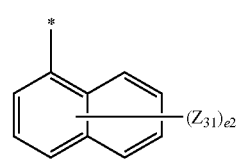

Formula 5-3

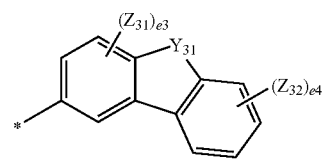

Formula 5-4

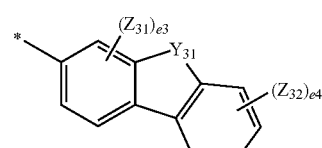

Formula 5-5

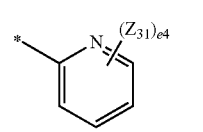

Formula 5-6

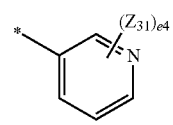

Formula 5-7

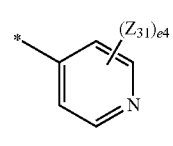

Formula 5-8

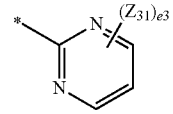

Formula 5-9

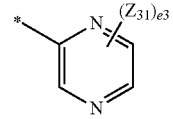

Formula 5-10

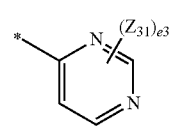

Formula 5-11

Formula 5-12

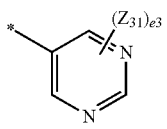

Formula 5-13

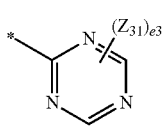

Formula 5-14

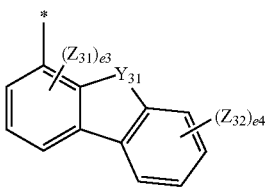

wherein in Formulae 5-1 to 5-14, $Y_{31}$ is O, S, $C(Z_{33})(Z_{34})$ or $N(Z_{35})$;

$Z_{31}$ to $Z_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a naphthyl group; and —Si($Q_{31}$)($Q_{32}$)($Q_{33}$), wherein $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

e1 may be an integer selected from 1 to 5; e2 may be an integer selected from 1 to 7; e3 may be an integer selected from 1 to 3; e4 may be an integer selected from 1 to 4; e5 may be 1 or 2; and * indicates a binding site with an adjacent atom.

According to some embodiments, $Ar_1$ to $Ar_8$ in Formula 1 may be each independently selected from Formulae 6-1 to 6-28 below:

Formula 6-1

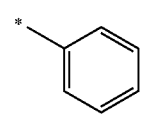

Formula 6-2

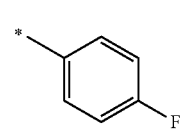

Formula 6-3

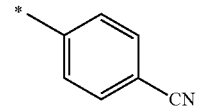

Formula 6-4

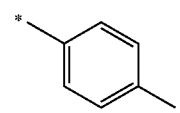

Formula 6-5

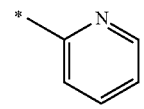

Formula 6-6

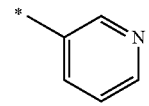

Formula 6-7

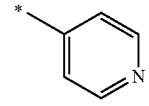

Formula 6-8

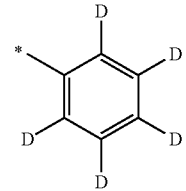

Formula 6-9

Formula 6-10

Formula 6-11

Formula 6-12

Formula 6-13

Formula 6-14

Formula 6-15

Formula 6-16

Formula 6-17

Formula 6-18

Formula 6-19

Formula 6-20

Formula 6-21

Formula 6-22

Formula 6-23

Formula 6-24

Formula 6-25

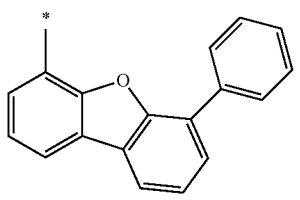

Formula 6-26

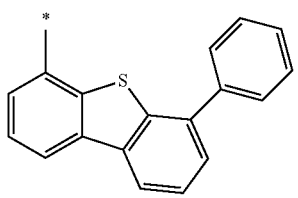

Formula 6-27

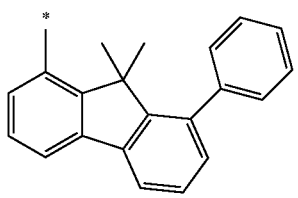

Formula 6-28

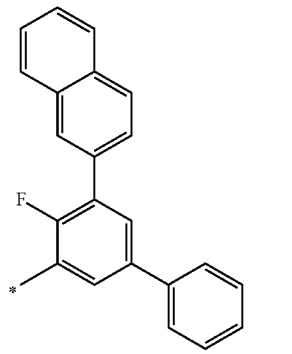

* in Formulae 6-1 to 6-28 indicates a binding site with an adjacent atom.

b1 in Formula 1 indicates the number of $X_1$, b2 indicates the number of $X_2$, b3 indicates the number of $X_3$, b1 and b2 are each independently an integer selected from 0 to 4; b3 is an integer selected from 0 to 3; and i) when $X_4$ is $R_4$, b1+b2+b3≥2, and ii) when $X_4$ is $-[(L_4)_{a4}-N(Ar_7)(Ar_5)]$, b1+b2+b3≥1.

In some embodiments, $X_4$ is $R_4$, and b1+b2+b3=2.
According to some embodiments, $X_4$ is $R_4$, and
b1=b2=1, and b3=0;
b1=b3=1, and b2=0; or
b2=b3=1, and b1=0.
According to some embodiments,
when b1≠0 and b2≠0, $X_1=X_2$,
when b1≠0 and b3≠0, $X_1=X_3$, or
when b2≠0 and b3≠0, $X_2=X_3$.

$R_1$ to $R_6$ in Formula 1 are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthiogroup, a substituted or unsubstituted $C_2$-$C_{60}$ heteroaryl group, a substituted or unsubstituted monovalent non-aromatic condensed polycyclic group, a substituted or unsubstituted monovalent non-aromatic heterocondensed polycyclic group, $-Si(Q_1)(Q_2)(Q_3)$, and $-B(Q_4)(Q_5)$;

In some embodiments, $R_1$ to $R_4$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, a substituted or unsubstituted monovalent non-aromatic condensed heteropolycyclic group, and $-Si(Q_1)(Q_2)(Q_3)$; and $R_5$ and $R_6$ in Formula 1 may be each independently selected form a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, and a substituted or unsubstituted monovalent non-aromatic condensed heteropolycyclic group.

In some embodiments, $R_5$ and $R_6$ in Formula 1 may not be linked to each other.

c1 in Formula 1 indicates the number of $R_1$, c2 indicates the number of $R_2$ and c3 indicates the number of $R_3$, c1 and c2 may be each independently an integer selected from 0 to 4, and c3 may be an integer selected from 0 to 3.

In some embodiments, a condensed cyclic compound represented by Formula 1 may be represented by one of Formulae 1-1 to 1-5 below:

<Formula 1-1>

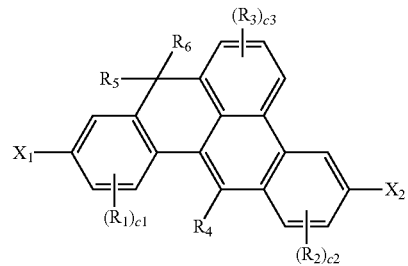

<Formula 1-2>

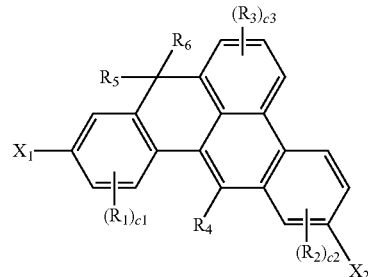

-continued

<Formula 1-3>

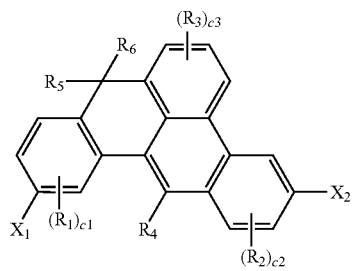

<Formula 1-4>

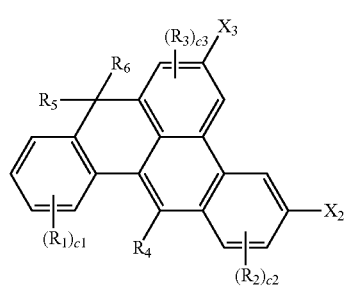

<Formula 1-5>

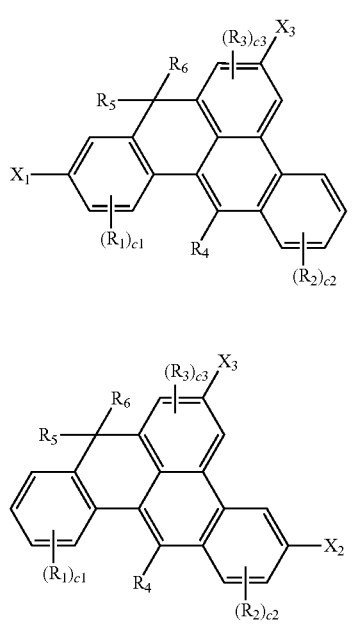

$X_1$ to $X_3$, $R_1$ to $R_6$, and c1 to c3 in Formulae 1-1 to 1-5 may be understood by referring to the descriptions provided herein.

In some embodiments, $L_1$ and $L_2$ in Formulae 1-1 to 1-5 may be each independently represented by one of Formulae 4-1 to 4-23 as illustrated above.

In some embodiments, $Ar_1$ to $Ar_4$ in Formulae 1-1 to 1-5 may be each independently represented by one of Formulae 6-1 to 6-28 as illustrated above.

In some embodiments, a condensed cyclic compound represented by Formula 1 may be represented by one of Formulae 1-21 to 1-24 below:

<Formula 1-21>

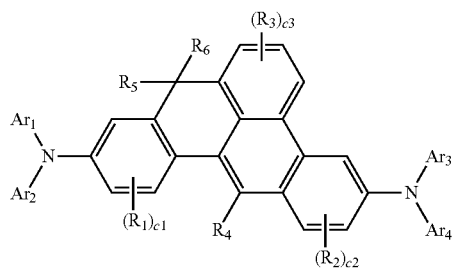

-continued

<Formula 1-22>

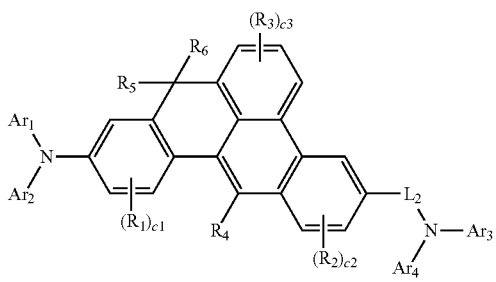

<Formula 1-23>

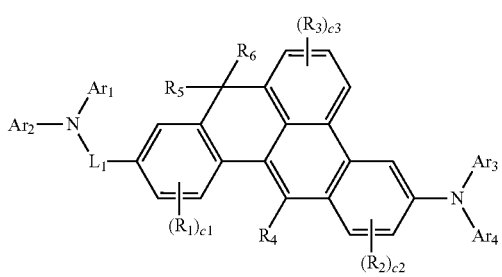

<Formula 1-24>

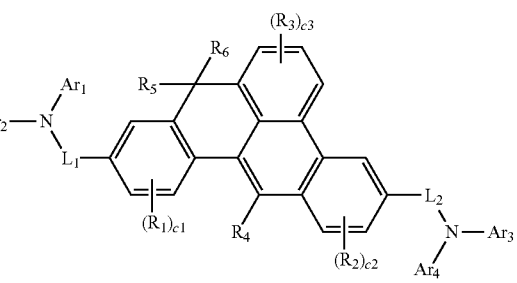

$L_1$, $L_2$, $Ar_1$ to $Ar_4$, and c1 to c3 in Formulae 1-21 to 1-24 may be understood by referring to the descriptions provided herein;

$R_1$ to $R_4$ in Formulae 1-21 to 1-24 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, a substituted or unsubstituted monovalent non-aromatic condensed heteropolycyclic group, and —Si(Q$_1$)(Q$_2$)(Q$_3$); and R$_5$ and R$_6$ may be each independently selected from a substituted or unsubstituted C$_1$-C$_{20}$ alkyl group, a substituted or unsubstituted C$_1$-C$_{20}$ alkoxy group, a substituted or unsubstituted C$_6$-C$_{20}$ aryl group, a substituted or unsubstituted C$_2$-C$_{20}$ heteroaryl group, a substituted or unsubstituted monovalent non-aromatic condensed polycyclic group, and a substituted or unsubstituted monovalent non-aromatic condensed heteropolycyclic group.

In some embodiments, Ar$_1$, Ar$_2$, Ar$_3$, and Ar$_4$ in Formulae 1-21 to 1-24 may be Ar$_1$=Ar$_2$=Ar$_3$=Ar$_4$;
Ar$_1$≠Ar$_2$, and Ar=Ar$_4$, and Ar$_2$=Ar$_3$;
Ar$_1$=A$_4$, and Ar$_2$≠Ar$_3$;
Ar$_1$≠A$_4$, and Ar$_2$=Ar$_3$;
Ar$_1$≠Ar$_2$, and Ar$_2$=Ar$_4$, and Ar$_1$=Ar$_3$;
Ar$_2$=Ar$_4$, and Ar$_1$≠Ar$_3$;
Ar$_2$≠Ar$_4$, and Ar$_1$=Ar$_3$;
Ar$_1$=Ar$_2$, and Ar$_3$≠Ar$_4$;
Ar$_1$≠Ar$_2$, and Ar$_3$=Ar$_4$; or
Ar$_1$≠Ar$_2$≠Ar$_3$≠Ar$_4$.

According to some embodiments, a condensed cyclic compound represented by Formula 1 may be represented by Formulae 1-31 or 1-32 below.

<Formula 1-31>

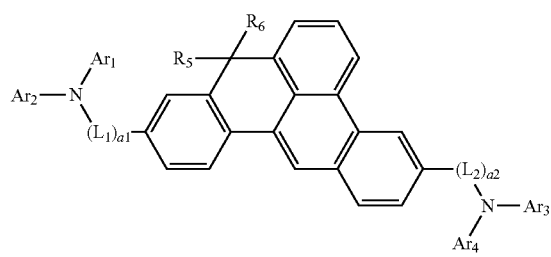

<Formula 1-32>

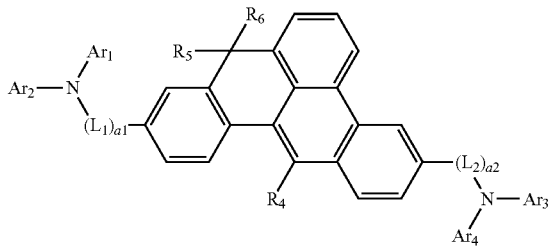

L$_1$, L$_2$, and Ar$_1$ to Ar$_4$ in Formulae 1-31 and 1-32 may be understood by referring to the descriptions provided herein;

R$_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted C$_1$-C$_{20}$ alkyl group, a substituted or unsubstituted C$_1$-C$_{20}$ alkoxy group, a substituted or unsubstituted C$_6$-C$_{20}$ aryl group, a substituted or unsubstituted C$_2$-C$_{20}$ heteroaryl group, a substituted or unsubstituted monovalent non-aromatic condensed polycyclic group, a substituted or unsubstituted monovalent non-aromatic condensed hetero-polycyclic group, and —Si(Q$_1$)(Q$_2$)(Q$_3$);

R$_5$ and R$_6$ may be each independently selected from a substituted or unsubstituted C$_1$-C$_{20}$ alkyl group, a substituted or unsubstituted C$_1$-C$_{20}$ alkoxy group, a substituted or unsubstituted C$_6$-C$_{20}$ aryl group, a substituted or unsubstituted C$_2$-C$_{20}$ heteroaryl group, a substituted or unsubstituted monovalent non-aromatic condensed polycyclic group, and a substituted or unsubstituted monovalent non-aromatic condensed heteropolycyclic group; and a1 and a2 may be each independently 0 or 1.

A condensed cyclic compound represented by Formula 1 may be one of Compounds 1 to 373 below. (herein Ph in Compounds below indicates a phenyl group):

1

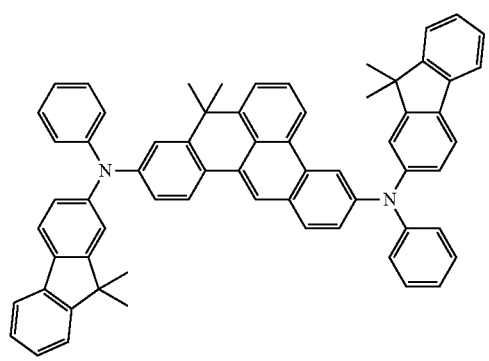

2

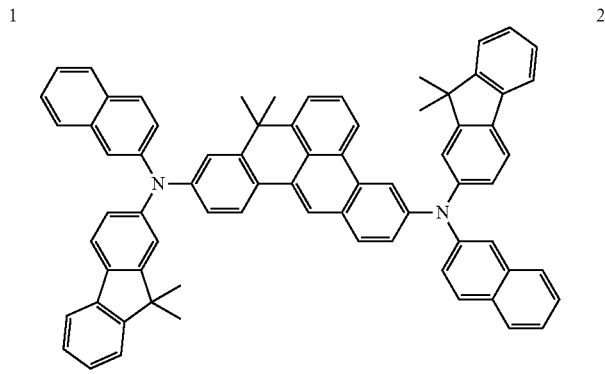

-continued
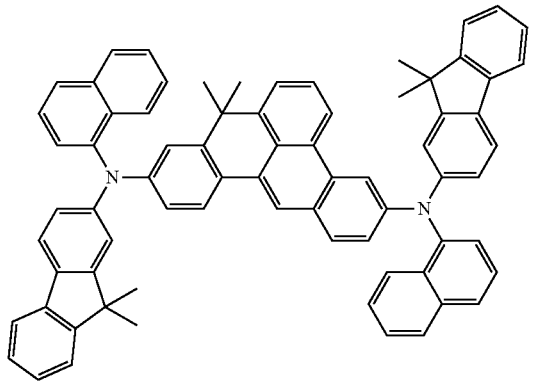
3
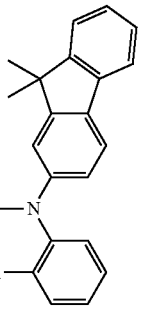
4
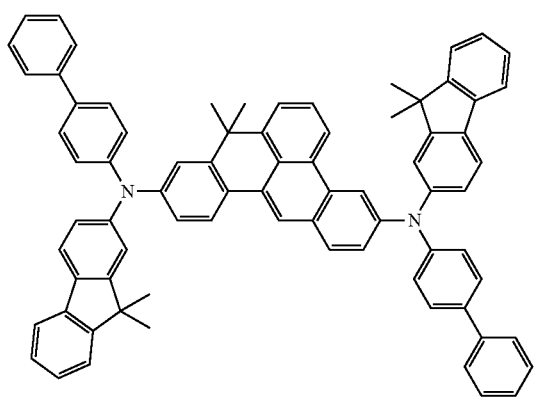
5
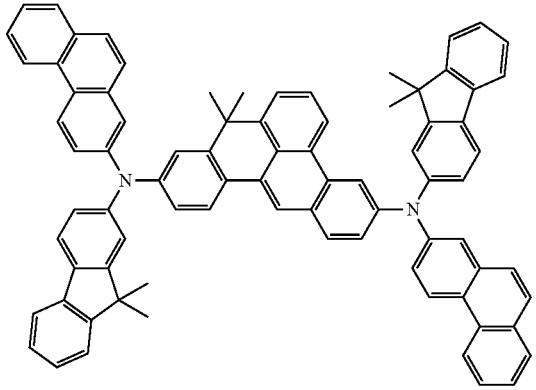
6
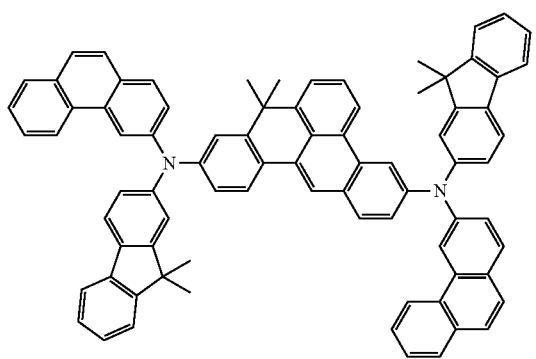
7
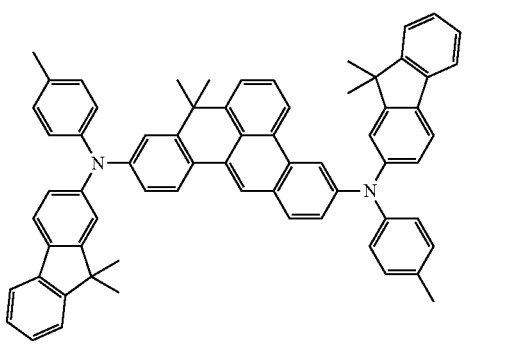
8
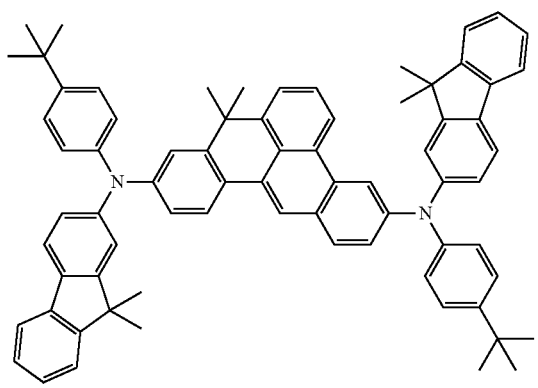
9
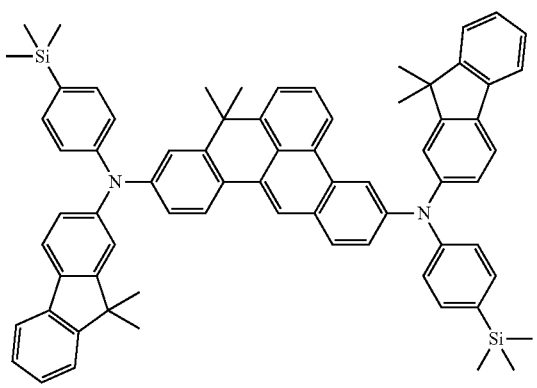
10

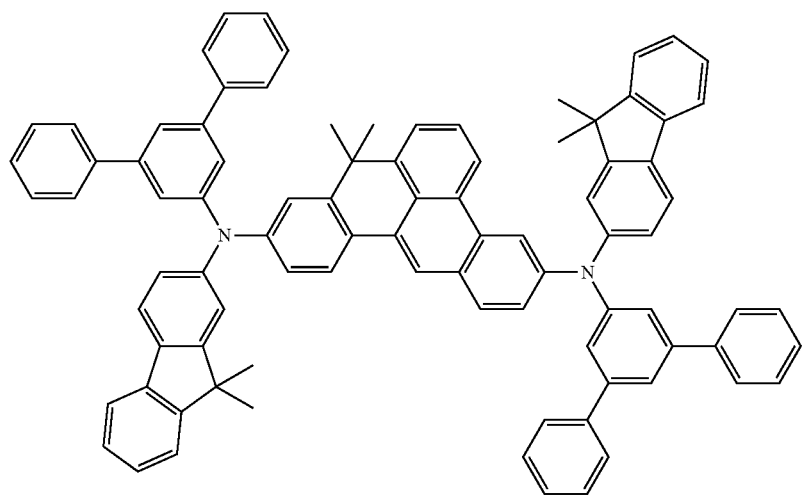
11
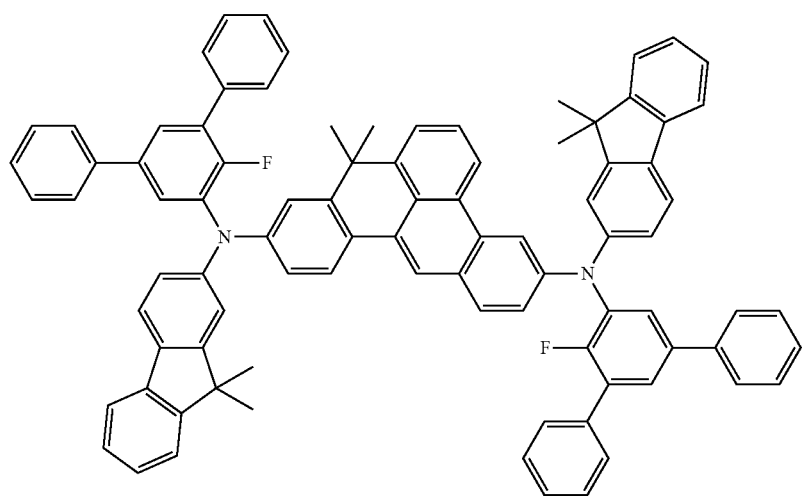
12
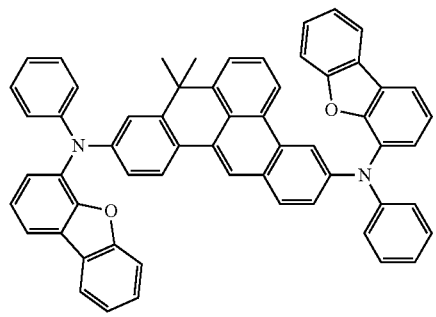
13
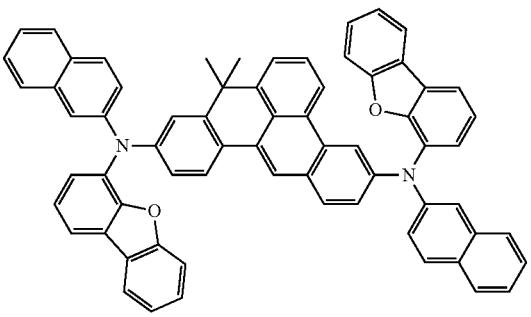
14

-continued
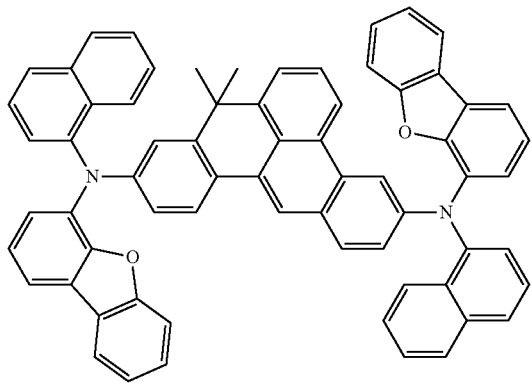
15
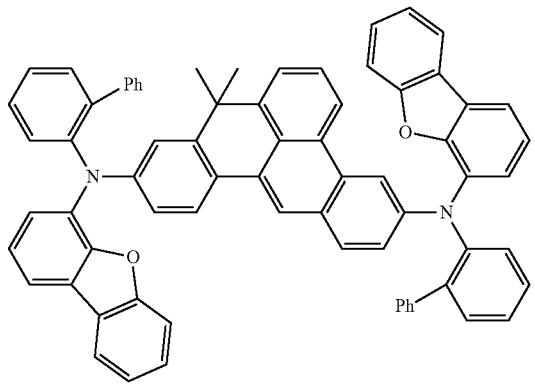
16
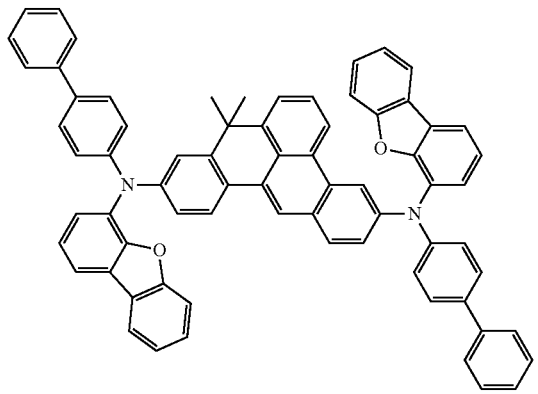
17
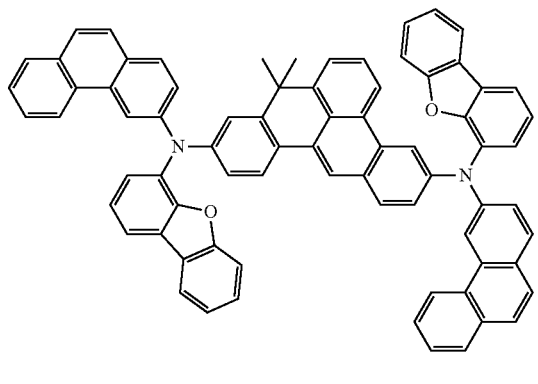
18
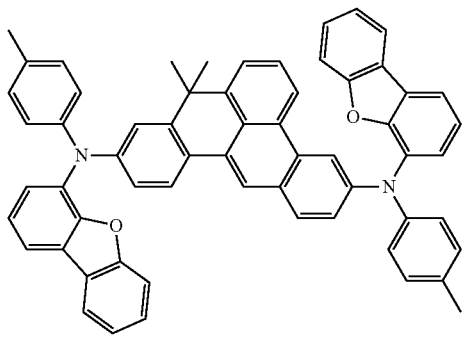
19
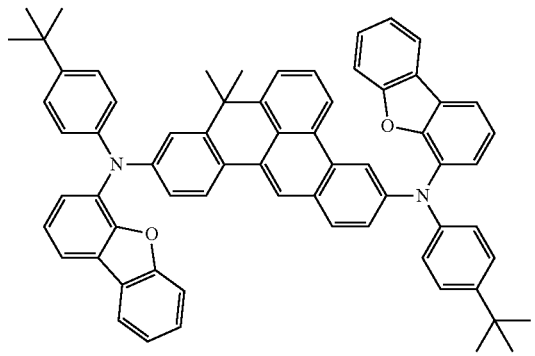
20
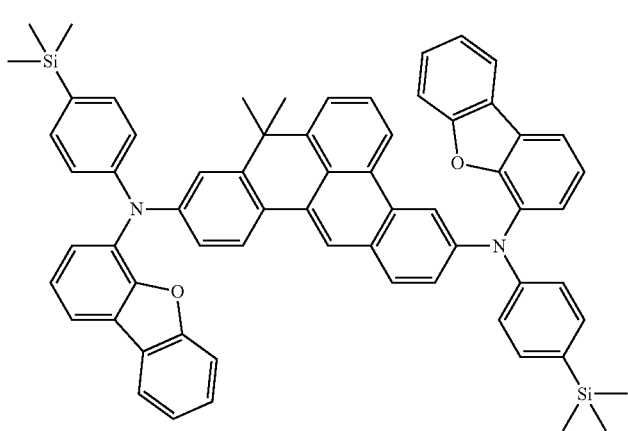
21

22
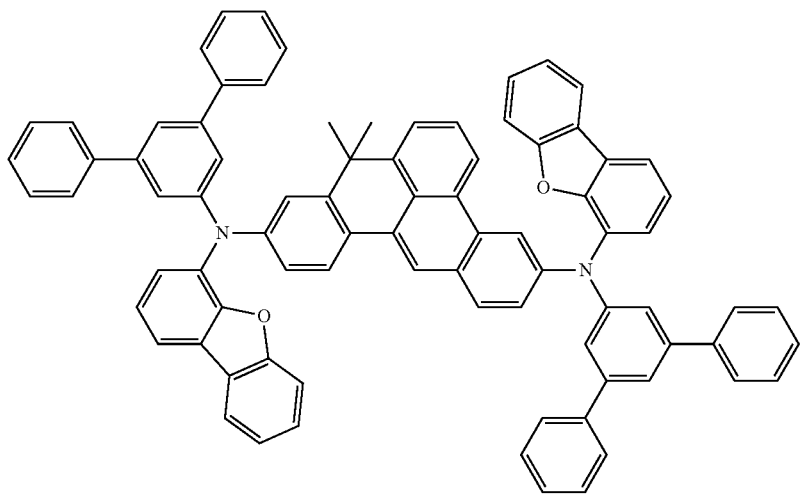
23
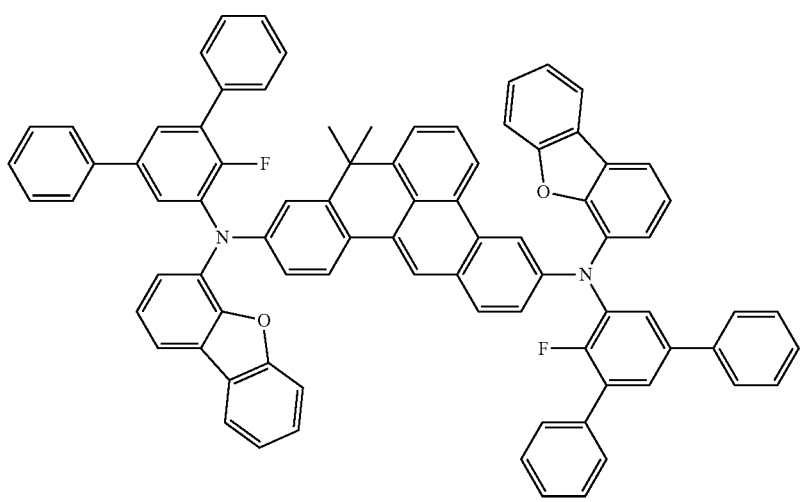
24
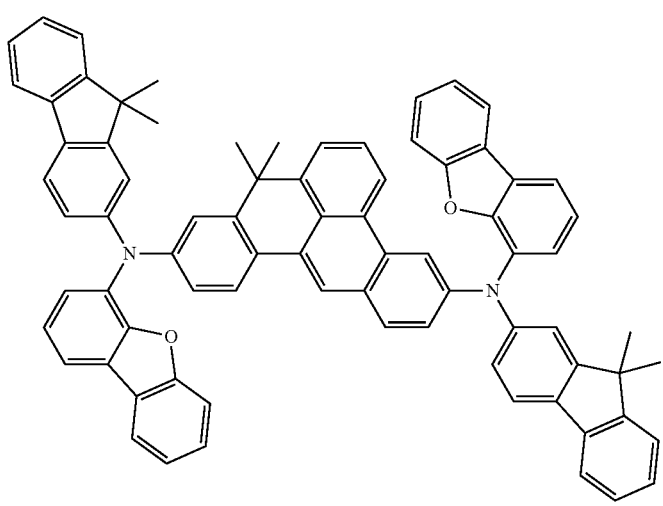

25
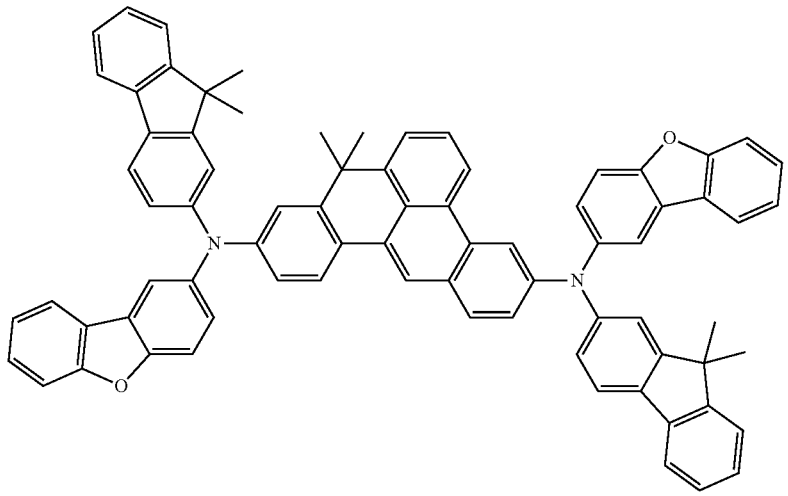
26
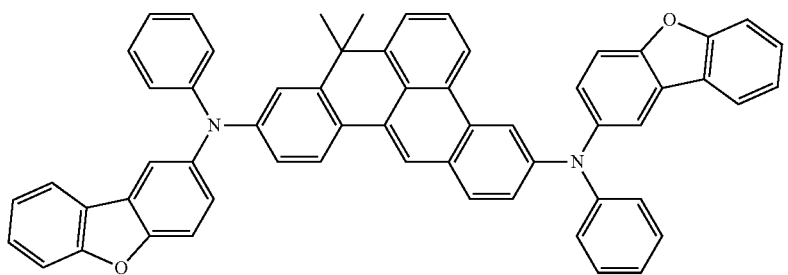
27
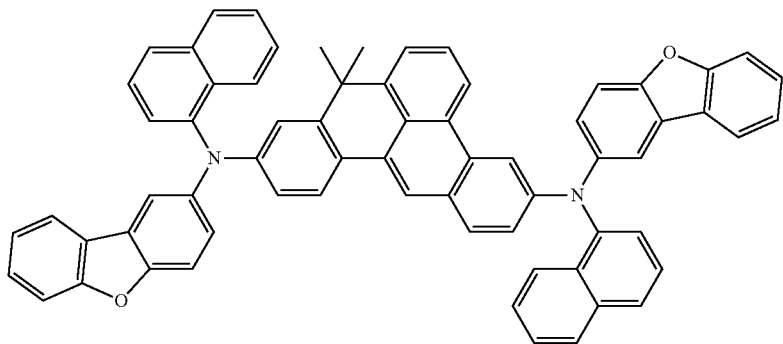
28
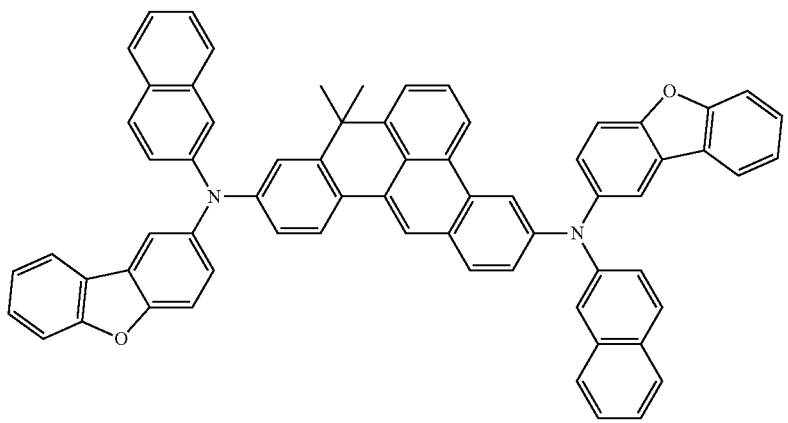

29
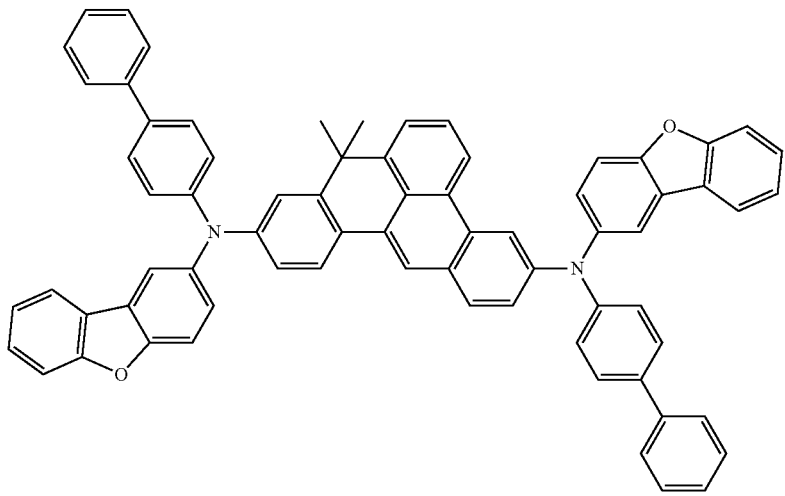
30
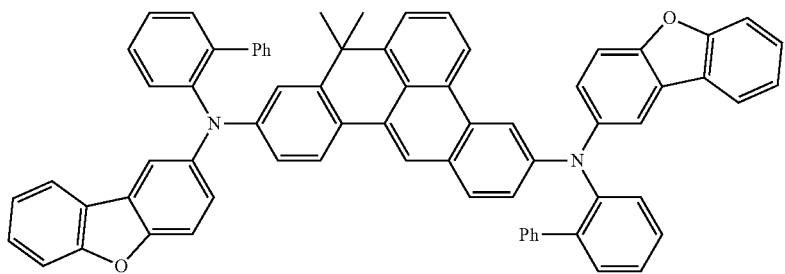
31
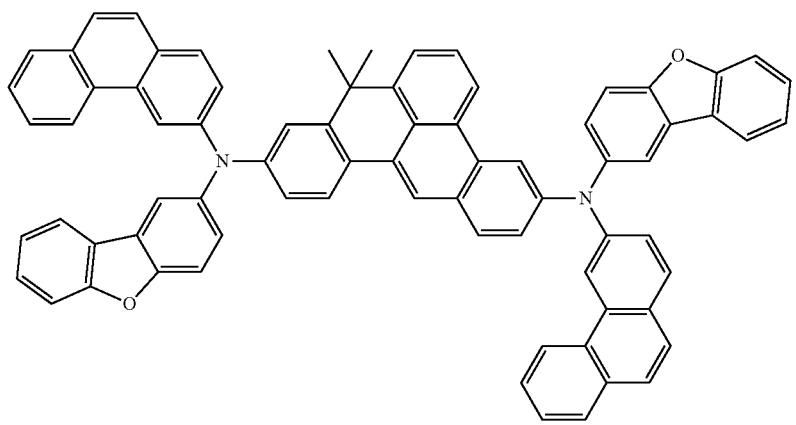
32
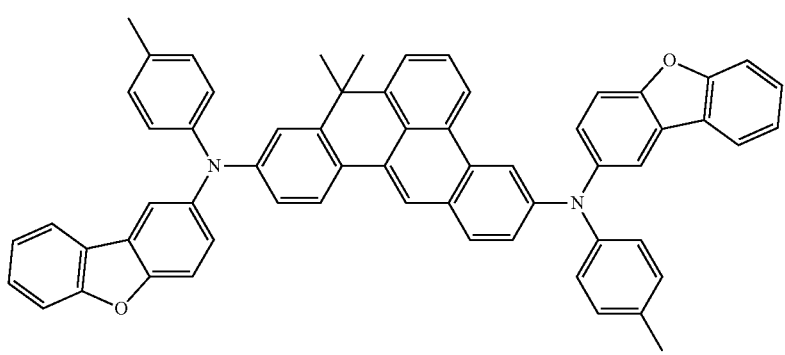

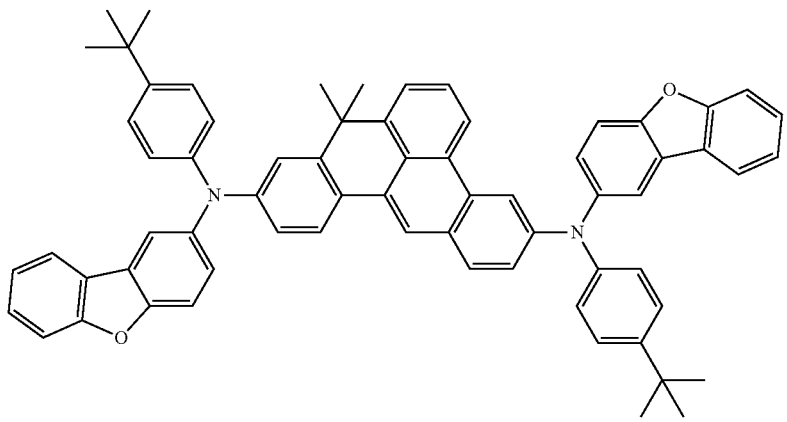
33
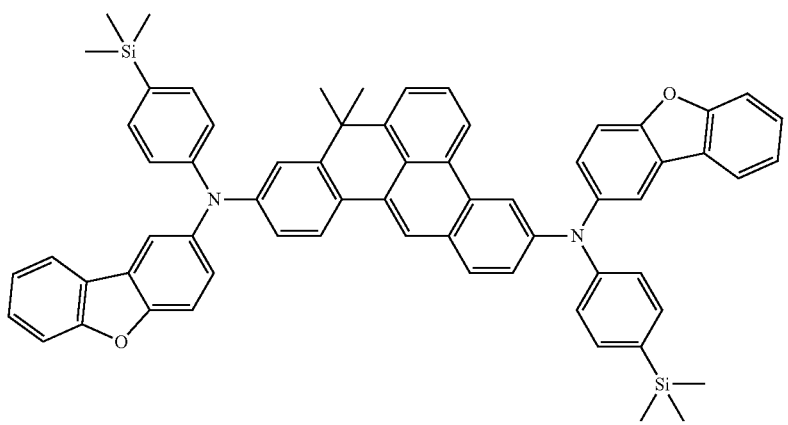
34
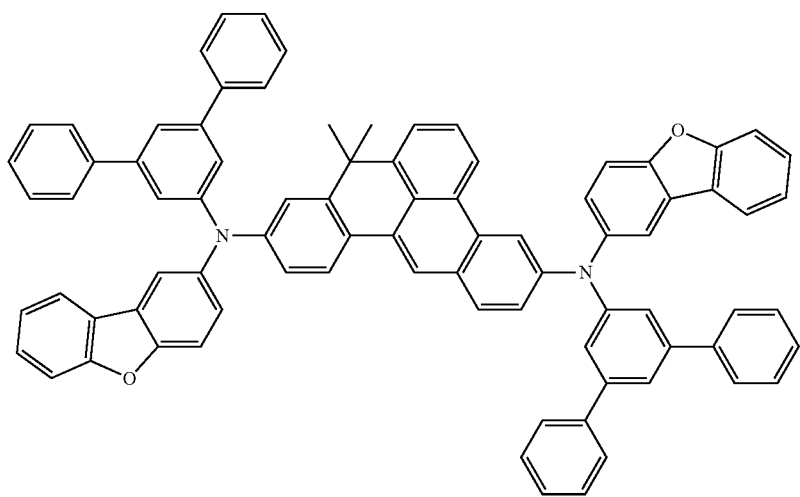
35

-continued
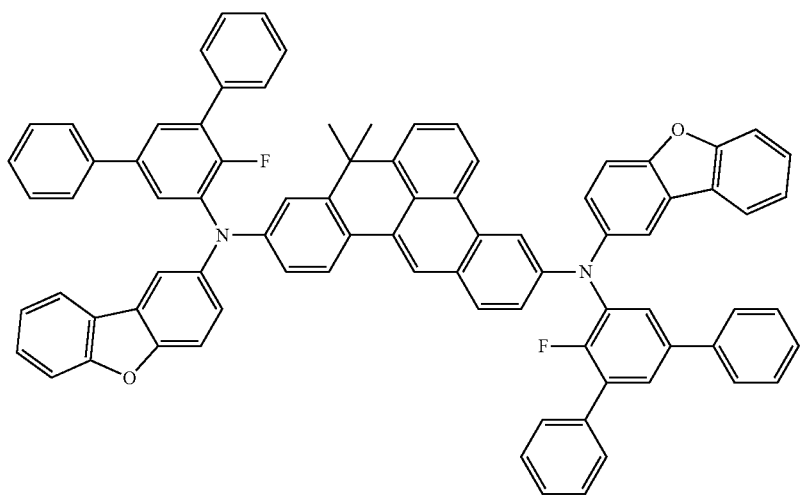
36
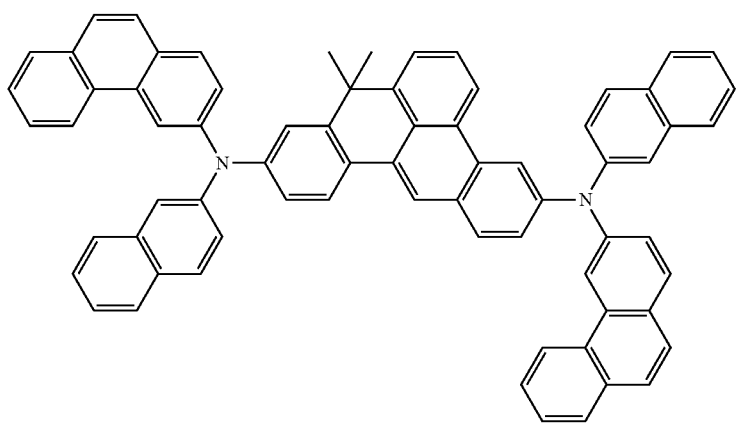
37
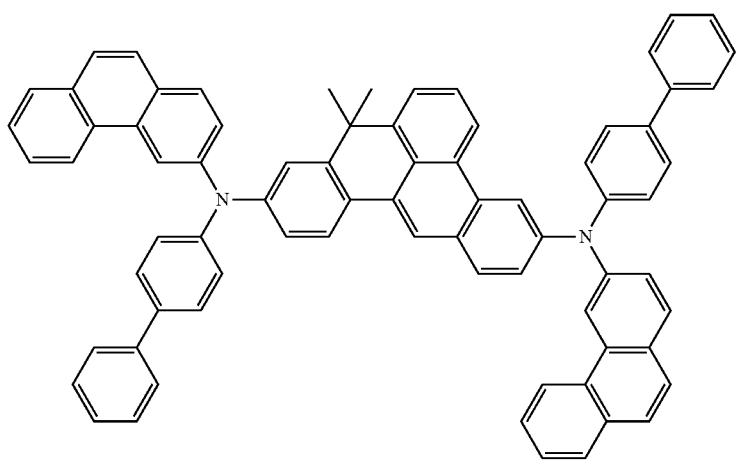
38

39
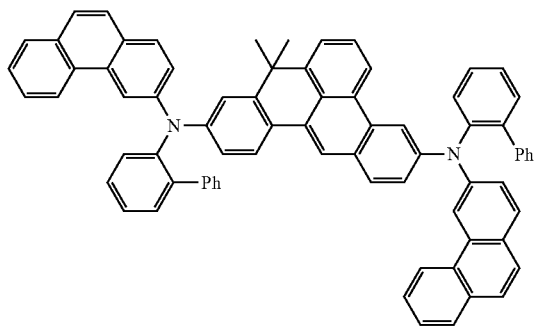
40
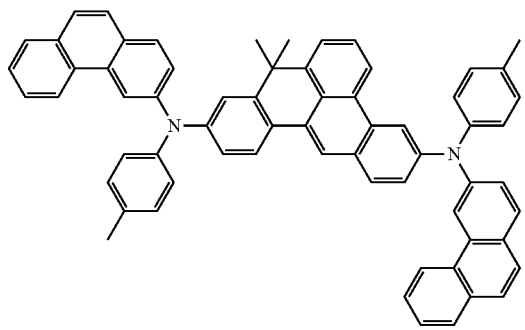
41
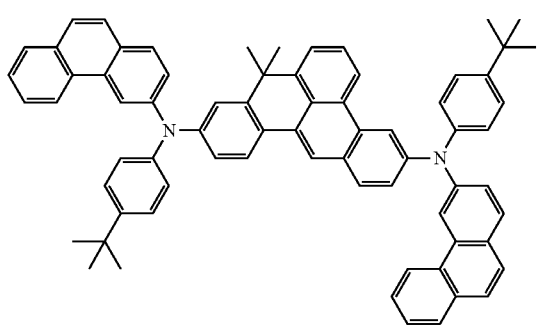
42
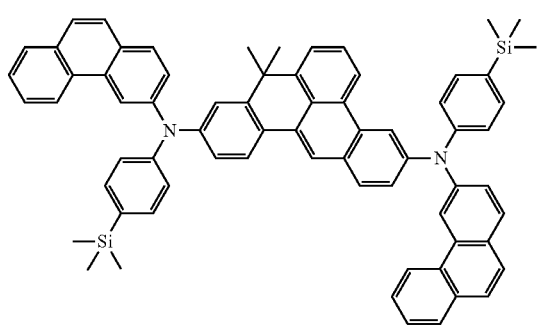
43
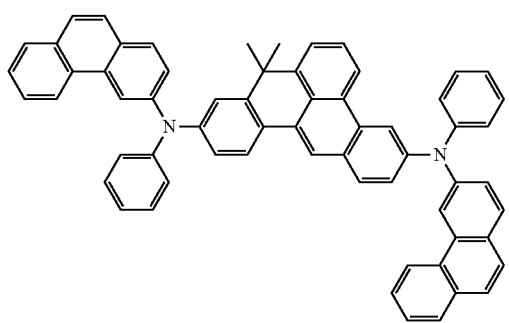
44
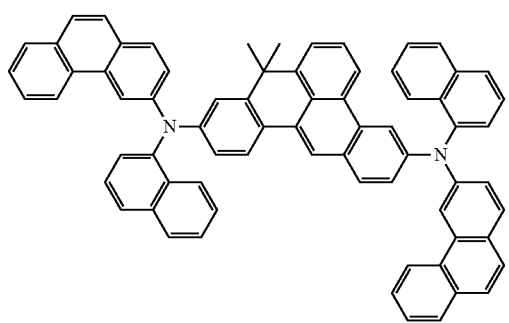
45
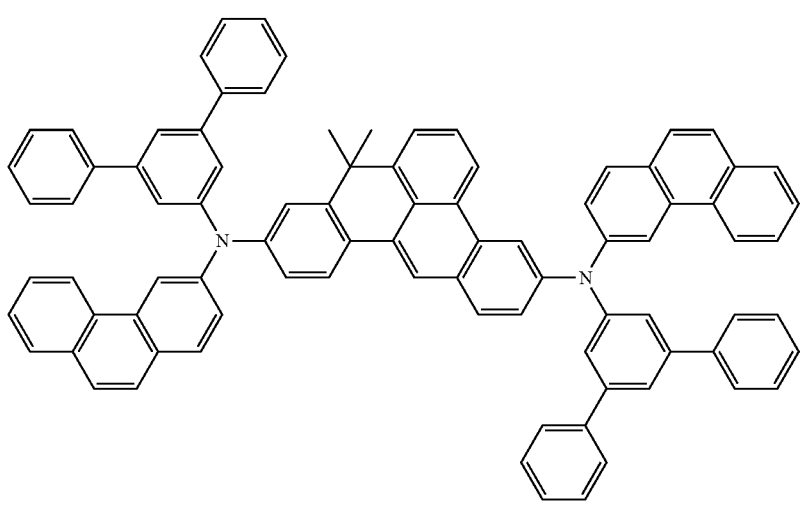

-continued
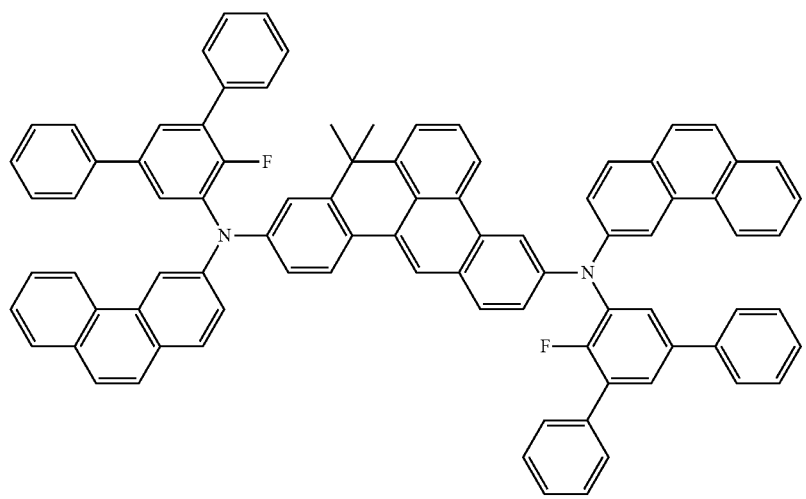
46
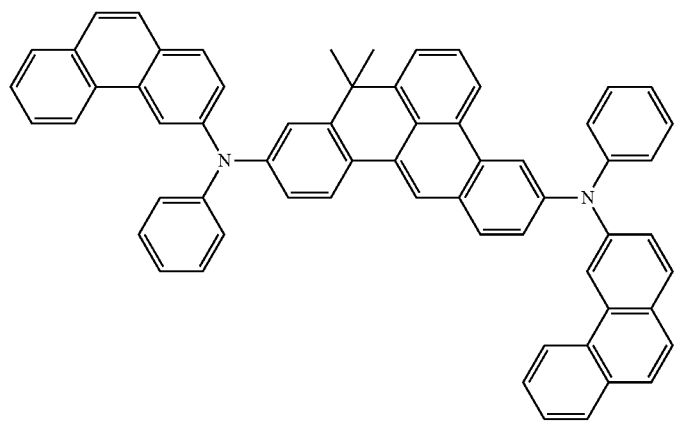
47
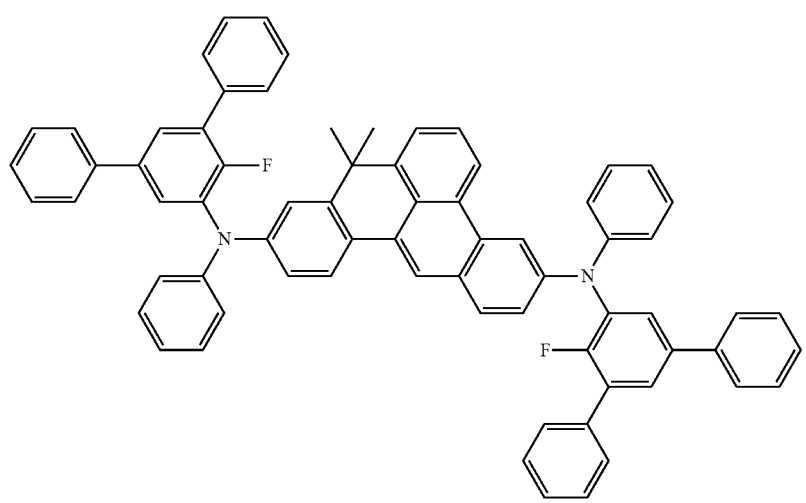
48

49
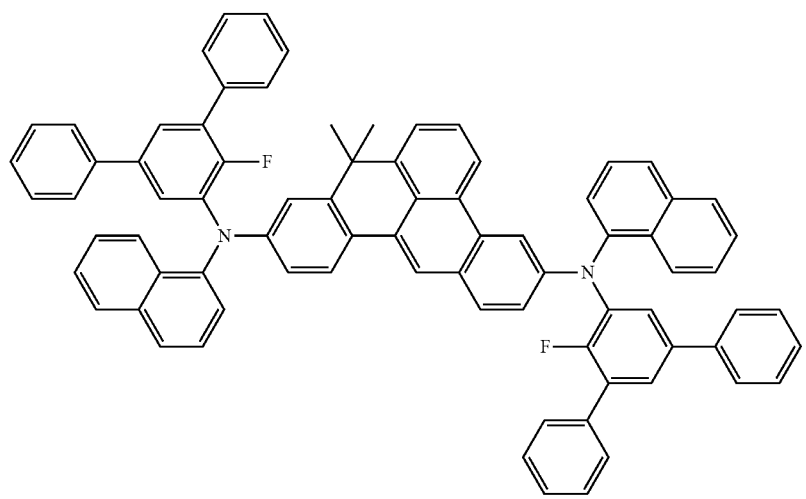
50
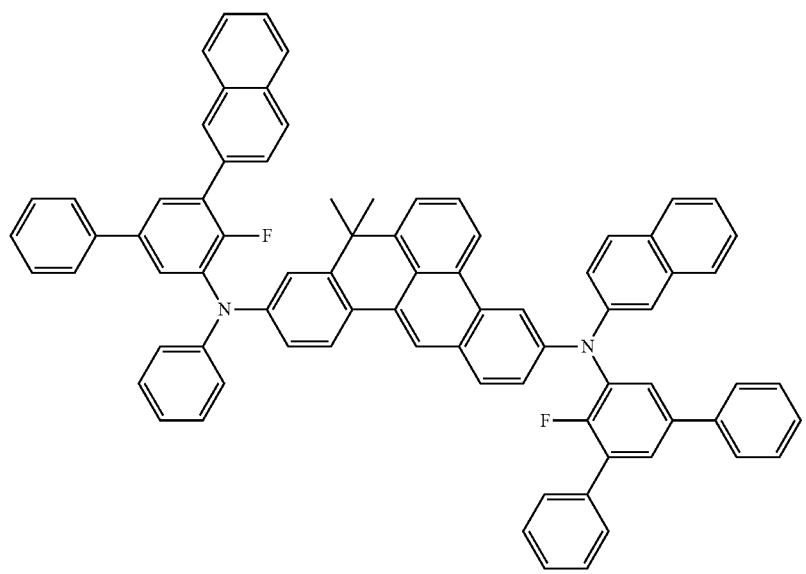
51
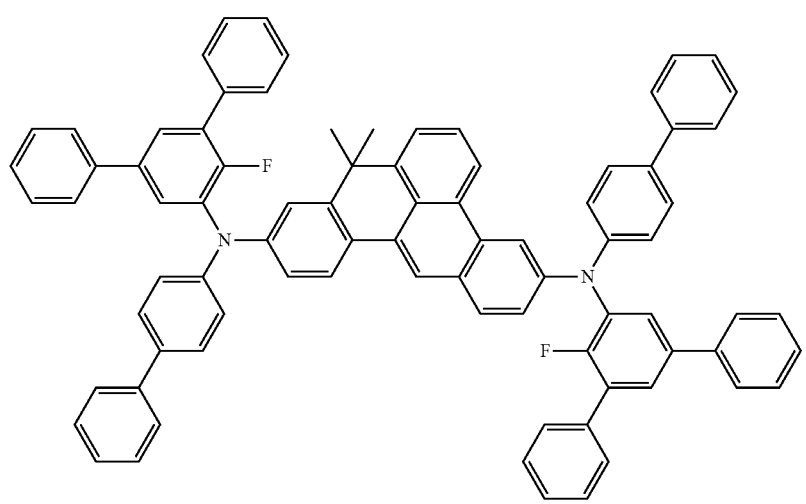

-continued
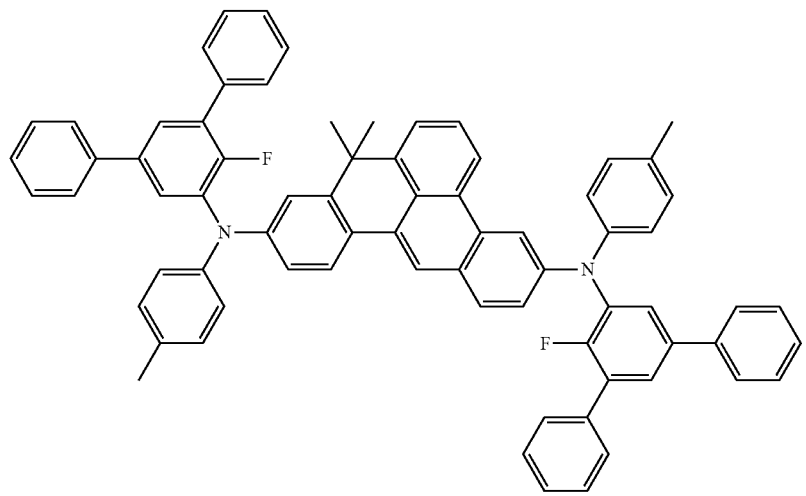
52
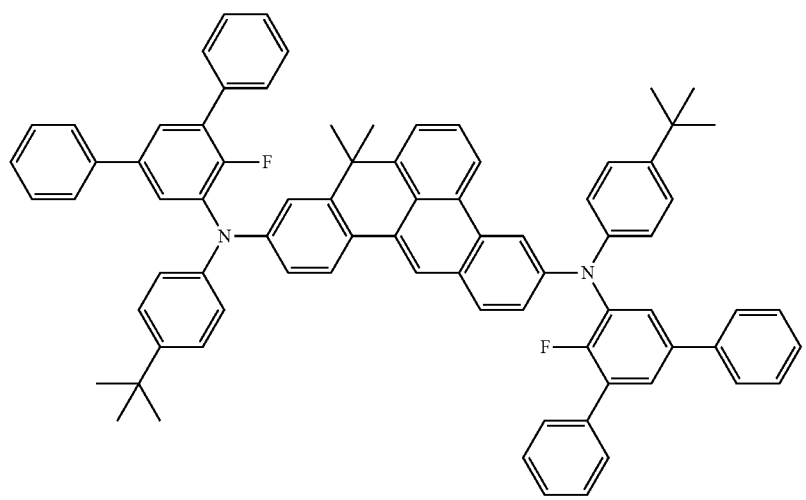
53
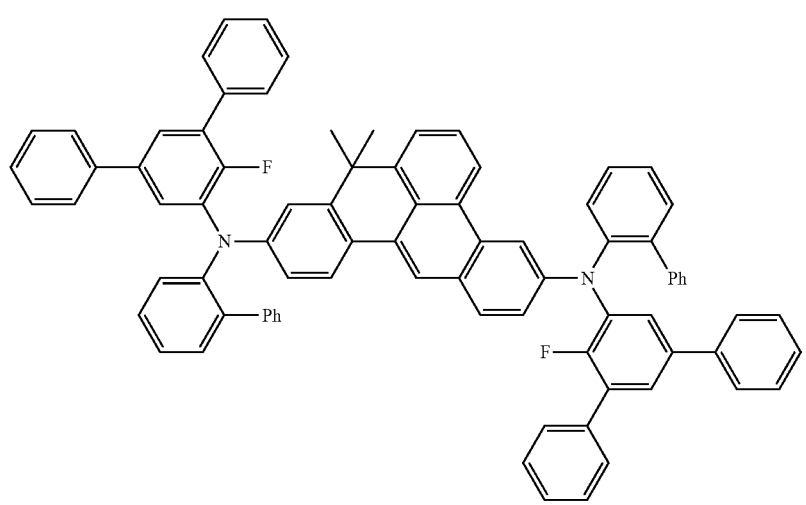
54

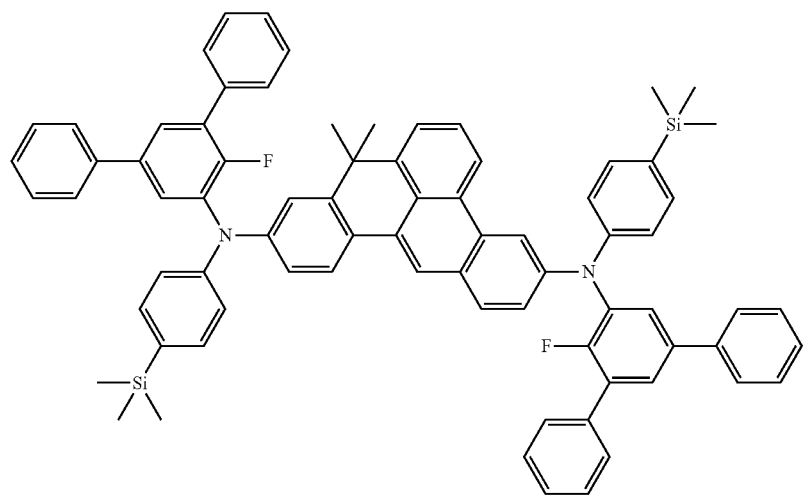
55
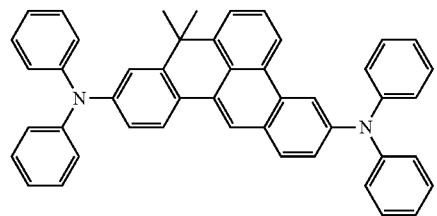
56
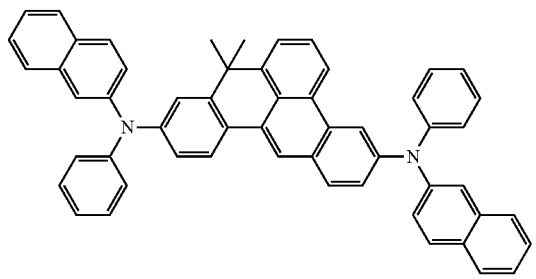
57
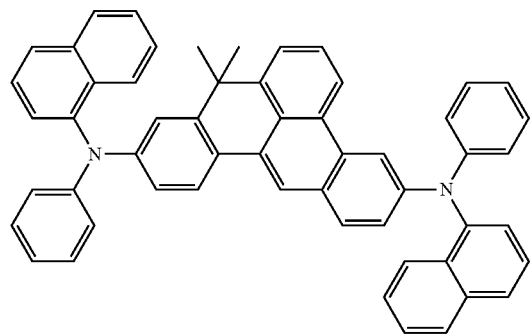
58
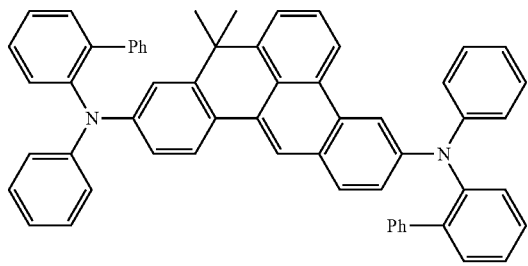
59
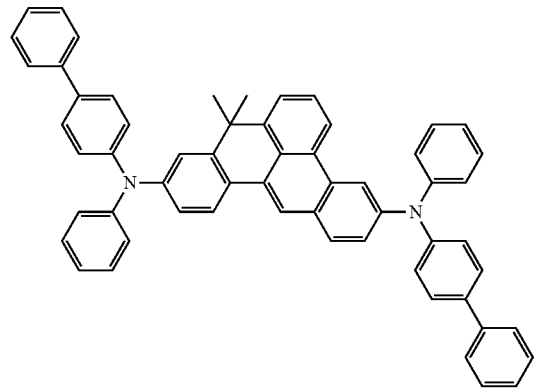
60
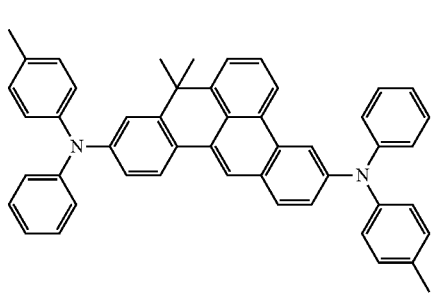
61

-continued
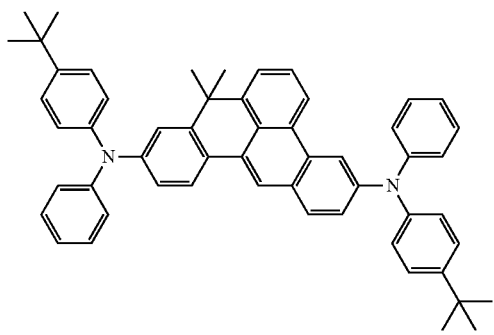
62
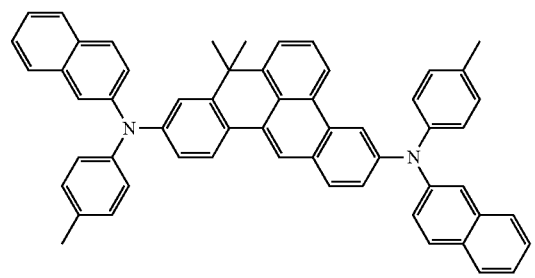
63
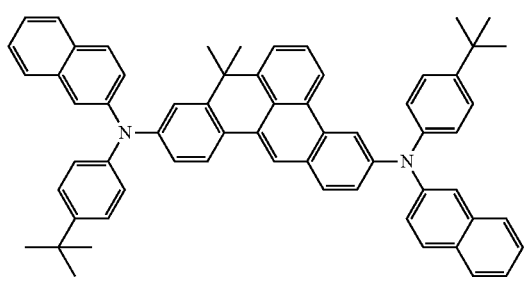
64
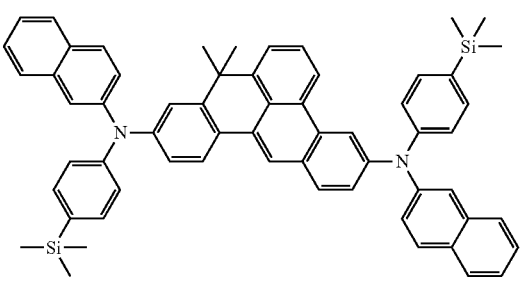
65
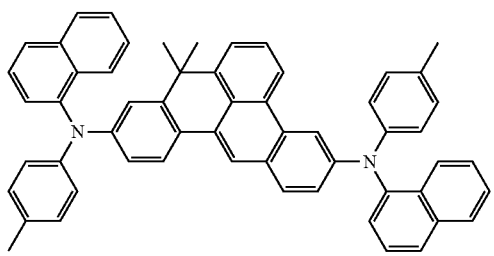
66
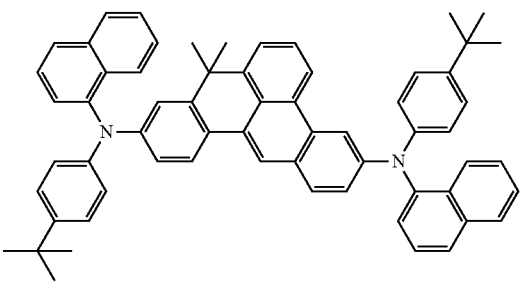
67
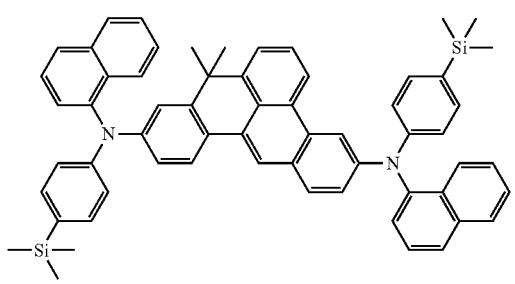
68
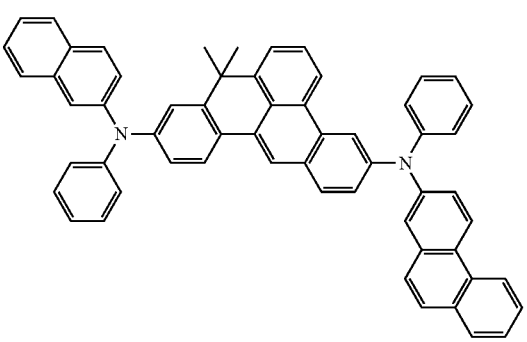
69

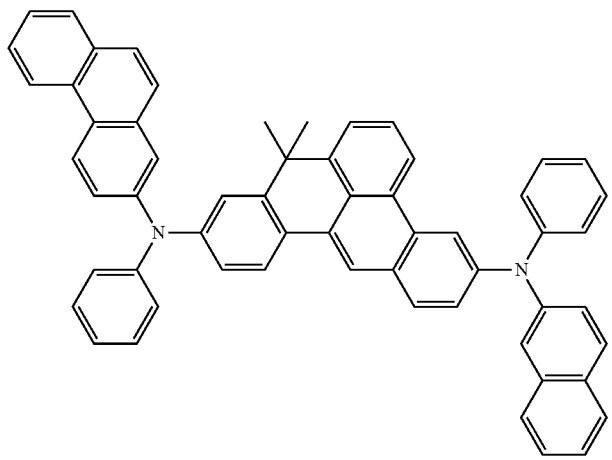
70
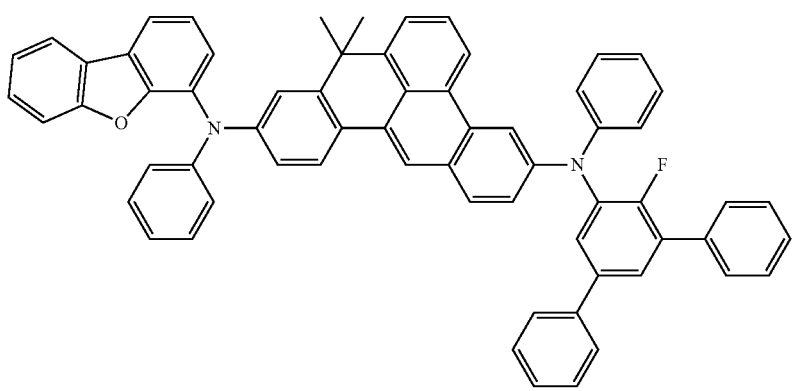
71
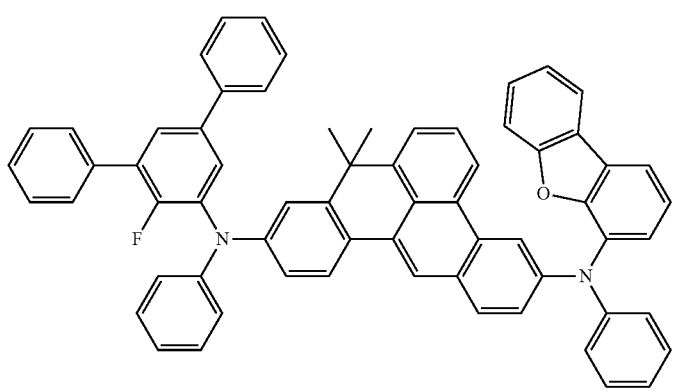
72

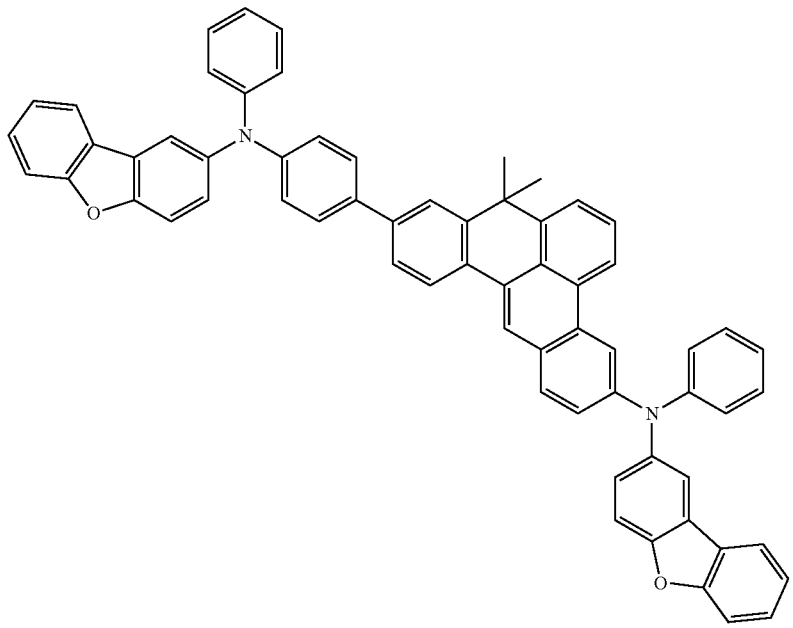
73
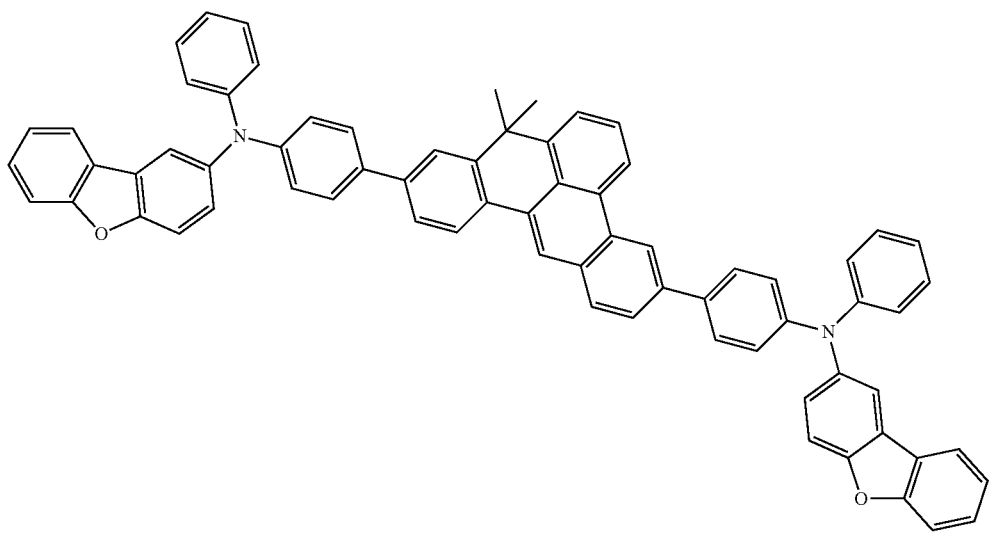
74
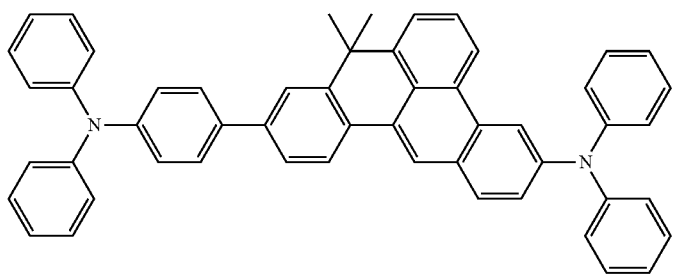
75

76
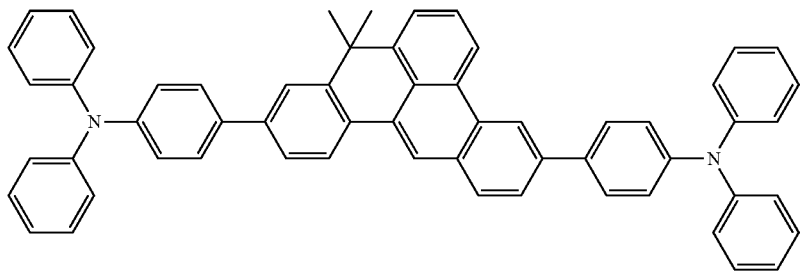
77
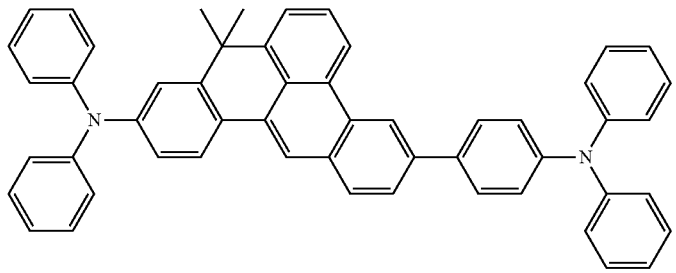
78
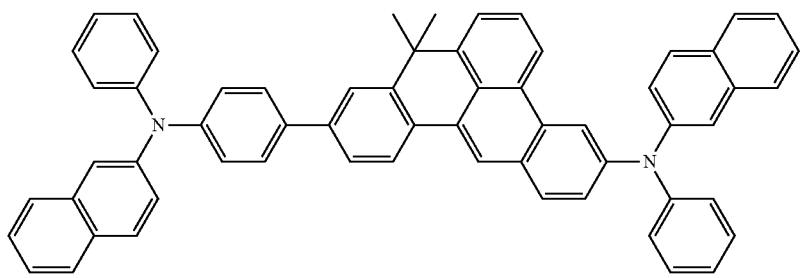
79
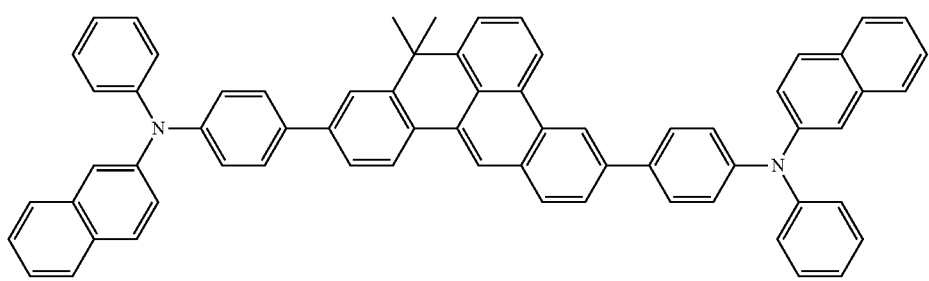
80
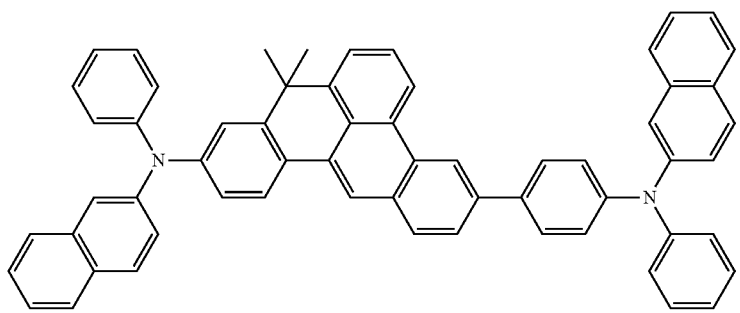

-continued
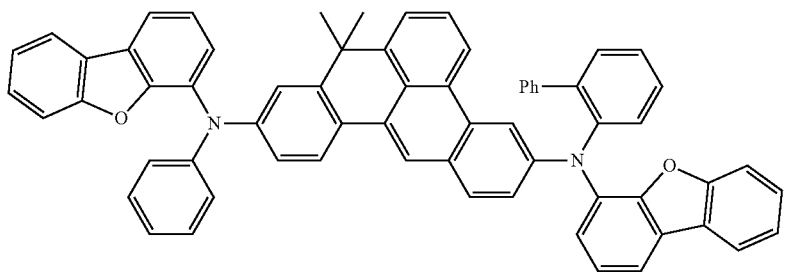
81
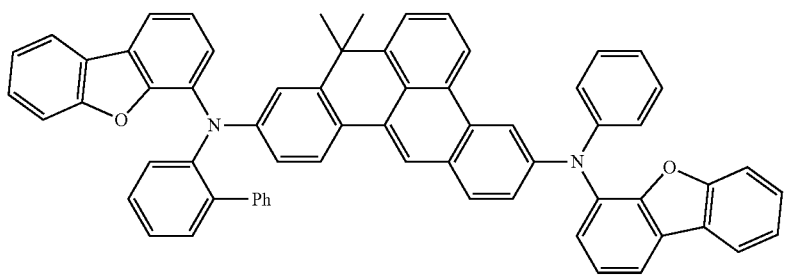
82
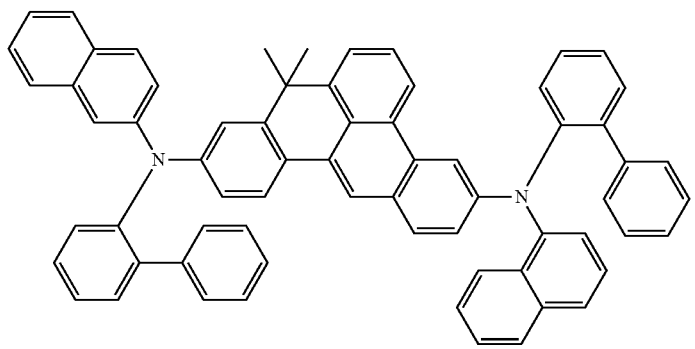
83
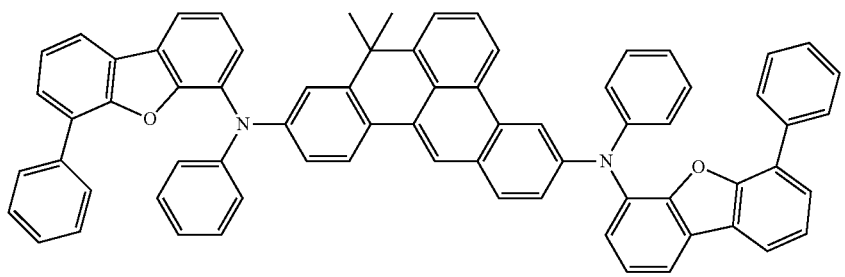
84
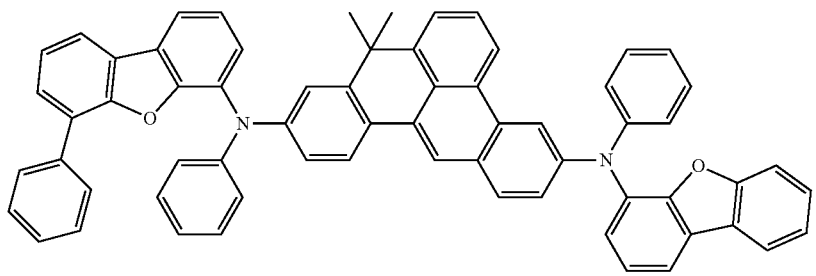
85

-continued
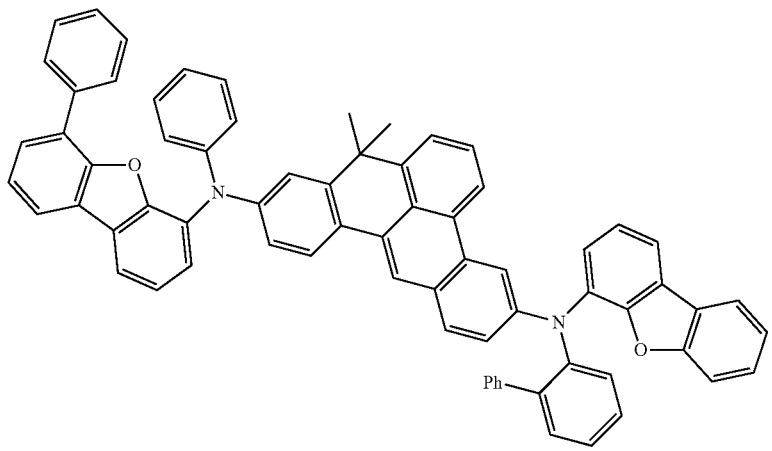
86
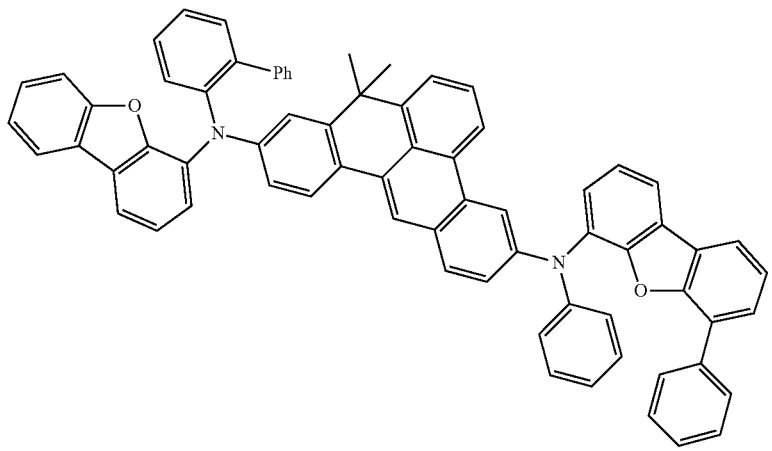
87
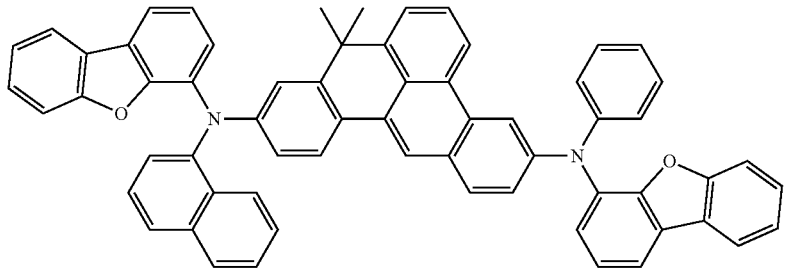
88
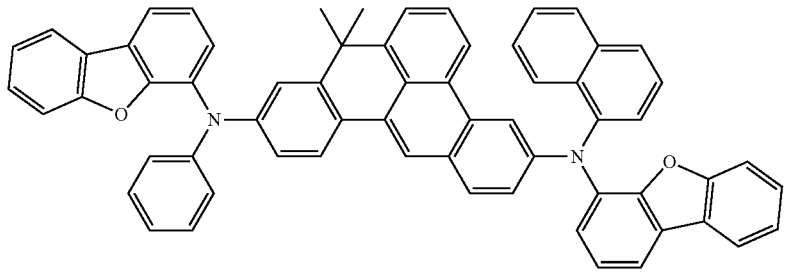
89

-continued
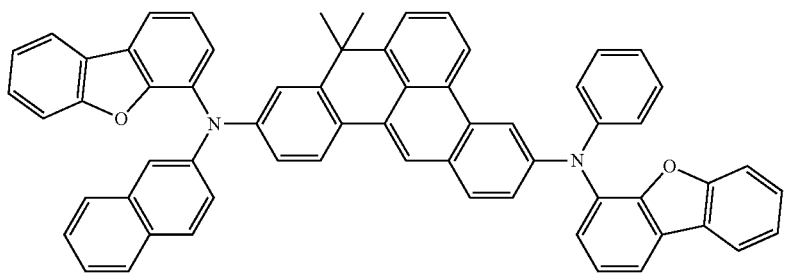
90
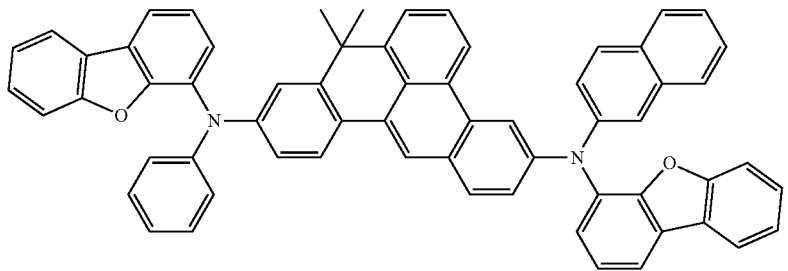
91
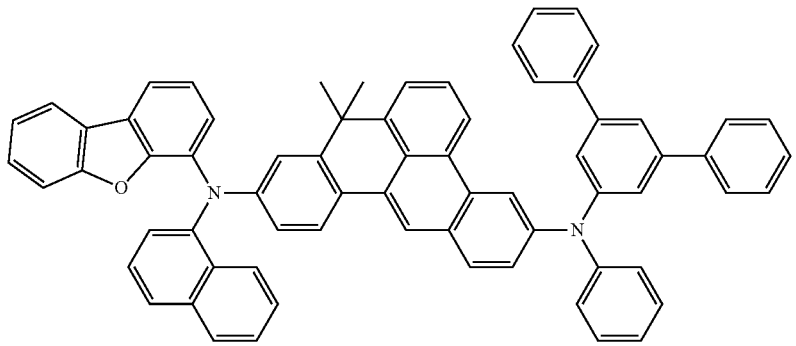
92
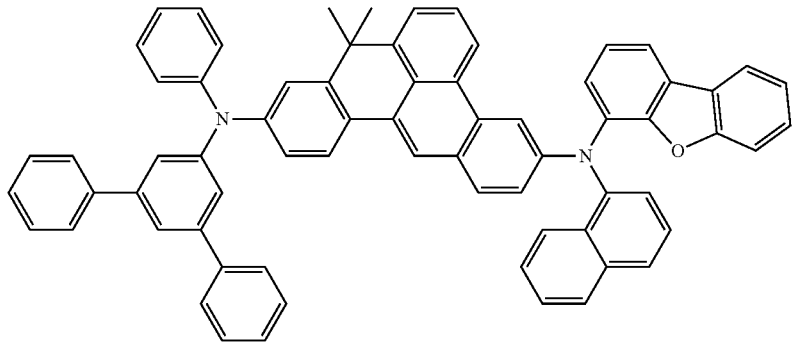
93
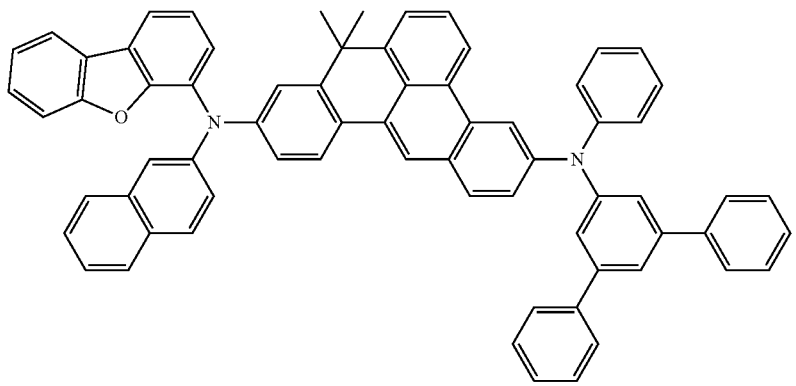
94

-continued
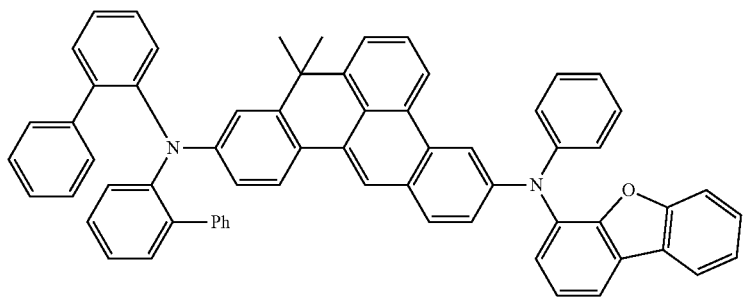
95
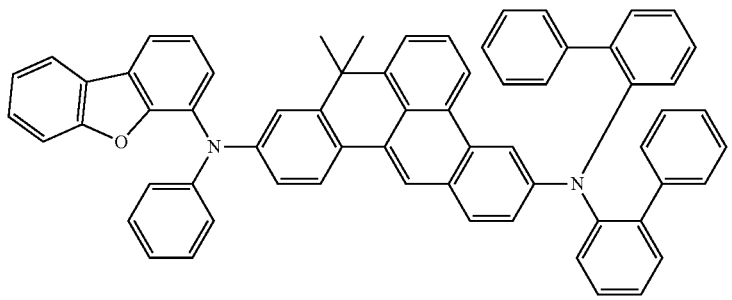
96
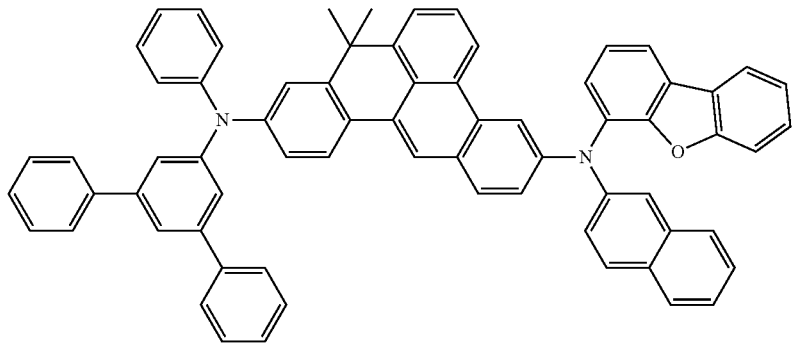
97
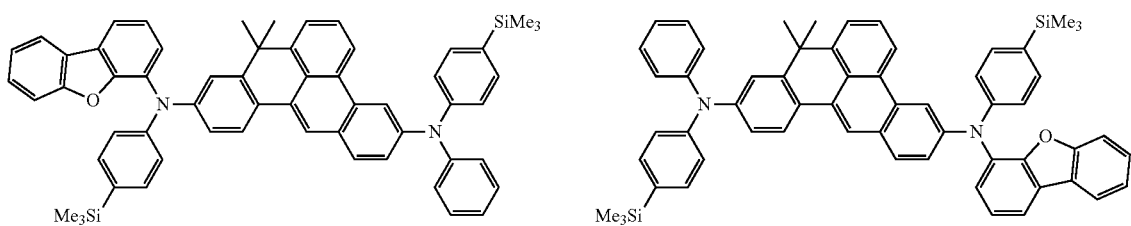
98   99
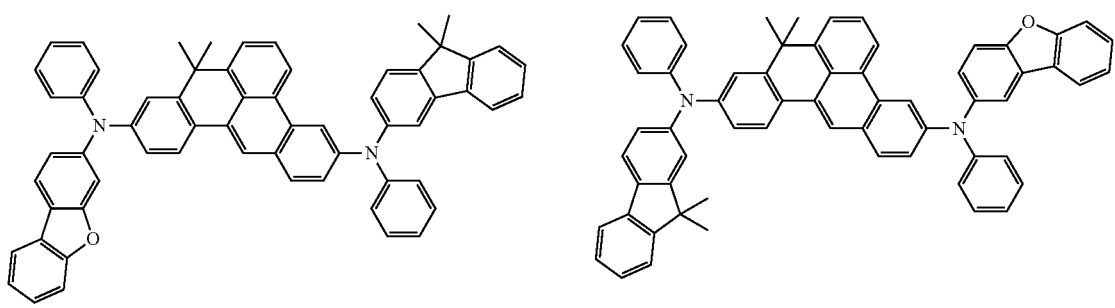
100   101

-continued
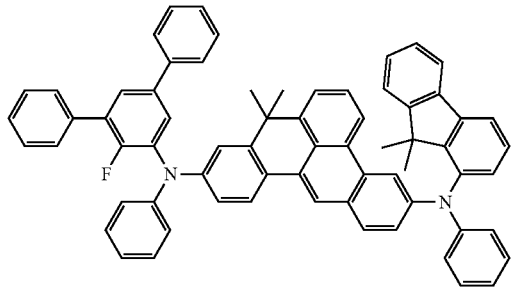
102
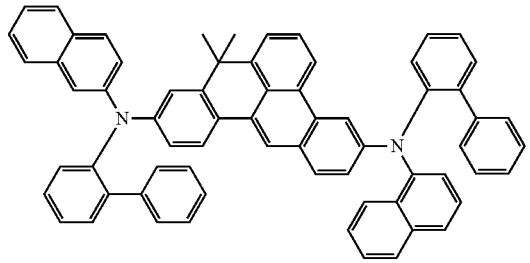
103
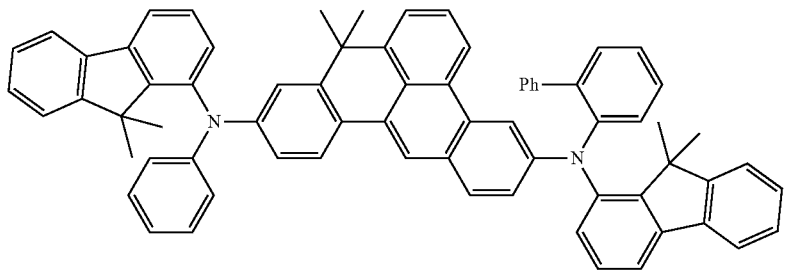
104
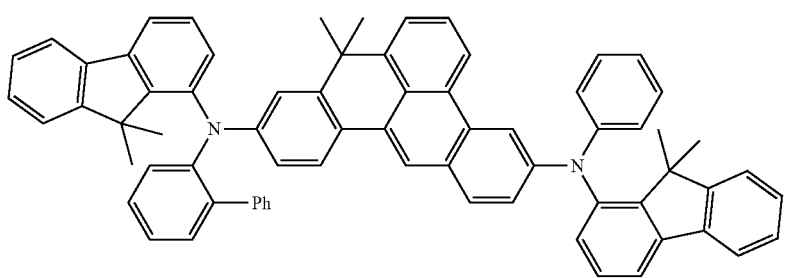
105
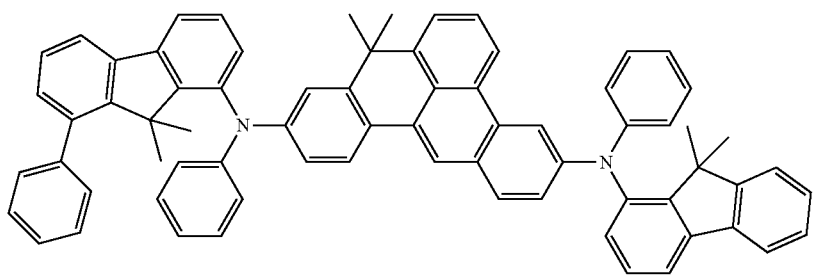
106
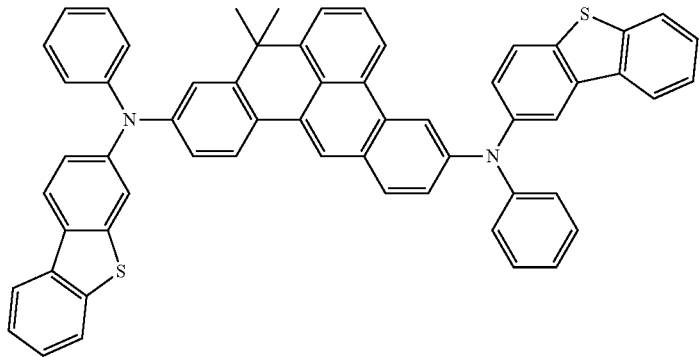
107

108
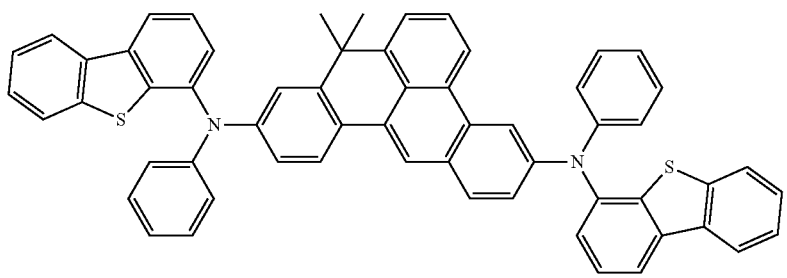
109
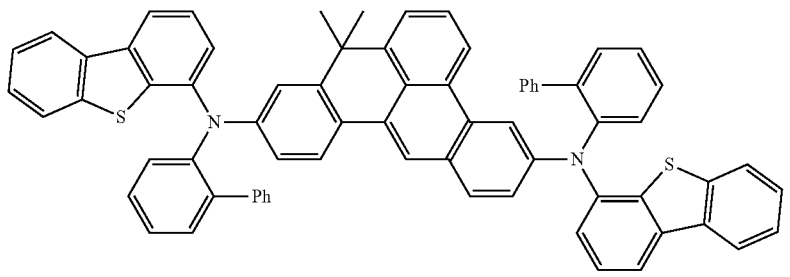
110
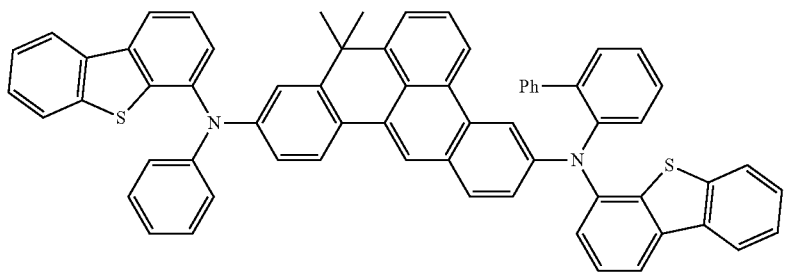
111
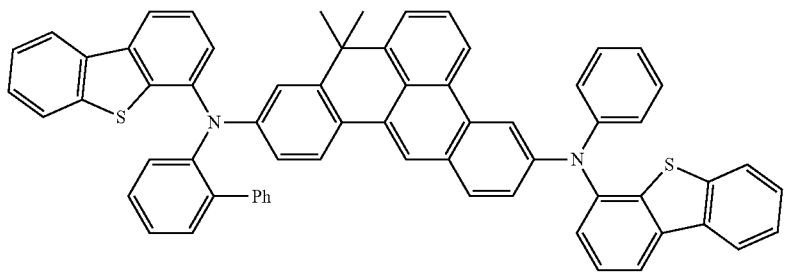
112
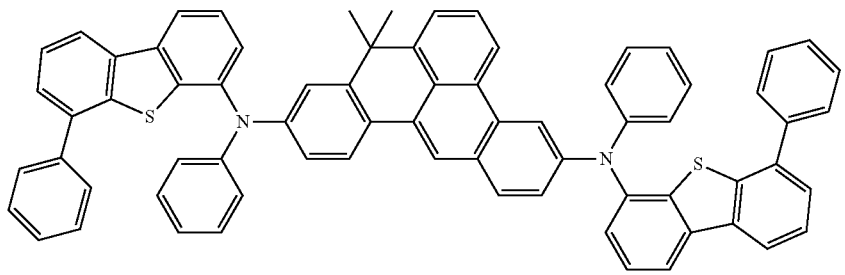

-continued
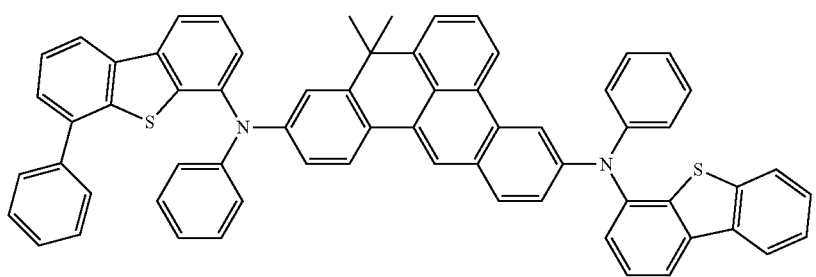
113
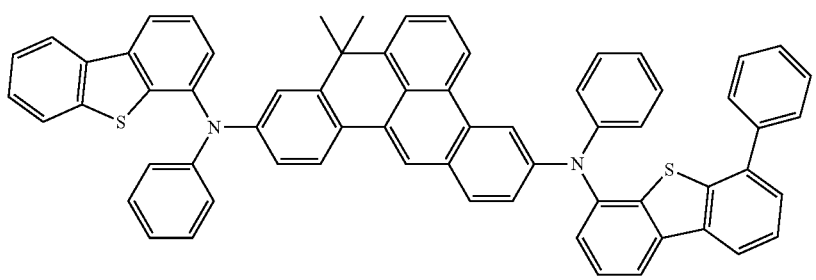
114
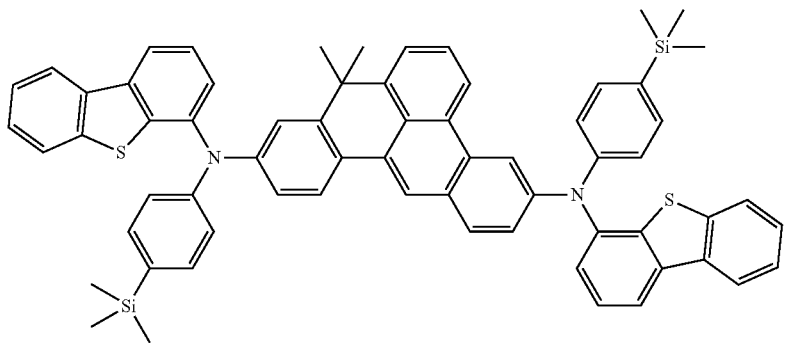
115
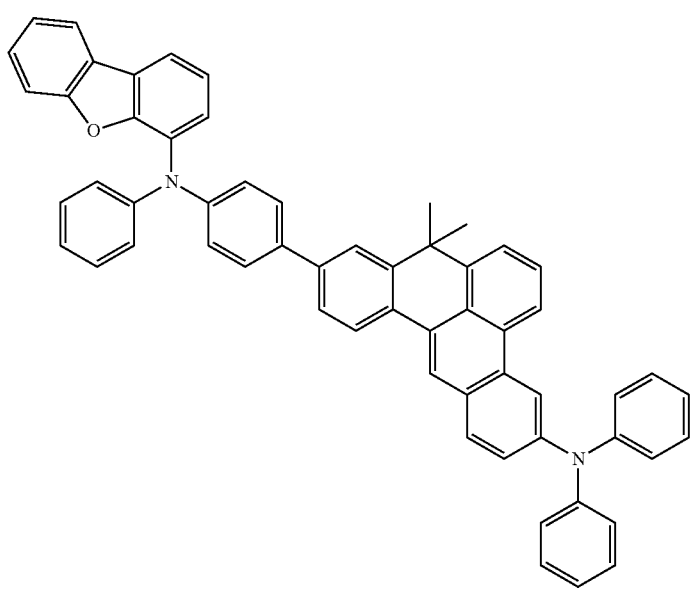
116

-continued
117
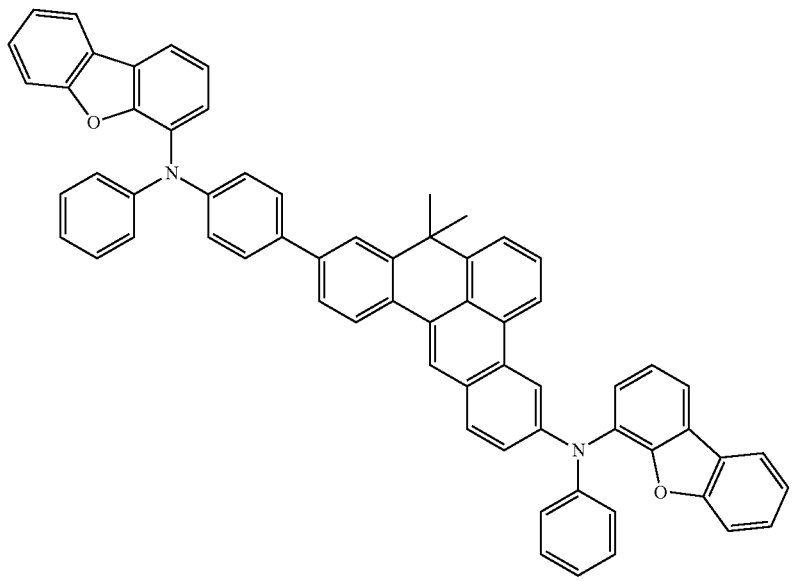
118
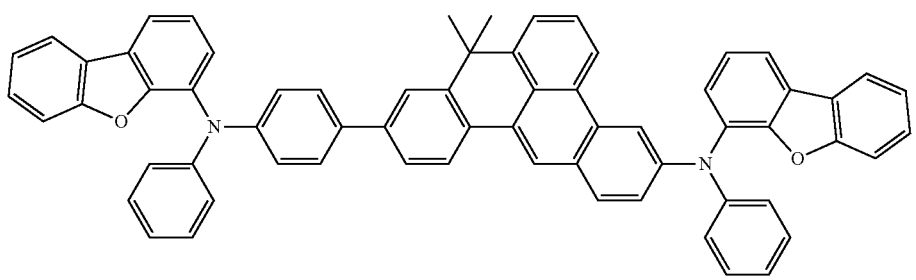
119
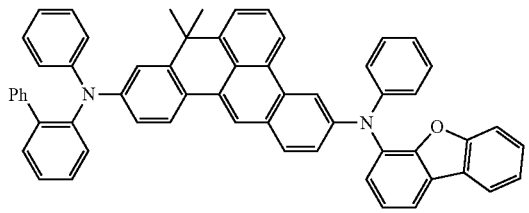
120
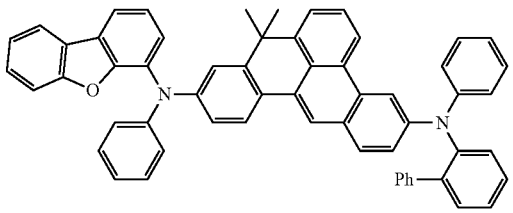
121
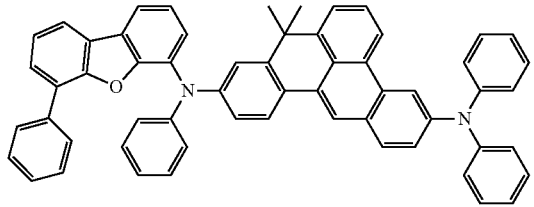
122
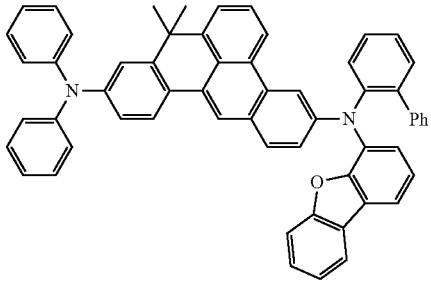
123
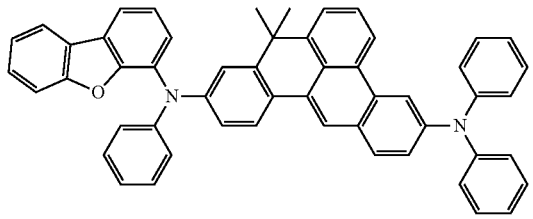
124
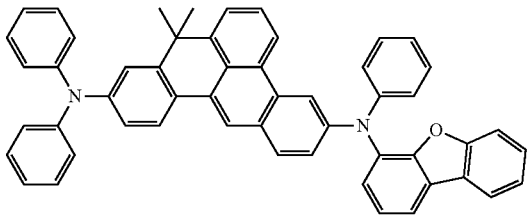

125
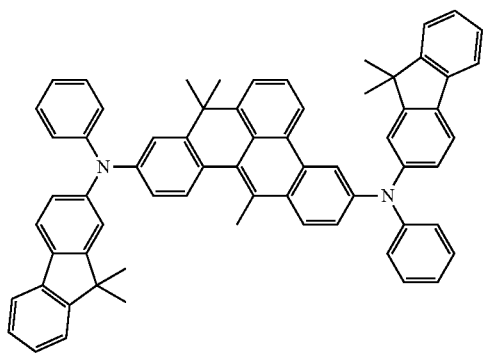
126
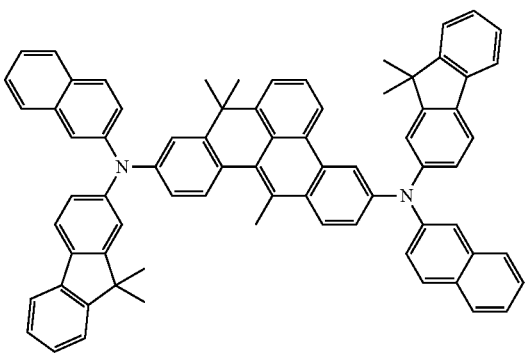
127
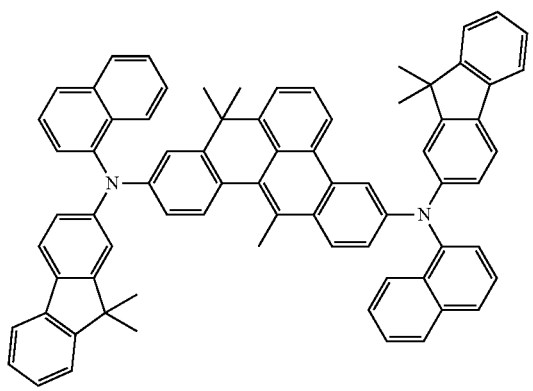
128
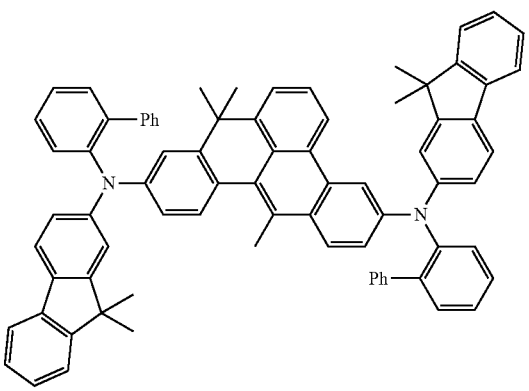
129
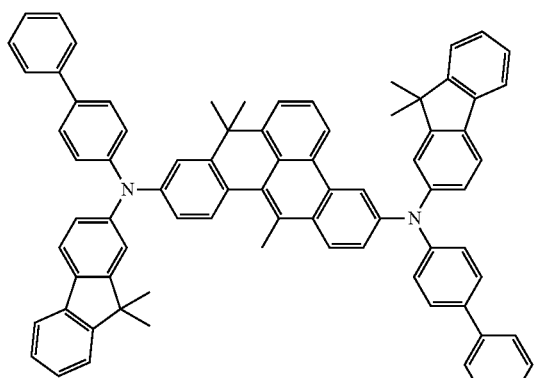
130
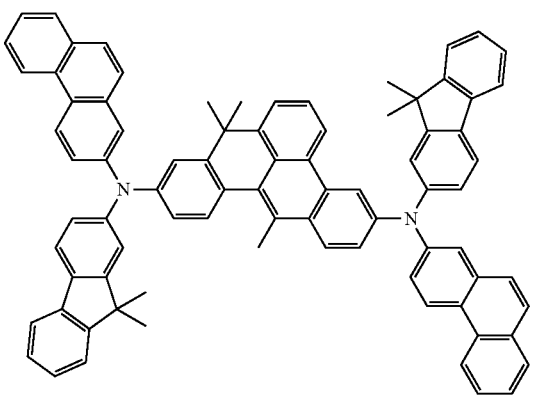
131
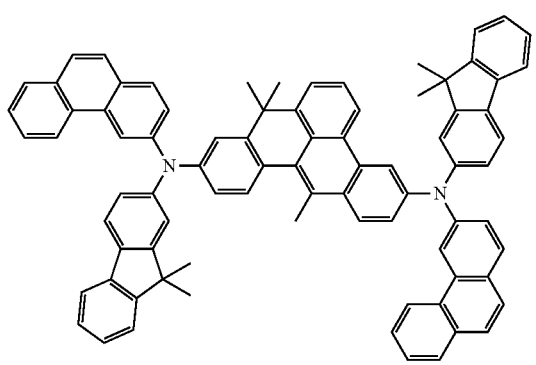
132
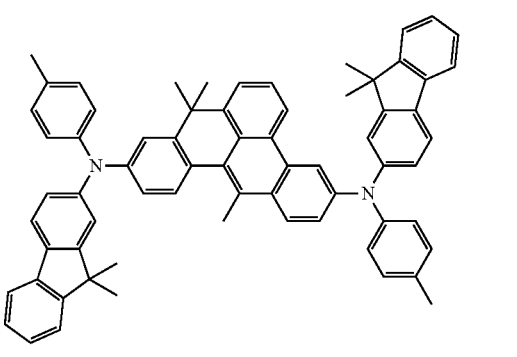

-continued
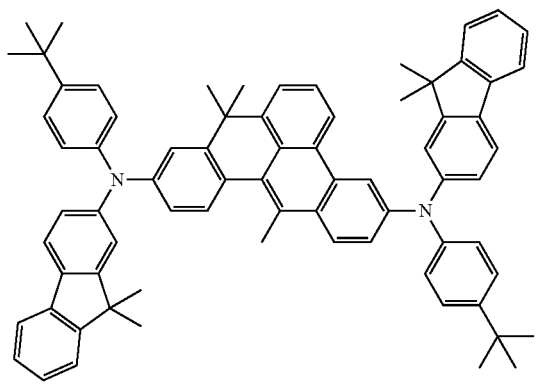
133
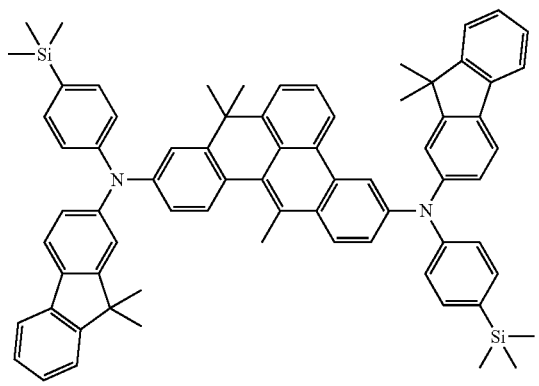
134
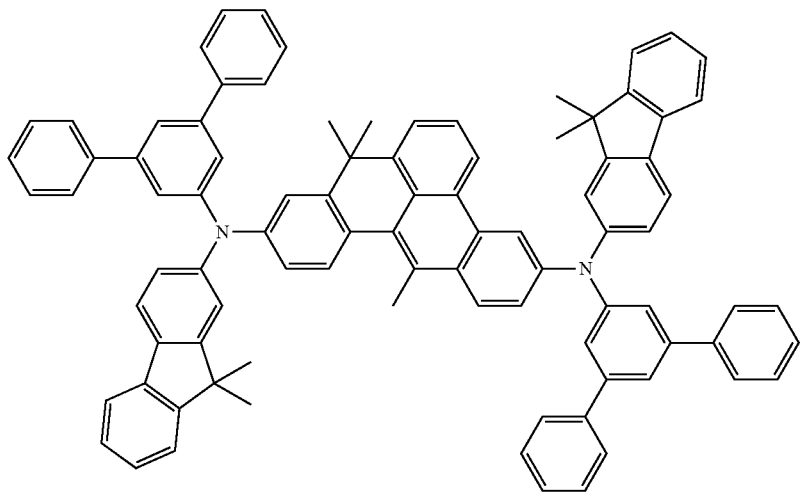
135
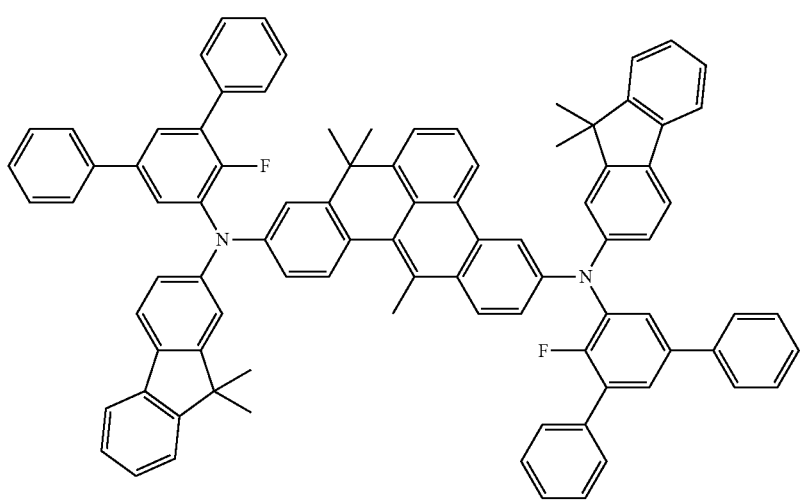
136

-continued
137
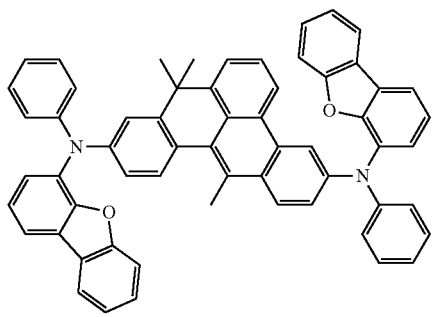
138
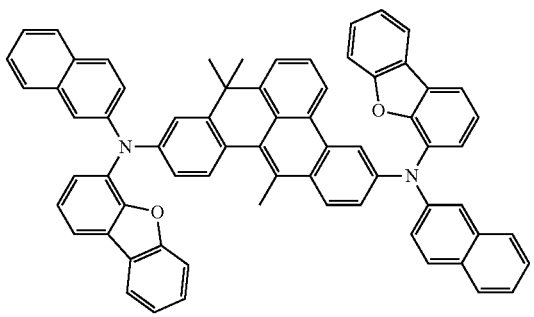
139
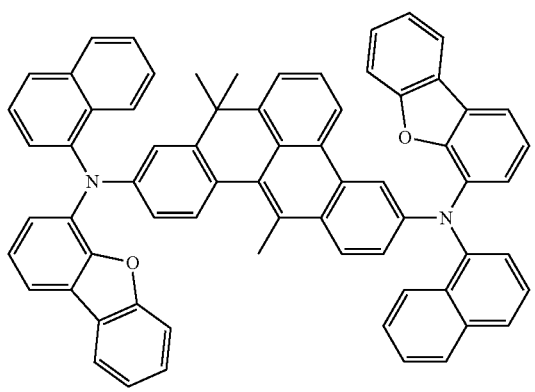
140
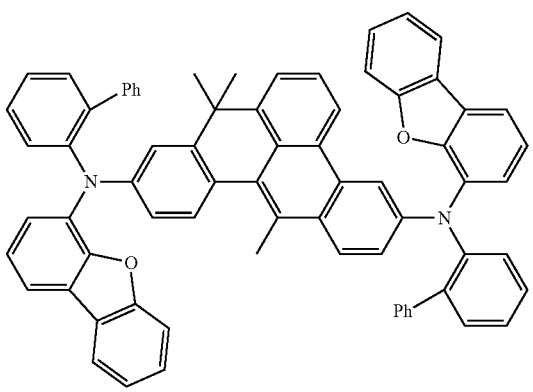
141
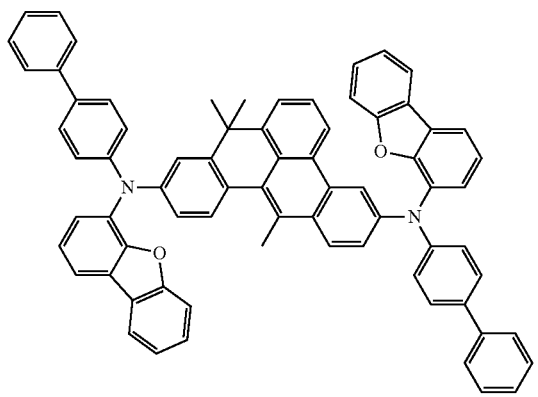
142
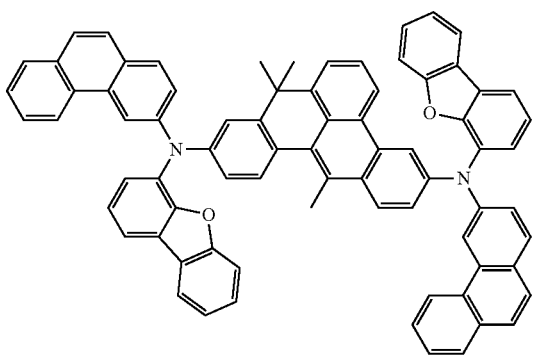
143
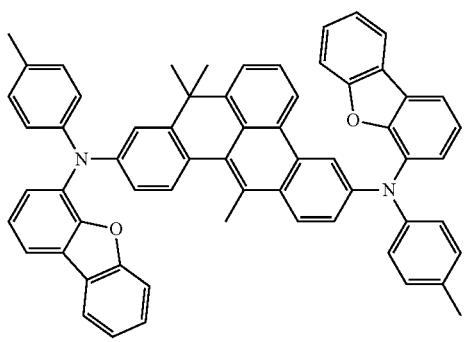
144
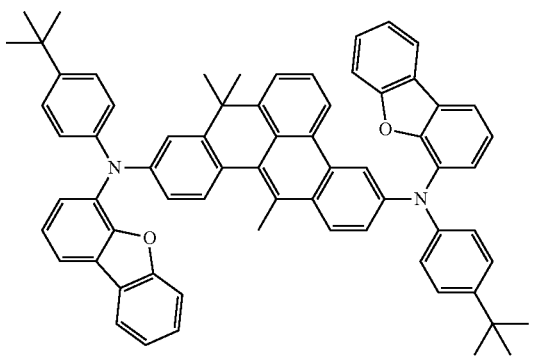

-continued
145
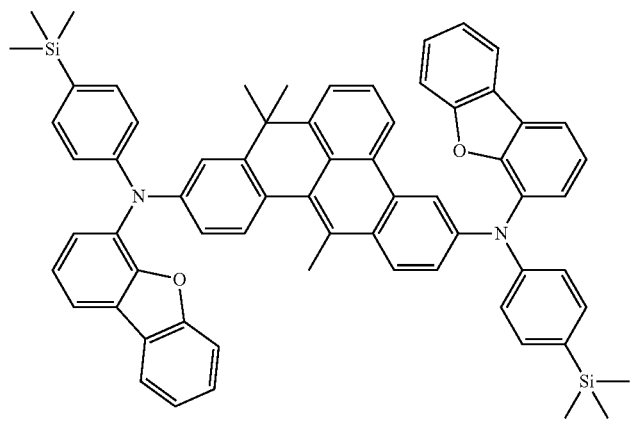
146
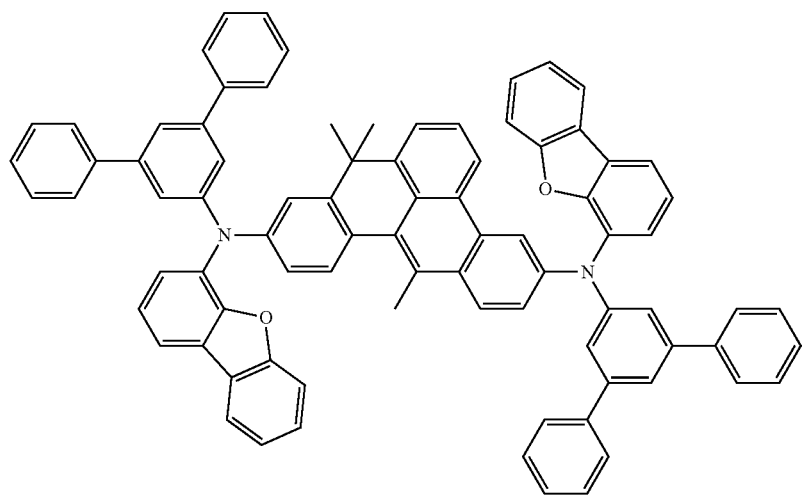
147
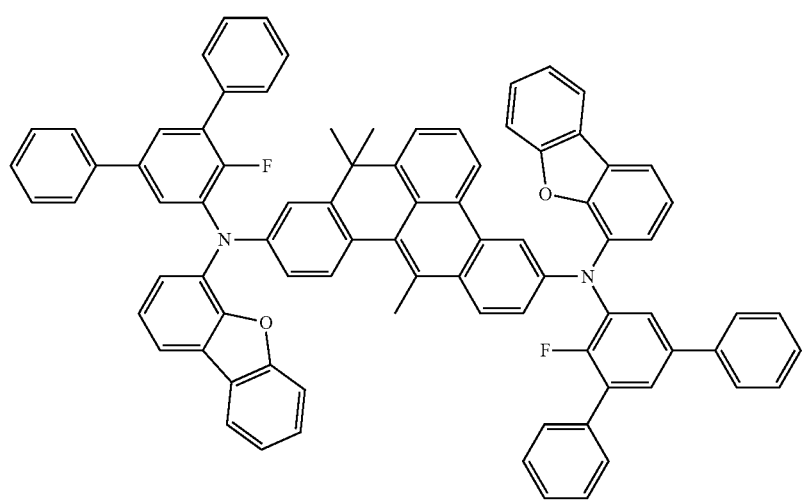

-continued
148
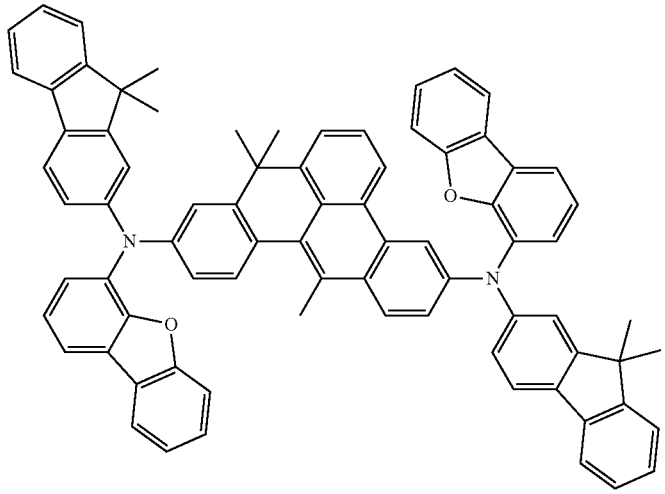
149
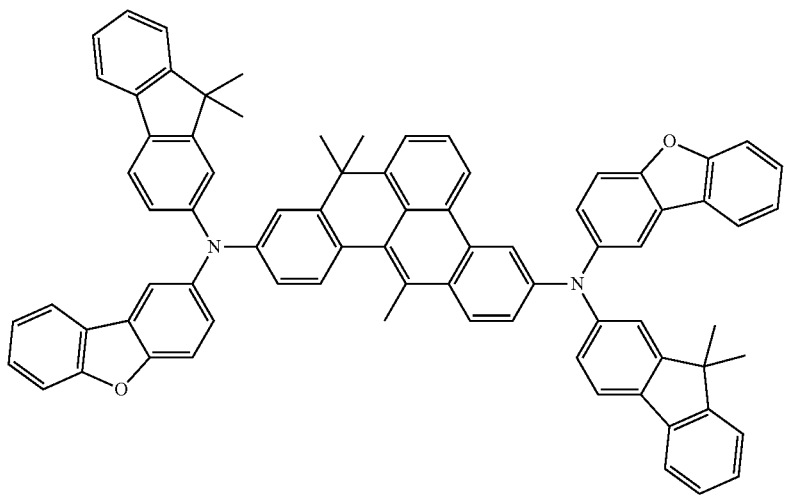
150
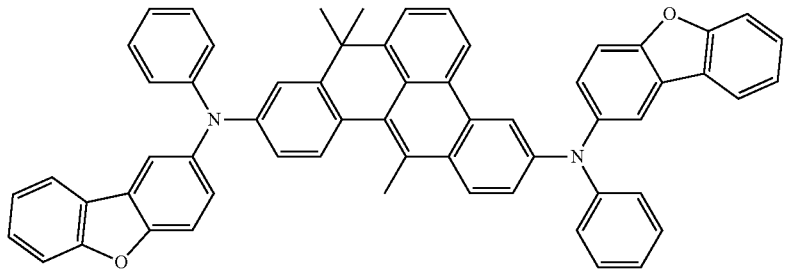
151
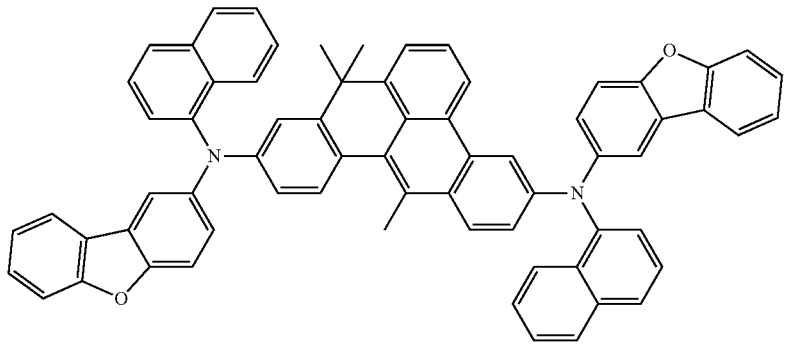

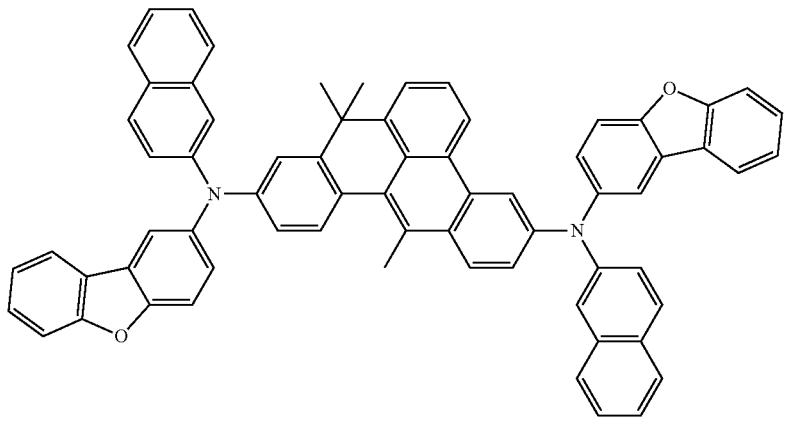
152
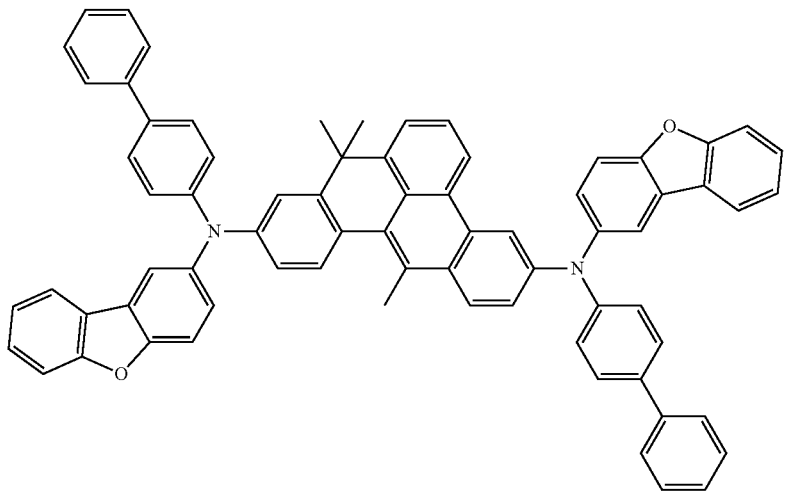
153
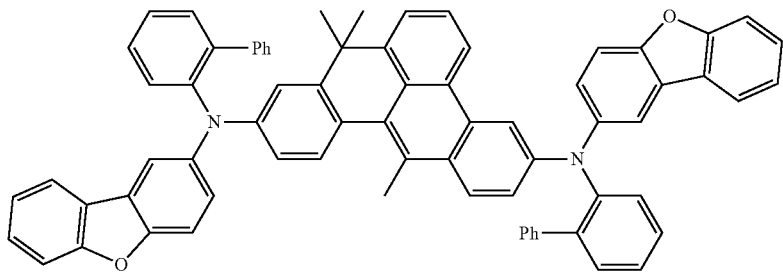
154
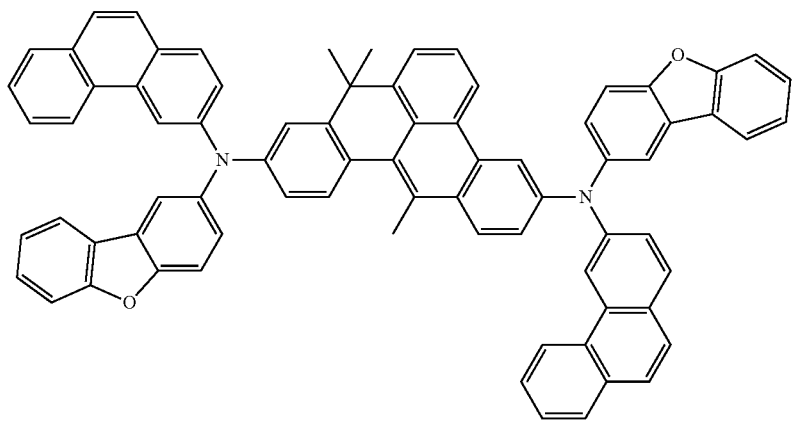
155

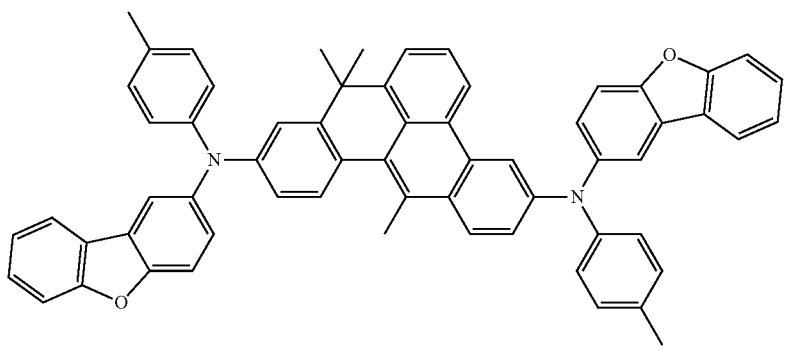
156
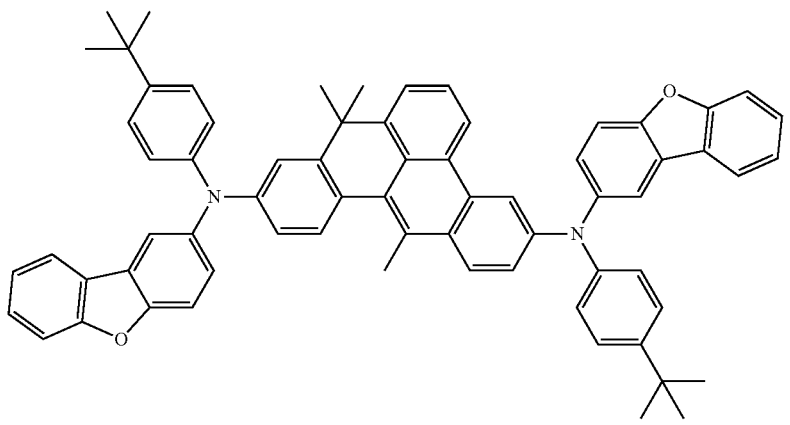
157
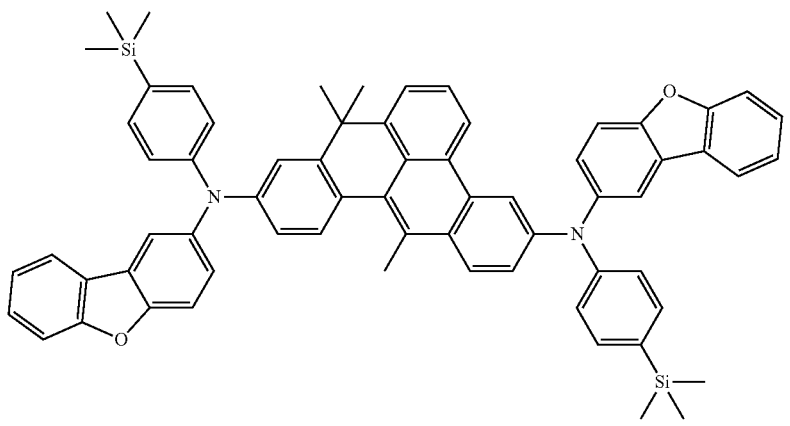
158

-continued
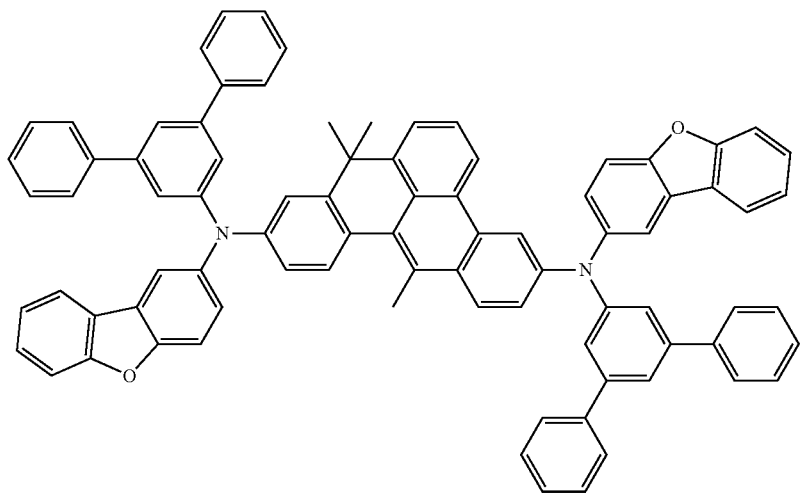
159

160
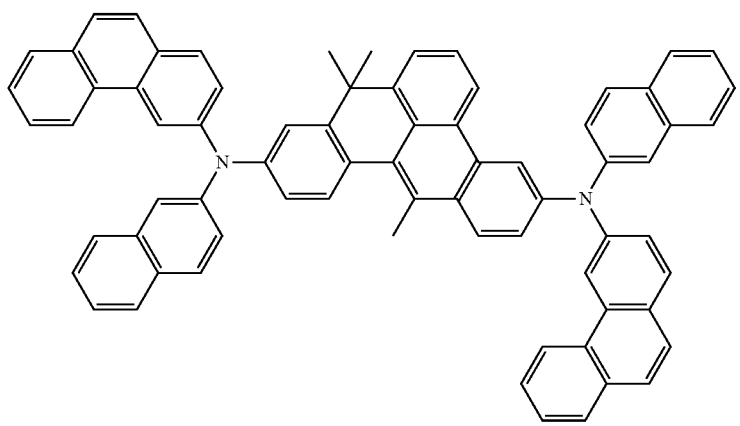
161

162
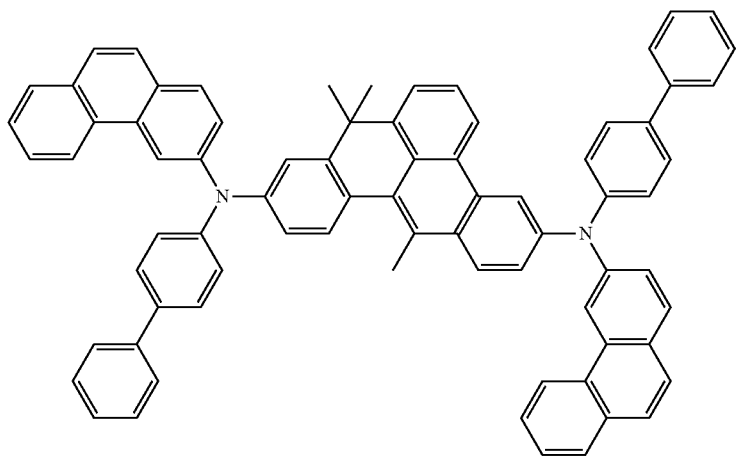
163 164
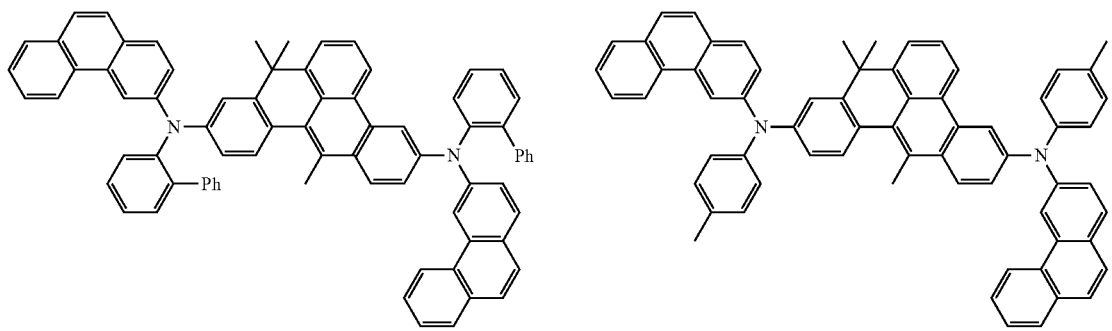
165 166
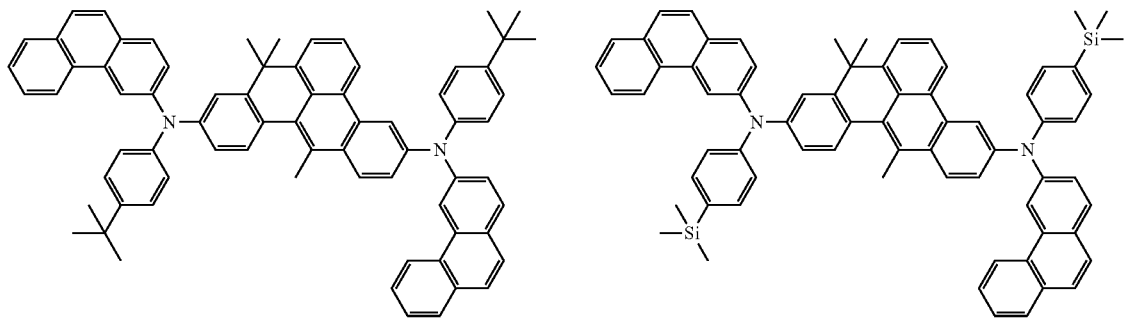
167 168
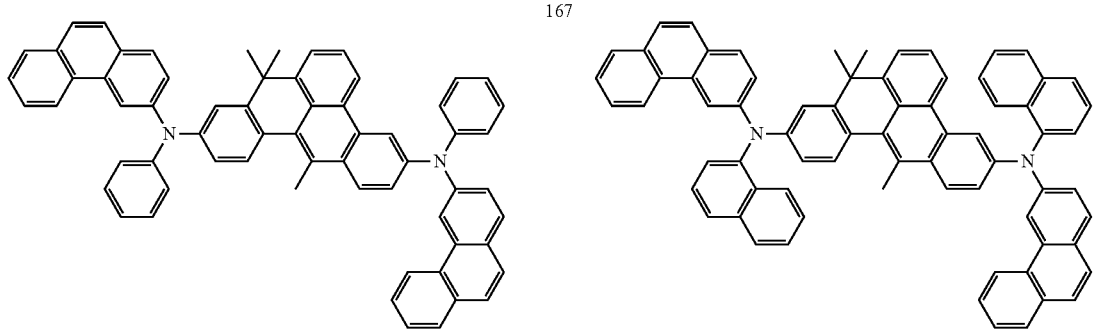

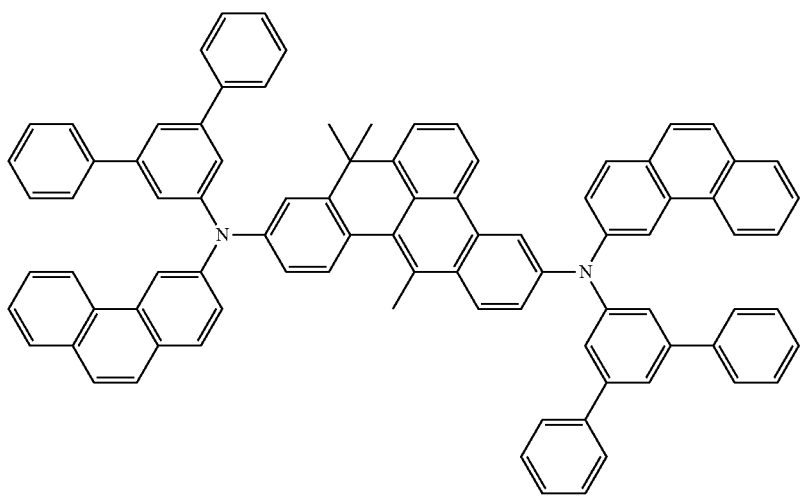
169
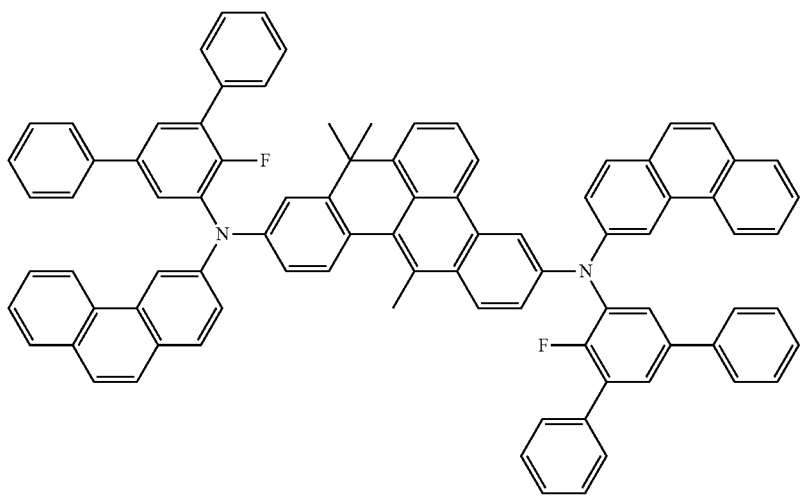
170
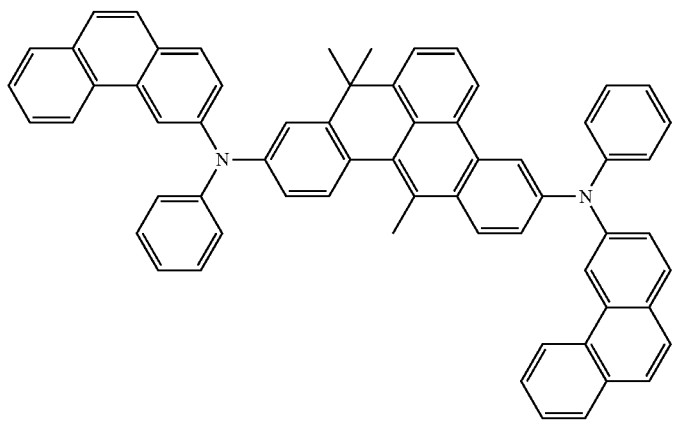
171

-continued
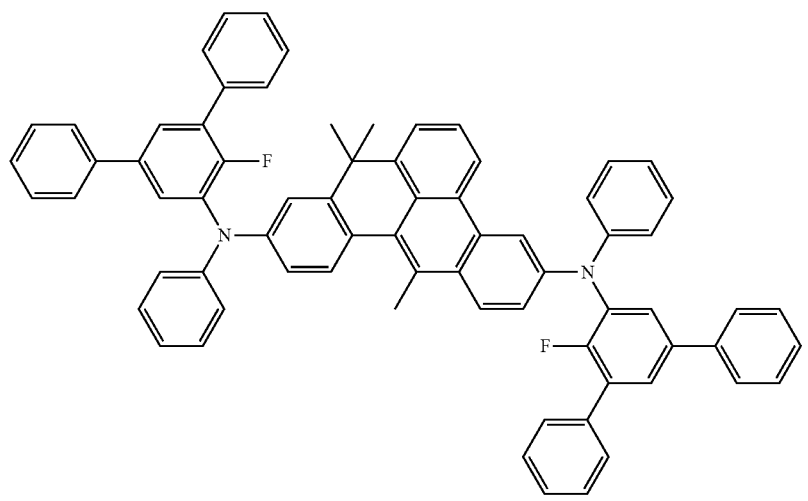
172

173
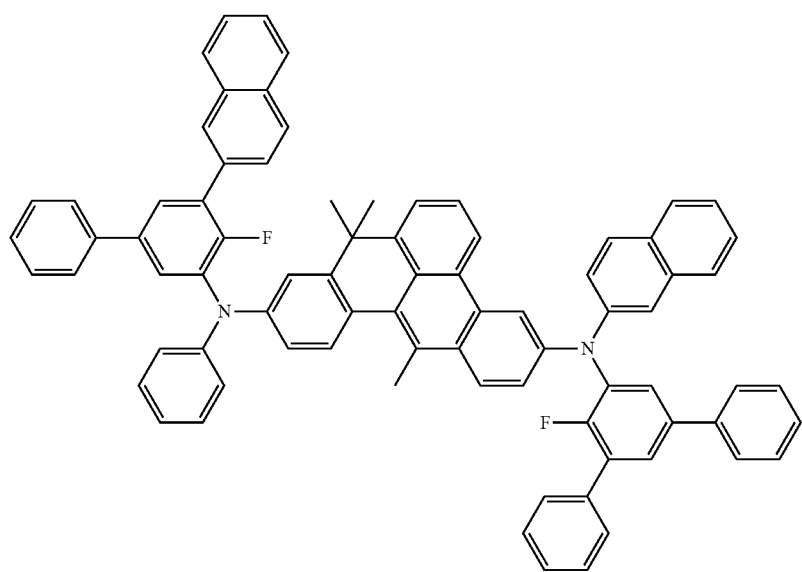
174

175
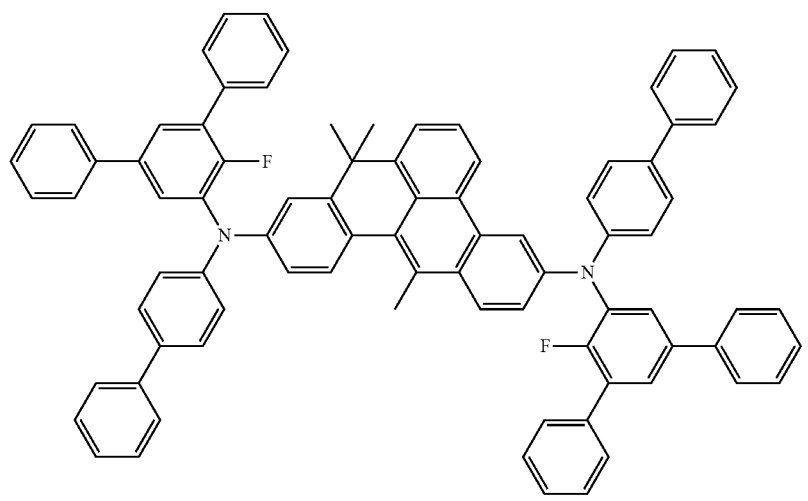
176
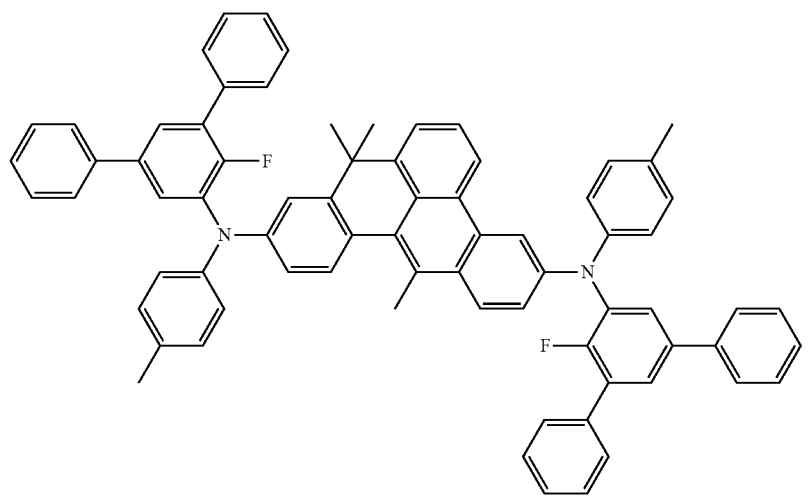
177
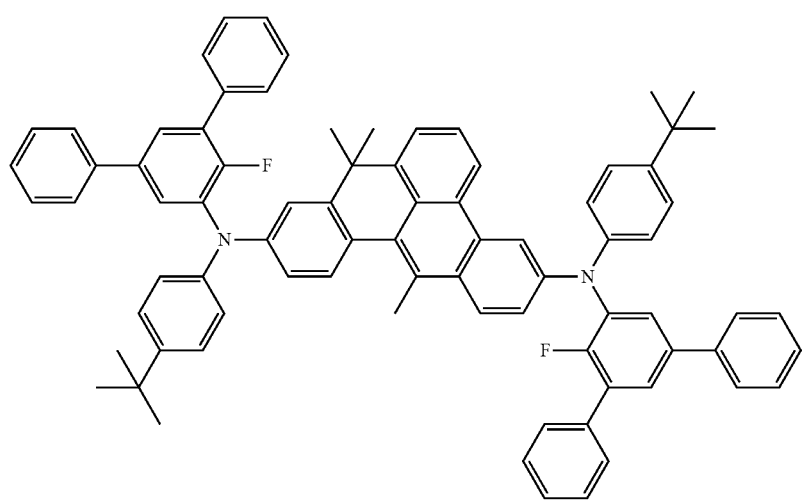

178
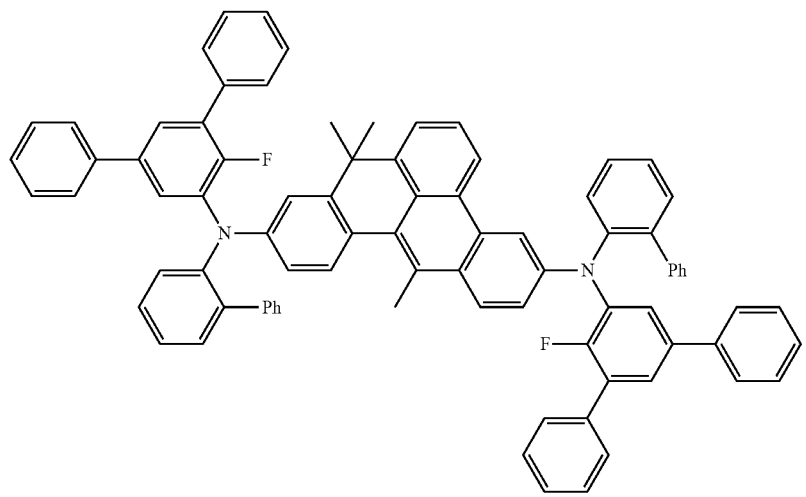
179
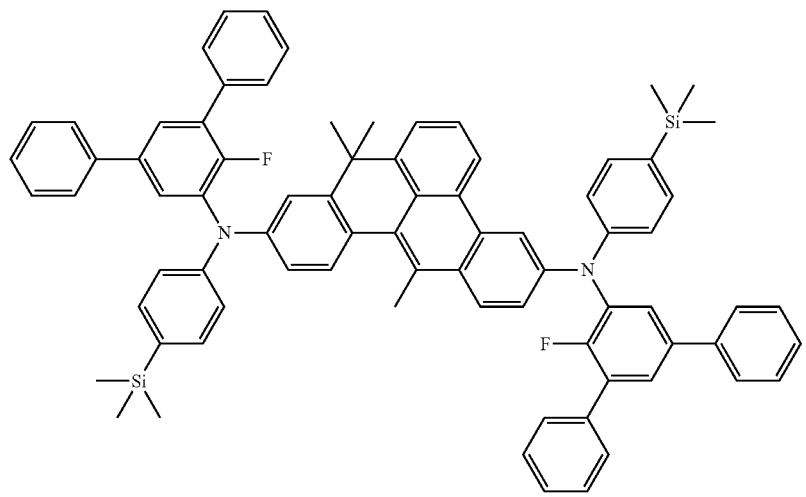
180
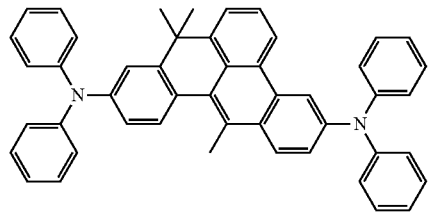
181
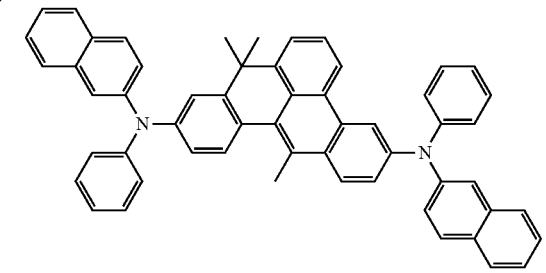
182
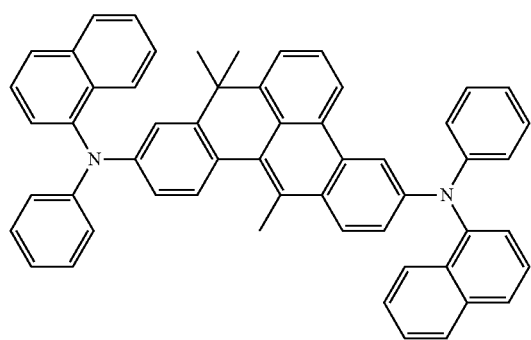
183
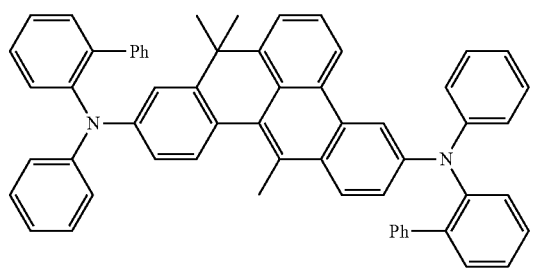

-continued
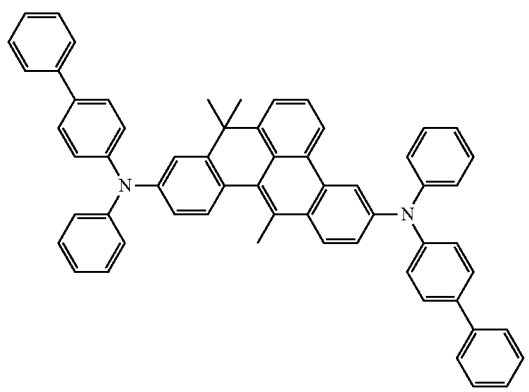
184
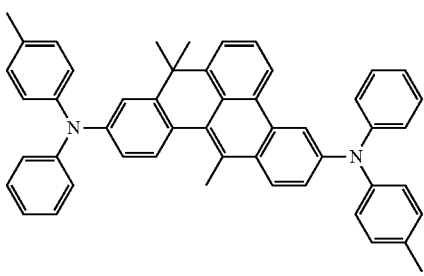
185
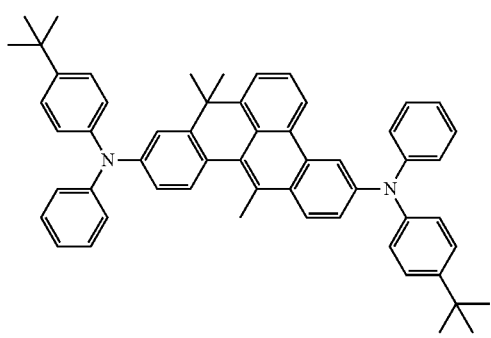
186
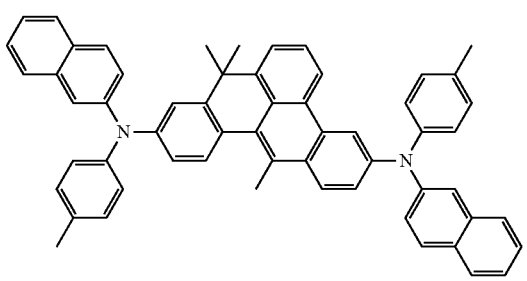
187
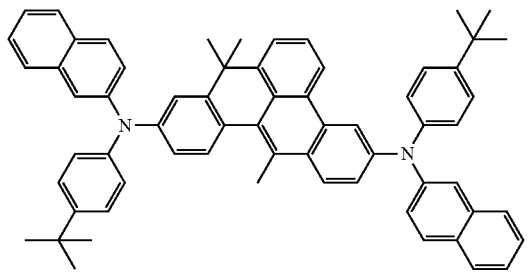
188
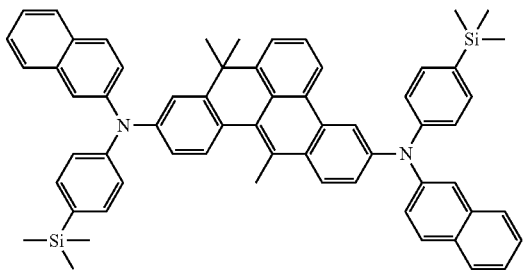
189
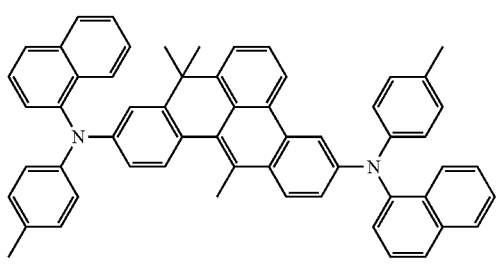
190
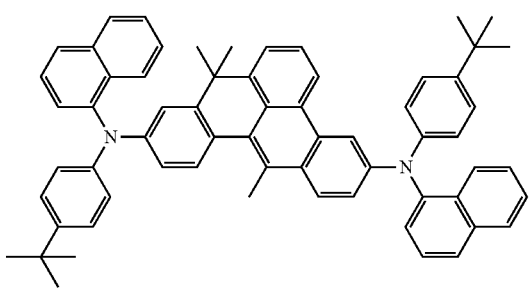
191
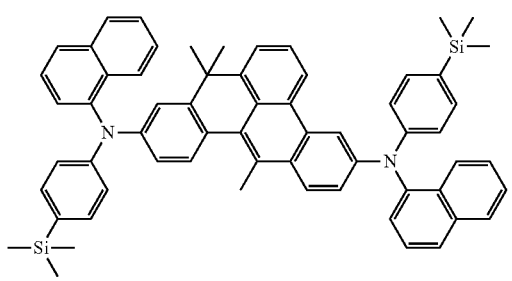
192
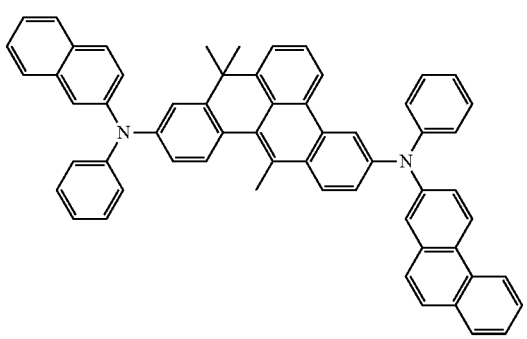
193

-continued
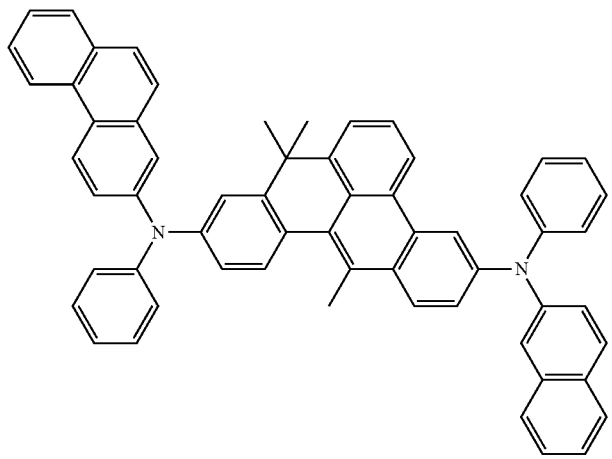
194
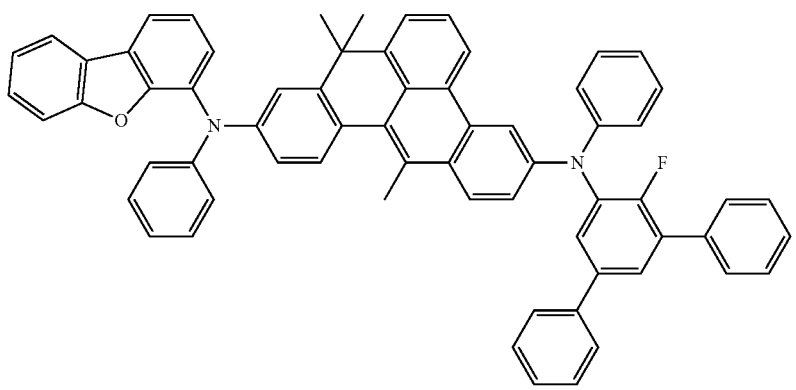
195
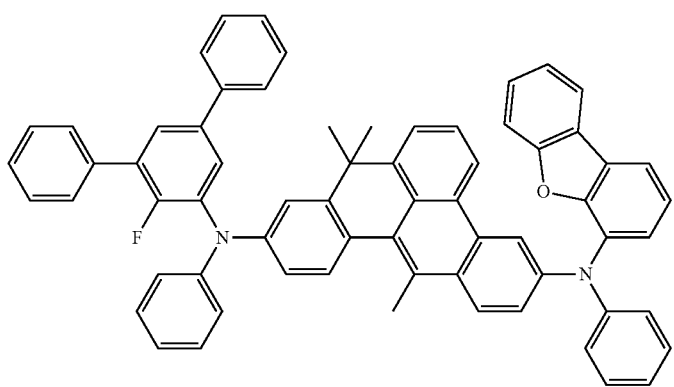
196

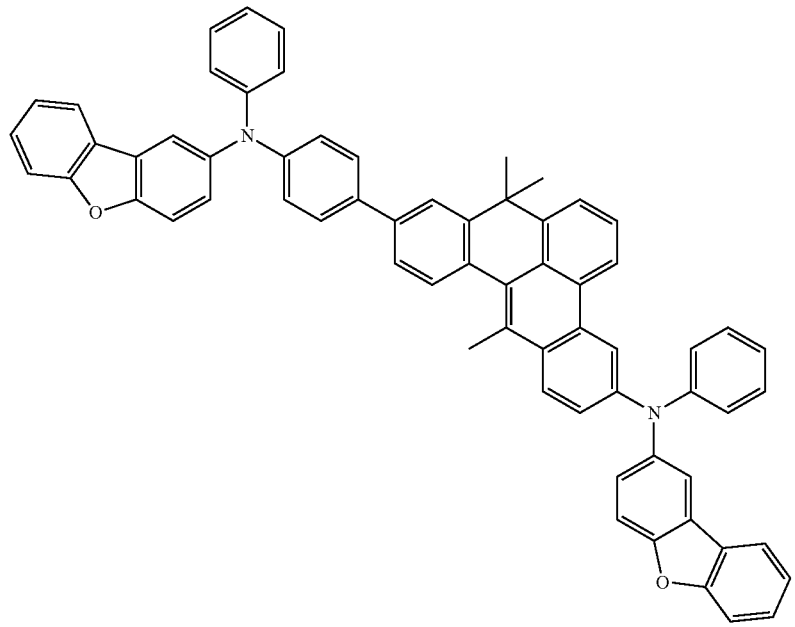
197
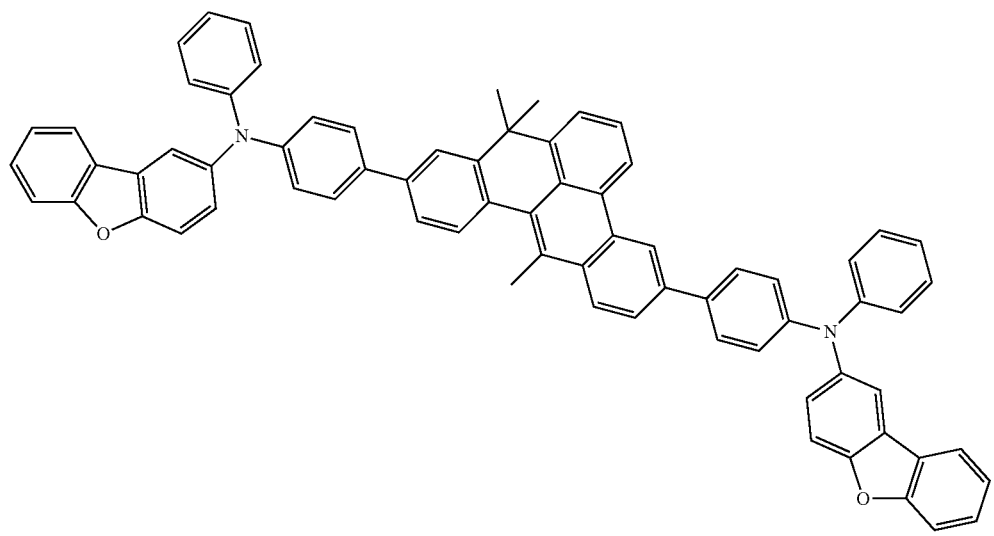
198
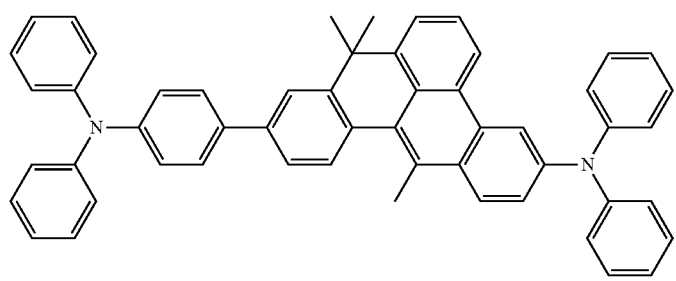
199

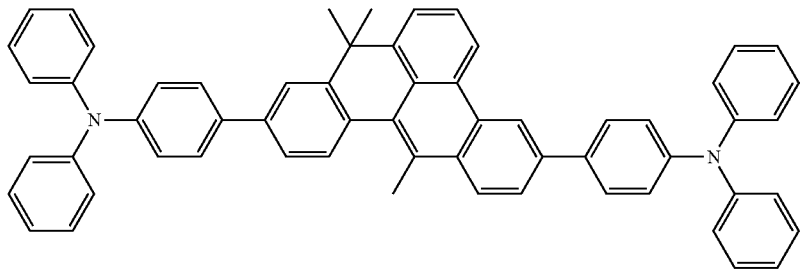
200
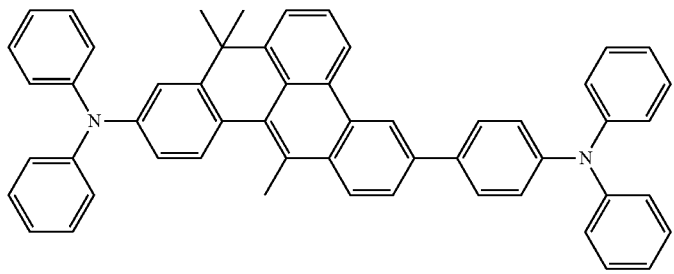
201
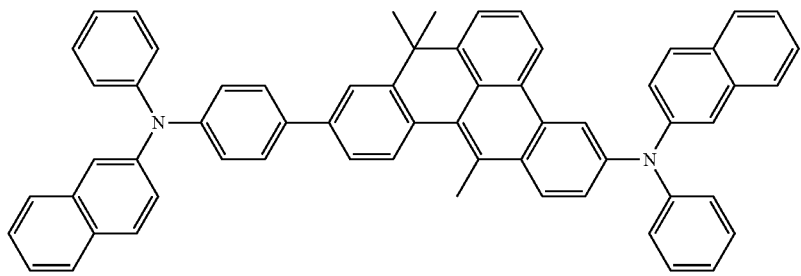
202
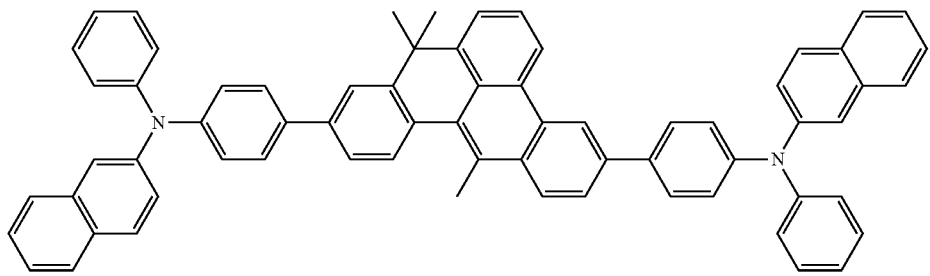
203
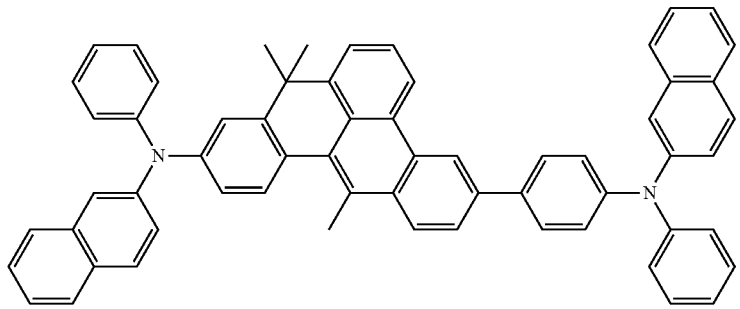
204

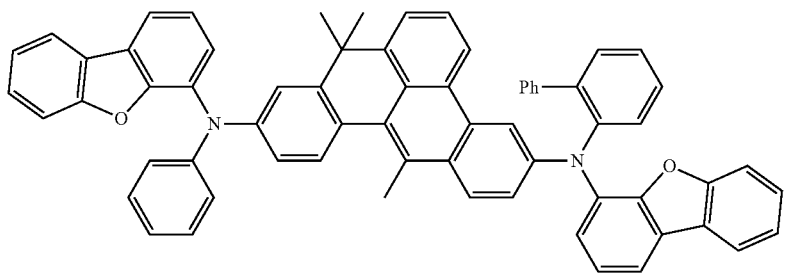
205
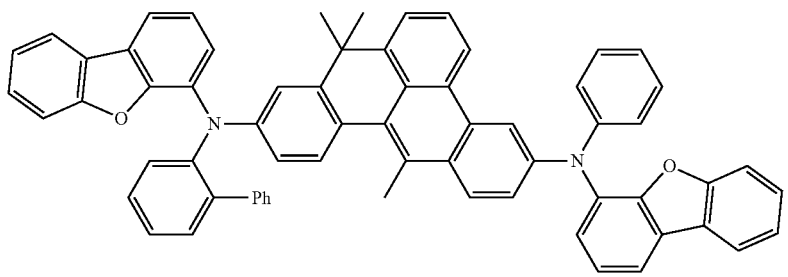
206
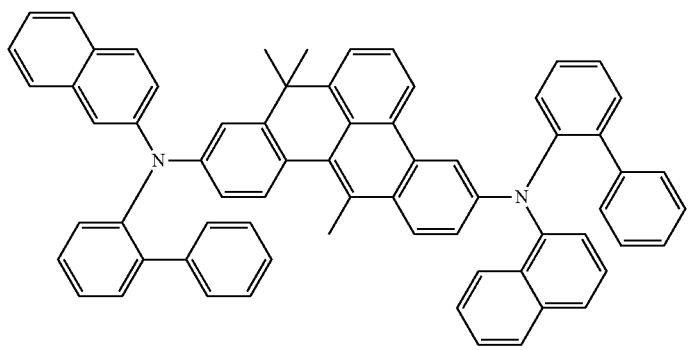
207
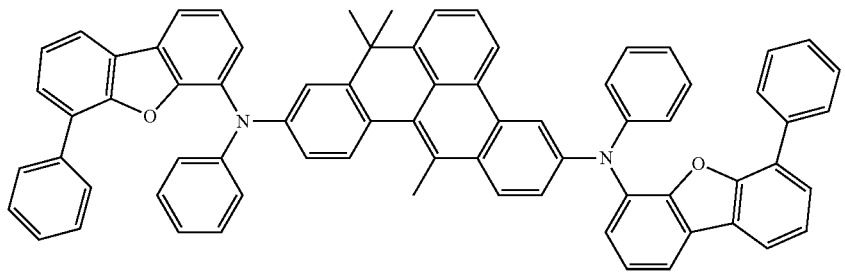
208
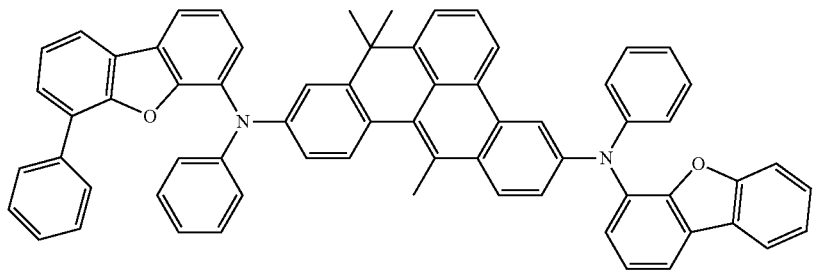
209

210
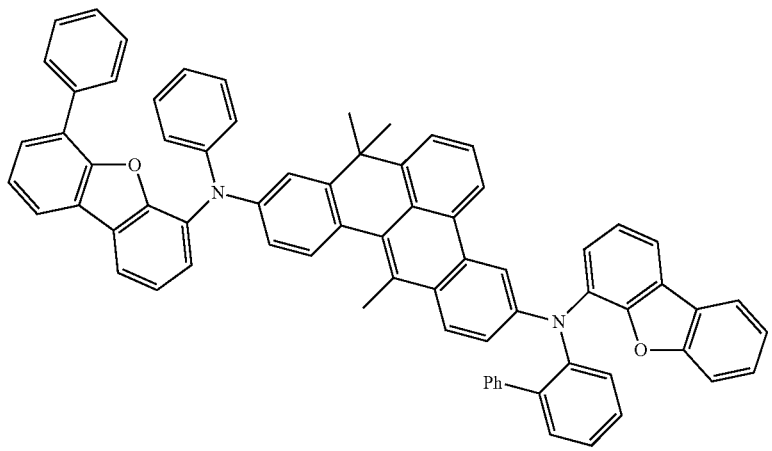
211
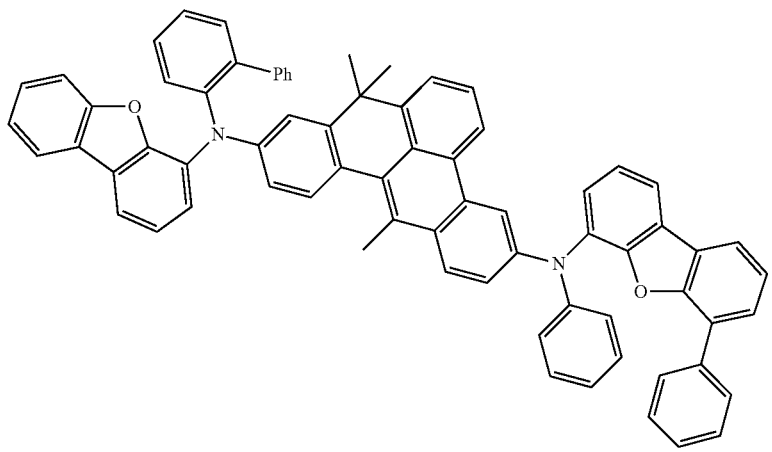
212
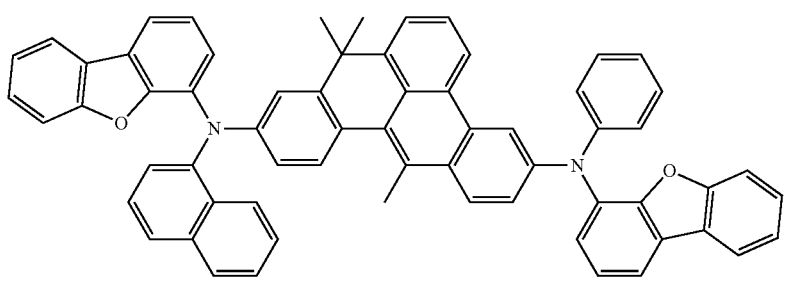
213
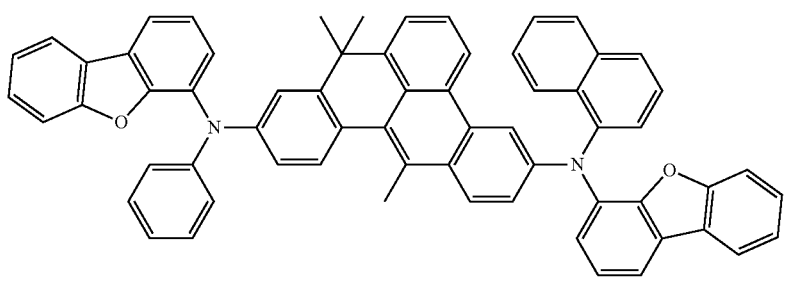

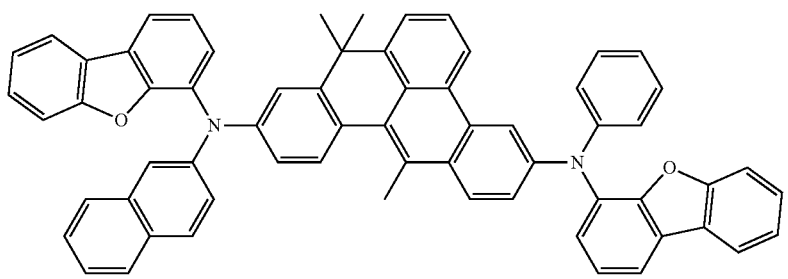
214
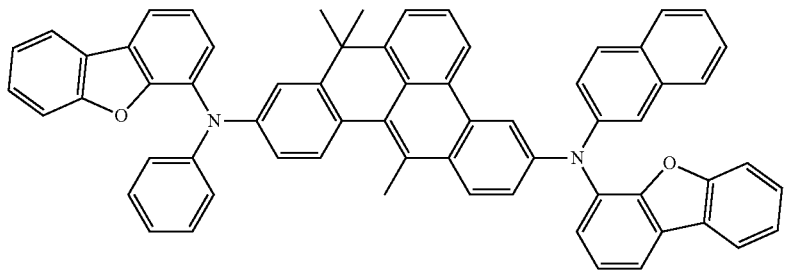
215
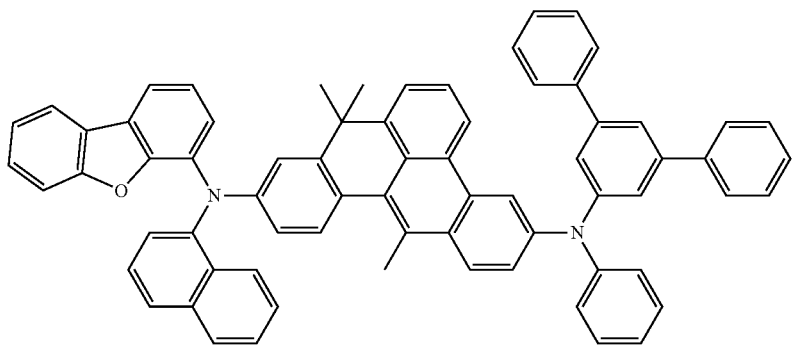
216
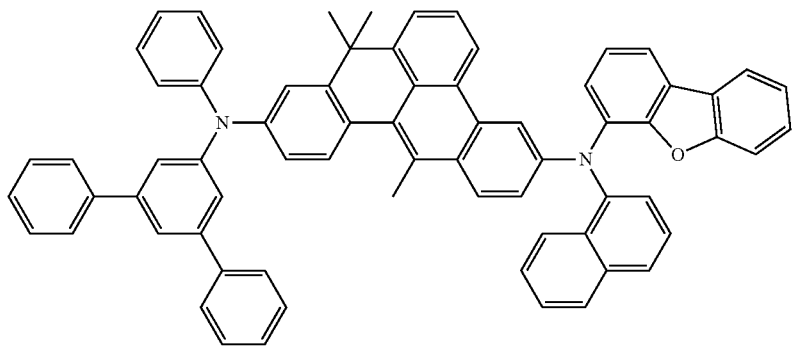
217
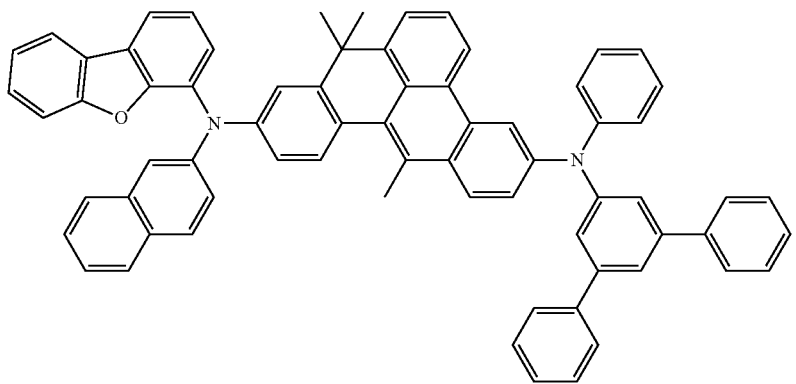
218

-continued
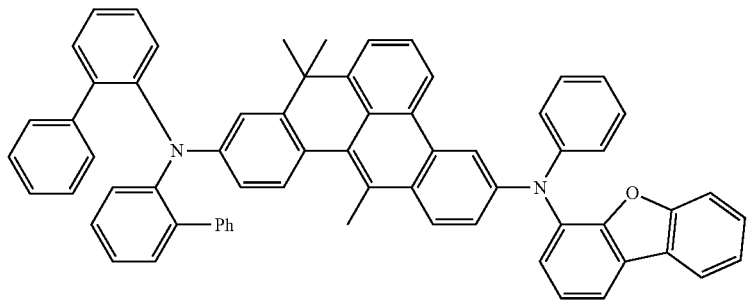
219
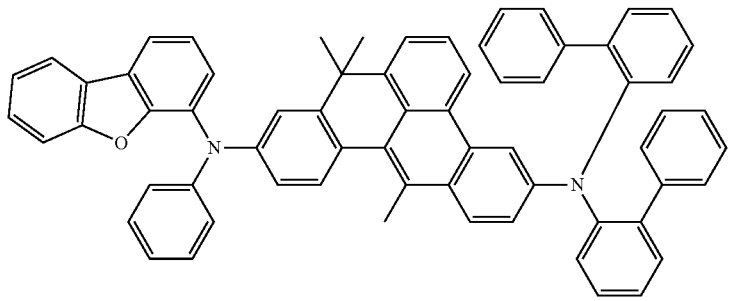
220
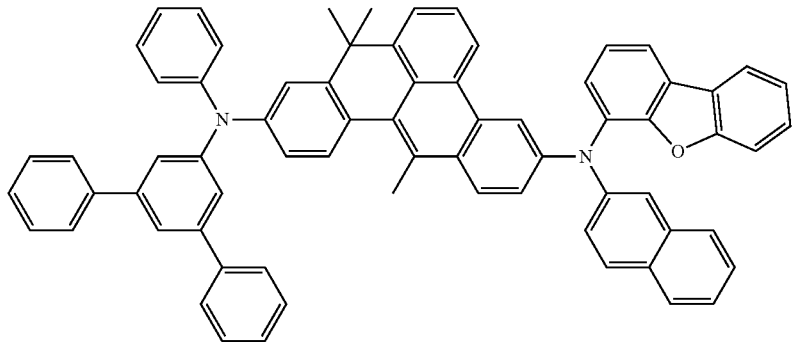
221
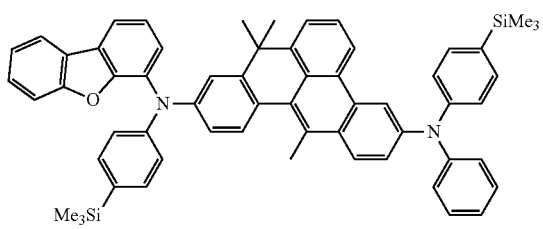
222
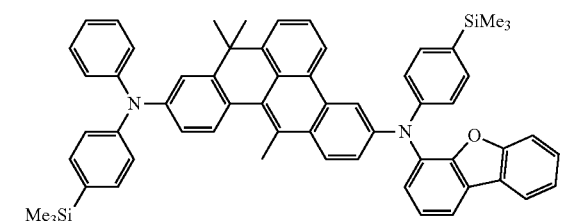
223
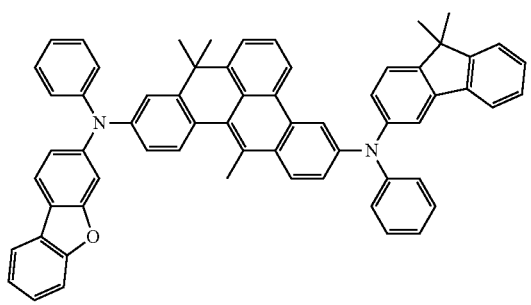
224
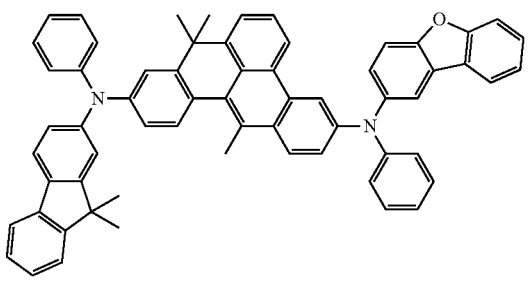
225

-continued
226
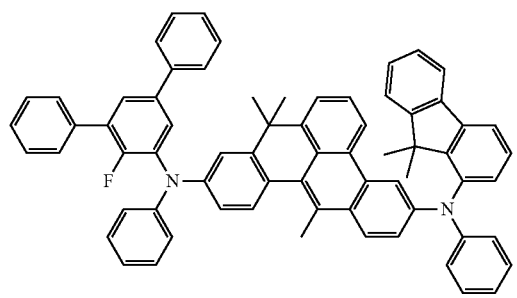
227
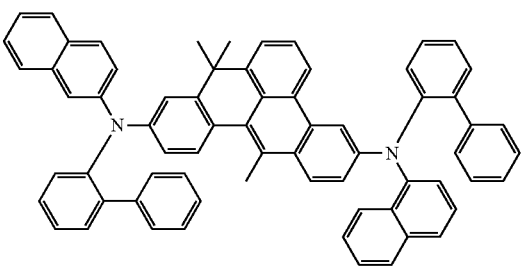
228
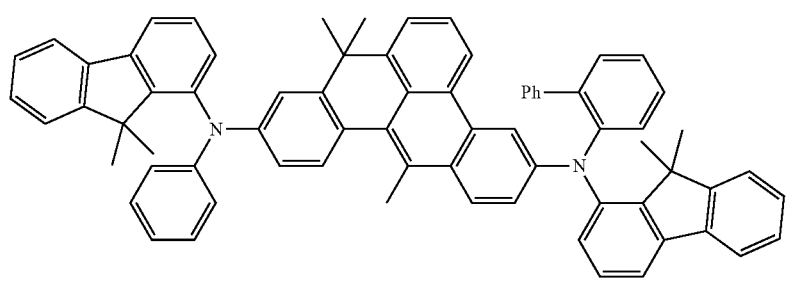
229
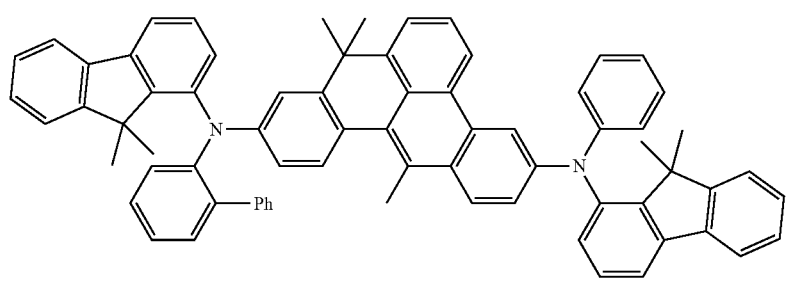
230
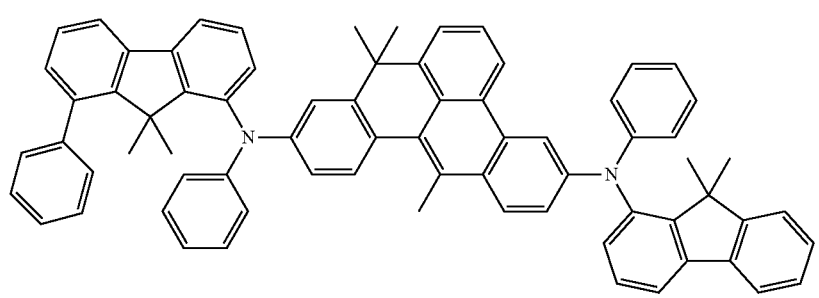
231
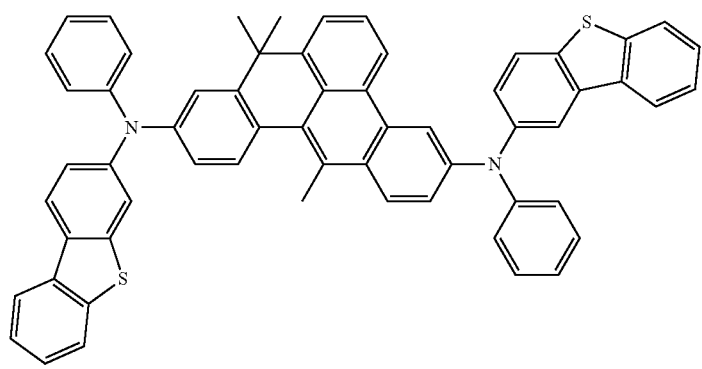

232
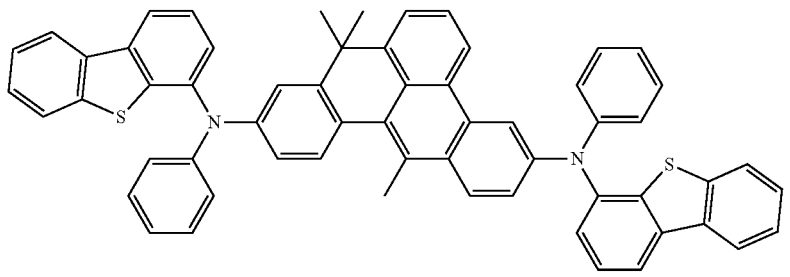
233
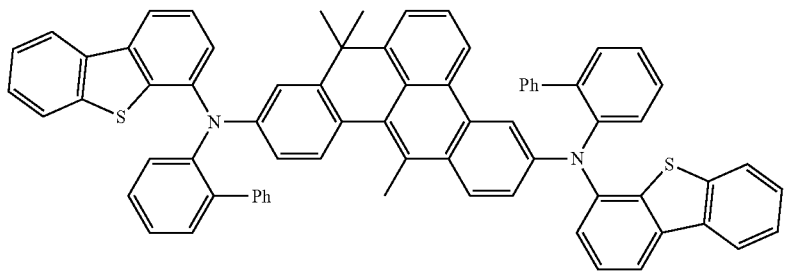
234
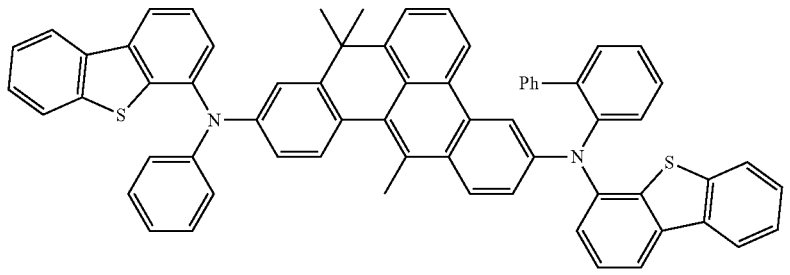
235
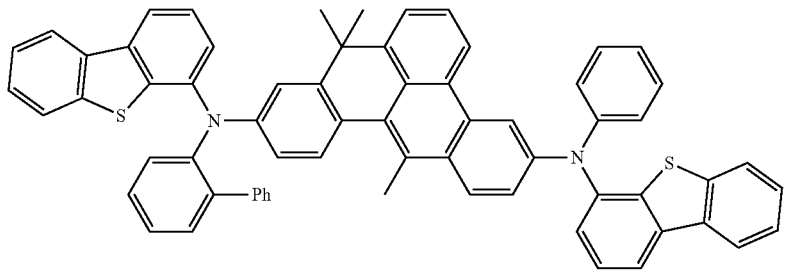
236
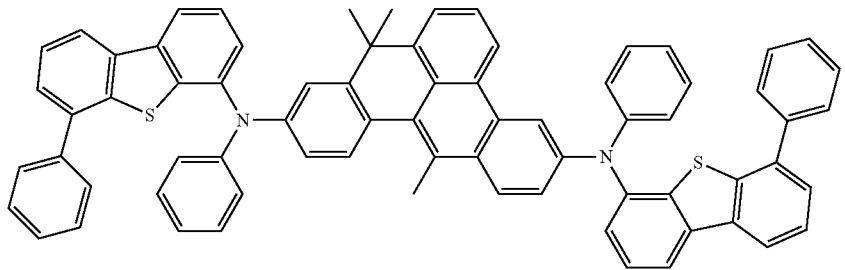

237
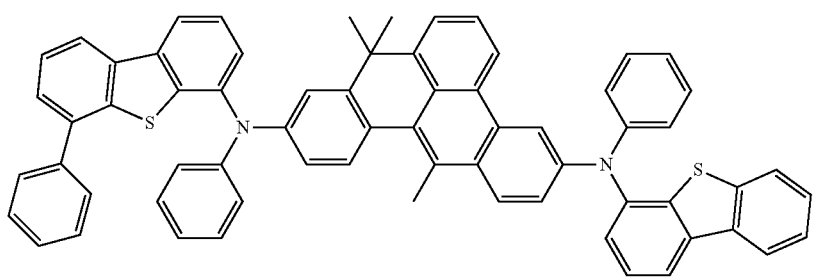
238
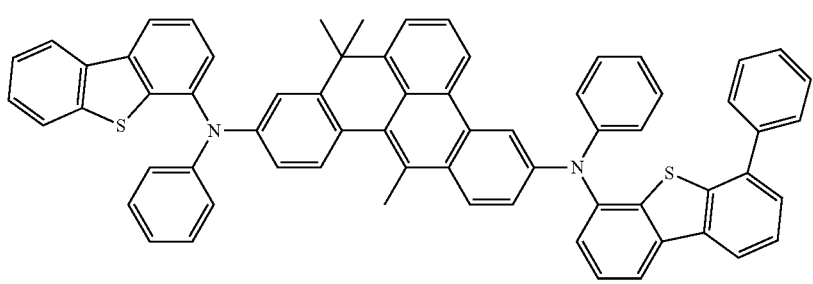
239
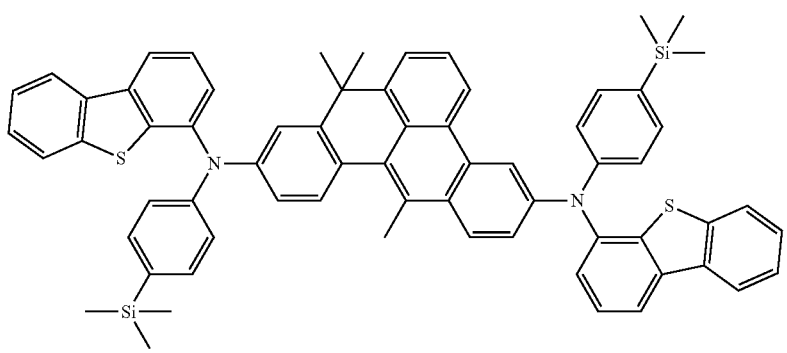
240
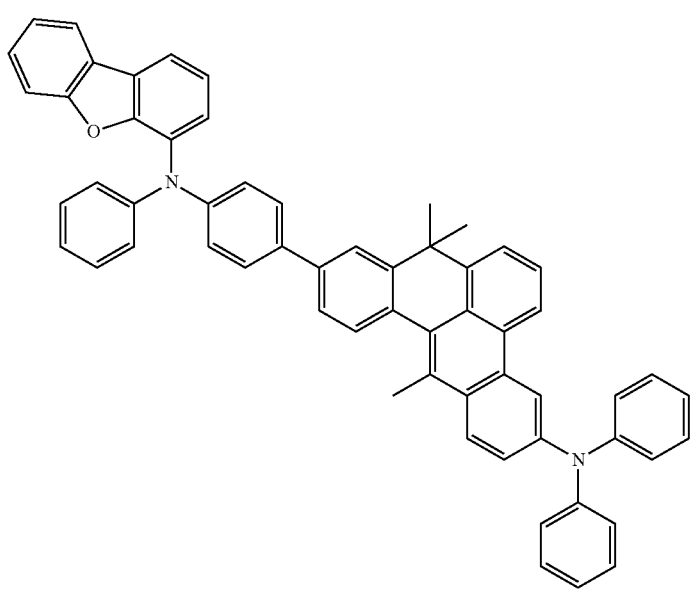

-continued
241
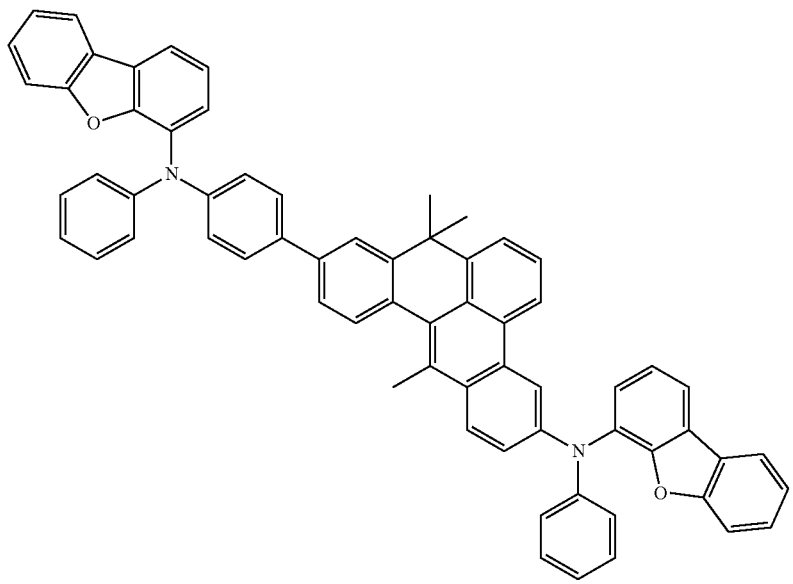
242
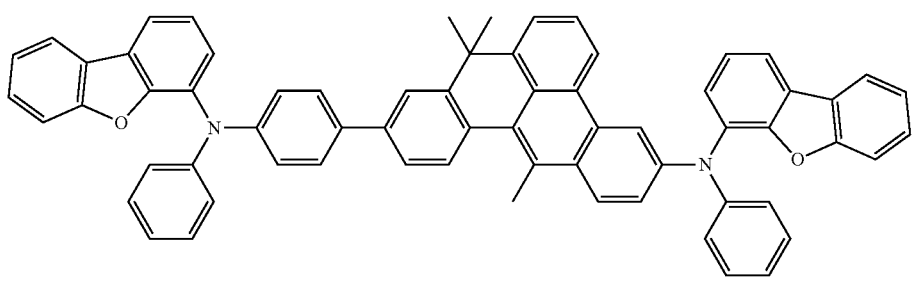
243
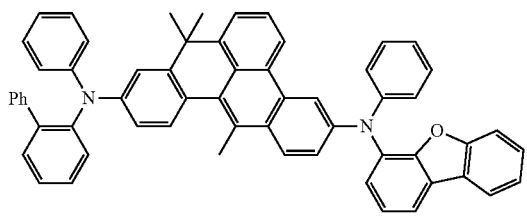
244
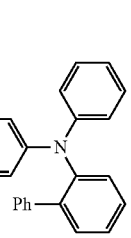
245
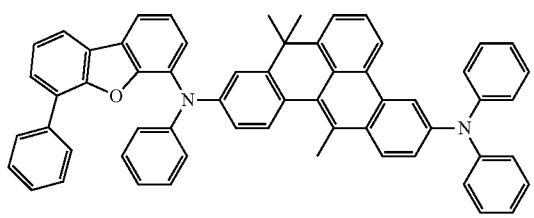
246
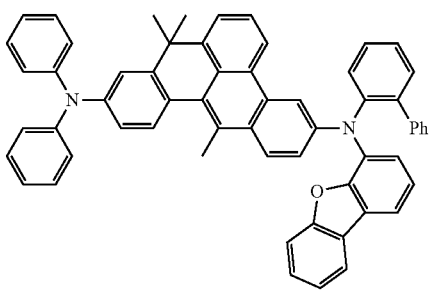
247
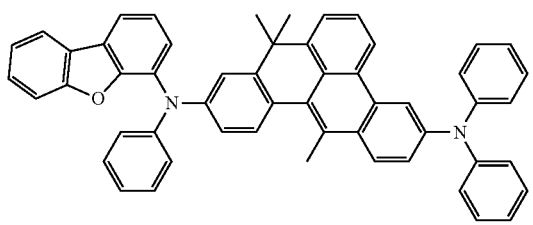
248
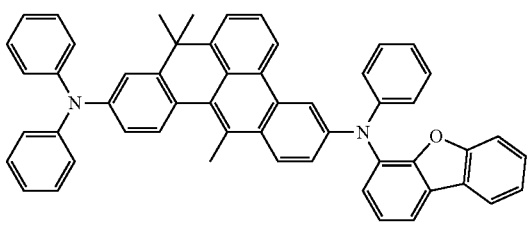

-continued
249
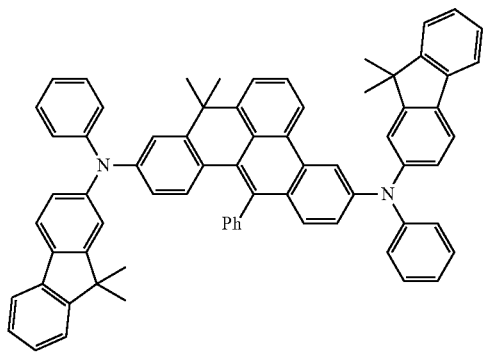
250
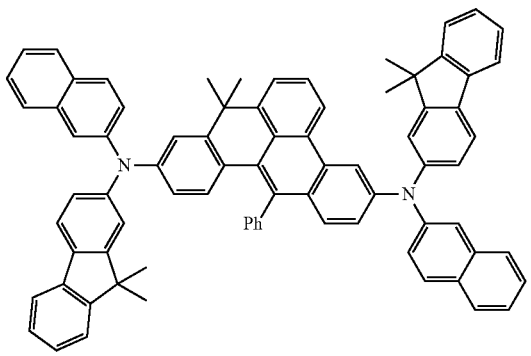
251
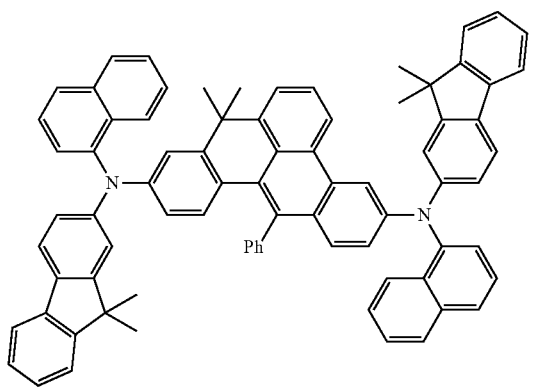
252
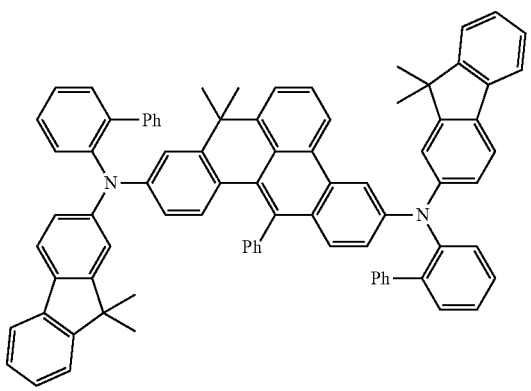
253
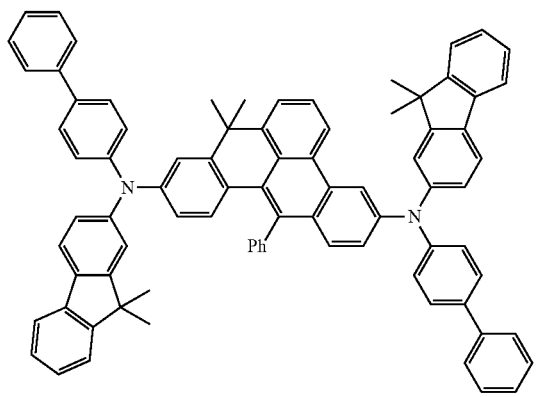
254
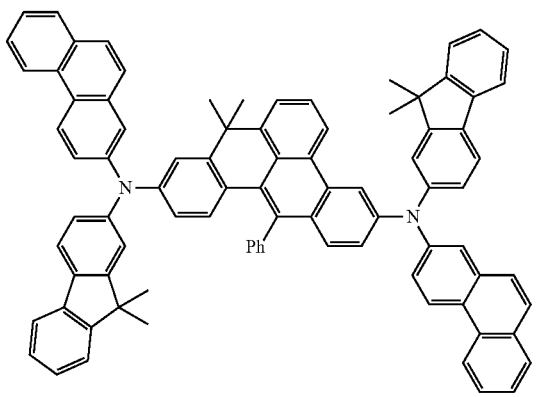
255
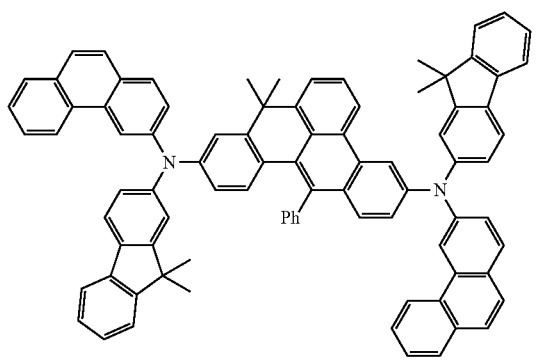
256
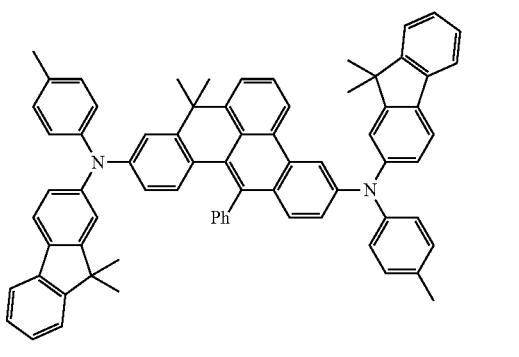

-continued
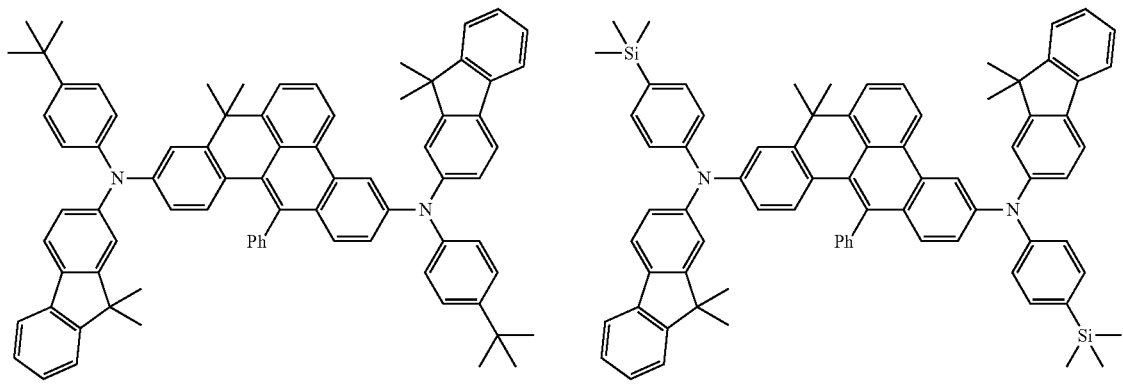
257 258
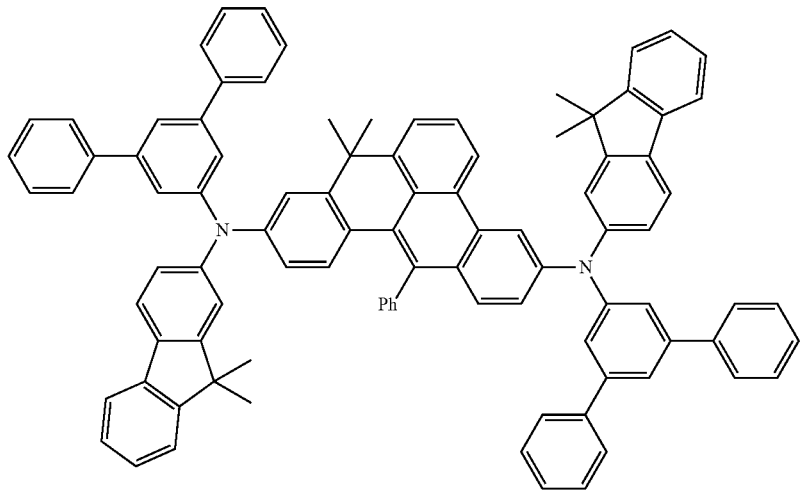
259
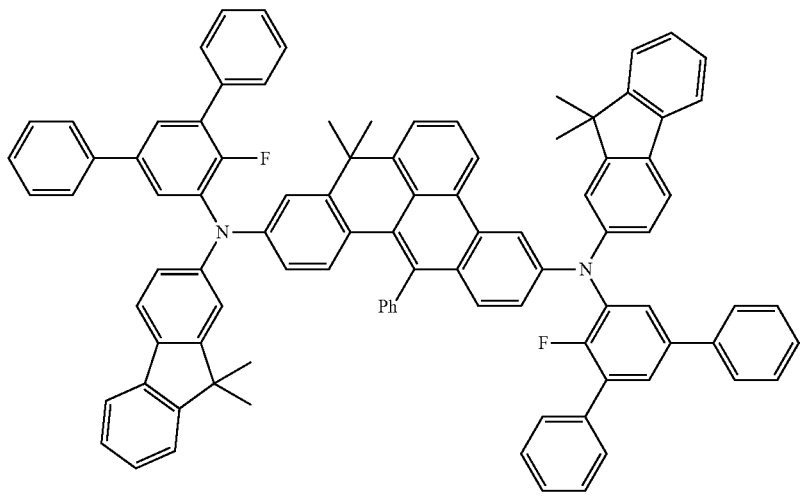
260

-continued
261
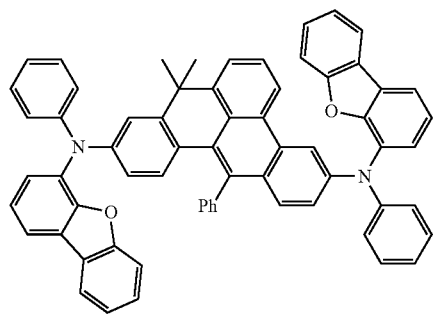
262
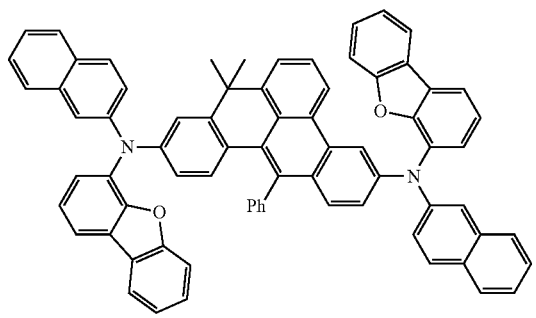
263
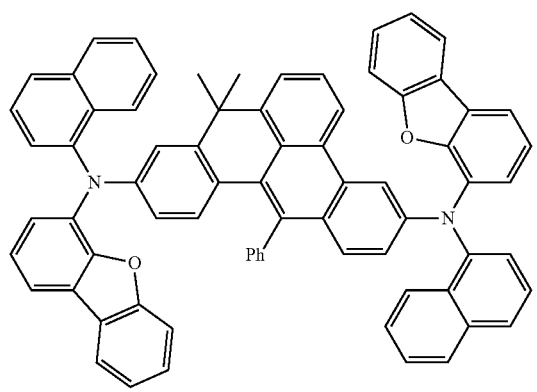
264
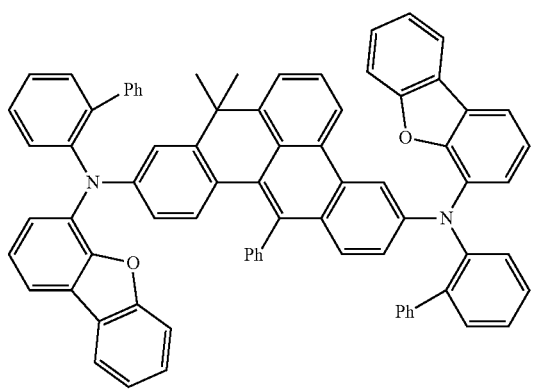
265
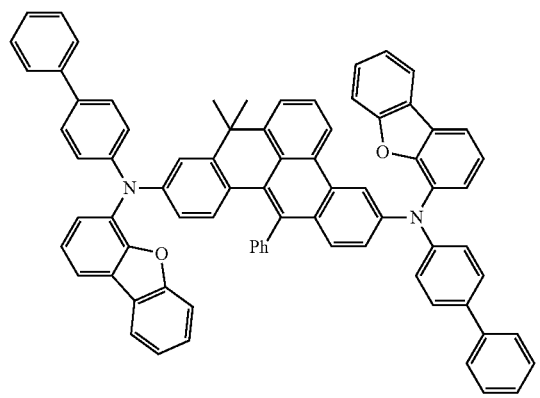
266
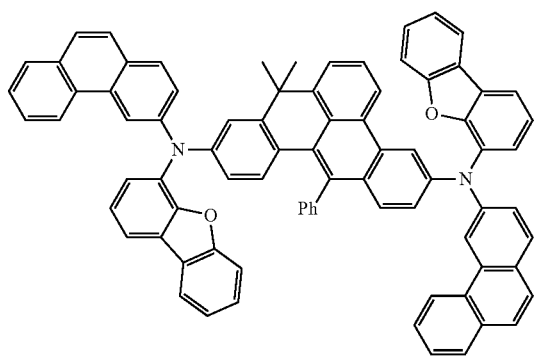
267
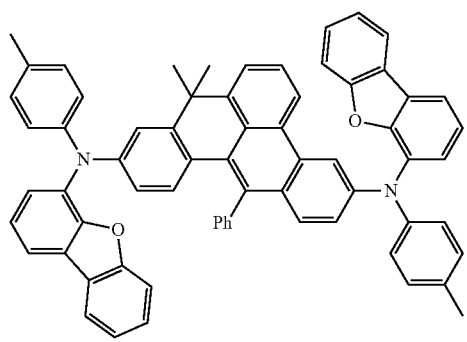
268
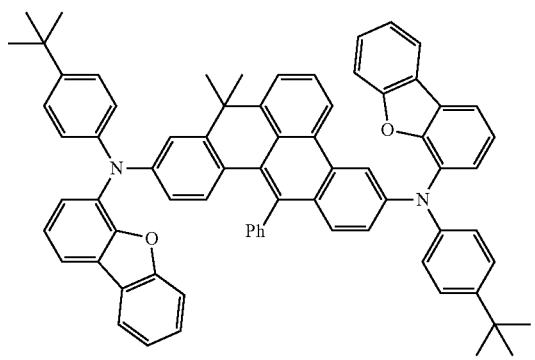

269
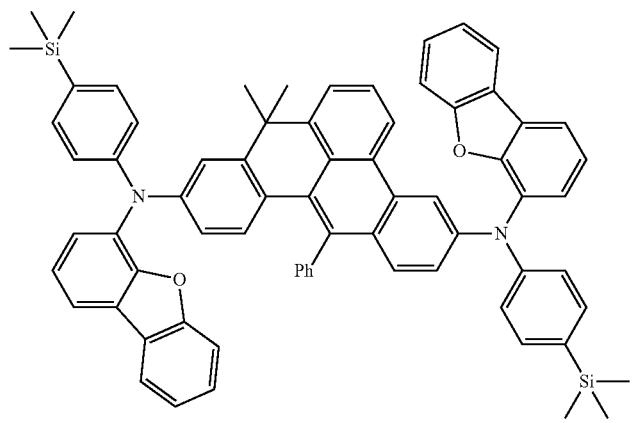
270
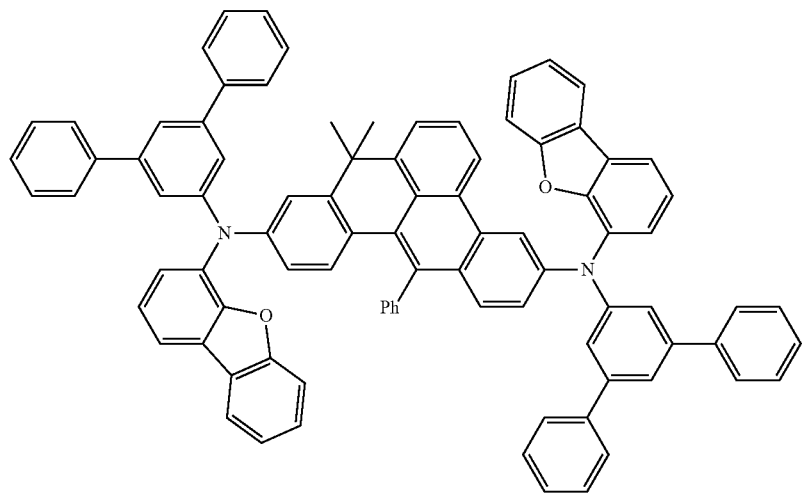
271
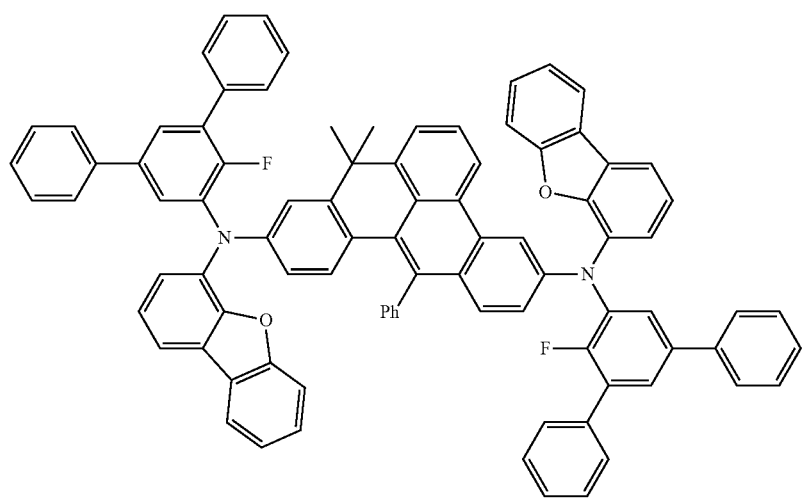

-continued
272
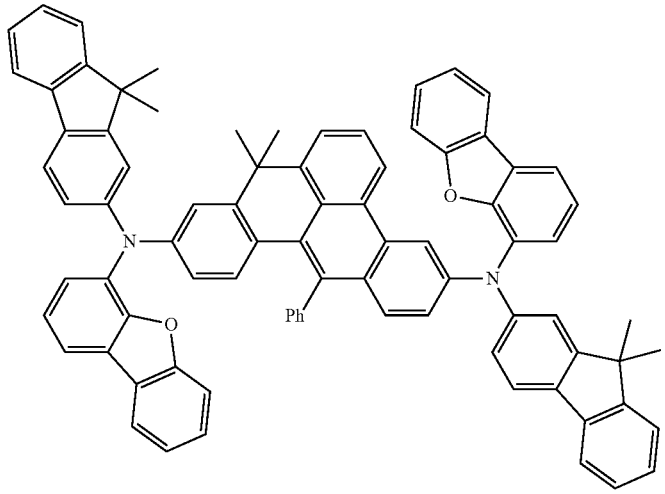
273
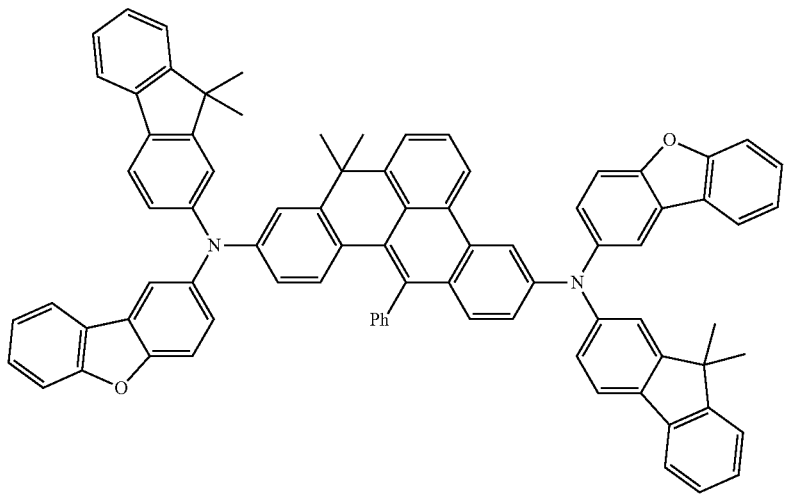
274
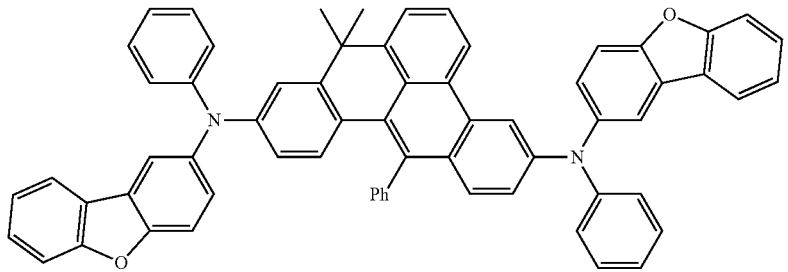
275
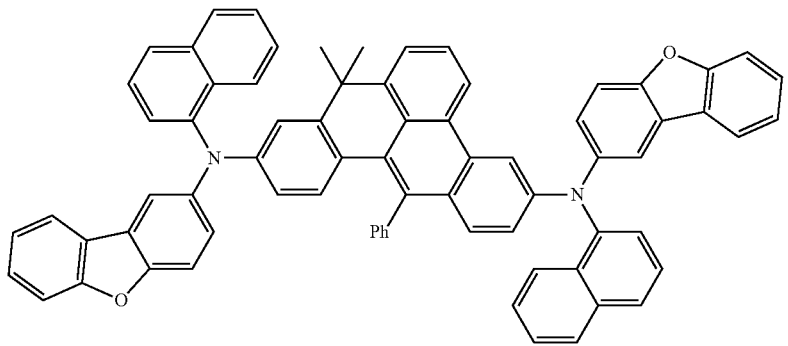

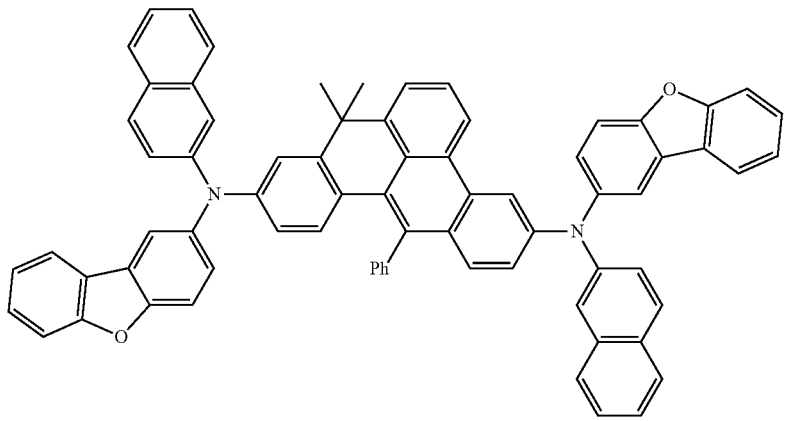
276
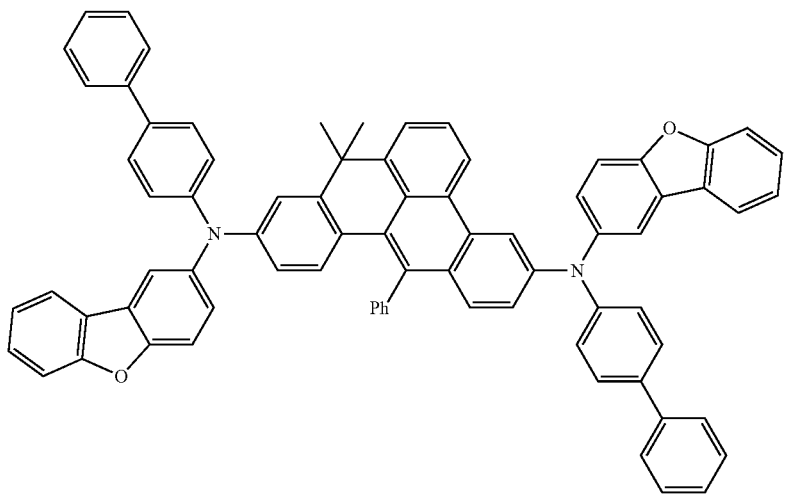
277
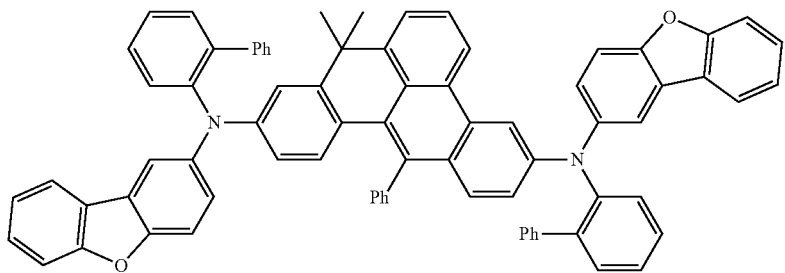
278
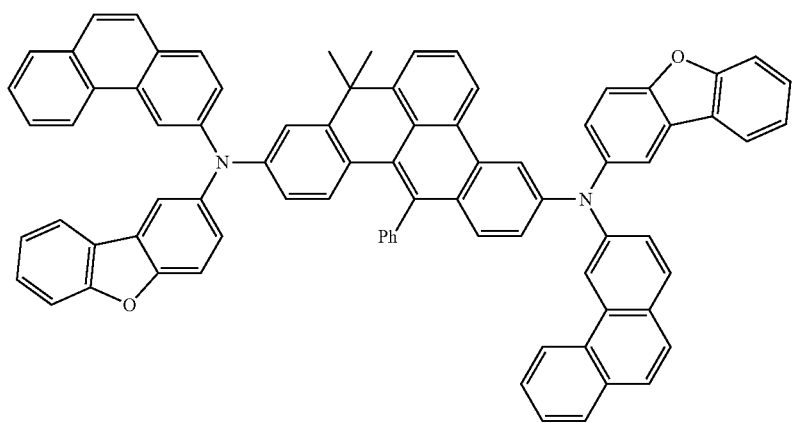
279

-continued
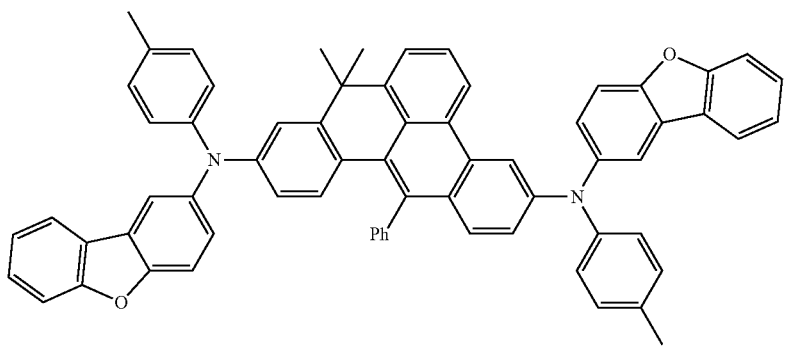
280
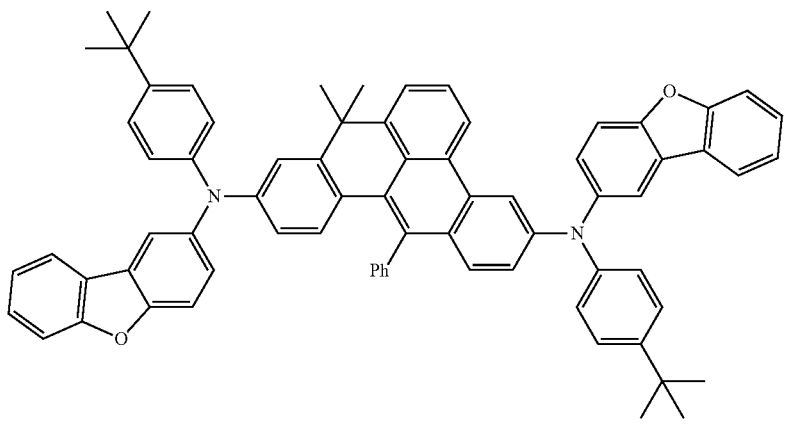
281
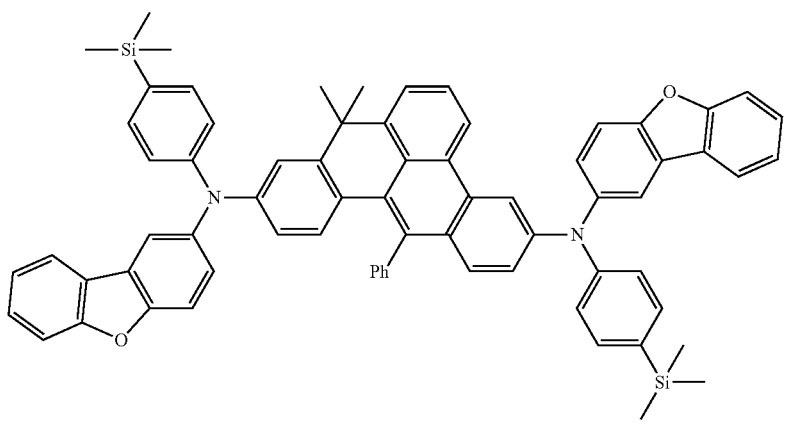
282

283
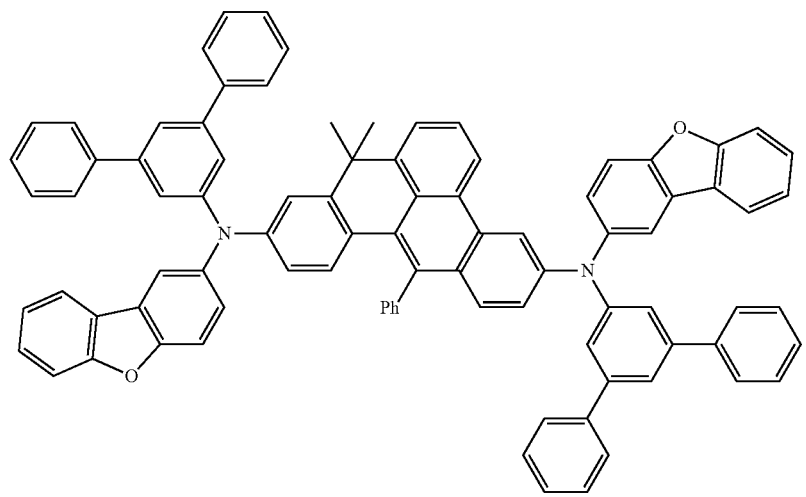
284
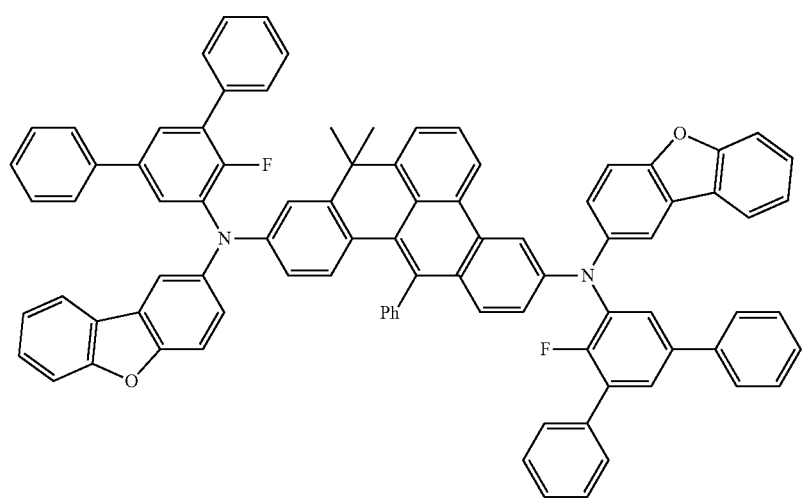
285
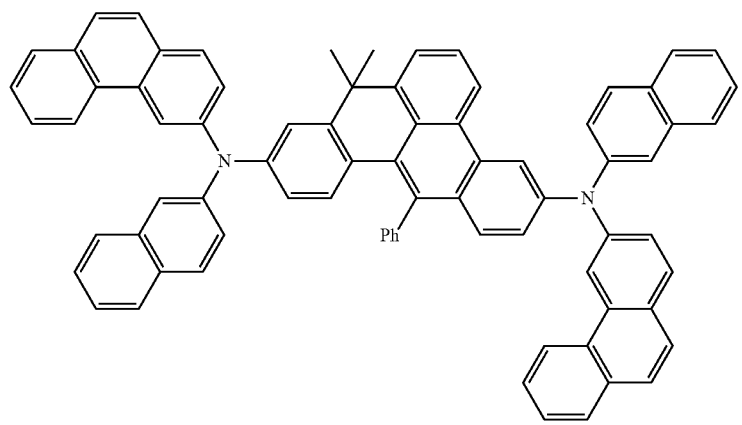

-continued
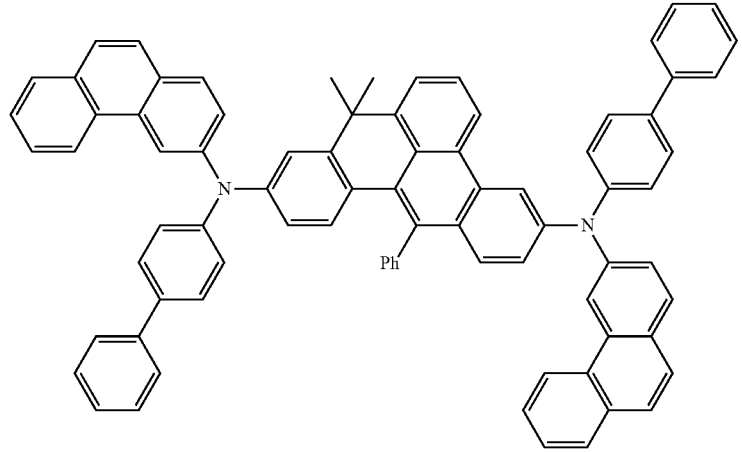
286
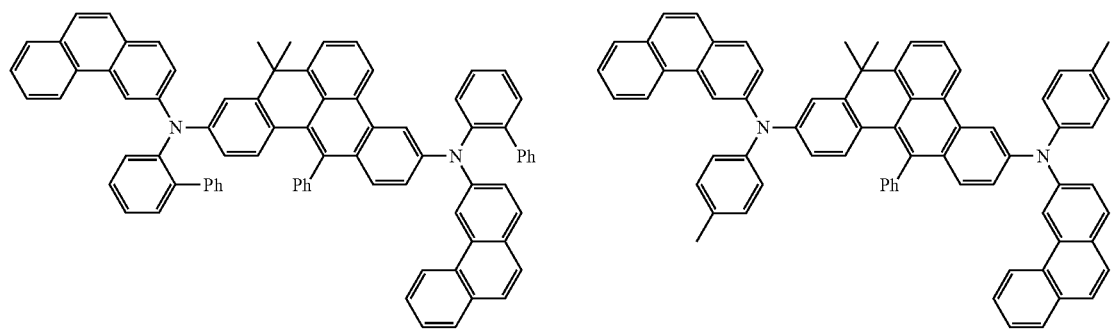
287 288
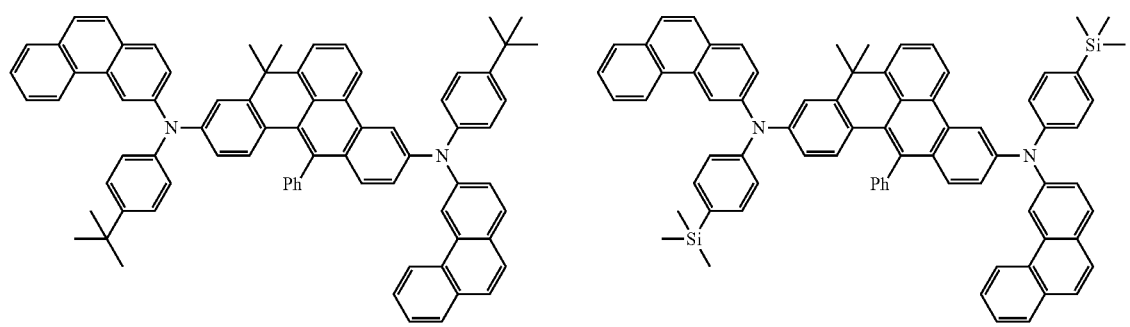
289 290
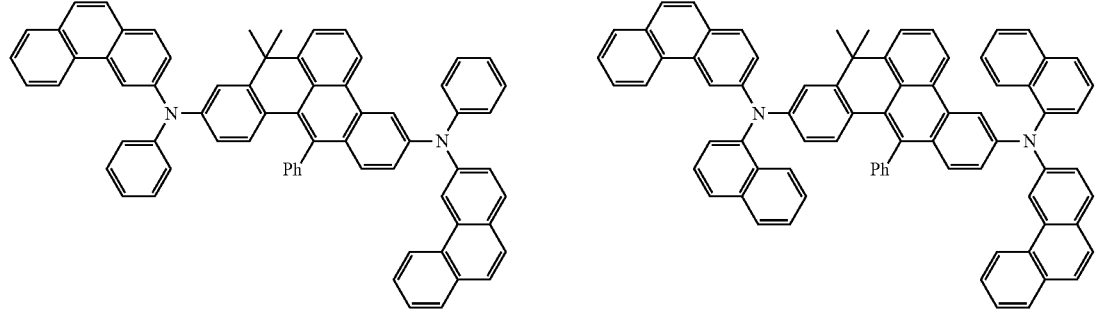
291 292

293
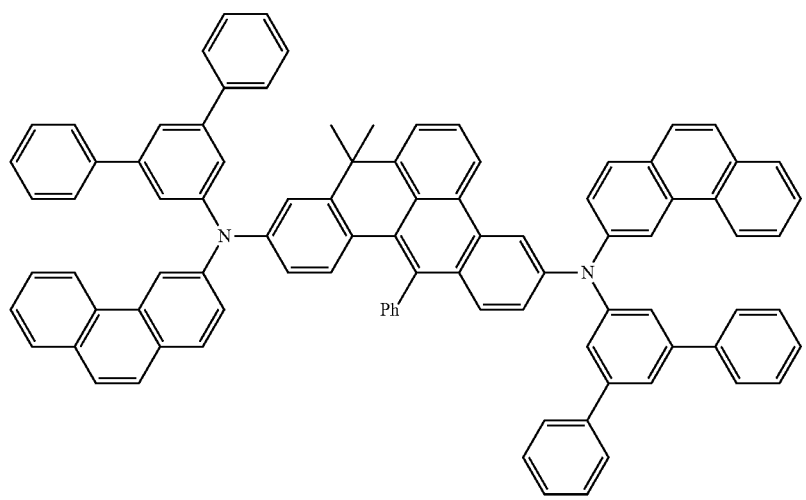
294
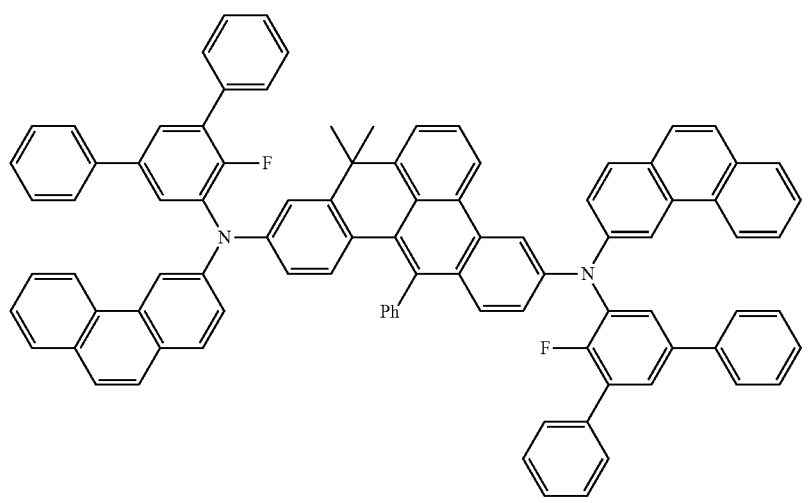
295
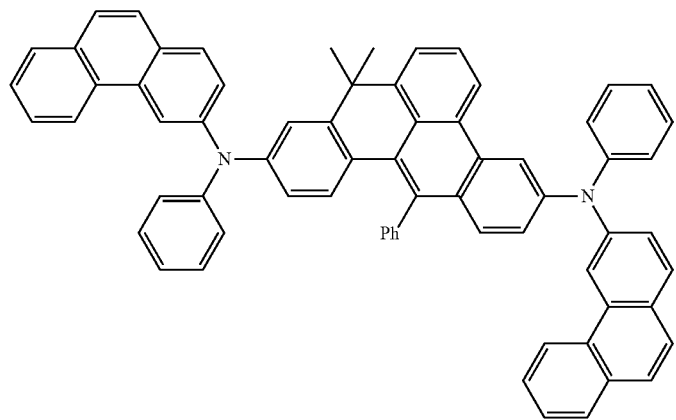

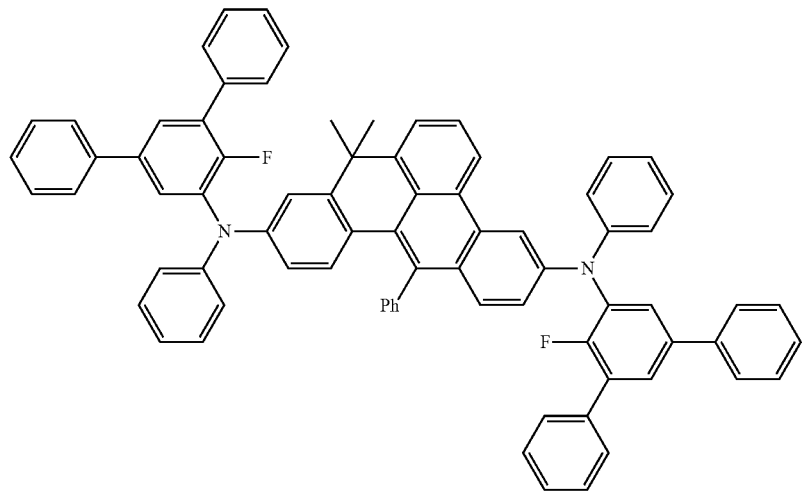
296
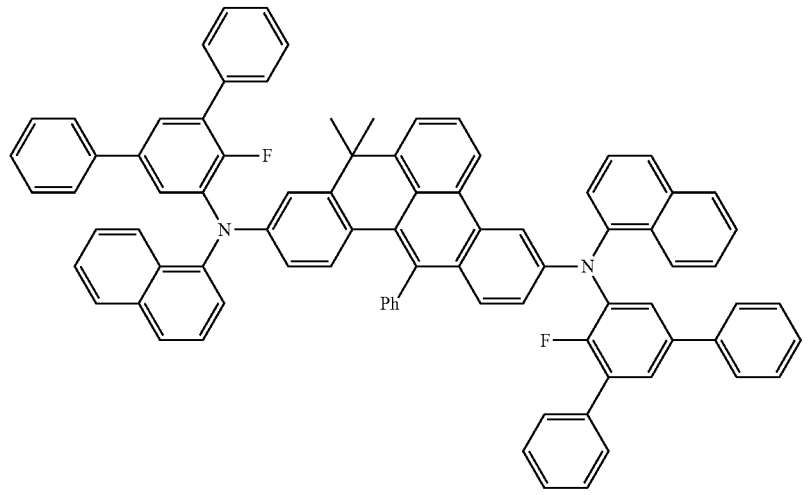
297
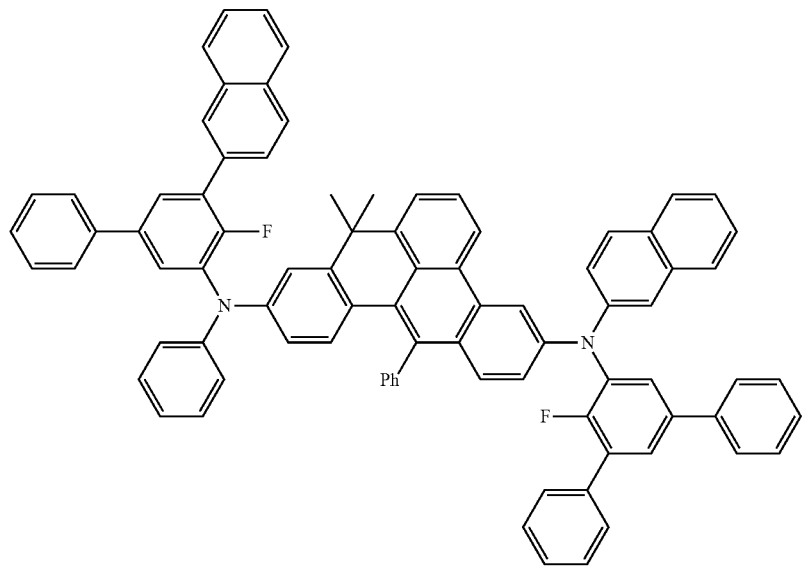
298

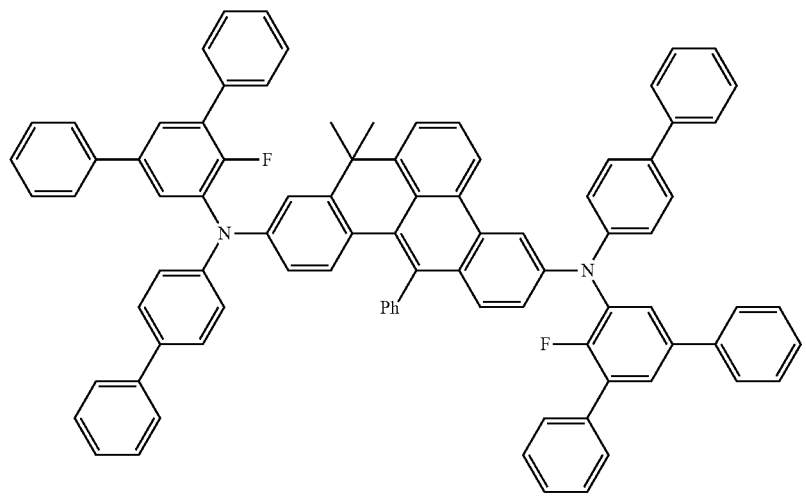
299
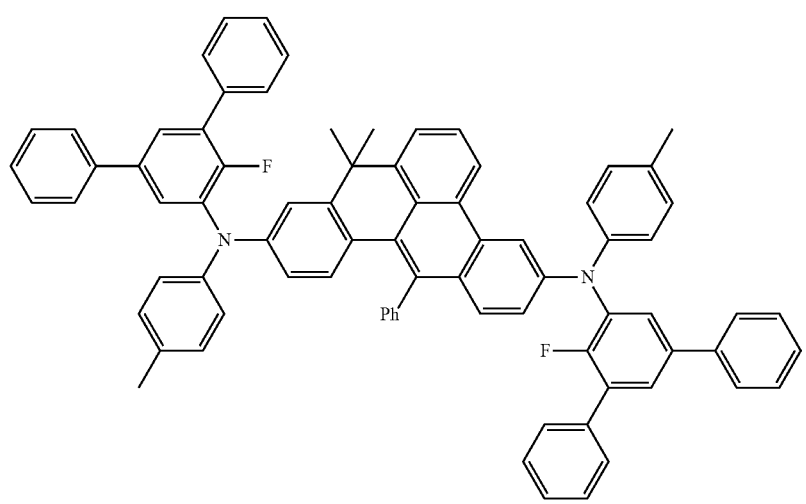
300
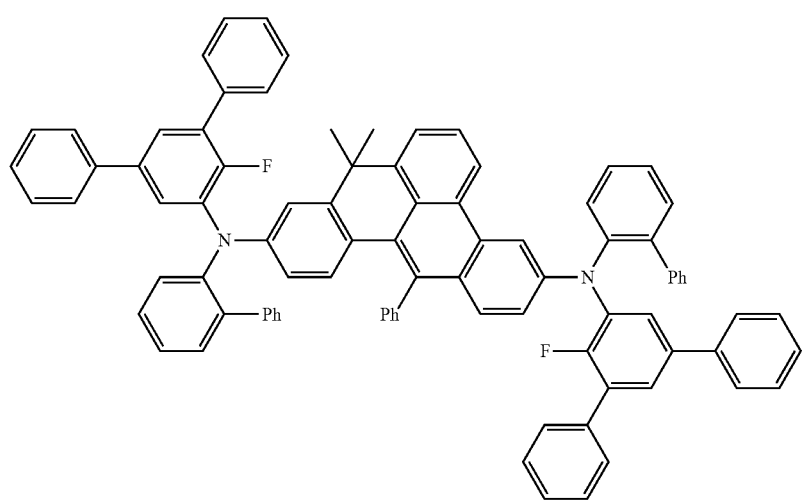
301

-continued
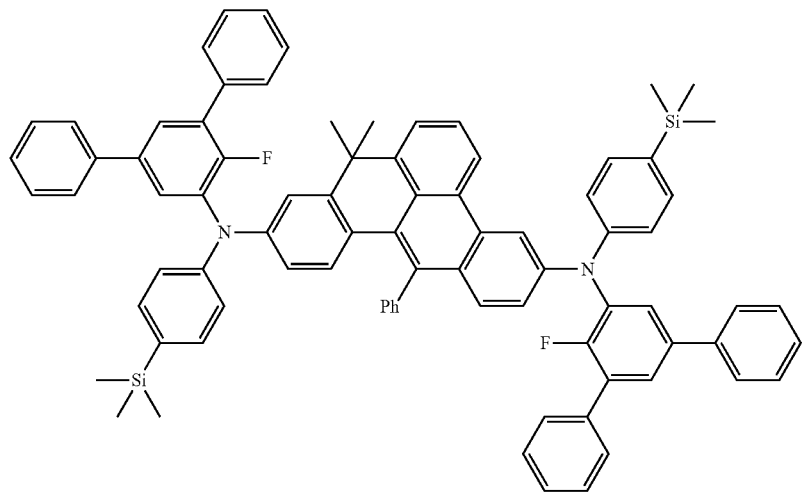
302
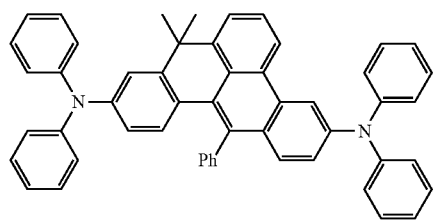
303
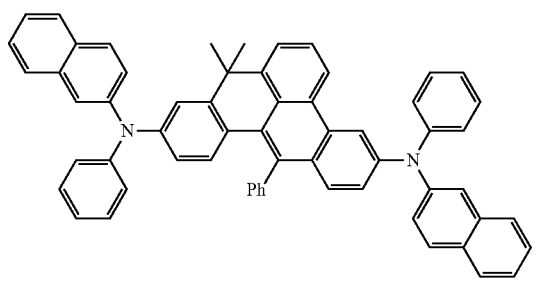
304
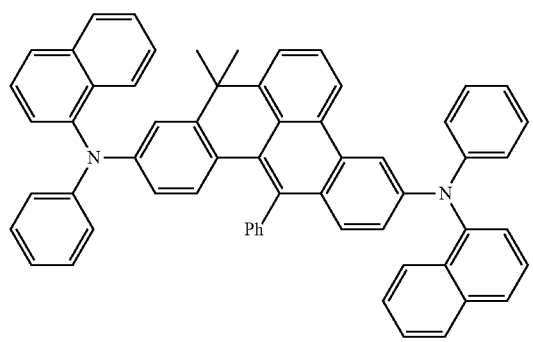
305
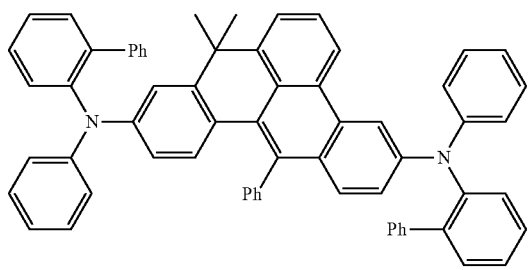
306
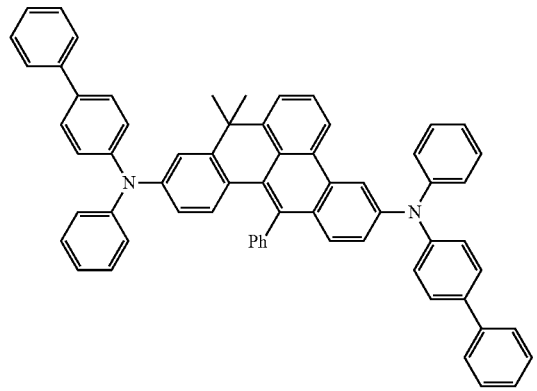
307
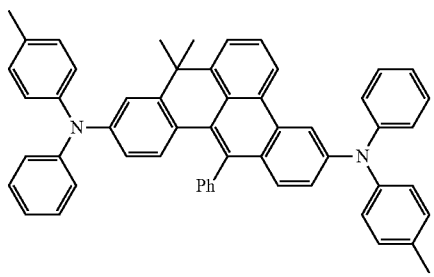
308

-continued
309
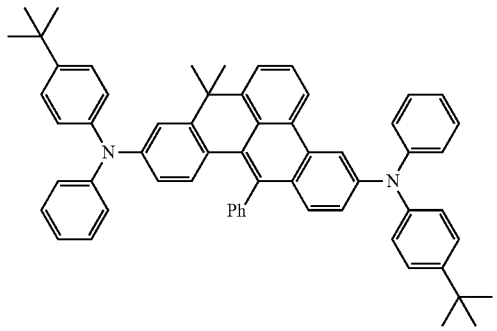
310
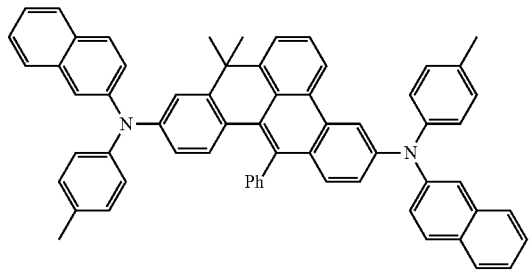
311
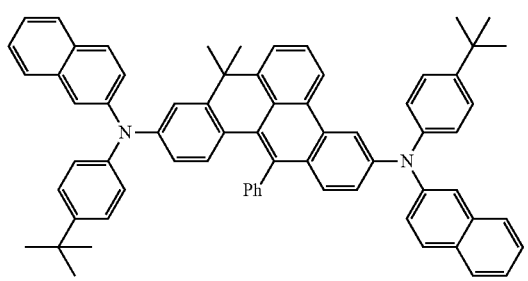
312
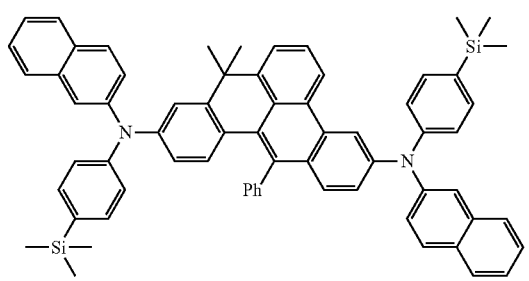
313
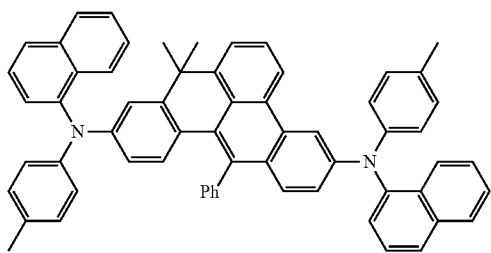
314
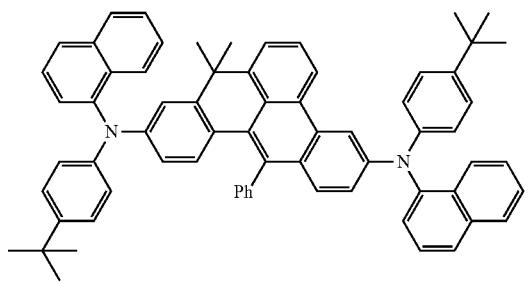
315
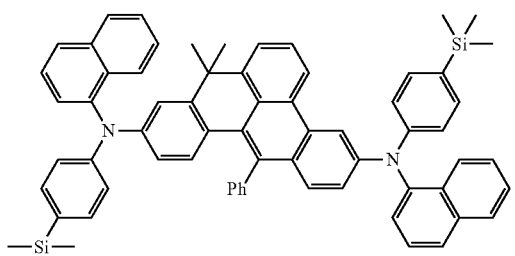
316
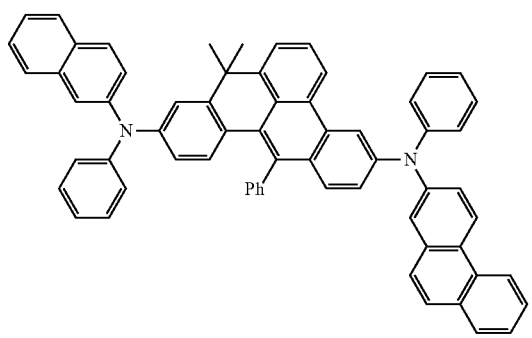

-continued
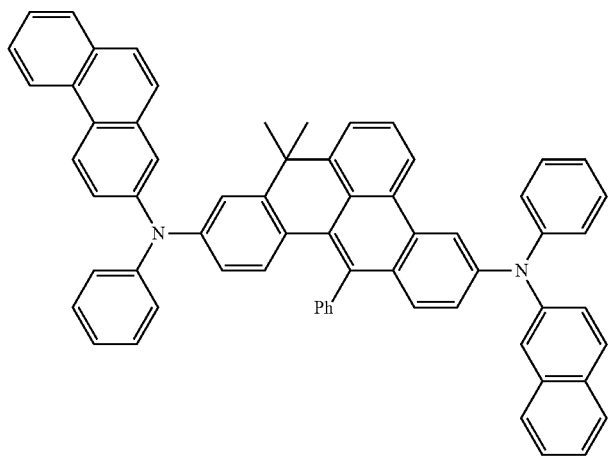
317
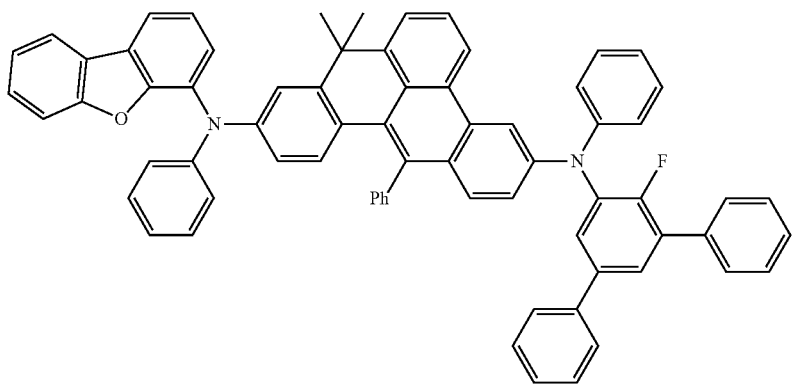
318
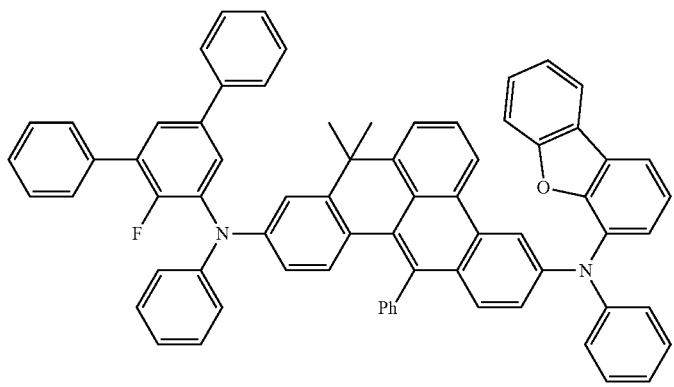
319

-continued
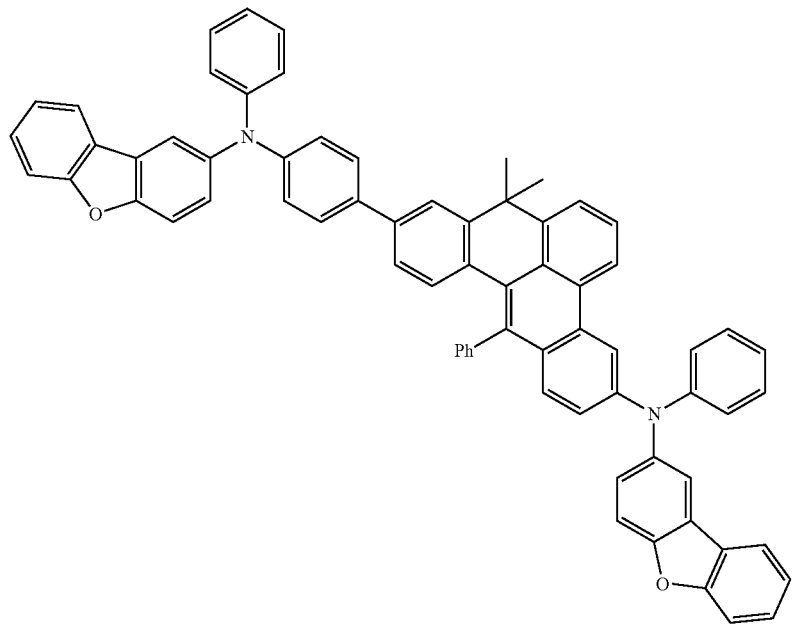
320
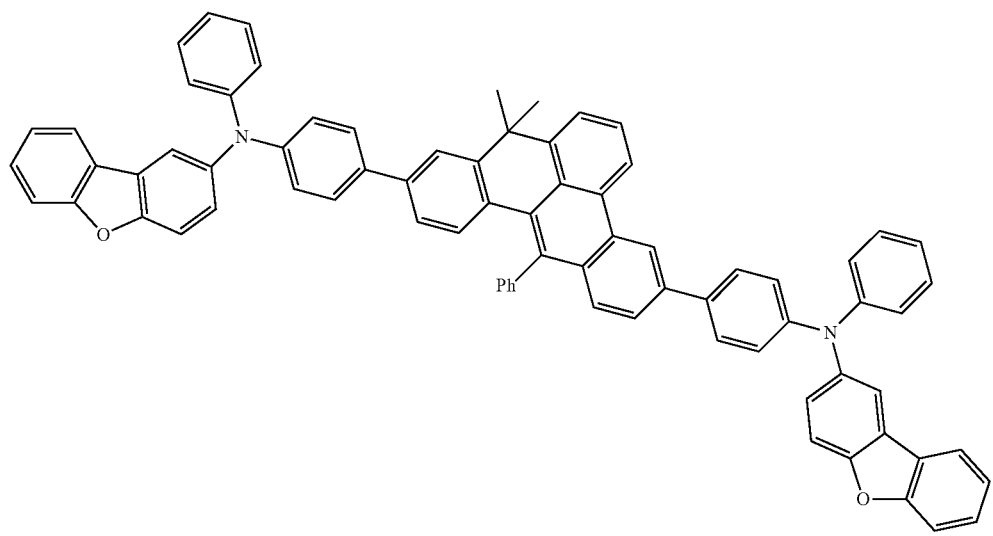
321
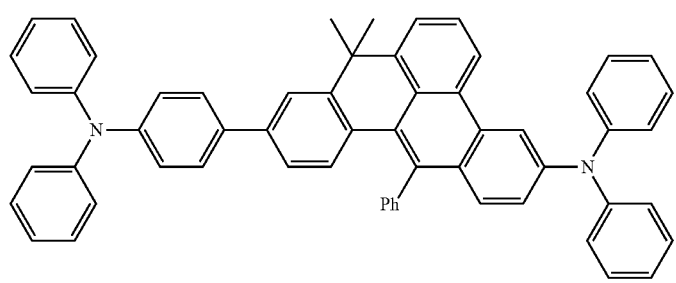
323

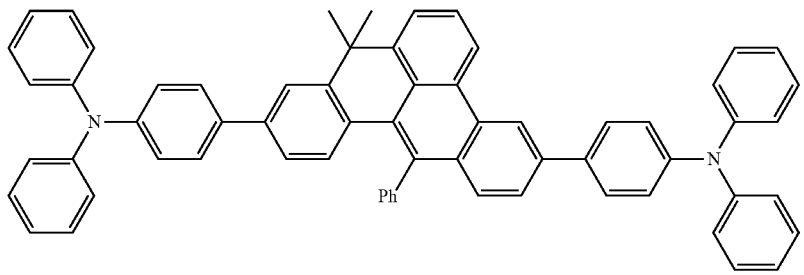
324
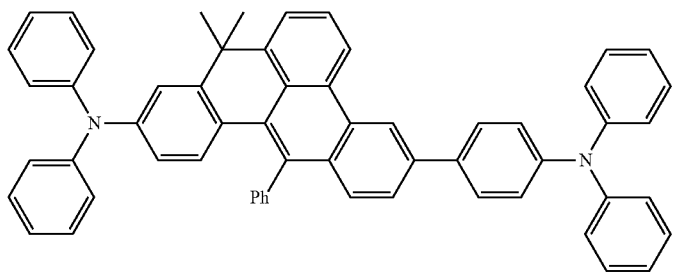
325
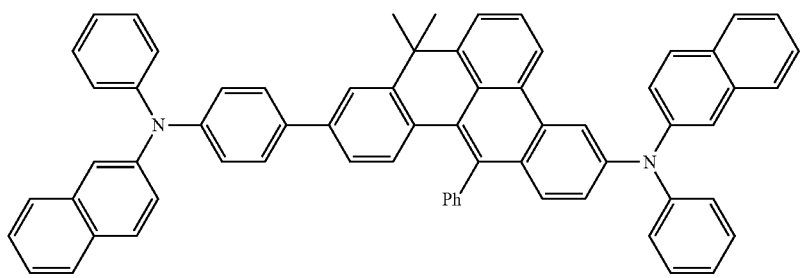
326
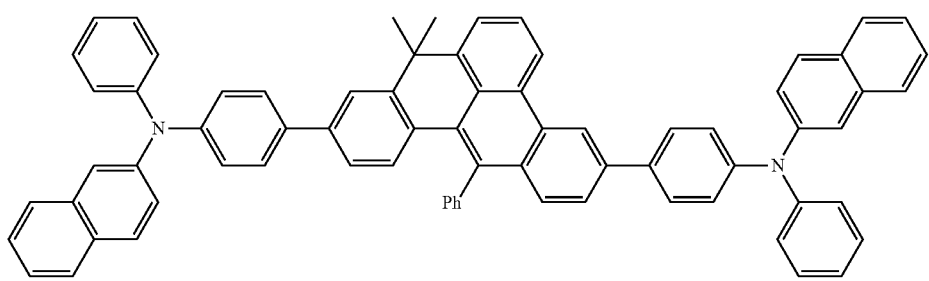
327
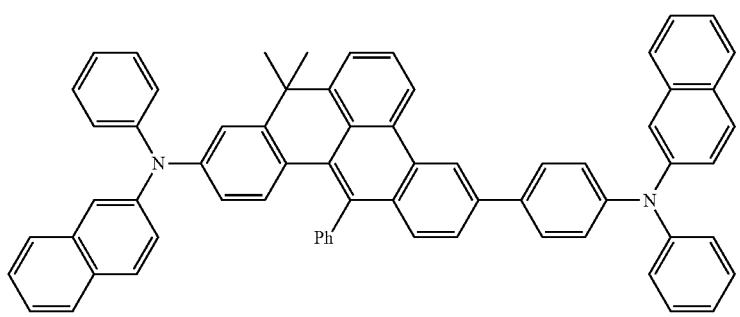
328

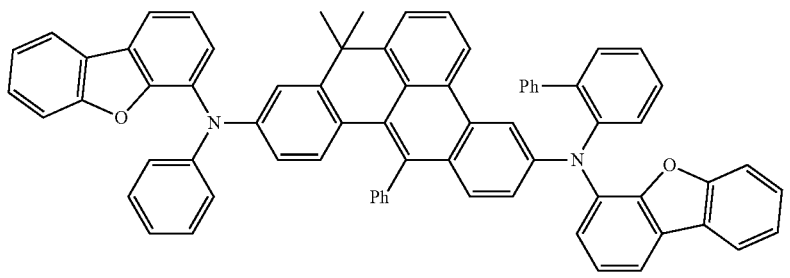
329
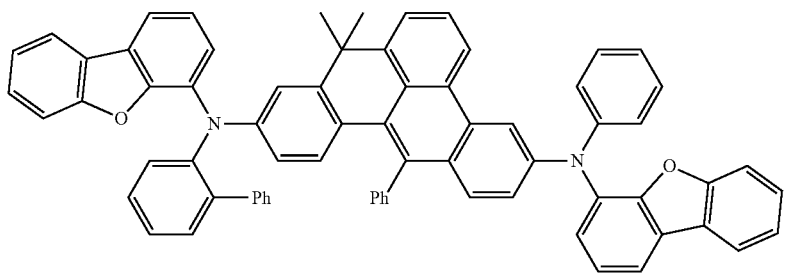
330
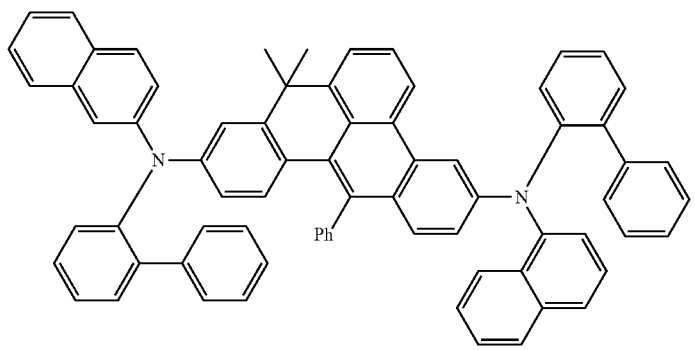
331
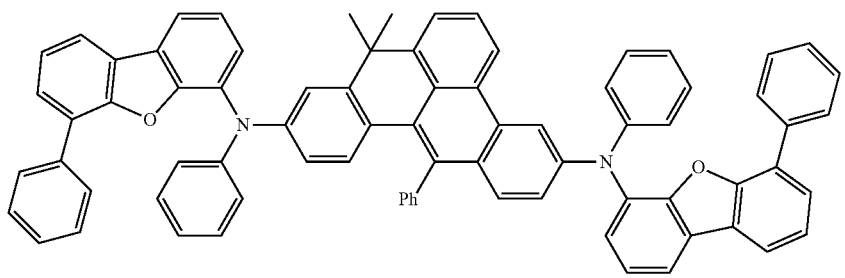
332
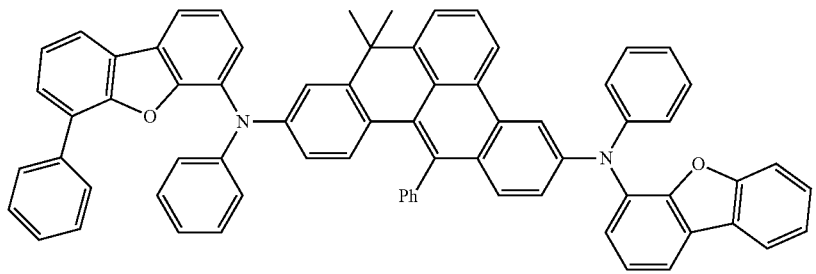
333

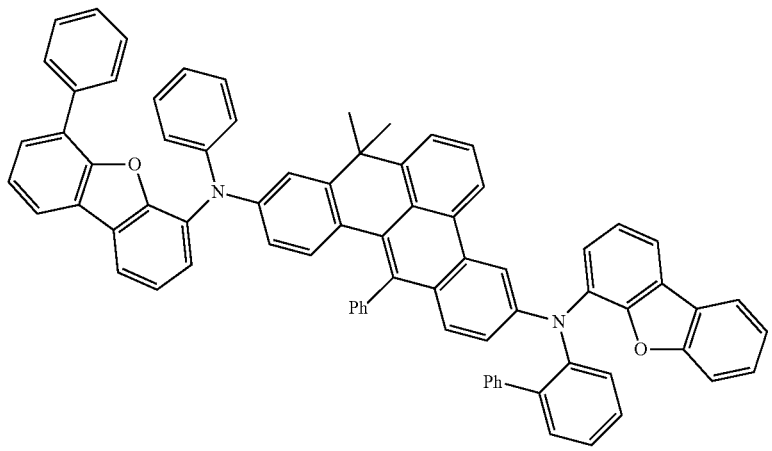
334
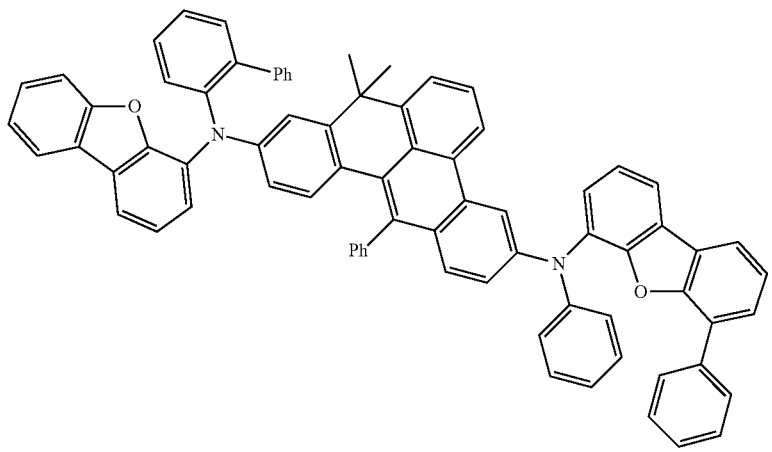
335
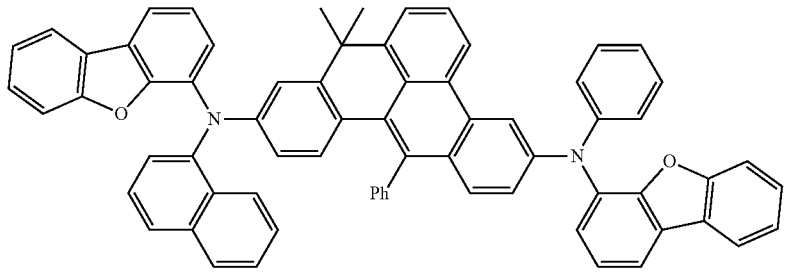
336
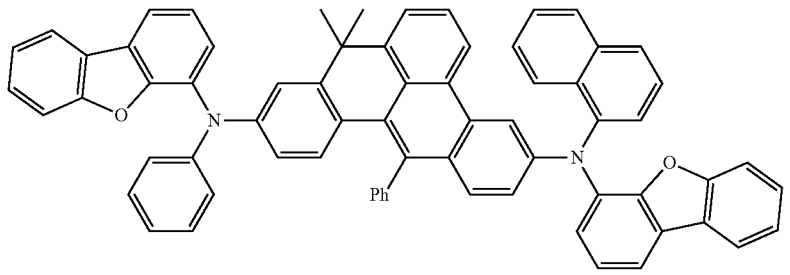
337

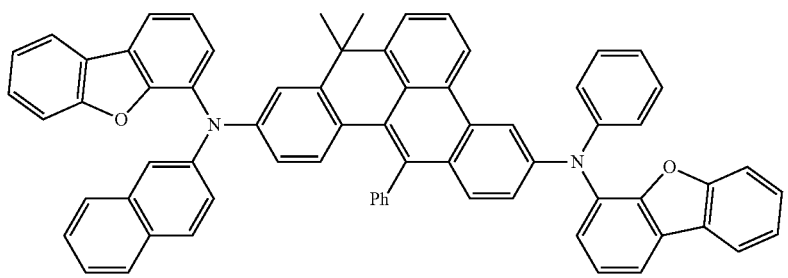
338
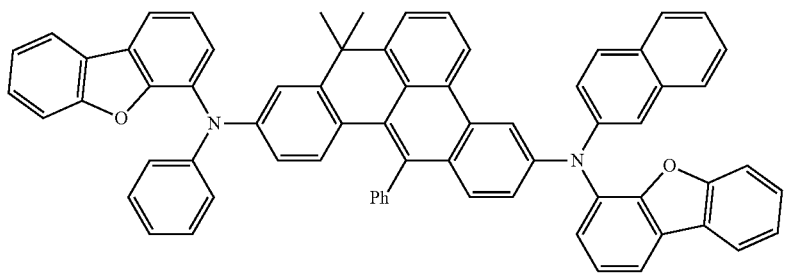
339
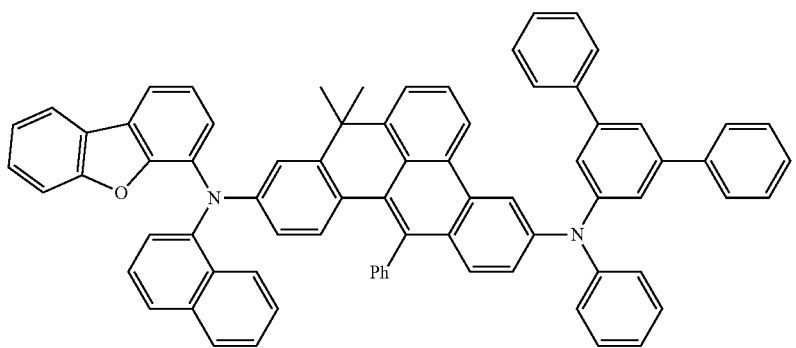
340
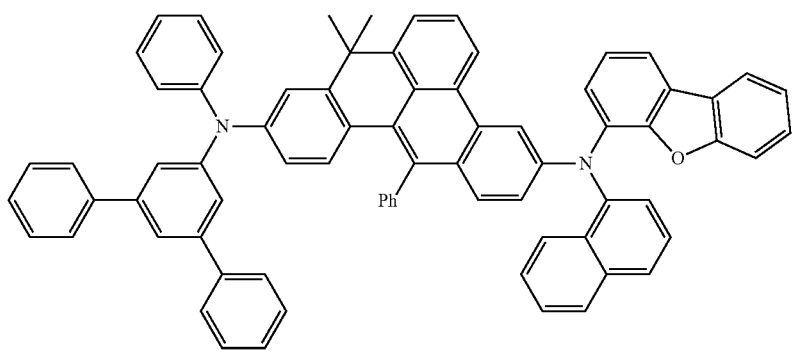
341
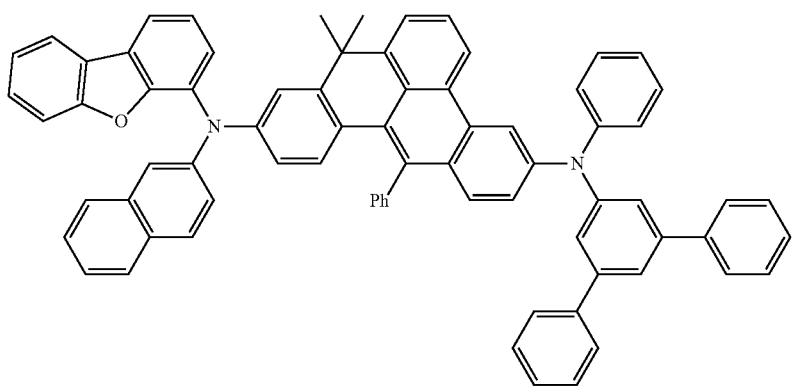
342

-continued
343
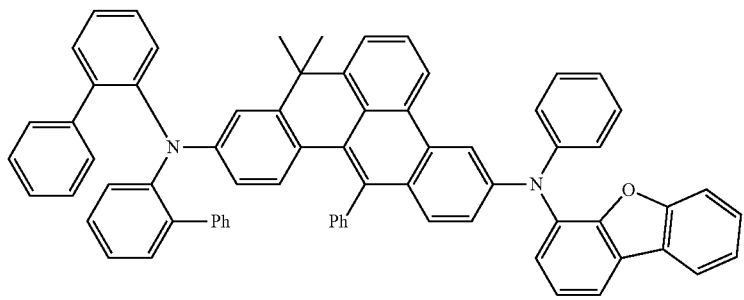
344
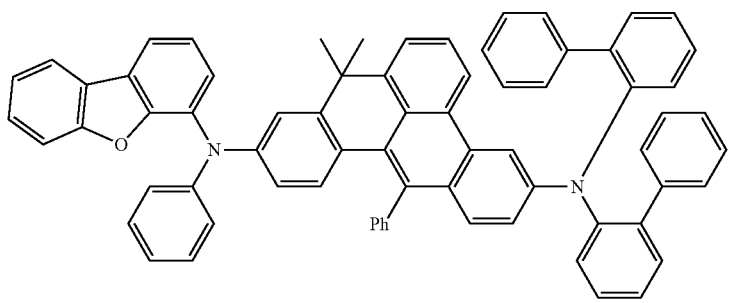
345
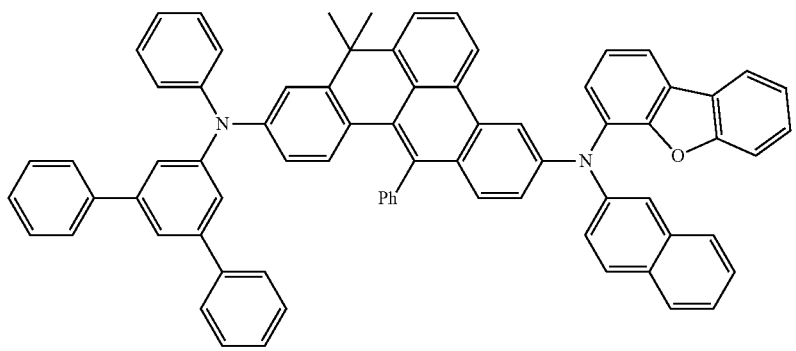
346
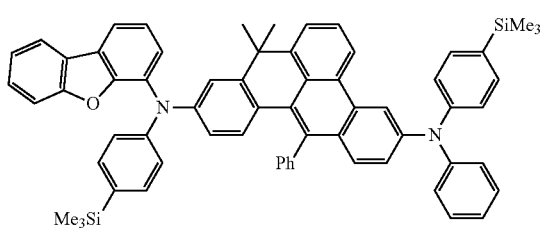
347
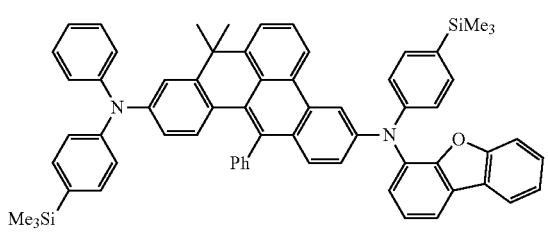
348
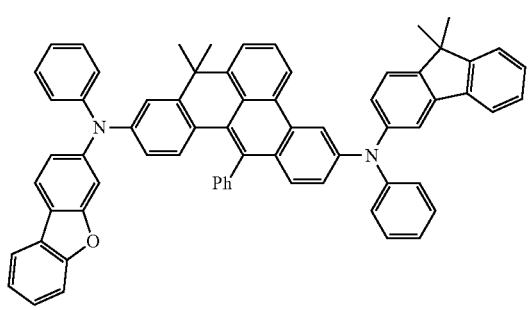
349
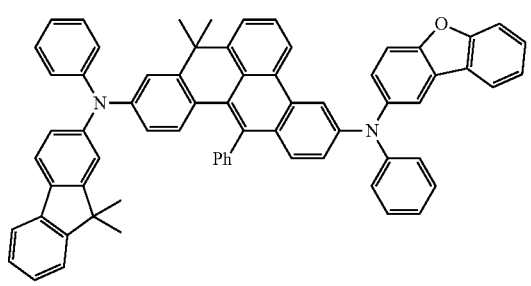

-continued
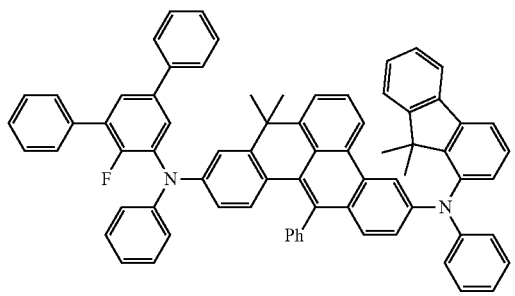
350
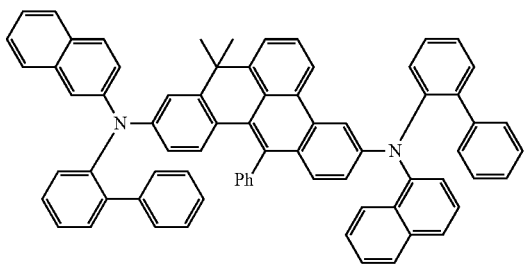
351
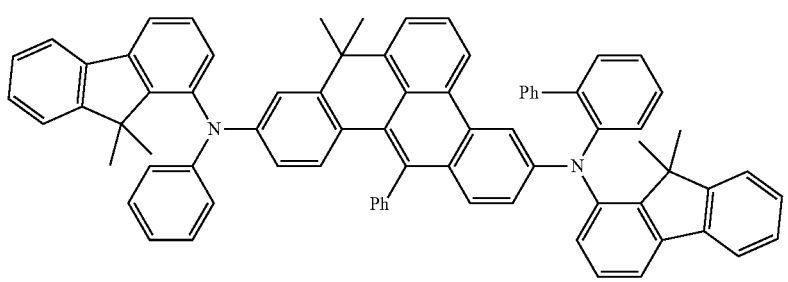
352
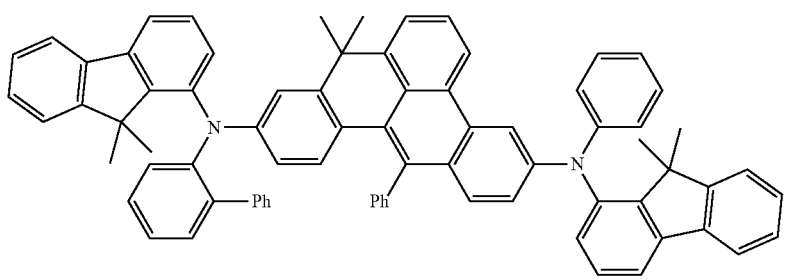
353
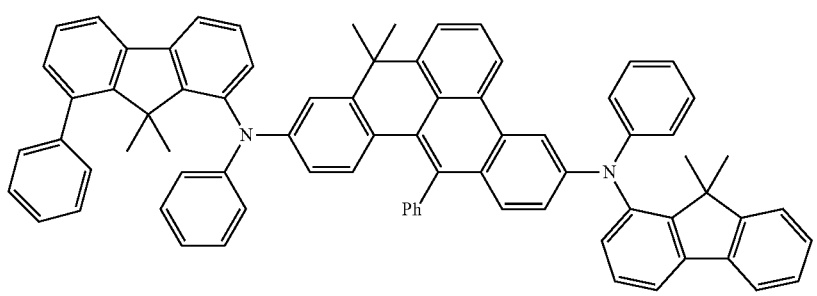
354
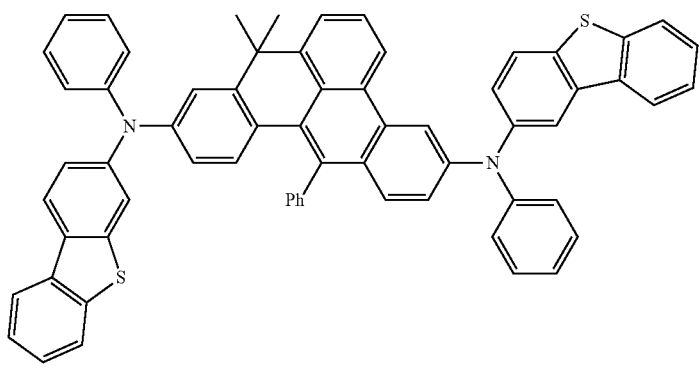
355

-continued
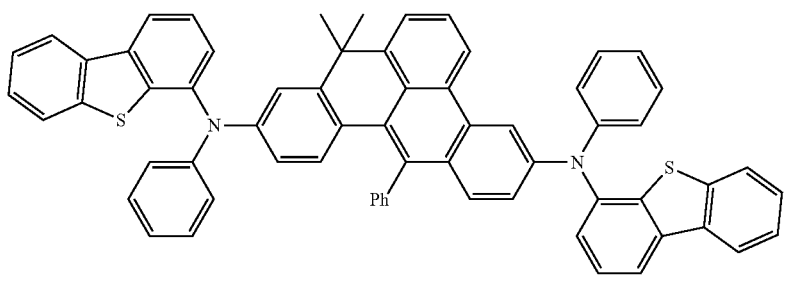
356
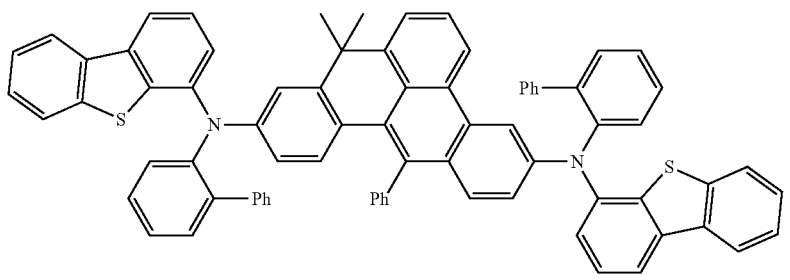
357
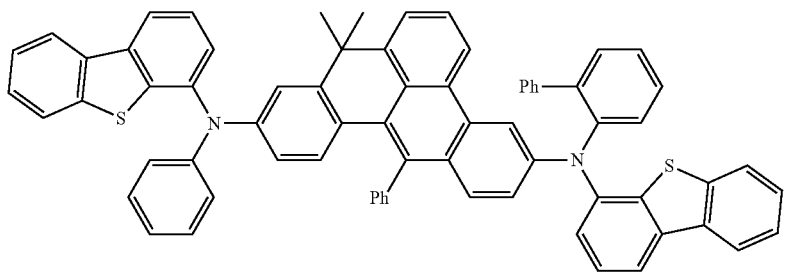
358
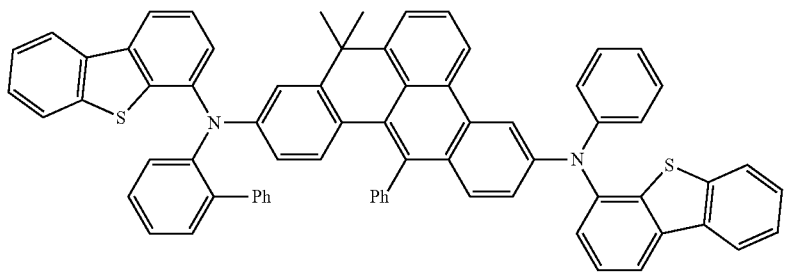
359
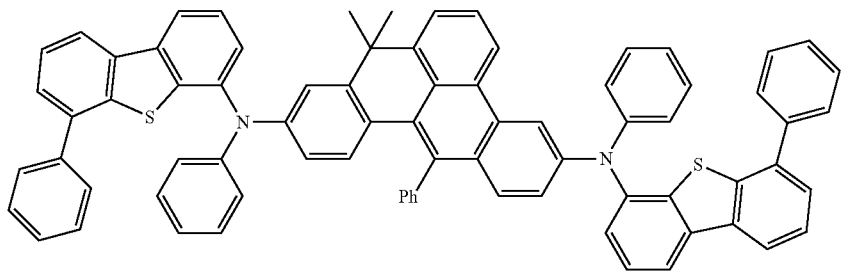
360

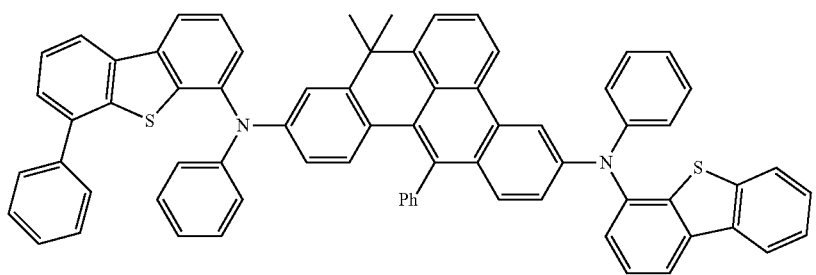
361
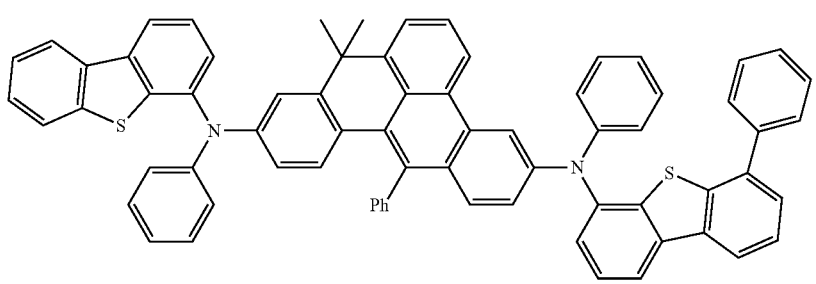
362
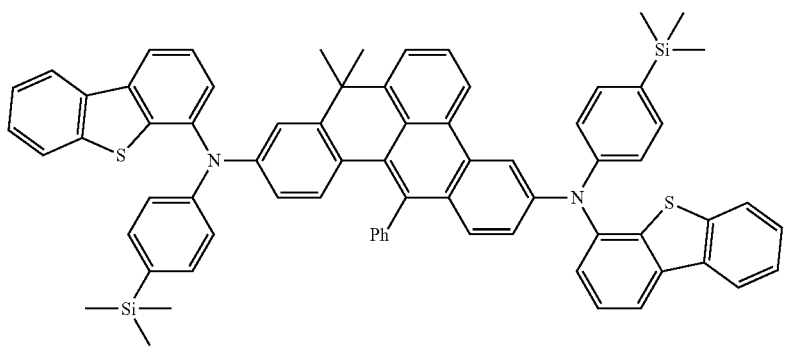
363
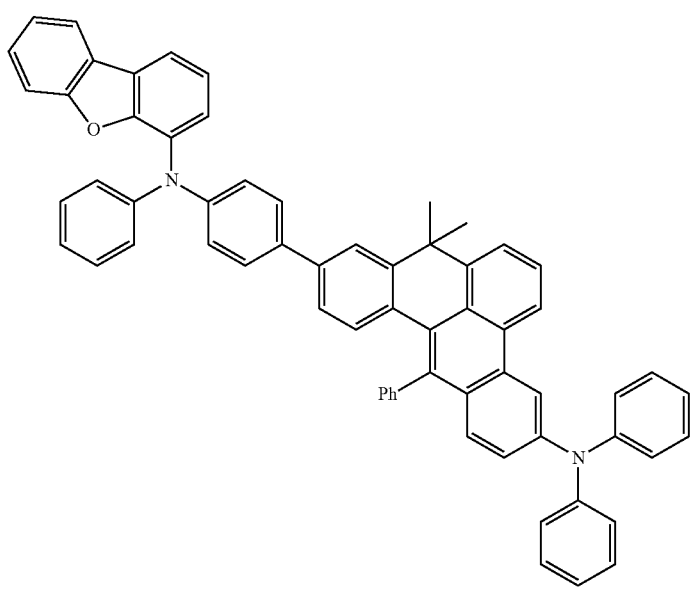
364

-continued
365
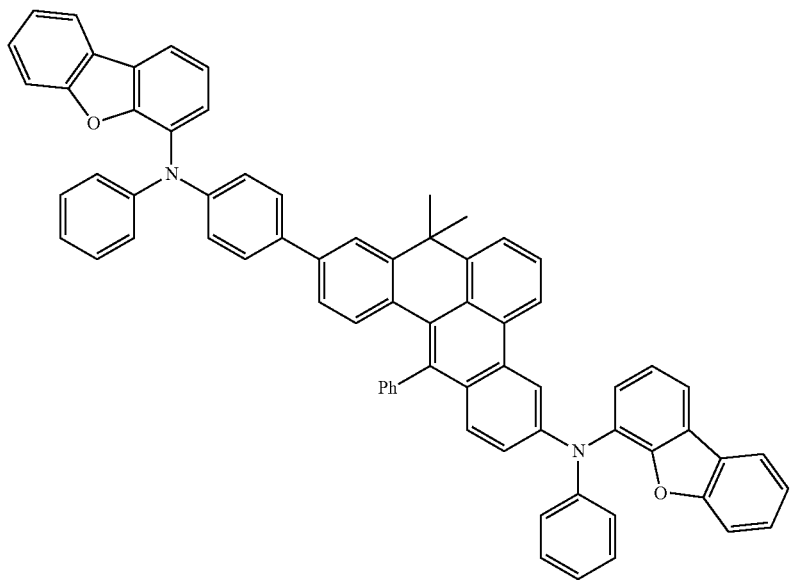
366
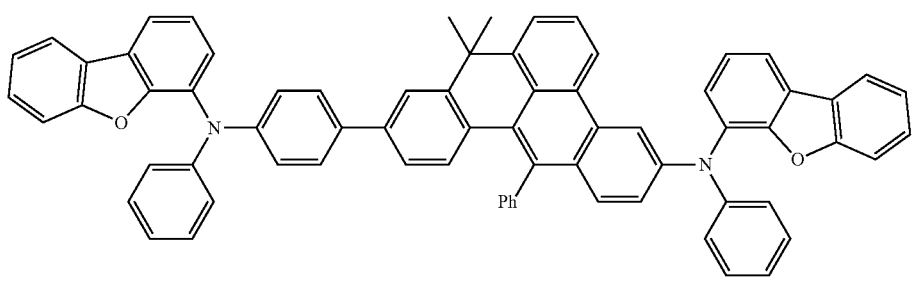
367 368
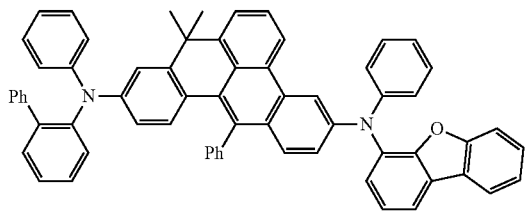
369 370
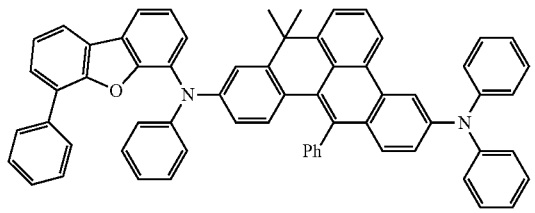
371 372
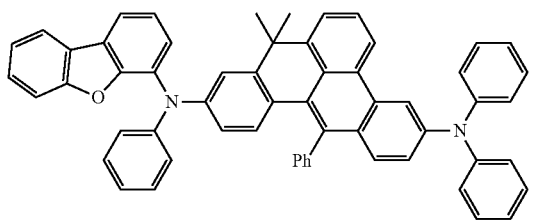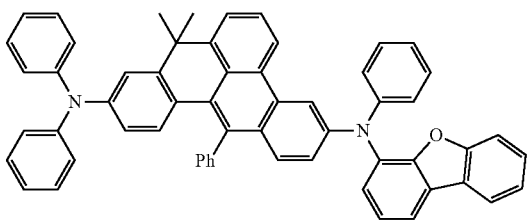

-continued

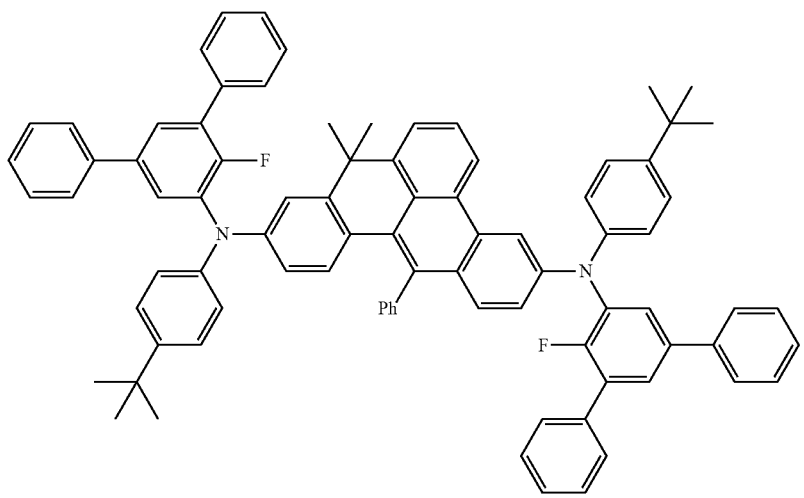

A condensed cyclic compound represented by Formula 1 includes a core represented by Formula 1' below; the core represented by Formula 1' below may have rich electrons, so that an organic light-emitting device including the condensed cyclic compound may have a high efficiency characteristic and when applied to an organic layer of organic light-emitting device, the core may contribute to emit blue light with a high color purity. Thus, an organic light-emitting device that includes a condensed cyclic compound represented by Formula having Formula 1' as the core may have a high efficiency characteristic.

<Formula 1'>

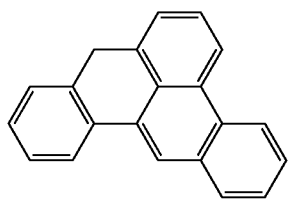

Also, b1 and b2 in Formula 1 are each independently an integer selected from 0 to 4, b3 is an integer selected from 0 to 3, and i) when $X_4$ is $R_4$, b1+b2+b3≥2, and ii) when $X_4$ is -[$(L_4)_{a4}$-N($Ar_7$)($Ar_5$)], b1+b2+b3≥1. Thus, the compound may have an electric characteristic suitable for materials for organic light-emitting device, such as a dopant in an emission layer.

The condensed cyclic compound represented by Formula 1 may be synthesized by using a known organic synthetic method. A synthesis method of the condensed cyclic compound may be obvious to one of ordinary skill in the art in view of the following embodiments.

The condensed cyclic compound represented by Formula 1 may be used between a pair of electrodes of an organic light-emitting device. For example, the condensed cyclic compound may be included an electron transport region, for example, an electron transport layer. Accordingly, an organic light-emitting device In some embodiments includes: a first electrode; a second electrode facing the first electrode; and an organic layer that is disposed between the first electrode and the second electrode and includes an emission layer, wherein the organic layer includes at least one of the condensed cyclic compounds described above.

The expression that "(an organic layer) includes at least one condensed cyclic compounds" used herein may include a case in which "(an organic layer) includes identical condensed cyclic compound represented by Formula 1 and a case in which two or more different condensed cyclic compounds represented by Formula 1.

For example, the organic layer may include, as the condensed cyclic compound, only Compound 1. In this regard, Compound 1 may exist in an emission layer of the organic light-emitting device. In another embodiment, the organic layer may include, as the condensed cyclic compound, Compound 1 and Compound 2. In this regard, Compound 1 and Compound 2 may exist in an identical layer (for example, Compound 1 and Compound 2 may all exist in an emission layer), or different layers (for example, Compound 1 may exist in an emission layer and Compound 2 may exist in an electron transport layer).

The organic layer includes i) a hole transport region that is disposed between the first electrode (anode) and the emission layer and includes at least one of a hole injection layer, a hole transport layer, a buffer layer, and an electron blocking layer, and ii) an electron transport region that is disposed between the emission layer and the second electrode (cathode) and includes at least one selected from a hole blocking layer, an electron transport layer, and an electron injection layer. The emission layer may include the condensed cyclic compound represented by Formula 1.

The term "organic layer" used herein refers to a single layer and/or a plurality of layers disposed between the first electrode and the second electrode of an organic light-emitting device. A material included in the "organic layer" is not limited to an organic material.

FIG. 1 is a schematic view of an organic light-emitting device 10 In some embodiments. The organic light-emitting device 10 includes a first electrode 110, an organic layer 150, and a second electrode 190.

Hereinafter, the structure of an organic light-emitting device according to an embodiment of the present disclosure and a method of manufacturing the same will be described with reference to FIG. 1.

Referring to FIG. 1, a substrate (not shown) may be additionally disposed under the first electrode 110 or above the second electrode 190. The substrate may be a glass substrate or transparent plastic substrate, each with excellent mechanical strength, thermal stability, transparency, surface smoothness, ease of handling, and water resistance.

For example, the first electrode 110 may be formed by depositing or sputtering a material for forming the first electrode on the substrate. When the first electrode 110 is an anode, the material for the first electrode may be selected from materials with a high work function to make holes be easily injected. The first electrode 110 may be a reflective electrode or a transmissive electrode. The material for the first electrode may be a transparent and highly conductive material, and examples of such a material are indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum (Al), aluminum-lithium (Al—Li), calcium (Ca), magnesium-indium (Mg—In), and magnesium-silver (Mg—Ag) may be used.

The first electrode 110 may have a single-layer structure, or a multi-layer structure including two or more layers. For example, the first electrode 110 may have a three-layered structure of ITO/Ag/ITO.

An organic layer 150 is disposed on the first electrode 110. The organic layer 150 may include an emission layer.

The organic layer 150 may further include a hole transport region disposed between the first electrode and the emission layer, and an electron transport region disposed between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL), as examples.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order, but are not limited thereto.

When the hole transport region includes a hole injection layer, the hole injection layer may be formed on the first electrode 110 by using various methods, such as vacuum deposition, spin coating casting, a Langmuir-Blodgett (LB) method, ink-jet printing, laser-printing, or laser-induced thermal imaging.

When a hole injection layer is formed by vacuum deposition, for example, the vacuum deposition may be performed at a temperature of a deposition temperature of about 100 to about 500° C., at a vacuum degree of about $10^{-8}$ to about $10^{-3}$ torr, and at a deposition rate of about 0.01 to about 100 Å/sec in consideration of a compound for a hole injection layer to be deposited, and the structure of a hole injection layer to be formed.

When a hole injection layer is formed by spin coating, the spin coating may be performed at a coating rate of about 2000 rpm to about 5000 rpm, and at a temperature of about 80° C. to 200° C. in consideration of a compound for a hole injection layer to be deposited, and the structure of a hole injection layer to be formed.

When the hole transport region includes a hole transport layer, the hole transport layer may be formed on the first electrode 110 or the hole injection layer by using various methods, such as vacuum deposition, spin coating, casting, a LB method, ink-jet printing, laser-printing, or laser-induced thermal imaging. When the hole transport layer is formed by using vacuum deposition and spin coating, the deposition and coating conditions of the hole transport layer may be understood referring to those of the hole injection layer.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (PANI/CSA), (polyaniline)/poly(4-styrenesulfonate) (Pani/PSS), a compound represented by Formula 201 below, and a compound represented by Formula 202 below:

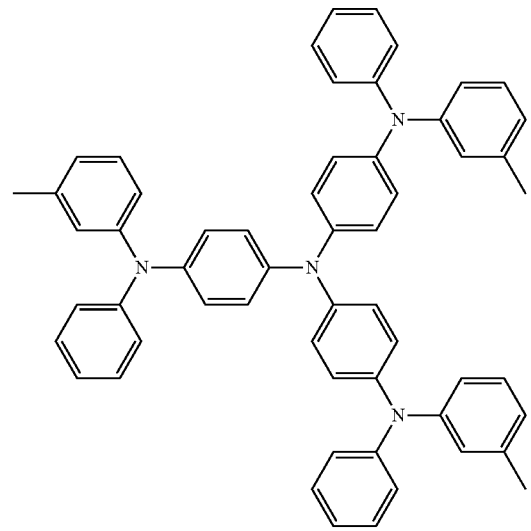

m-MTDATA

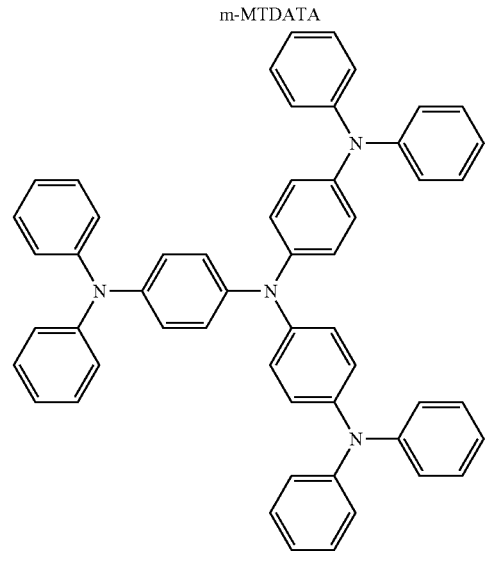

TDATA

-continued
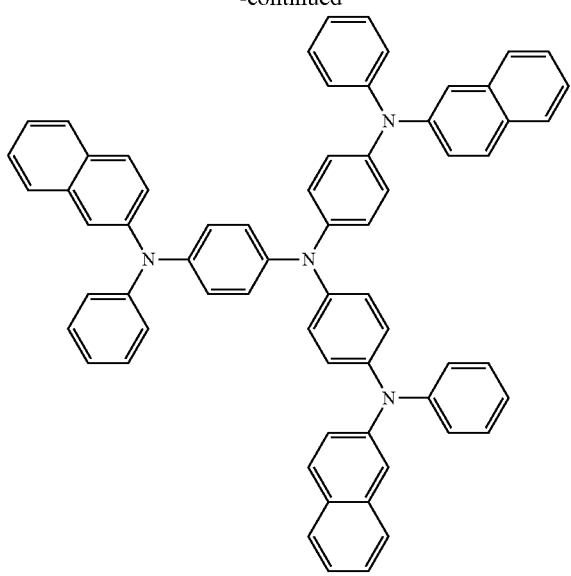
2-TNATA
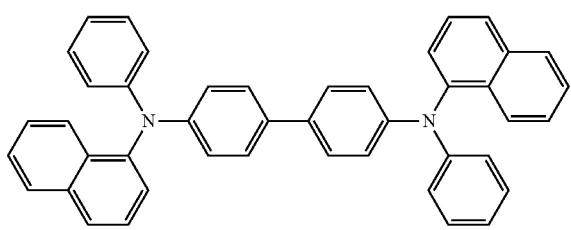
NPB
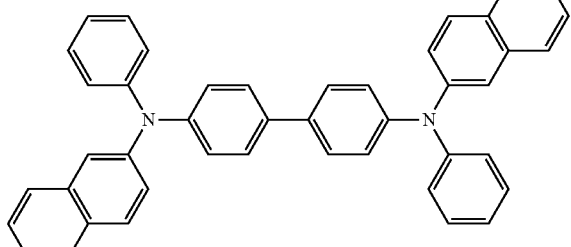
β-NPB
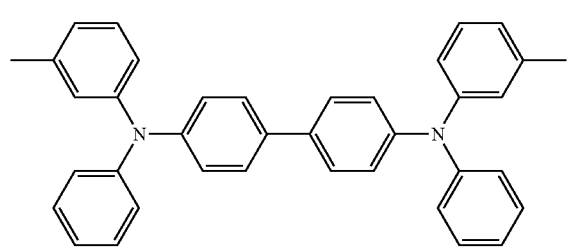
TPD
-continued
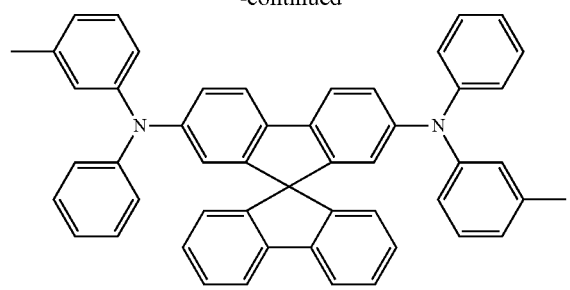
Spiro-TPD
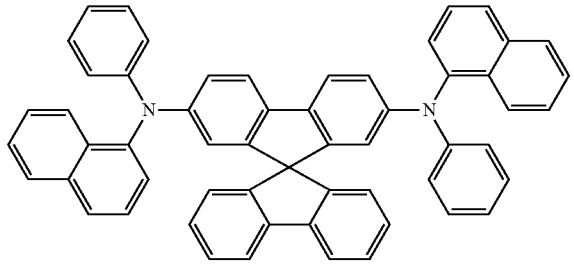
Spiro-NPB
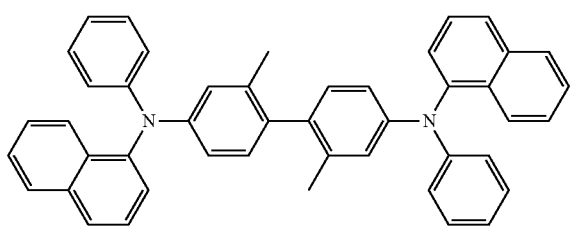
α-NPB
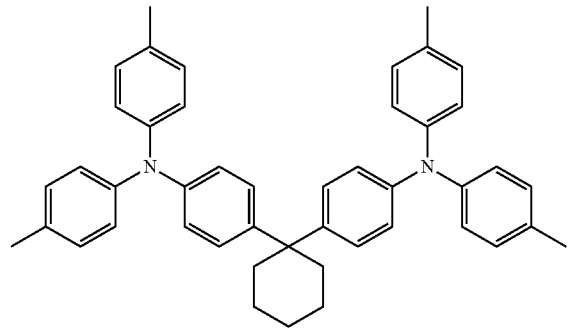
TAPC
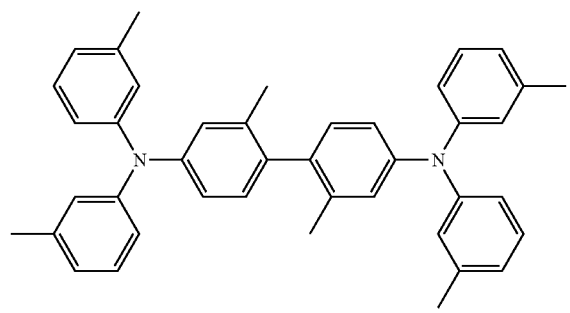
HMTPD
<Formula 201>
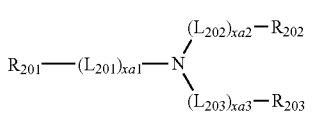

-continued

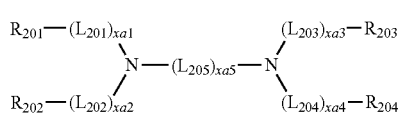
<Formula 202> wherein in Formulae 201 and 202, $L_{201}$ to $L_{205}$ may be understood by each independently referring to the descriptions of $L_1$ to $L_4$ provided herein;

xa1 to xa4 may be each independently selected from 0, 1, 2, and 3;

xa5 may be selected from 1, 2, 3, 4, and 5; and $R_{201}$ to $R_{204}$ are selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group.

wherein in Formulae 201 and 202, $L_{201}$ to $L_{205}$ may be each independently selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

$R_{201}$ to $R_{204}$ are each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, as examples.

The compound represented by Formula 201 may be represented by Formula 201A:

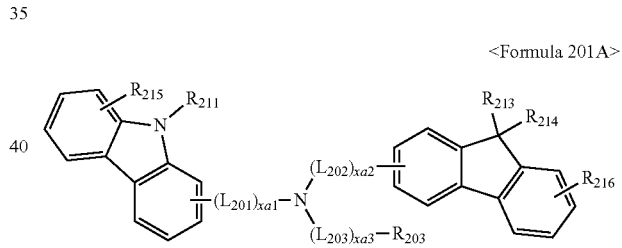
<Formula 201A>

For example, the compound represented by Formula 201 may be represented by Formula 201A-1 below:

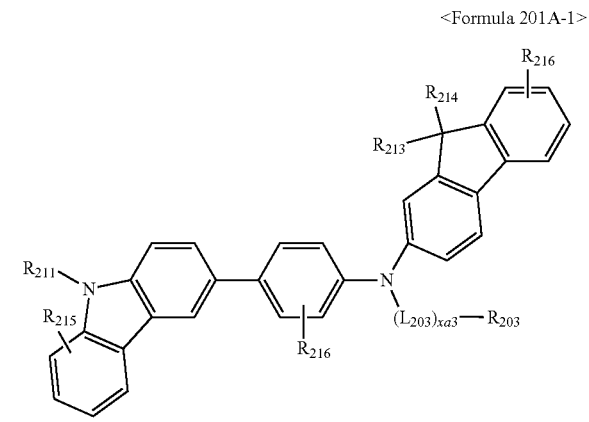
<Formula 201A-1>

For example, the compound represented by Formula 202 may be represented by Formula 202A below:

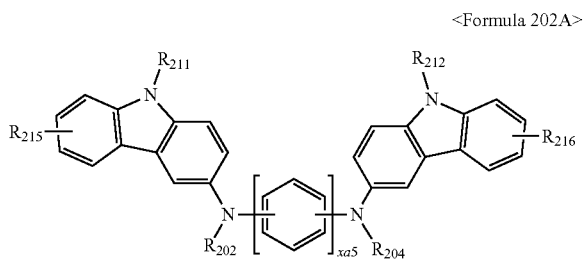

<Formula 202A>

$L_{201}$ to $L_{203}$, xa1 to xa3, xa5 and $R_{202}$ to $R_{204}$ in Formula 201A, 201A-1 and 202A may be understood by referring to the descriptions provided herein whereas $R_{211}$ may be understood by referring to the description of $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

For example, in Formulae 201A, 201A-1, and 202A, $L_{201}$ to $L_{203}$ may be each independently selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$, and $R_{212}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ are each independently selected from
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

$R_{213}$ and $R_{214}$ in Formulae 201A and 201A-1 may bind to each other to form a saturated or unsaturated ring.

The compound represented by Formula 201, and the compound represented by Formula 202 may each be selected from compounds HT1 to HT20 illustrated below, as examples.

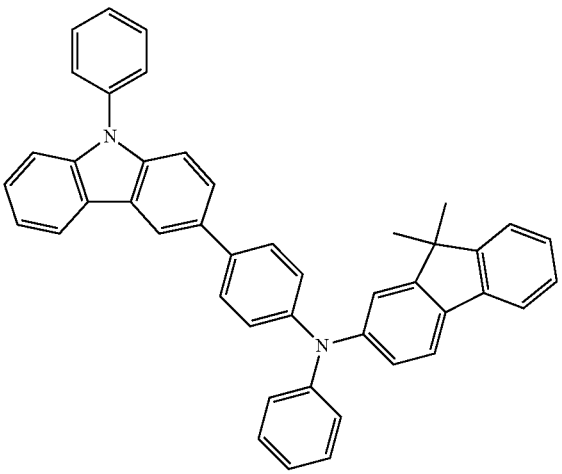

HT1

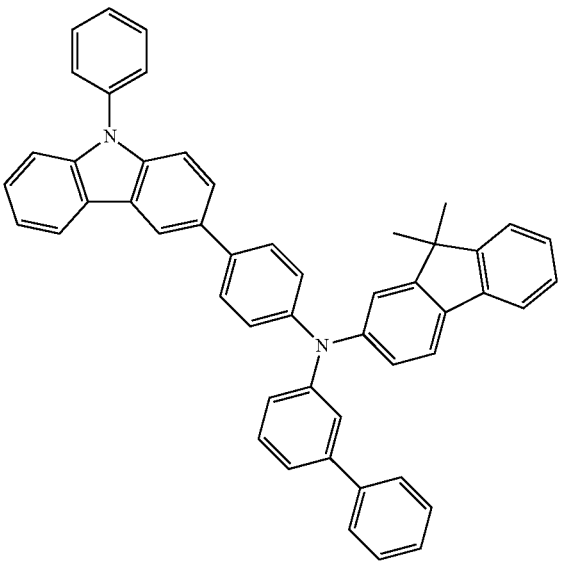

HT2

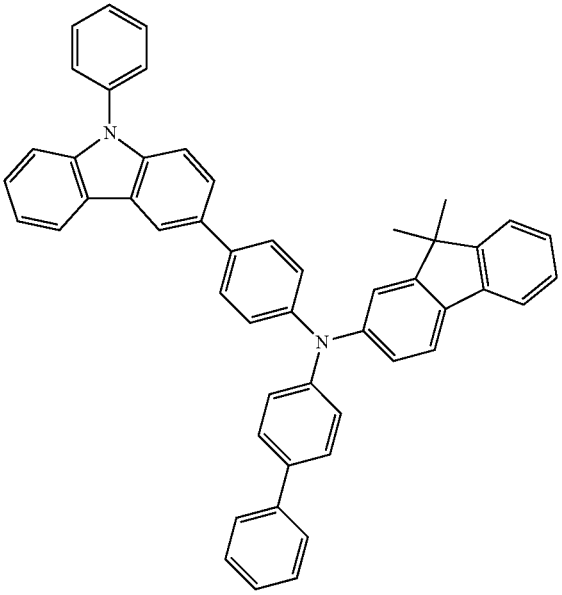

HT3

HT4
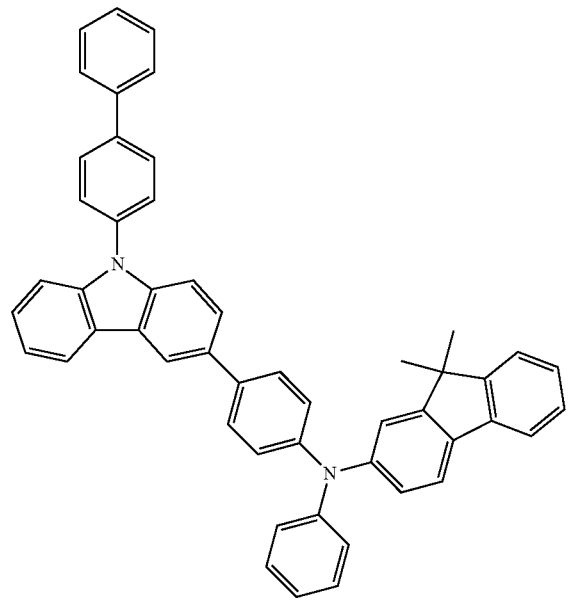
HT6
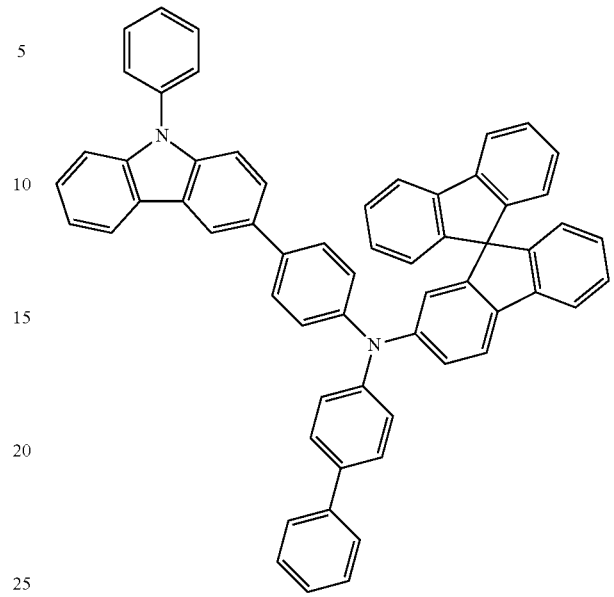
HT5
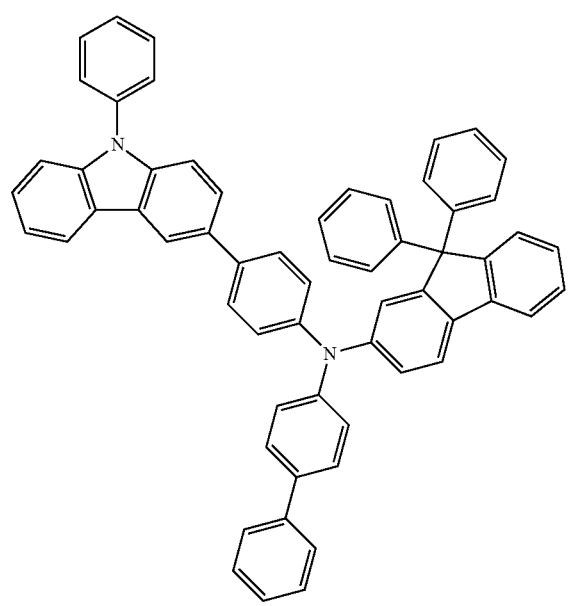
HT7

HT8
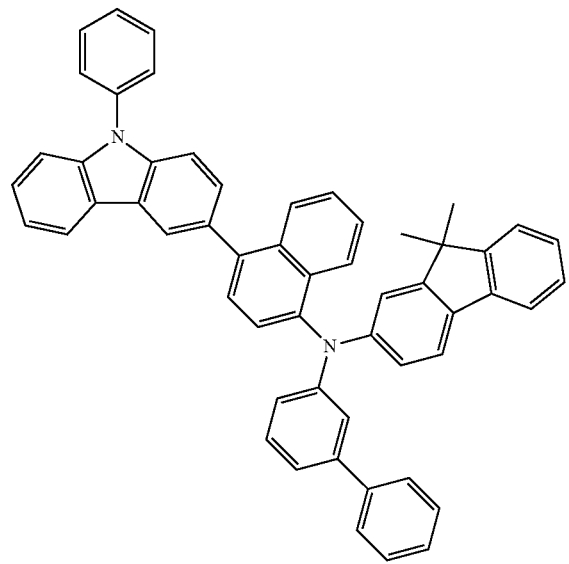
HT10
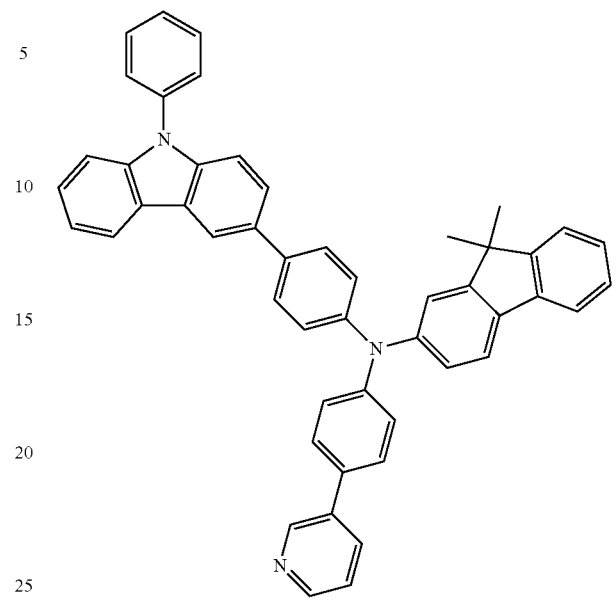
HT9
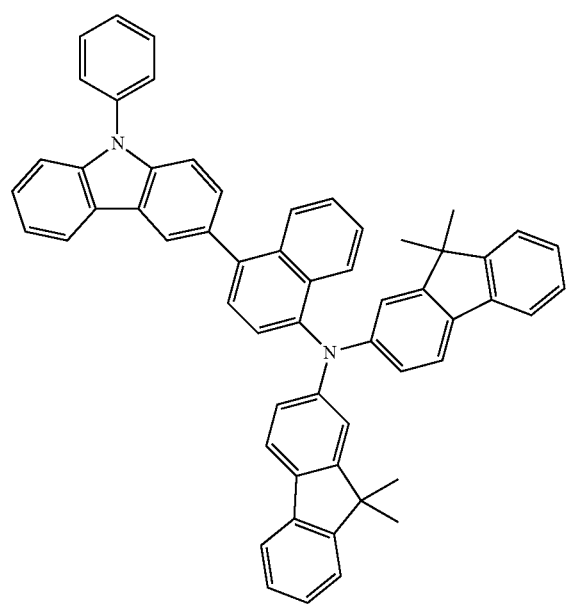
HT11
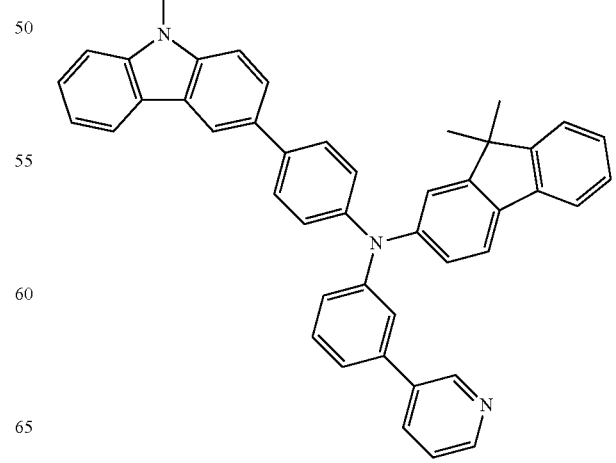

HT12
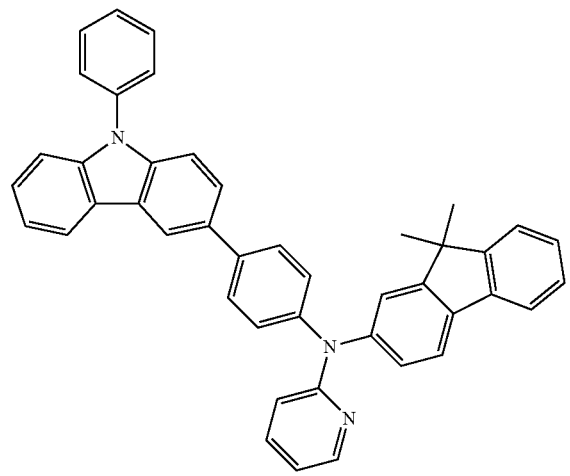
HT13
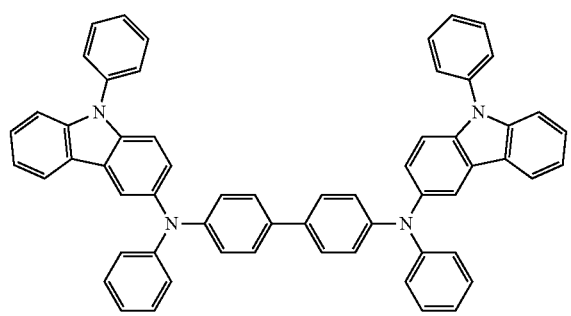
HT14
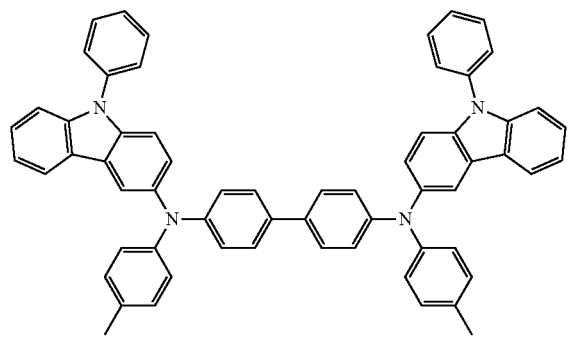
HT15
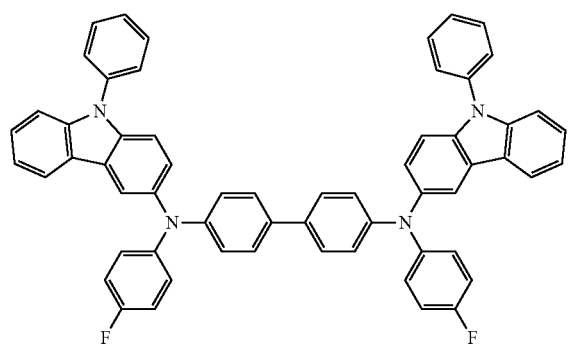
HT16
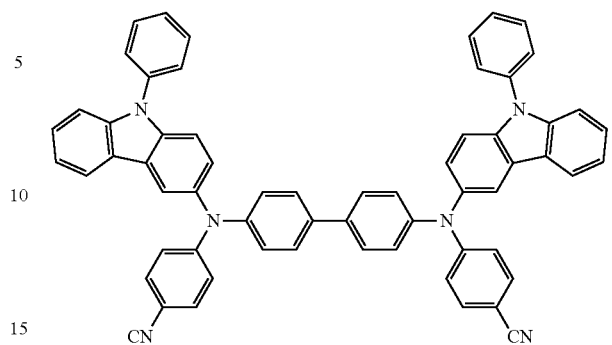
HT17
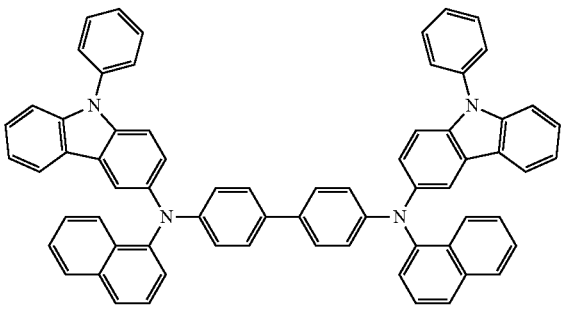
HT18
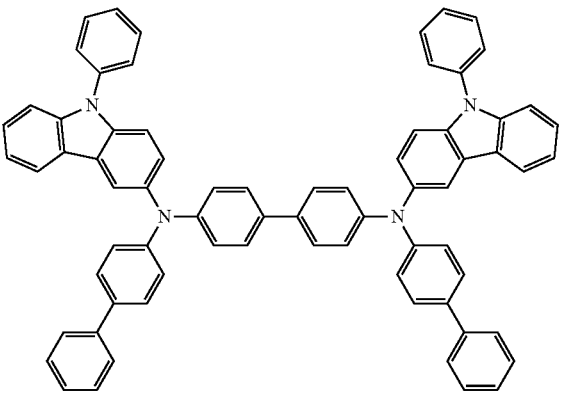
HT19
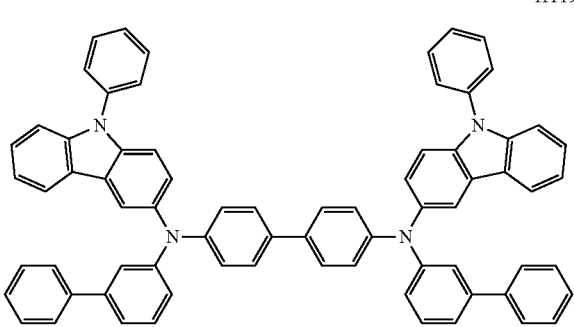

HT20

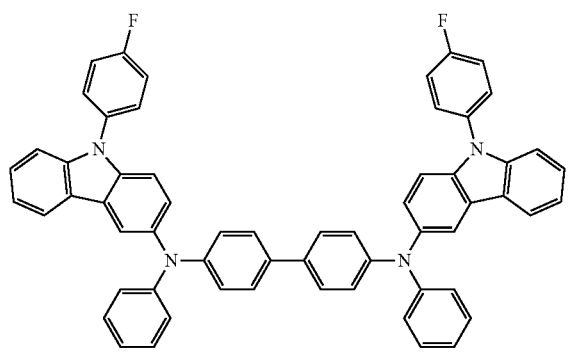

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, as examples. Examples of the p-dopant include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

<Compound HT-D1>

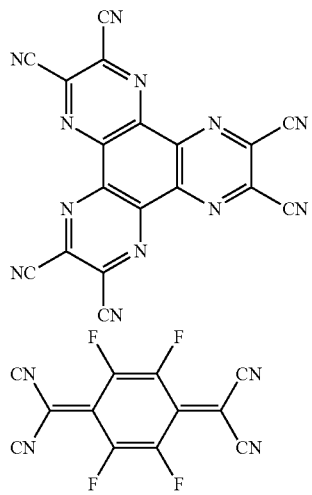

<F4-TCNQ>

The hole transport region may further include, in addition to the hole injection layer and the hole transport layer, at least one of a buffer layer and an electron blocking layer. Since the buffer layer may compensate for an optical resonance distance according to a wavelength of light emitted from the emission layer, light-emission efficiency of a formed organic light-emitting device may be improved. For use as a material included in the buffer layer, materials that are included in the hole transport region may be used. The electron blocking layer prevents injection of electrons from the electron transport region.

An emission layer is formed on the first electrode 110 or the hole transport region by using various methods, such as vacuum deposition, spin coating, casting, a LB method, ink-jet printing, laser-printing, or laser-induced thermal imaging. When the emission layer is formed by vacuum deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In some embodiments, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include the condensed cyclic compound represented by Formula 1.

The emission layer may include a host and a dopant. Here, the dopant may include the condensed cyclic compound represented by Formula 1.

The host may include at least one selected from TPBi, TBADN, AND (also referred to as "DNA"), CBP, CDBP, and TCP:

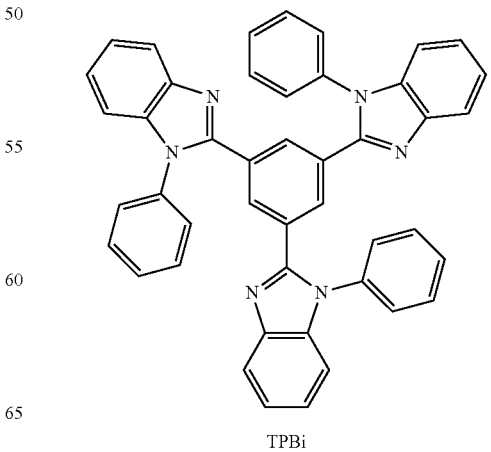

TPBi

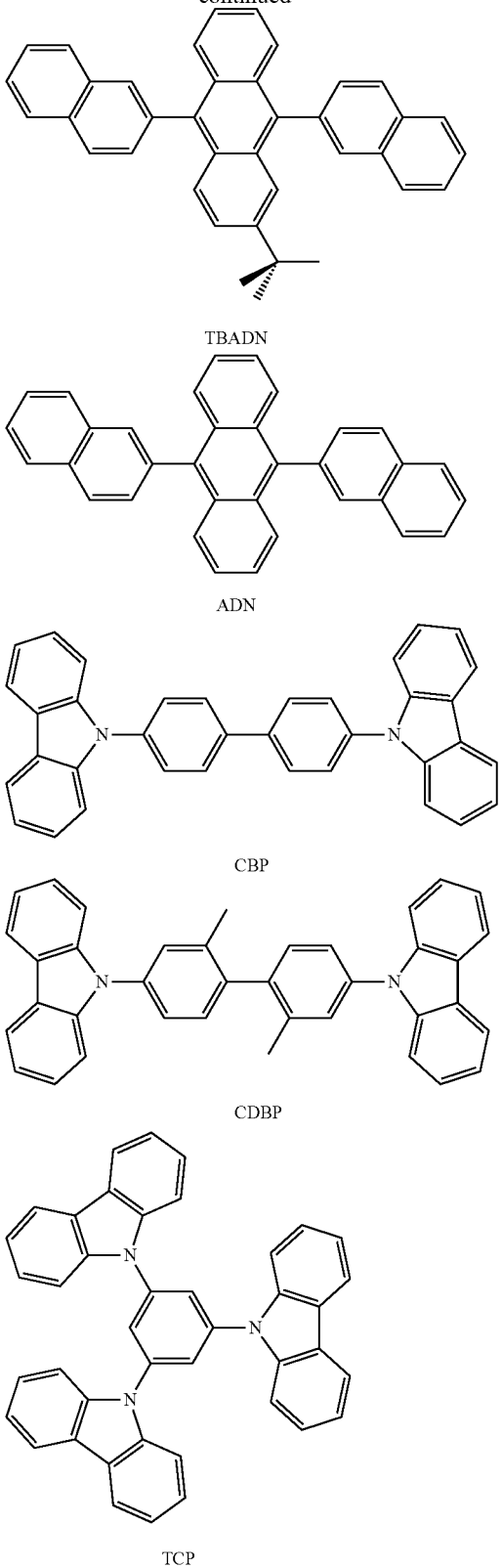

TBADN

ADN

CBP

CDBP

TCP

According to another embodiment, the host may include a compound represented by Formula 301 below.

$Ar_{301}\text{-}[(L_{301})_{xb1}\text{-}R_{301}]_{xb2}$ <Formula 301> wherein in Formula 301, $Ar_{301}$ may be selected from

A naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, aheptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$heterocycloalkenyl group, a C6-C60 aryl group, a C6-C60 aryloxy group, a C6-C60 arylthio group, a $C2$-$C_{60}$ heteroaryl group, a monovalent non-aromatic condensed polycyclic group, a monovalent non-aromatic condensed heteropolycyclic group, and —Si$(Q_{301})(Q_{302})(Q_{303})$ ($Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group;

$L_{301}$ may be understood by referring to the description provided in connection with $L_{201}$;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

xb1 may be selected from 0, 1, 2, and 3; and
xb2 may be selected from 1, 2, 3, and 4.
wherein in Formula 301,
$L_{301}$ may be selected from
a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl, as examples.

For example, the host may include a compound represented by Formula 301A below:

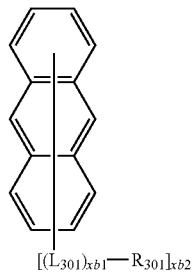

<Formula 301A>

Substituents of Formula 301A may be understood by corresponding descriptions provided herein.

The compound represented by Formula 301 may include at least one of Compounds H1 to H42, as examples:

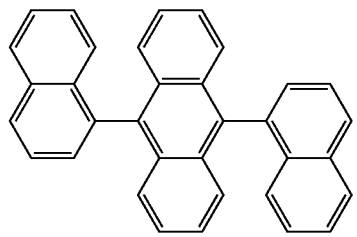

H1

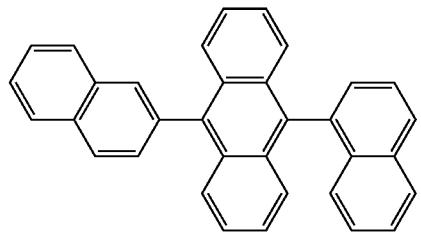

H2

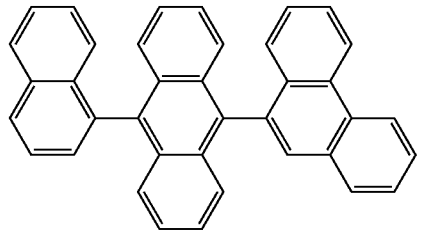

H3

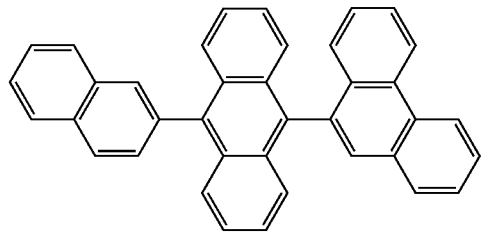

H4

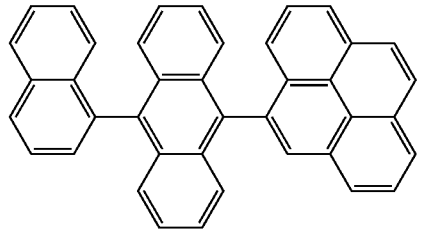

H5

-continued
H6
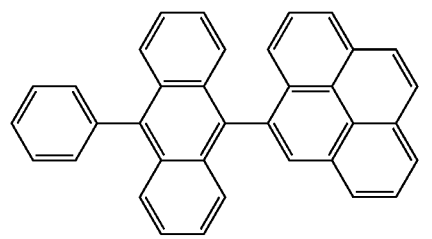
H7
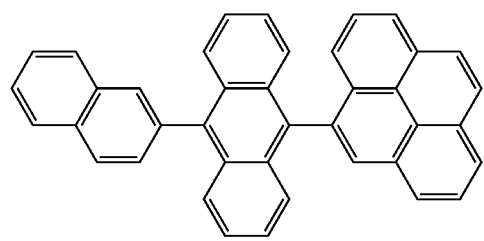
H8
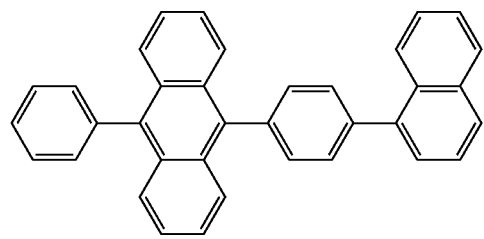
H9
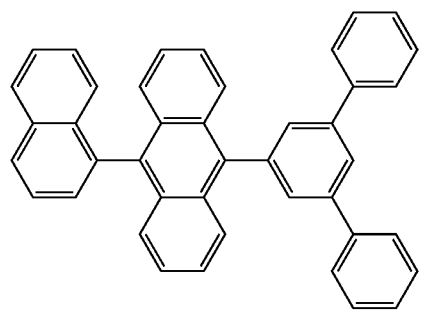
H10
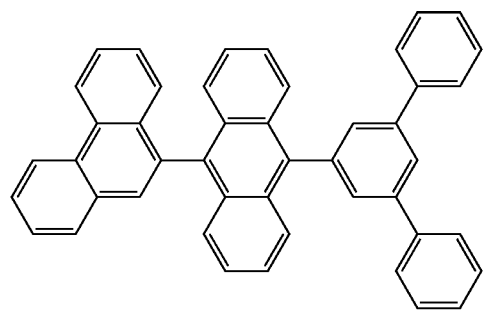
H11
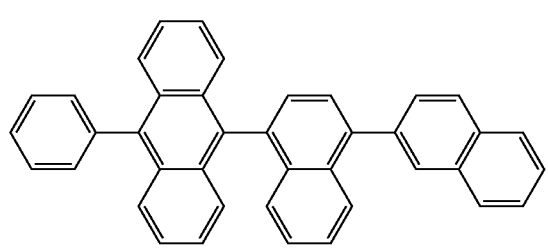
-continued
H12
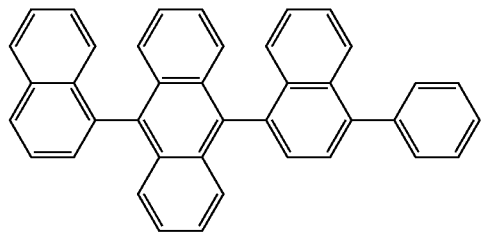
H13
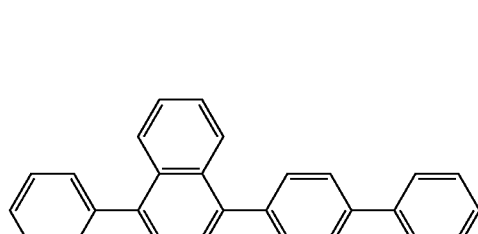
H14
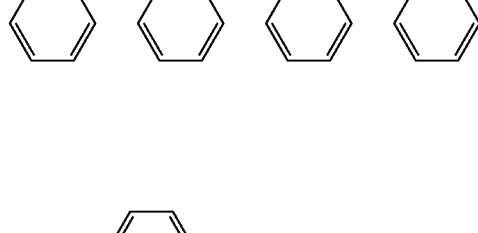
H15
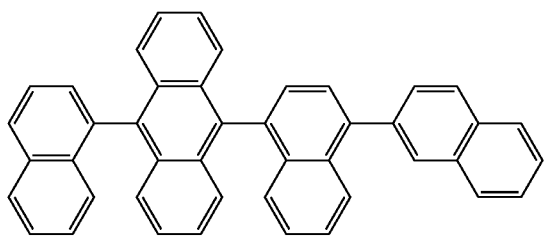
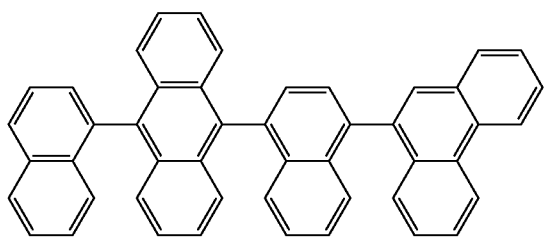
H16
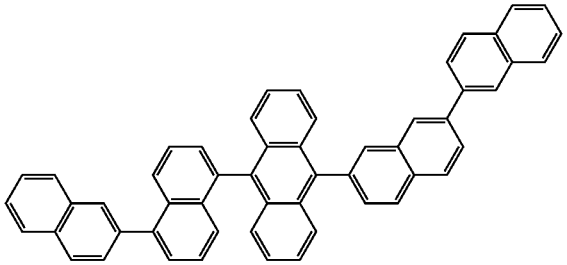

203
-continued
H17
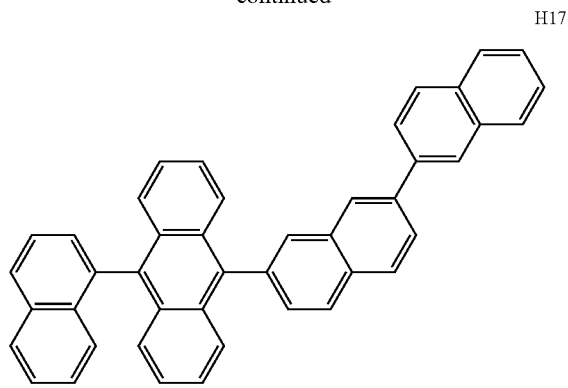
H18
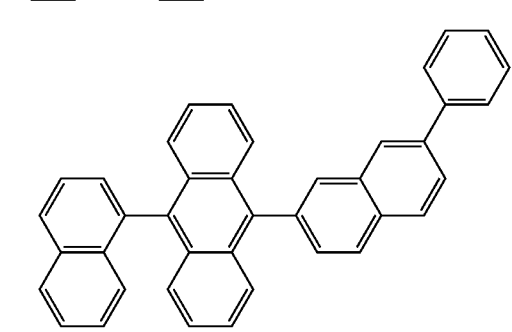
H19
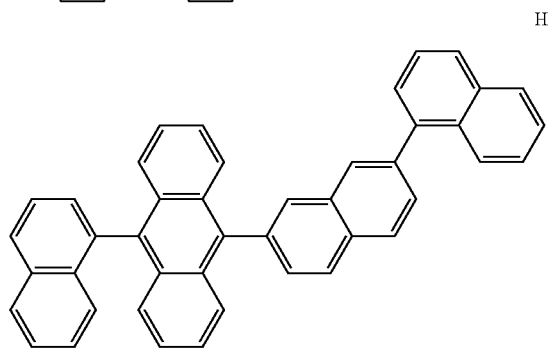
H20
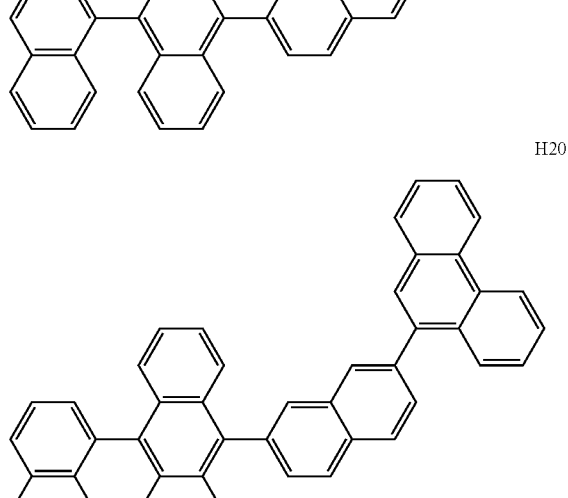
H21
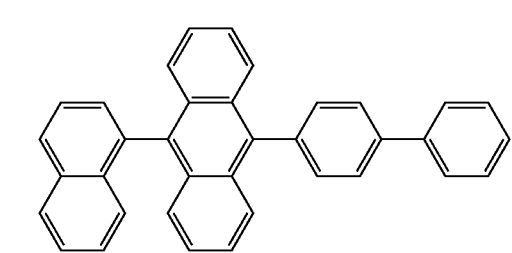
204
-continued
H22
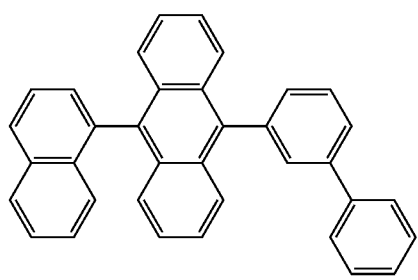
H23
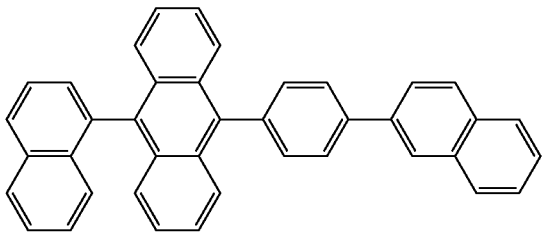
H24
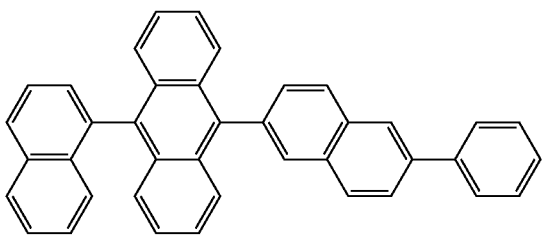
H25
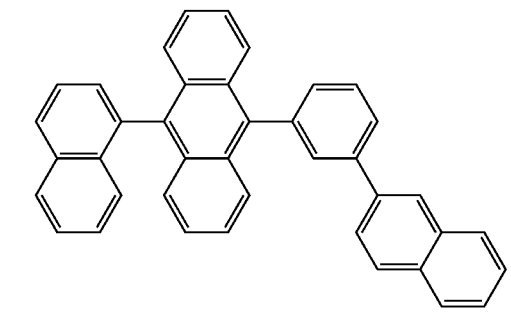
H26
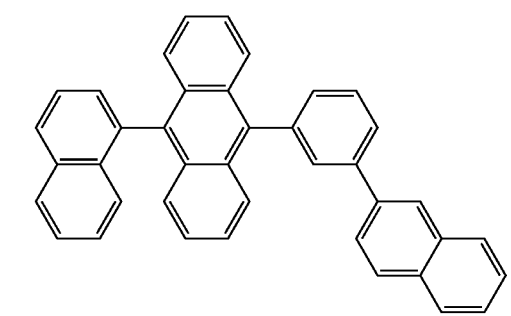

205
-continued
H27
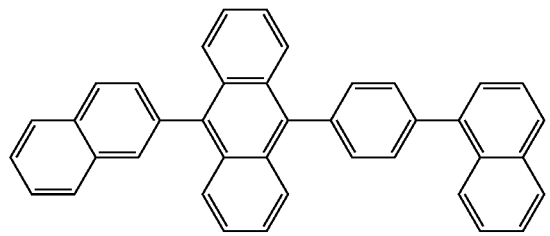
H28
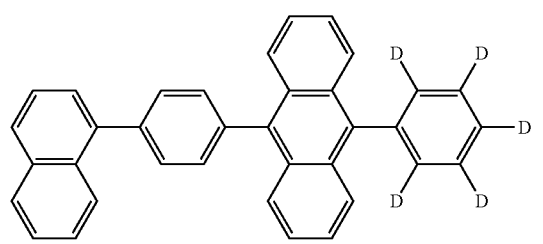
H29
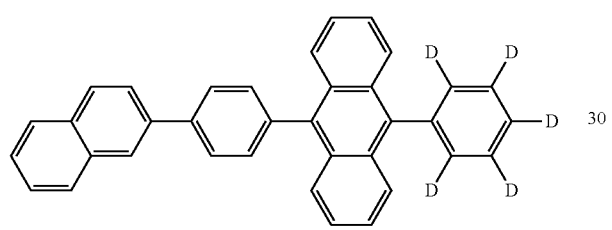
H30
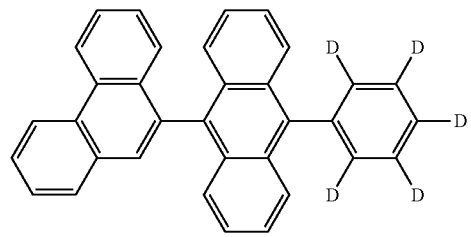
H31
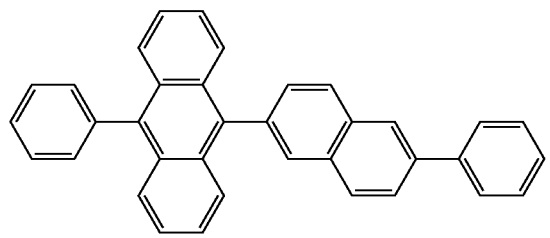
H32
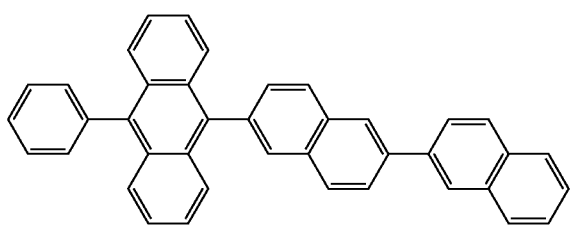
206
-continued
H33
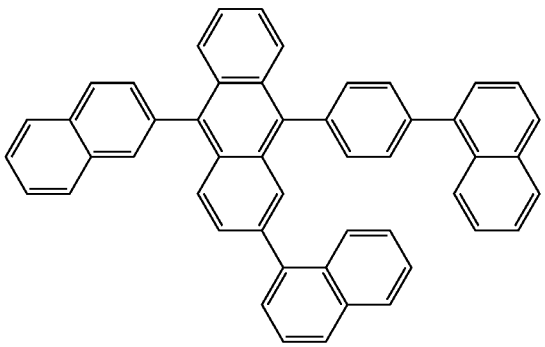
H34
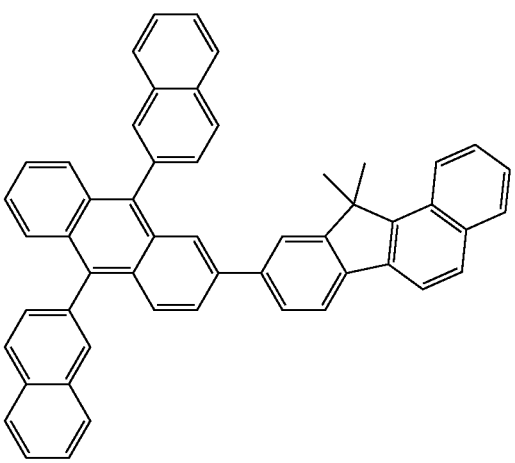
H35
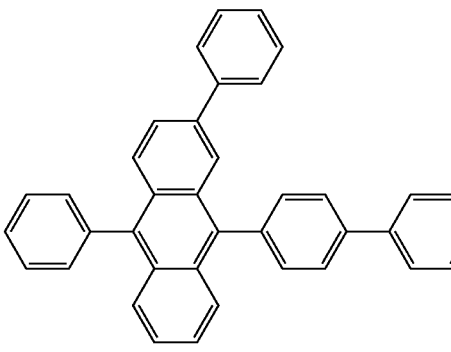

207
-continued
H36
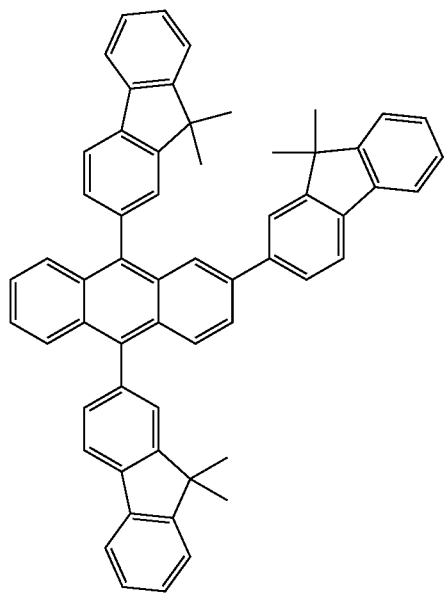
H37
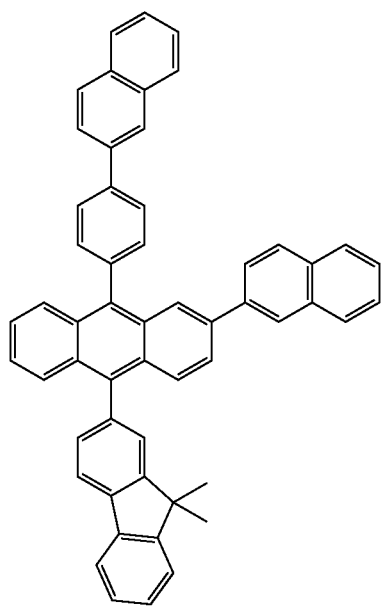
H38
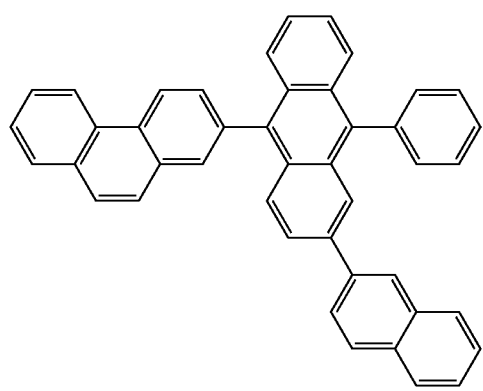
208
-continued
H39
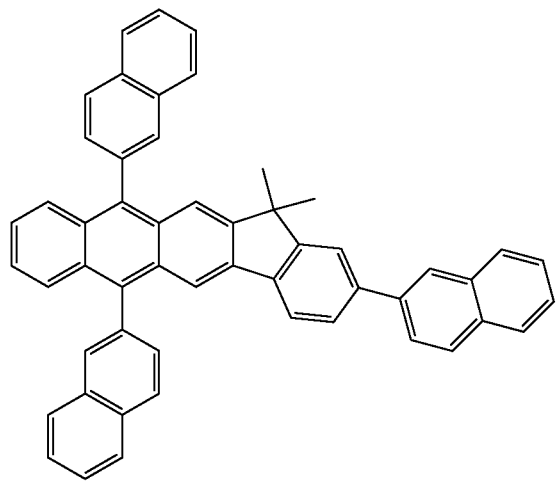
H40
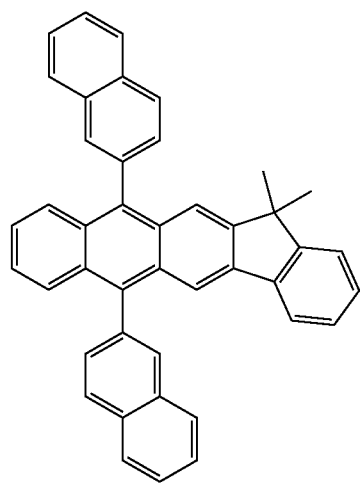
H41
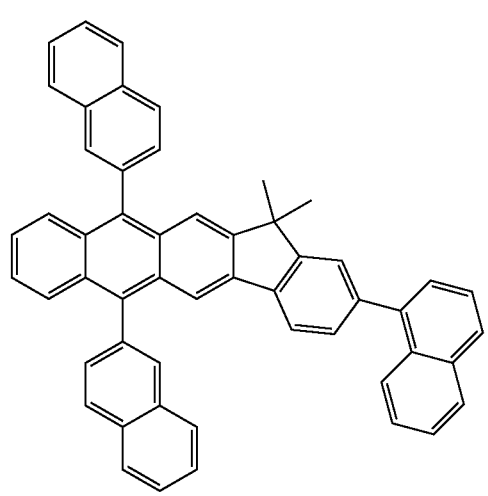

H42
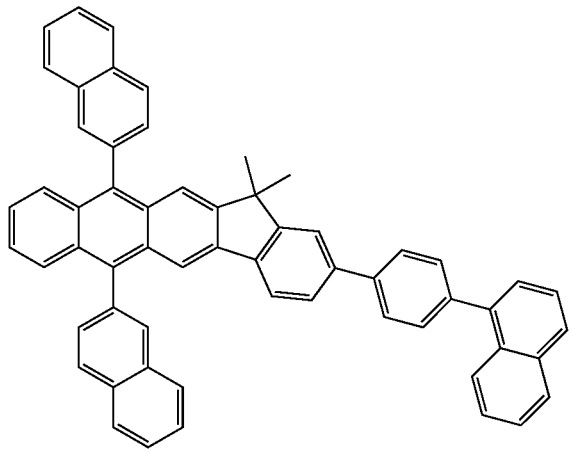
According to another embodiment, the host may include at least one of Compounds H43 to H49 below, as examples:
H43
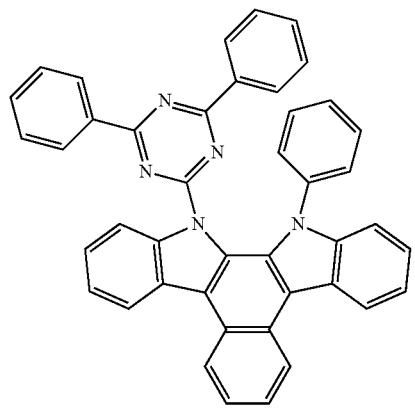
H44
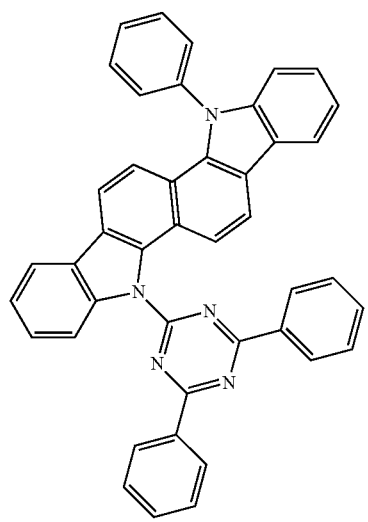
H45
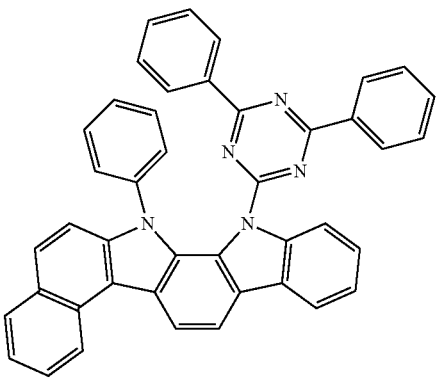
H46
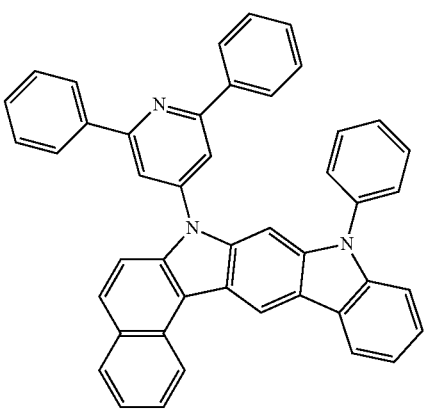
H47
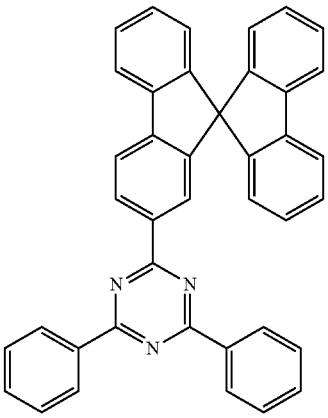
H48
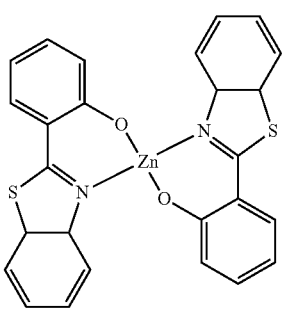

H49

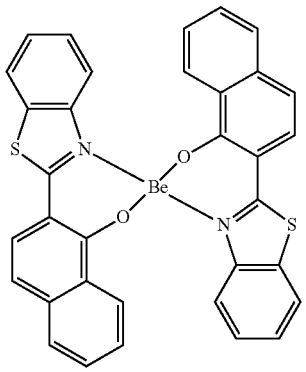

The dopant may be at least one selected from a fluorescent dopant and a phosphorescent dopant. When the dopant includes a fluorescent dopant, the fluorescent dopant may include the condensed cyclic compound represented by Formula 1.

The phosphorescent dopant may include an organometallic complex represented by Formula 401 below:

<Formula 401>

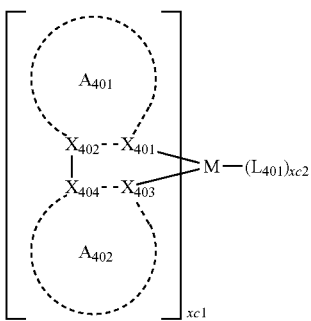

wherein in Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently nitrogen or carbon;

$A_{401}$ and $A_{402}$ rings may be each independently selected from a substituted or unsubstituted benzene, a substituted or unsubstituted naphthalene, a substituted or unsubstituted fluorenene, a substituted or unsubstituted spiro-fluorenene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazol, a substituted or unsubstituted benzoimidazole, a substituted or unsubstituted benzofuran, a substituted or unsubstituted benzothiophene, a substituted or unsubstituted isobenzothiophene, a substituted or unsubstituted benzooxazole, a substituted or unsubstituted isobenzooxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and a substituent of at least one selected from the substituted benzene, substituted naphthalene, substituted fluorenene, substituted spiro-fluorenene, substituted indene, substituted pyrrol, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazol, substituted benzoimidazole, substituted benzofuran, substituted benzothiophene, substituted isobenzothiophene, substituted benzooxazole, substituted isobenzooxazole, substituted triazole, substituted oxadiazole, substituted triazine, substituted dibenzofuran, and substituted dibenzothiophene may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{401}$)($Q_{402}$), —Si($Q_{403}$)($Q_{404}$)($Q_{405}$), or —B($Q_{406}$)($Q_{407}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, $-N(Q_{411})(Q_{412})$, $-Si(Q_{413})(Q_{414})(Q_{415})$, and $-B(Q_{416})(Q_{417})$; and $-N(Q_{421})(Q_{422})$, $-Si(Q_{423})(Q_{424})(Q_{425})$, and $-B(Q_{426})(Q_{427})$; and $L_{401}$ may be an organic ligand;
xc1 may be 1, 2, or 3; and
xc2 may be 0, 1, 2, or 3.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptandionate, or hexafluoroacetonate), a carboxylic acid ligand (for example, picolinate, dimethyl-3-pyrazolecarboxylate, or benzoate), a carbon monooxide ligand, an isonitrile ligand, a cyano ligand, and a phosphorous ligand (for example, phosphine, and phosphite), as examples.

When $A_{401}$ in Formula 401 has two or more substituents, the substituents of $A_{402}$ may bind to each other to form a saturated or unsaturated ring.

When $A_{402}$ in Formula 402 has two or more substituents, the substituents of $A_{402}$ may bind to each other to form a saturated or unsaturated ring.

When xc1 in Formula 401 is two or more, a plurality of ligands

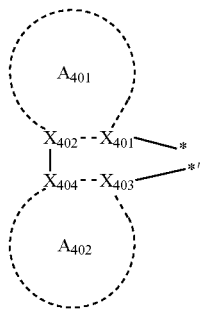

in Formula 401 may be identical or different. When xc1 in Formula 401 is two or more, $A_{401}$ and $A_{402}$ may directly link to $A_{401}$ and $A_{402}$ of a different neighboring ligand or may link to $A_{401}$ and $A_{402}$ of a different neighboring ligand via a linking group (e.g. a $C_1$-$C_5$ alkylene group, $-N(R')-$ (here, R' is a $C_1$-$C_{10}$ alkyl group or a $C_6$-$C_{20}$ aryl group) or $-C(=O)-$) therebetween.

The fluorescent dopant may include at least one selected from DPAVBi, BDAVBi, TBPe, DCM, DCJTB, Coumarin 6, and C545T, each illustrated below, in addition to the condensed cyclic compound represented by Formula 1.

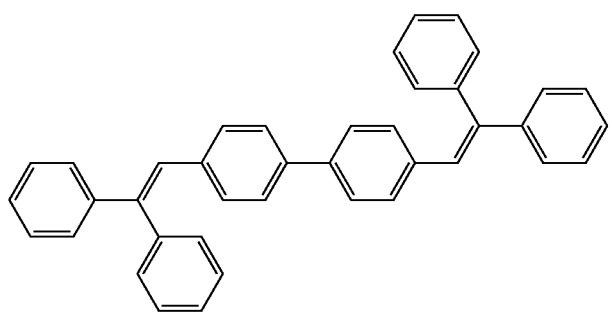

DPVBi

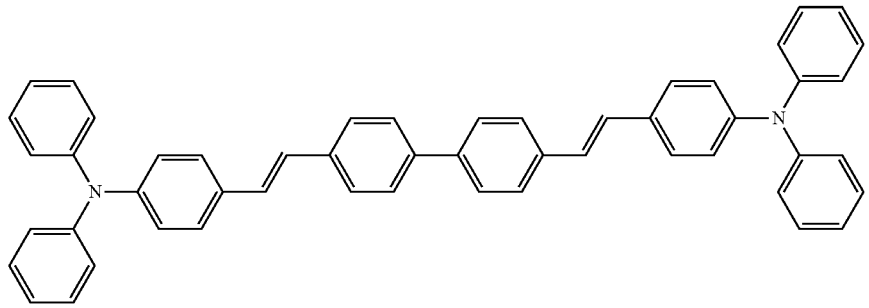

DPAVBi

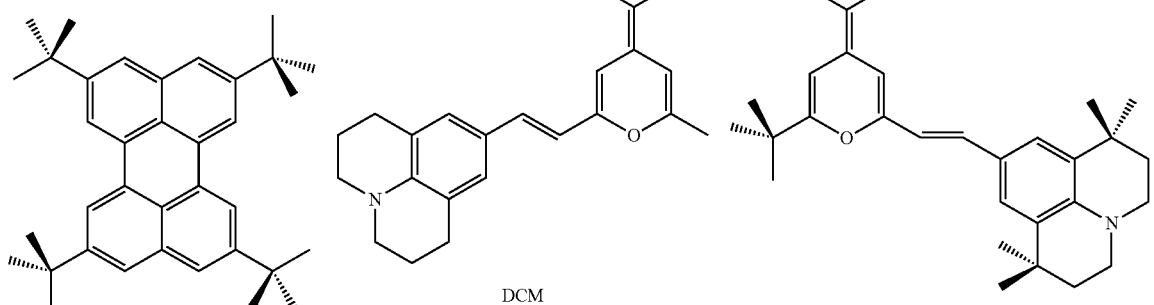

TBPe          DCM          DCJTB

Coumarin 6

C545T

An amount of the dopant in the emission layer may be, for example, in a range of about 0.01 to about 15 parts by weight based on 100 parts by weight of the host.

A thickness of the emission layer may be in a range of about 100 Å to about 1000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include, for example, at least one selected from a hole blocking layer, an electron transport layer (ETL), and an electron injection layer.

For example, the electron transport region may have a structure of electron transport layer/electron injection layer or a structure of hole blocking layer/electron transport layer/electron injection layer, wherein layers of each structure are sequentially stacked from the emission layer in the stated order.

According to an embodiment, the organic layer 150 of the organic light-emitting device includes an electron transport region disposed between the emission layer and the second electrode 190, wherein the electron transport region includes the condensed cyclic compound represented by Formula 1.

The electron transport region may include a hole blocking layer. The hole blocking layer may be formed, when the emission layer includes a phosphorescent dopant, to prevent diffusion of excitons or holes into an electron transport layer.

When the electron transport region includes a hole blocking layer, the hole blocking layer may be formed on the emission layer by using various methods, such as vacuum deposition, spin coating casting, a LB method, ink-jet printing, laser-printing, or laser-induced thermal imaging. When the hole blocking layer is formed by vacuum deposition or spin coating, deposition and coating conditions for the hole blocking layer may be determined by referring to the deposition and coating conditions for the hole injection layer.

The hole blocking layer may include, for example, at least one of BCP and Bphen.

BCP

Bphen

A thickness of the hole blocking layer may be in a range of about 20 Å to about 1000 Å, for example, about 30 Å to about 300 Å. When the thickness of the hole blocking layer is within these ranges, the hole blocking layer may have improved hole blocking ability without a substantial increase in driving voltage.

The electron transport region may include an electron transport layer. The electron transport layer may be formed on the emission layer or the hole blocking layer by using various methods, such as vacuum deposition, spin coating casting, a LB method, ink-jet printing, laser-printing, or laser-induced thermal imaging. When an electron transport layer is formed by vacuum deposition or spin coating, deposition and coating conditions for the electron transport layer may be determined by referring to the deposition and coating conditions for the hole injection layer.

According to an embodiment, the organic layer 150 of the organic light-emitting device may include an electron transport region disposed between the emission layer and the second electrode 190. The electron transport region may include at least one selected from an electron transport layer and an electron injection layer.

The electron transport layer may further include at least one selected from BCP, Alq$_3$

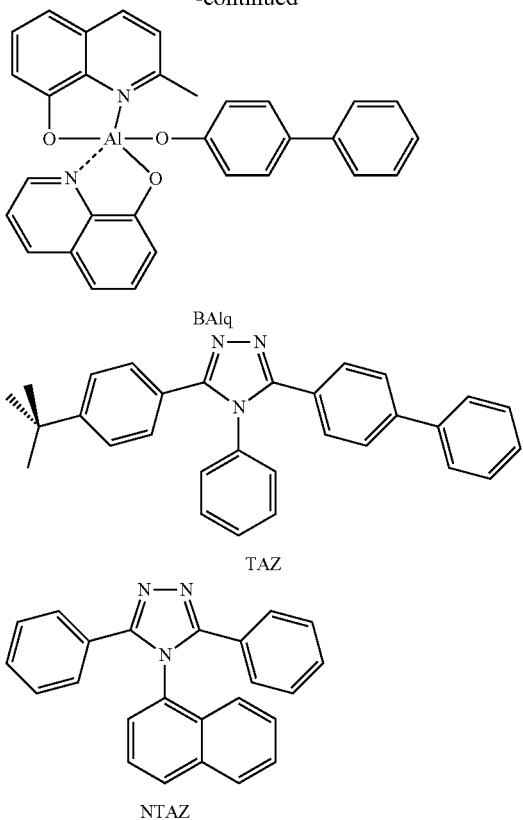

BAlq

TAZ

NTAZ

According to another embodiment, the electron transport layer may include at least one compound selected from a compound represented by Formula 601 and a compound represented by Formula 602 illustrated below:

$$Ar_{601}-[(L_{601})_{xe1}-E_{601}]_{xe2}$$  <Formula 601> wherein in Formula 601, $Ar_{601}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, aheptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group and —Si($Q_{301}$)($Q_{302}$)($Q_{303}$) ($Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group;

$L_{601}$ may be understood by referring to the description provided in connection with $L_{201}$;

$E_{601}$ may be selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and xe2 may be selected from 1, 2, 3, and 4.

<Formula 602>

$$R_{616}-(L_{616})_{xe616}-\underset{\underset{X_{612}}{\overset{X_{611}}{\vert}}}{\overset{(L_{614})_{xe614}-R_{614}}{\vert}}\overset{X_{613}}{\underset{(L_{615})_{xe615}-R_{615}}{}}$$

wherein in Formula 602, $X_{611}$ is N or C-$(L_{611})_{xe611}$-$R_{611}$, $X_{612}$ is N or C-$(L_{612})_{xe612}$-$R_{612}$, $X_{613}$ is N or C-$(L_{613})_{xe613}$-$R_{613}$ and, at least one of $X_{611}$ to $X_{613}$ is N;

$L_{611}$ to $L_{616}$ may be understood by referring to the description provided herein in connection with $L_{201}$;

$R_{611}$ to $R_{616}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xe611 to xe616 may be each independently selected from 0, 1, 2, and 3.

The compound represented by Formula 601 and the compound represented by Formula 602 may each be selected from Compounds ET1 to ET15 illustrated below.

ET1
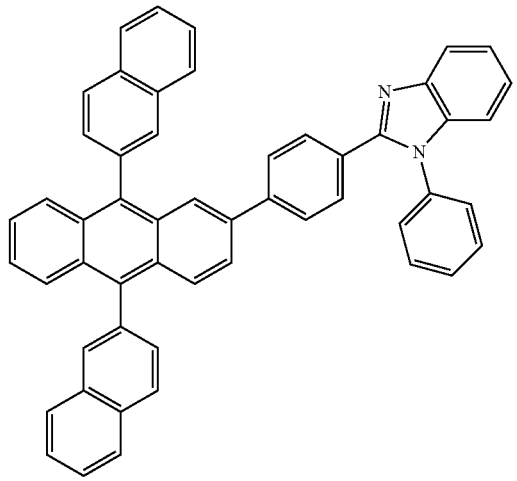

ET2
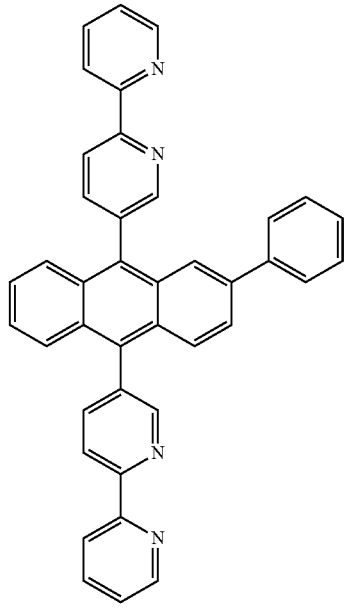

ET3
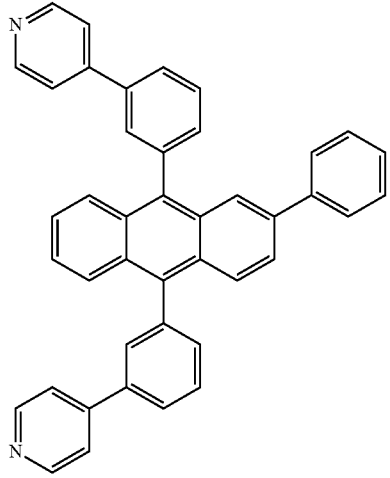

221
-continued
222
-continued
ET4
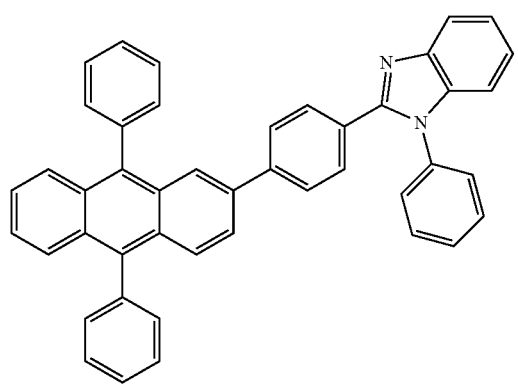
ET7
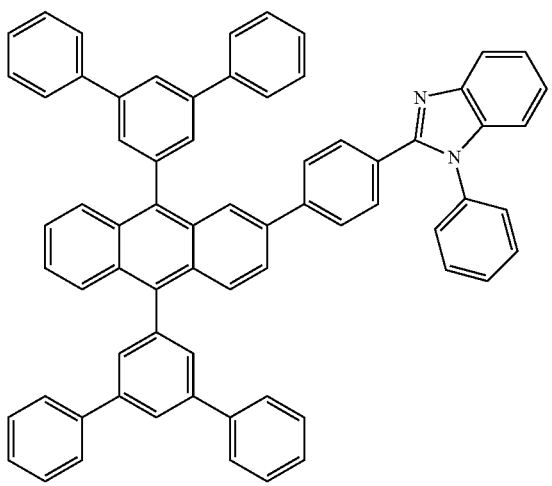
ET5
ET8
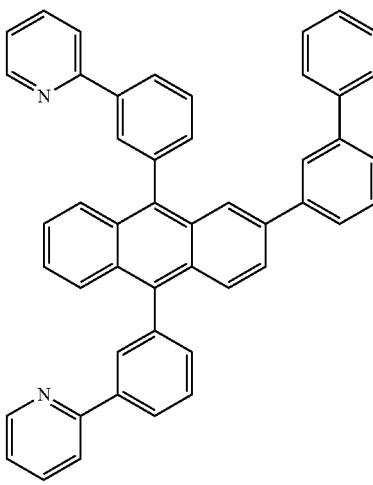
ET6
ET9
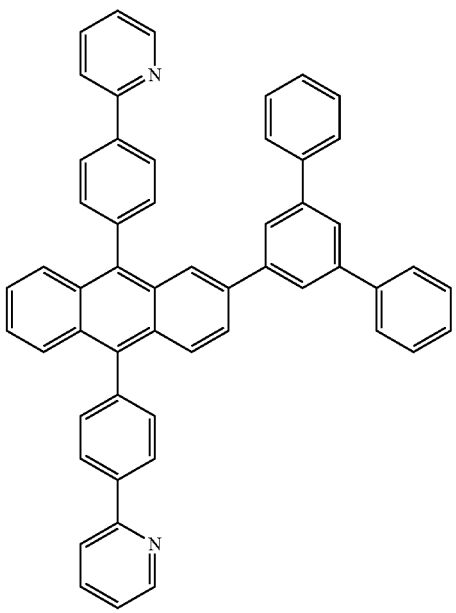

ET10
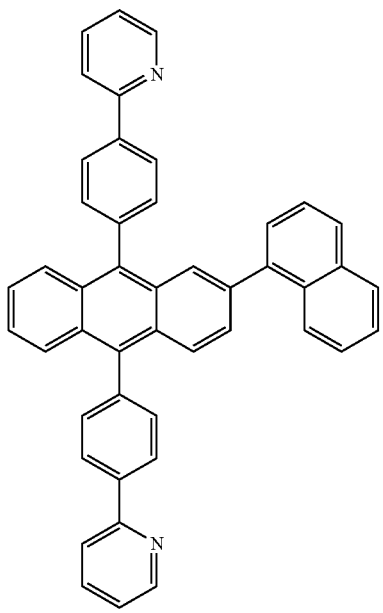

ET11
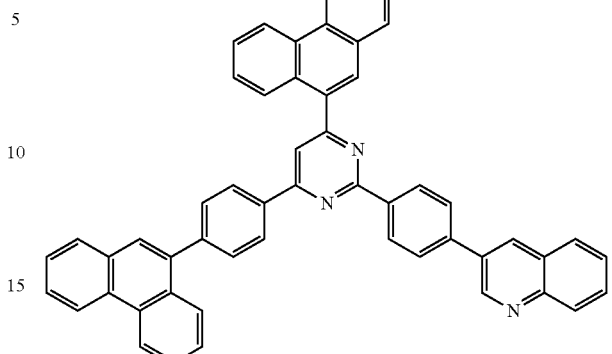

ET12
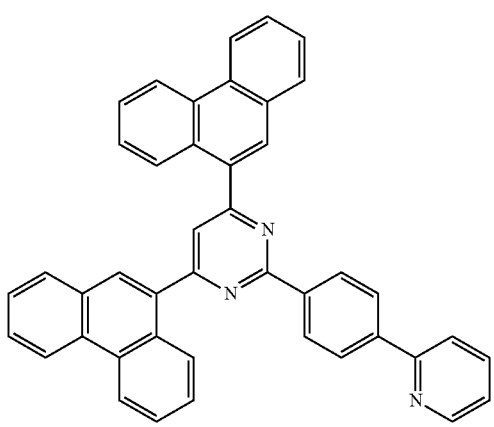

ET13
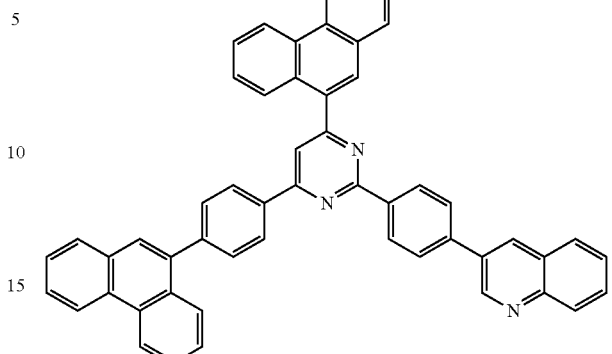

ET14
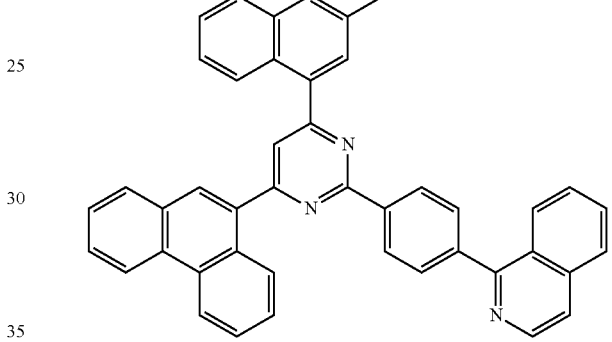

ET15
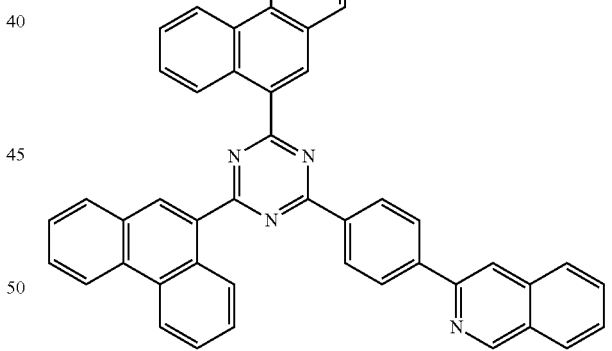

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

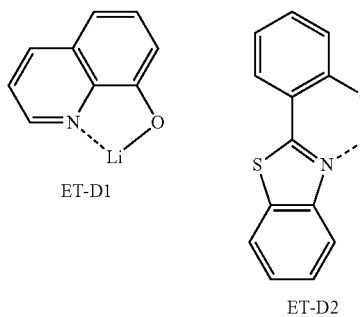

ET-D1

ET-D2

The electron transport region may include an electron injection layer that allows electrons to be easily provided from the second electrode 190.

The electron injection layer may be formed on the electron transport layer by using various methods, such as vacuum deposition, spin coating casting, a LB method, ink-jet printing, laser-printing, or laser-induced thermal imaging. When an electron injection layer is formed by vacuum deposition or spin coating, deposition and coating conditions for the electron injection layer may be determined by referring to the deposition and coating conditions for the hole injection layer.

The electron injection layer may include at least one selected from, LiF, NaCl, CsF, $Li_2O$, BaO, and LiQ.

A thickness of the electron injection layer may be in a range of about 1 Å to about 100 Å, about 3 Å to about 90 Å. When the thickness of the electron injection layer is within the range described above, the electron injection layer may have satisfactory electron injection characteristics without a substantial increase in driving voltage.

The second electrode 190 is disposed on the organic layer 150 having such a structure. The second electrode 190 may be a cathode that is an electron injection electrode, and in this regard, a material for forming the second electrode 190 may be a material having a low work function, and such a material may be metal, alloy, an electrically conductive compound, or a mixture thereof. Detailed examples of the second electrode 190 are lithium ($Li$), magnesium (Mg), aluminum (Al), aluminum-lithium (Al—Li), calcium (Ca), magnesium-indium (Mg—In), or magnesium-silver (Mg—Ag). According to another embodiment, the material for forming the second electrode 190 may be ITO or IZO. The second electrode 190 may be a reflective electrode, a semi-transmissive electrode, or a transmissive electrode.

Hereinbefore, the organic light-emitting device has been described with reference to FIG. 1, but in other implementations, other suitable configurations may be provided.

A $C_1$-$C_{60}$ alkyl group used herein refers to a linear or branched aliphatic hydrocarbon monovalent group having 1 to 60 carbon atoms, and detailed examples thereof are a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as a $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or terminal of the $C_2$-$C_{60}$ alkyl group.

Detailed examples thereof include an ethenyl group, a propenyl group, and a butenyl group. A $C_2$-$C_{60}$ alkenylene group used herein refers to a divalent group having the same structure as a $C_2$-$C_{60}$ alkenyl group.

A $C_2$-$C_{60}$ alkynyl group used herein refers to a hydrocarbon group formed by substituting at least one carbon trip bond in the middle or terminal of the $C_2$-$C_{60}$ alkyl group, and detailed examples thereof are an ethynyl group, and a propynyl group. A $C_2$-$C_{60}$ alkynylene group used herein refers to a divalent group having the same structure as a $C_2$-$C_{60}$ alkynyl group.

A $C_3$-$C_{10}$ cycloalkyl group used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as a $C_3$-$C_{10}$ cycloalkyl group.

A $C_2$-$C_{10}$ heterocycloalkyl group used herein refers to a monovalent monocyclic group having at least one hetero atom selected from N, O, P, and S as a ring-forming atom and 2 to 10 carbon atoms, and detailed examples thereof are a tetrahydrofuranyl group, and a tetrahydrothiophenyl group. A $C_2$-$C_{10}$ heterocycloalkylene group used herein refers to a divalent group having the same structure as a $C_2$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity, and detailed examples thereof are a cyclopentenyl group, a cyclohexenyl group, and a cycloheptenyl group. A $C_3$-$C_{10}$ cycloalkenylene group used herein refers to a divalent group having the same structure as a $C_3$-$C_{10}$ cycloalkenyl group.

A $C_2$-$C_{10}$ heterocycloalkenyl group used herein refers to a monovalent monocyclic group that has at least one hetero atom selected from N, O, P, and S as a ring-forming atom, 2 to 10 carbon atoms, and at least one double bond in its ring. Detailed examples of the $C_2$-$C_{10}$ heterocycloalkenyl group are a 2,3-hydrofuranyl group and a 2,3-hydrothiophenyl group. A $C_2$-$C_{10}$ heterocycloalkenylene group used herein refers to a divalent group having the same structure as a $C_2$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monovalent group having a carbocyclic aromatic system that has at least one hetero atom selected from N, O, P, and S as a ring-forming atom, and 2 to 60 carbon atoms. A $C_2$-$C_{60}$ heteroarylene group used herein refers to a divalent group having a carbocyclic aromatic system that has at least one hetero atom selected from N, O, P, and S as a ring-forming atom, and 2 to 60 carbon atoms. Examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group used herein refers to a monovalent group (for example, having 8 to 60 carbon atoms) that has two or more rings condensed to each other, only carbon atoms as a ring forming atom, and non-aromacity in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group (for example, having 2 to 60 carbon atoms) that has two or more rings condensed to each other, has a heteroatom selected from N, O P, and S, other than carbon atoms, as a ring forming atom, and has non-aromacity in the entire molecular structure. An example of the monovalent non-aromatic condensed hetero-polycyclic group is a carbazolyl group. A divalent non-aromatic condensed hetero-polycyclic group used herein refers to a divalent group having the same structure as the monovalent non-aromatic condensed heteropolycyclic group.

As used herein, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$B(Q_{14})(Q_{15})$, and —$N(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$B(Q_{24})(Q_{25})$, and —$N(Q_{26})(Q_{27})$; and —$Si(Q_{31})(Q_{32})(Q_{33})$, —$B(Q_{34})(Q_{35})$, and —$N(Q_{36})(Q_{37})$;

wherein $Q_{11}$ to $Q_{17}$, $Q_{21}$ to $Q_{27}$, and $Q_{31}$ to $Q_{37}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, or a monovalent non-aromatic condensed hetero-polycyclic group.

For example, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed hetero-polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —Si($Q_{11}$)($Q_{12}$)($Q_3$), —B($Q_{14}$)($Q_{15}$), and —N($Q_{16}$)($Q_{17}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$);

wherein $Q_{1l}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

"Ph" used herein refers to a phenyl group, "Me" refers to a methyl group, "Et" refers to an ethyl group, and "ter-Bu" or "But" refers to a tert-butyl group.

Hereinafter, an organic light-emitting device according to an embodiment will be described in detail with reference to the following Synthesis Examples, Examples, and Comparative Examples. The wording "B was used instead of A" used in describing Synthesis Examples means that a molar equivalent of A was identical to a molar equivalent of B.

The Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments.

Further, it will be understood that the embodiments are not limited to the particular details described in the Examples and Comparative Examples.

Synthesis Example 1

Synthesis of Compound 1

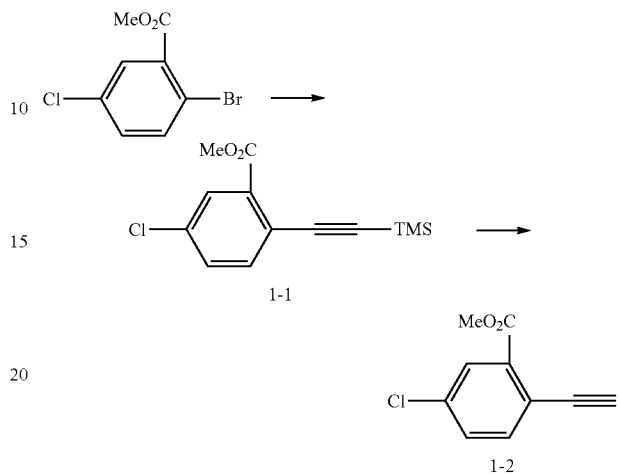

Synthesis of Intermediate 1-1

10 g (40 mmol) of methyl 2-bromo-5-chlorobenzoate was dissolved in 20 ml of triethylamine, and then 6 g (60 mmol) of ethynyltrimethylsilane, 2.3 g (2 mmol) of Pd(PPh$_3$)$_4$ and 760 mg (4 mmol) of CuI were added dropwise thereto in sequence. After a reaction solution was stirred at 50° C. for 4 hours, the reaction solution was cooled to 0° C. and diluted in diethyl ether to neutralize with 1N HCl. An organic layer was separated by using diethyl ether, and dried by using anhydrous magnesium sulfate, and then filtered and distilled under reduced pressure. The obtained residue was separated and purified by silicagel column chromatography to produce 10.7 g (yield of 99%) of Intermediate 1-1. The obtained compound was identified by liquid chromatography-mass spectrometry (LC-MS).

$C_{13}H_{15}ClO_2Si$: M$^+$ calc'd: 266.80. found: 266.82.

Synthesis of Intermediate 1-2

10.7 g (40 mmol) of Intermediate 1-1 was dissolved in tetrahydrofuran, 50 ml of TBAF 1N was added dropwise thereto, and then the result was stirred for 4 hours. Water was added to a reaction solution to terminate a reaction, and then an extraction process was performed thereon three times by using ethylacetate, and then the result was dried by using anhydrous magnesium sulfate and then distilled under reduced pressure. The obtained residue was separated and purified by silicagel column chromatography to produce 7.8 g (yield of 99%) of Intermediate 1-2. The obtained compound was identified by LC-MS. $C_{10}H_7ClO_2$: M$^+$ calc'd: 194.61. found: 194.61.

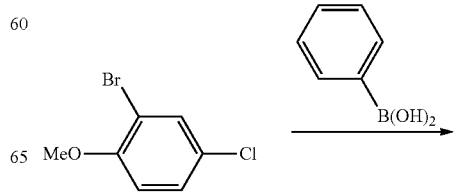

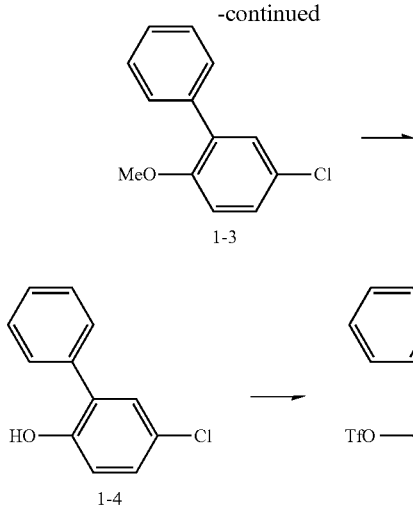

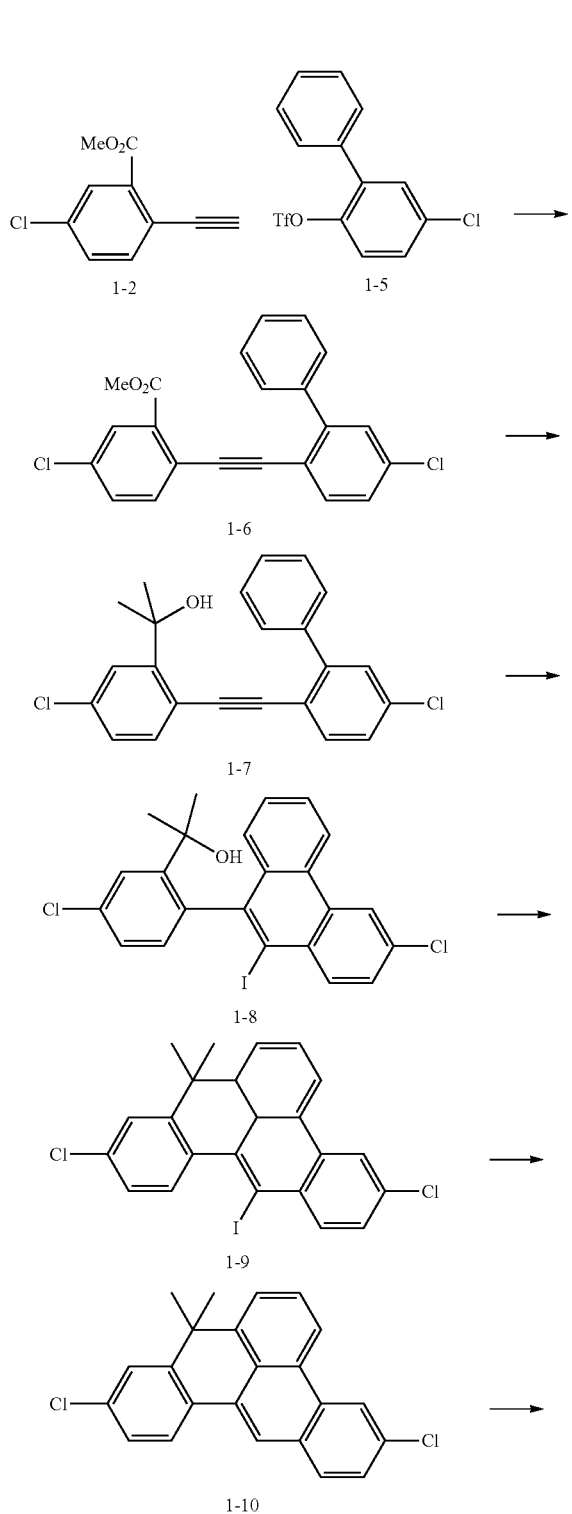

was extracted therefrom by using methylenechloride. The obtained organic layer was dried by using anhydrous magnesium sulfate, and then filtered and distilled under reduced pressure. The obtained was separated and purified by silicagel column chromatography to produce 12 g (yield of 99%) of Intermediate 1-5. The obtained compound was identified by LC-MS. $C_{13}H_8ClF_3O_3S$: $M^+$ calc'd: 335.98. found 335.99.

Synthesis of Intermediate 1-3

10 g (45 mmol) of 2-bromo-4-chloro-1-methoxybenzene and 7.5 g (37 mmol) of phenylboronic acid were dissolved in 100 ml of tetrahydrofuran and 30 ml of water, 2.6 g (2.3 mmol) of $Pd(PPh_3)_4$ and 18 g (130 mmol) of $K_2CO_3$ were added dropwise thereto. A reaction solution was stirred at 70° C. for 3 hours, and then slowly cooled to room temperature. An organic layer was separated by using diethyl ether, and dried by using anhydrous magnesium sulfate, and then filtered and distilled under reduced pressure. The obtained residue was separated and purified by silicagel column chromatography to produce Intermediate 1-3 9.7 g (yield of 99%). The obtained compound was identified by LC-MS. $C_{13}H_{11}ClO$: $M^+$ calc'd: 218.05. found: 218.04.

Synthesis of Intermediate 1-4

9.7 g (33 mmol) of Intermediate 1-3 was dissolved in methylenechloride, and 50 ml of $BBr_3$1N was slowly added dropwise thereto at 0° C. A reaction solution was heated to room temperature and stirred for 5 hours. A saturated sodium bicarbonate solution was added to the reaction solution at 0° C. to terminate a reaction, and then an organic layer was separated therefrom by using methylenechloride. The obtained organic layer was dried by using anhydrous magnesium sulfate, and filtered and distilled under reduced pressure. The obtained residue was separated and purified by silicagel column chromatography to produce 8.2 g (yield of 89%) of Intermediate 1-4. The obtained compound was identified by LC-MS. $C_{12}H_9ClO$: $M^+$ calc'd: 204.03. found 204.5.

Synthesis of Intermediate 1-5

8.2 g (29 mmol) of Intermediate 1-4 was dissolved in 80 ml of methylenechloride, and 8.7 ml (62 mmol) of triethylamine and 7 ml (42 mmol) of trifluoromethanesulfonic anhydride were added dropwise thereto in sequence. A reaction solution was stirred at 0° C. for 30 minutes, water was added to terminate a reaction, and then an organic layer

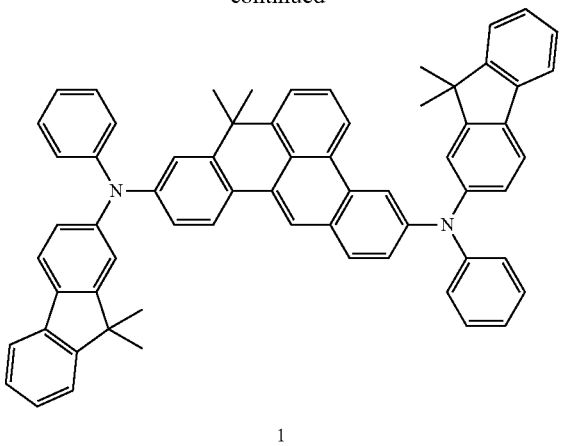

1

Synthesis of Intermediate 1-6

7.8 g (40 mmol) of Intermediate 1-2 and 13.4 g (40 mmol) of Intermediate 1-5 were dissolved in dimethylformamide (DMF), triethylamine and Pd(PPh$_3$)$_4$ were added dropwise thereto in sequence. The result was stirred at room temperature for 15 hours, and water was added dropwise thereto to terminate a reaction, and then an organic layer was extracted therefrom by using diethyl ether. The obtained organic layer was dried by using anhydrous magnesium sulfate, and then filtered and distilled under reduced pressure. The obtained residue was separated and purified by silicagel column chromatography to produce 9.5 g (yield of 63%) of Intermediate 1-6. The obtained compound was identified by LC-MS. $C_{22}H_{14}Cl_2O_2$: M$^+$ calc'd: 380.04. found: 380.05.

Synthesis of Intermediate 1-7

9.5 g (25 mmol) of Intermediate 1-6 was dissolved in 150 ml of tetrahydrofuran, and 75 ml of methyl magnesiumchloride 1N was slowly added dropwise thereto at −78° C. A reaction solution was slowly heated to room temperature and stirred for 7 hours. 1N HCl was added to terminate a reaction and an extraction process was performed thereon by using diethyl ether. An organic layer was separated therefrom, dried by using anhydrous magnesium sulfate, and then filtered and distilled under reduced pressure. The obtained residue was separated and purified by silicagel column chromatography to produce 7.6 g (yield of 80%) of Intermediate 1-7. The obtained compound was identified by LC-MS. $C_{23}H_{18}Cl_2O$: M$^+$ calc'd: 380.07. found: 380.06.

Synthesis of Intermediate 1-8

7.6 g (20 mmol) of Intermediate 1-7 was dissolved in 120 ml of methylenechloride, and 3.9 g (24 mmol) of iodine monochloride dissolved in 10 ml of methylenechloride was slowly added dropwise thereto at −78° C. After 30 minutes, an aqueous saturated sodium thiosulfate solution was added thereto to terminate a reaction, and an extraction process was performed thereon by using methylenechloride. An organic layer was separated therefrom, and dried by using anhydrous magnesium sulfate, and then filtered and distilled under reduced pressure. The obtained residue was separated and purified by silicagel column chromatography to produce 9.7 g (yield of 96%) of Intermediate 1-8. The obtained compound was identified by LC-MS. $C_{23}H_{17}Cl_2IO$: M$^+$ calc'd: 505.97. found: 505.99.

Synthesis of Intermediate 1-9

9.7 g (19.1 mmol) of Intermediate 1-8 was dissolved in dichloromethane (80 ml) and cooled to 0° C. TFA 0.1 ml was added dropwise to a reaction solution, and the reaction solution was stirred for 30 minutes, and then 1 ml of triethylamine was added thereto to terminate a reaction. The residue obtained by filtering under reduced pressure was separated and purified by silicagel column chromatography to produce 8.1 g (yield of 86%) of Intermediate 1-9. The obtained compound was identified by LC-MS. $C_{23}H_{15}Cl_2I$: M$^+$ calc'd: 487.96. found: 487.98.

Synthesis of Intermediate 1-10

8.1 g (16.5 mmol) of Intermediate 1-9 was dissolved in 80 ml of tetrahydrofuran, and 9 ml of n-BuLi 2.4M was slowly added thereto at −78° C. The result was stirred at room temperature for 30 minutes and an aqueous saturated ammonium chloride solution was added thereto to terminate a reaction. The extraction process was performed thereon three times by using diethyl ether, and thus an organic layer was separated. The separated organic layer was dried by using anhydrous magnesium sulfate, and then filtered and distilled under reduced pressure. The obtained residue was separated and purified by silicagel column chromatography to produce 5.9 g (yield of 86%) of Intermediate 1-10. The obtained compound was identified by LC-MS. $C_{23}H_{16}Cl_2$: M$^+$ calc'd: 362.06. found: 362.07.

Synthesis of Compound 1

1 g (2.7 mmol) of Intermediate 1-10, 1.6 g (5.6 mmol) of 9,9-dimethyl-N-phenyl-9H-fluorene-2-amine, 0.09 g (0.14 mmol) of Pd$_2$(dba)$_3$, 0.02 g (0.28 mmol) of PtBu$_3$ and 0.56 g (3 mmol) of KOtBu were dissolved in 50 mL of toluene, and the result was stirred at 85° C. for 2 hours. A reaction solution was cooled to room temperature and water was added to terminate a reaction and then the extraction process was performed thereon three times by using ethyl acetate. The obtained organic layer was dried by using anhydrous magnesium sulfate and distilled under reduced pressure, and then the obtained residue was separated and purified by silicagel column chromatography to produce 1.9 g (yield of 82%) of Compound 1. The obtained compound was identified by LC-MS and nuclear magnetic resonance (NMR).

Synthesis Example 2

Synthesis of Compound 10

2.1 g (yield of 78%) of Compound 10 was obtained in the same manner as in Synthesis Example 1, except that in synthesizing Compound 1, 2.0 g (5.7 mmol) of 9,9-dimethyl-N-(4-(trimethylsilyl)phenyl)-9H-fluorene-2-amine was used instead of 9,9-dimethyl-N-phenyl-9H-fluorene-2-amine. The obtained compound was identified by LC-MS and NMR.

Synthesis Example 3

Synthesis of Compound 13

1.6 g (yield of 74%) of Compound 13 was obtained in the same manner as in Synthesis Example 1, except that in synthesizing Compound 1, 1.5 g (5.6 mmol) of N-phenyldibenzo[b,d]furan-4-amine was used instead of 9,9-dimethyl-N-phenyl-9H-fluorene-2-amine. The obtained Compound was identified by LC-MS and NMR.

Synthesis Example 4

Synthesis of Compound 25

1.9 g (yield of 67%) of Compound 25 was obtained in the same manner as in Synthesis Example 1, except that in synthesizing Compound 1, 2.1 g (5.6 mmol) of N-(9,9-dimethyl-9H-fluorene-2-yl)dibenzo[b,d]furan-2-amine was used instead of 9,9-dimethyl-N-phenyl-9H-fluorene-2-amine. The obtained compound was identified by LC-MS and NMR.

Synthesis Example 5

Synthesis of Compound 40

1.6 g (yield of 70%) of Compound 40 was obtained in the same manner as in Synthesis Example 1, except that in synthesizing Compound 1, 1.6 g (5.6 mmol) of N-(p-tolyl)phenanthrene-3-amine was used instead of 9,9-dimethyl-N-phenyl-9H-fluorene-2-amine. The obtained compound was identified by LC-MS and NMR.

Synthesis Example 6

Synthesis of Compound 125

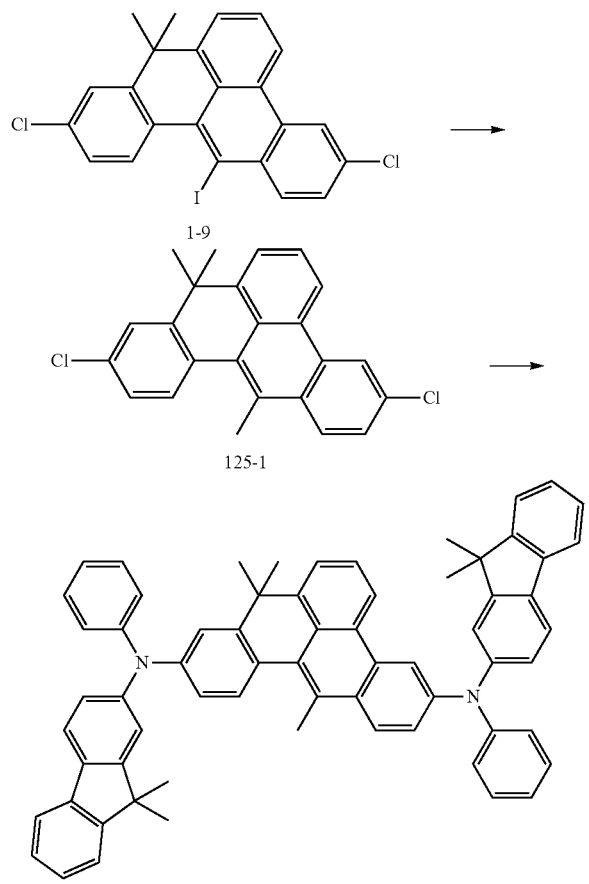

Synthesis of Intermediate 125-1

5 g (10 mmol) of Intermediate 1-9 was dissolved in tetrahydrofuran (100 ml) and cooled to −78° C., and then n-BuLi (2.5M, 4.8 ml) was slowly added dropwise thereto. While maintaining the temperature, the result was stirred for an hour and 1.2 ml (20 mmol) of iodomethane was added dropwise thereto. Next, the result was slowly heated to room temperature and then stirred for 20 hours. An aqueous saturated sodium thiosulfate solution was added thereto to terminate a reaction and the extraction process was performed thereon three times by using diethyl ether. Then, the result was dried by using anhydrous magnesium sulfate. The residue obtained after filtering and distilling under reduced pressure was separately purified by column chromatography to produce 2.7 g (yield of 72%) of Intermediate 125-1. The obtained compound was identified by LC-MS. $C_{24}H_{18}Cl_2$: $M^+$ calc'd: 376.08. found: 377.08.

Synthesis of Compound 125

2 g (yield of 70%) of Compound 125 was obtained in the same manner as in Synthesis Example 1, except that 1 g (2.7 mmol) of Intermediate 125-1 was used instead of Intermediate 1-9. The obtained compound was identified by LC-MS and NMR.

Synthesis Example 7

Synthesis of Compound 129

2.1 g (yield of 76%) of Compound 129 was obtained in the same manner as in Synthesis Example 1, except that 1 g (2.7 mmol) of Intermediate 125-1 was used instead of Intermediate 1-9, and 2 g (5.6 mmol) of N-([1,1'-biphenyl]-4-yl)-9,9-dimethyl-9H-fluorene-2-amine was used instead of 9,9-dimethyl-N-phenyl-9H-fluorene-2-amine. The obtained compound was identified by LC-MS and NMR.

Synthesis Example 8

Synthesis of Compound 137

1.59 g (yield of 72%) of Compound 137 was obtained in the same manner as in Synthesis Example 1, except that 1 g (2.7 mmol) of Intermediate 125-1 was used instead of Intermediate 1-9, and 1.45 g (5.6 mmol) of N-phenyldibenzo[b,d]furan-4-amine was used instead of 9,9-dimethyl-N-phenyl-9H-fluorene-2-amine. The obtained compound was identified by LC-MS and NMR.

Synthesis Example 9

Synthesis of Compound 186

1.5 g (yield of 74%) of Compound 186 was obtained in the same manner as in Synthesis Example 1, except that 1 g (2.7 mmol) of Intermediate 125-1 was used instead of Intermediate 1-9, and 1.26 g (5.6 mmol) of 4-(tert-butyl)-N-phenylaniline was used instead of 9,9-dimethyl-N-phenyl-9H-fluorene-2-amine. The obtained compound was identified by LC-MS and NMR.

Synthesis Example 10

Synthesis of Compound 253

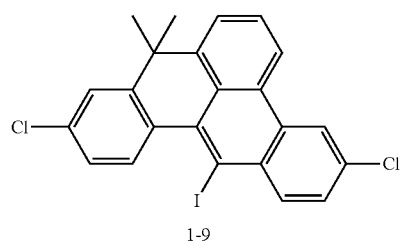

1-9

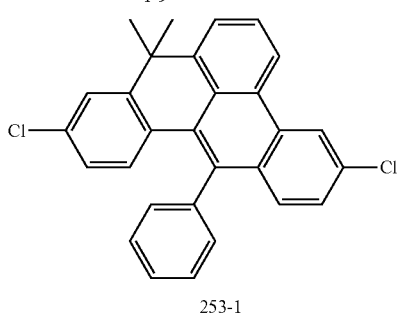

253-1

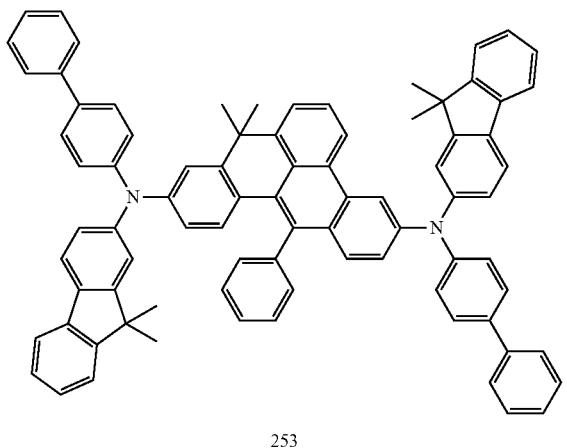

253

Synthesis of Intermediate 253-1

5 g (10 mmol) of Intermediate 1-9 and 1.5 g (12 mmol) of phenylboronic acid were dissolved in 50 ml of tetrahydrofuran and 15 ml of water, 577 mg (0.5 mmol) of Pd(PPh$_3$)$_4$ and 4.2 g (30 mmol) of K$_2$CO$_3$ were added dropwise thereto. A reaction solution was stirred at 70° C. for 3 hours and slowly cooled to room temperature. An organic layer was separated therefrom by using diethyl ether and dried by using anhydrous magnesium sulfate, and then filtered and distilled under reduced pressure. The obtained residue was separated and purified by silicagel column chromatography to produce 2.94 g (yield of 67%) of Intermediate 253-1. The obtained compound was identified by LC-MS and NMR. C$_{29}$H$_{20}$Cl$_2$: M$^+$ calc'd: 438.09. found: 438.10.

Synthesis of Compound 253

2 g (yield of 85%) of Compound 253 was obtained in the same manner as in Synthesis Example 1, except that 1 g (2.2 mmol) of Intermediate 253-1 was used instead of Intermediate 1-9, and 1.66 g (4.6 mmol) of N-([1,1'-biphenyl]-4-yl)-9,9-dimethyl-9H-fluorene-2-amine was used instead of 9,9-dimethyl-N-phenyl-9H-fluorene-2-amine. The obtained compound was identified by LC-MS and NMR.

Synthesis Example 11

Synthesis of Compound 257

1.85 g (yield of 80%) of Compound 257 was obtained in the same manner as in Synthesis Example 1, except that 1 g (2.2 mmol) of Intermediate 253-1 was used instead of Intermediate 1-9, and 1 g (4.6 mmol) of N-(4-(tert-butyl)phenyl)-9,9-dimethyl-9H-fluorene-2-amine was used instead of 9,9-dimethyl-N-phenyl-9H-fluorene-2-amine. The obtained compound was identified by LC-MS and NMR.

Compounds 1, 10, 13, 25, 40, 125, 129, 137, 186, 253, and 257 synthesized in Synthesis Examples 1 to 11 were identified by $^1$H NMR and LC-MS. Results thereof are shown in Table 1 below.

TABLE 1

| Compound | $^1$H NMR (CDCl$_3$, 400 MHz) | LC-MS found | LC-MS calc. |
|---|---|---|---|
| 1 | 8.66 (s, 1H), 8.25 (dd, 1H), 7.88 (t, 2H), 7.77 (d, 2H), 7.50-7.30 (m, 7H), 7.18-7.01 (m, 9H), 6.73-6.61 (m, 6H), 6.49 (d, 1H) 6.41 (d, 1H), 6.30 (dd, 4H) 1.63 (s, 6H), 1.61 (s, 12H) | 860.42 | 860.41 |
| 10 | 8.66 (s, 1H), 8.25 (d, 1H), 7.88 (t, 2H), 7.77 (d, 2H), 7.50-7.30 (m, 7H), 7.14-7.09 (m, 9H), 6.76-6.45 (m, 10H), 1.63 (s, 6H), 1.61 (s, 12H), 0.24 (s, 18H) | 1004.49 | 1004.49 |
| 13 | 8.66 (s, 1H), 8.25 (d, 1H), 7.85-7.81 (m, 4H), 7.69-7.64 (m, 5H), 7.49-7.38 (m, 6H), 7.08-6.96 (m, 8H), 6.76 (s, 1H), 6.65-6.58 (m, 3H), 6.42 (d, 1H), 6.30-6.21 (m, 4H), 1.63 (s, 6H) | 808.33 | 808.31 |
| 25 | 8.66 (s, 1H), 8.25 (d, 1H), 7.92-7.64 (m, 8H), 7.55-7.30 (m, 15H), 7.13-6.98 (m, 7H), 6.80-6.51 (m, 6H), 1.63 (s, 6H), 1.61 (s, 12H) | 1040.43 | 1040.43 |
| 40 | 8.66 (s, 1H), 8.37 (d, 2H), 8.25 (s, 1H), 7.94-7.85 (m, 5H), 7.73-7.41 (m, 14H), 7.20-6.96 (m, 7H), 6.82-6.46 (m, 6H), 2.29 (s, 6H), 1.63 (s, 6H) | 856.40 | 856.38 |

TABLE 1-continued

| Compound | ¹H NMR (CDCl₃, 400 MHz) | LC-MS found | LC-MS calc. |
|---|---|---|---|
| 125 | 8.18 (d, 1H), 8.01-7.93 (m, 3H), 7.77 (d, 2H), 7.48-7.30 (m, 6H), 7.14-7.05 (m, 8H), 6.79-6.63 (m, 7H), 6.49 (d, 1H), 6.41 (d, 1H), 6.30-6.19 (m, 4H), 3.11 (s, 3H), 1.63 (s, 6H), 1.61 (s, 12H) | 874.46 | 874.43 |
| 129 | 8.18 (d, 1H), 8.02-7.94 (m, 3H), 7.77 (d, 2H), 7.58 (m, 4H), 7.51-7.29 (m, 16H), 7.14-7.08 (m, 4H), 6.84-6.72 (m, 5H), 6.60-6.45 (m, 6H), 3.11 (s, 3H), 1.63 (s, 6H), 1.61 (s, 12H) | 1026.48 | 1026.49 |
| 137 | 8.18 (d, 1H), 8.00 (d, 1H), 7.95 (d, 1H), 7.83-7.81 (m, 2H), 7.70-7.64 (m, 5H), 7.49-7.38 (m, 6H), 7.08-6.96 (m, 7H), 6.82-6.61 (m, 5H), 6.41-6.21 (m, 5H), 3.11 (s, 3H), 1.63 (s, 6H) | 822.31 | 822.32 |
| 186 | 8.18 (d, 1H), 7.98-7.94 (m, 2H), 7.51-7.39 (m, 3H), 7.26-7.23 (m, 4H), 7.08-7.04 (m, 4H), 6.82-6.63 (m, 5H), 6.52-6.47 (m, 4H), 6.31 (dd, 2H), 6.21 (dd, 2H), 3.11 (s, 3H), 1.63 (s, 6H), 1.50 (s, 18H) | 754.43 | 754.43 |
| 253 | 8.03-7.92 (m, 4H), 7.86-7.75 (m, 3H), 7.58-7.30 (m, 24H), 7.14-7.08 (m, 4H), 6.76-6.73 (m, 3H), 6.60-6.32 (m, 8H), 1.61 (s, 6H), 1.60 (s, 12H) | 1088.56 | 1088.51 |
| 257 | 8.03-7.92 (m, 4H), 7.86-7.75 (m, 3H), 7.55-7.25 (m, 14H), 7.14-7.08 (m, 4H), 6.76-6.72 (m, 3H), 6.52-6.45 (m, 7H), 6.34 (dd, 1H), 1.61 (s, 6H), 1.60 (s, 12H), 1.50 (s, 18H) | 1048.56 | 1048.57 |

Example 1

An ITO glass substrate (a product of Corning Co., Ltd) with an ITO layer having a thickness of 15 Ω/cm² (1,200 Å) thereon was cut to a size of 50 mm×50 mm×0.7 mm, and then, sonicated by using isopropyl alcohol and pure water each for 5 minutes, and cleaned by the exposure to ultraviolet rays for 30 minutes, and then ozone, and the ITO glass substrate was mounted on a vacuum deposition apparatus.

2-TNATA was deposited on the ITO anode to form a hole injection layer having a thickness of 600 Å, and NPB was deposited on the hole injection layer to form a hole transport layer having a thickness of 300 Å, and then DNA (host) and Compound 1 (dopant) were co-deposited on the hole transport layer in a weight ratio of 98:2 to form an emission layer having a thickness of 300 Å.

Thereafter, Alq₃ was deposited on the emission layer to form an electron transport layer having a thickness of 300 Å, and LiF was deposited on the electron transport layer to form an electron injection layer having a thickness of 10 Å, and Al was deposited on the electron injection layer to form a cathode having a thickness of 3,000 Å, thereby completing the manufacture of an organic light-emitting device.

Example 2

An organic light-emitting device was manufactured in the same manner as in Example 1, except that in forming an emission layer, as a dopant, Compound 10 was used instead of Compound 1.

Example 3

An organic light-emitting device was manufactured in the same manner as in Example 1, except that in forming an emission layer, as a dopant, Compound 13 was used instead of Compound 1.

Example 4

An organic light-emitting device was manufactured in the same manner as in Example 1, except that in forming an emission layer, as a dopant, Compound 25 was used instead of Compound 1.

Example 5

An organic light-emitting device was manufactured in the same manner as in Example 1, except that in forming an emission layer, as a dopant, Compound 40 was used instead of Compound 1.

Example 6

An organic light-emitting device was manufactured in the same manner as in Example 1, except that in forming an emission layer, as a dopant, Compound 125 was used instead of Compound 1.

Example 7

An organic light-emitting device was manufactured in the same manner as in Example 1, except that in forming an emission layer, as a dopant, Compound 129 was used instead of Compound 1.

Example 8

An organic light-emitting device was manufactured in the same manner as in Example 1, except that in forming an emission layer, as a dopant, Compound 137 was used instead of Compound 1.

Example 9

An organic light-emitting device was manufactured in the same manner as in Example 1, except that in forming an emission layer, as a dopant, Compound 186 was used instead of Compound 1.

Example 10

An organic light-emitting device was manufactured in the same manner as in Example 1, except that in forming an emission layer, as a dopant, Compound 253 was used instead of Compound 1.

Example 11

An organic light-emitting device was manufactured in the same manner as in Example 1, except that in forming an emission layer, as a dopant, Compound 257 was used instead of Compound 1.

Comparative Example 1

An organic light-emitting device was manufactured in the same manner as in Example 1, except that in forming an emission layer, as a dopant, Compound A below was used instead of Compound 1.

<Compound A>

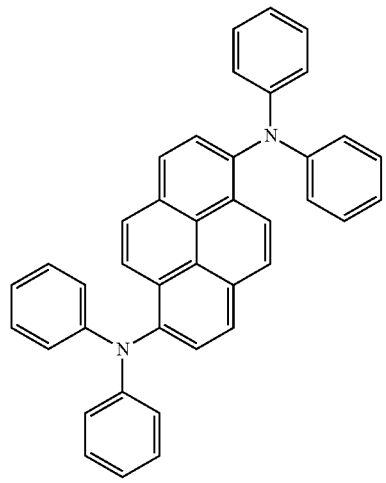

Comparative Example 2

An organic light-emitting device was manufactured in the same manner as in Example 1, except that in forming an emission layer, as a dopant, Compound B below was used instead of Compound 1.

<Compound B>

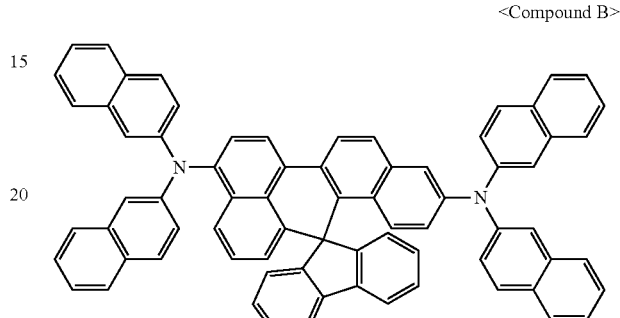

Evaluation Example 1

The driving voltage, current density, brightness, efficiency, and half-lifespan of the organic light-emitting devices manufactured according to Examples 1 to 11, and Comparative Examples 1 and 2 were measured by using Keithley SMU 236 and a brightness photometer PR650, and results thereof are shown in Table 2. The half-lifespan is a period of time that is taken until the brightness of the organic light-emitting device was 50% of initial brightness.

TABLE 2

| | Dopant of emission layer | Driving voltage (V) | Current Density (mA/cm$^2$) | Brightness (cd/m$^2$) | Efficiency (cd/A) | Emission color | Half lifespan (hr @100 mA/cm$^2$) |
|---|---|---|---|---|---|---|---|
| Example 1 | Compound 1 | 5.73 | 50 | 3340 | 6.68 | Blue | 357 |
| Example 2 | Compound 10 | 5.86 | 50 | 3310 | 6.62 | Blue | 335 |
| Example 3 | Compound 13 | 5.85 | 50 | 3315 | 6.63 | Blue | 321 |
| Example 4 | Compound 25 | 5.96 | 50 | 3290 | 6.58 | Blue | 348 |
| Example 5 | Compound 40 | 5.72 | 50 | 3185 | 6.37 | Blue | 312 |
| Example 6 | Compound 125 | 5.72 | 50 | 3135 | 6.27 | Blue | 311 |
| Example 7 | Compound 129 | 5.81 | 50 | 3190 | 6.38 | Blue | 307 |
| Example 8 | Compound 137 | 5.79 | 50 | 3245 | 6.49 | Blue | 334 |
| Example 9 | Compound 186 | 5.98 | 50 | 3260 | 6.52 | Blue | 326 |
| Example 10 | Compound 253 | 5.87 | 50 | 3215 | 6.43 | Blue | 307 |
| Example 11 | Compound 257 | 5.79 | 50 | 3140 | 6.28 | Blue | 308 |
| Comparative Example 1 | Compound A | 7.01 | 50 | 2645 | 5.29 | Blue | 258 |
| Comparative Example 2 | Compound B | 7.21 | 50 | 2470 | 4.94 | Blue | 238 |

Referring to Table 2, it was found that the organic light-emitting devices manufactured according to Examples 1 to 11 exhibited lower driving voltage, higher brightness, higher efficiency, and longer half-lifespan, compared to the organic light-emitting devices manufactured according to Comparative Examples 1 and 2.

By way of summation and review, embodiments provide a condensed cyclic compound and an organic light-emitting device including the same. As described above, according to the one or more of the above embodiments, an organic light-emitting device including the compound according to embodiments may have a low driving voltage, high efficiency, high brightness, and long lifespan.

Example embodiments have been disclosed herein, and although specific terms are employed, they are used and are to be interpreted in a generic and descriptive sense only and not for purpose of limitation. Accordingly, it will be understood by those of skill in the art that various changes in form and details may be made without departing from the spirit and scope thereof as set forth in the following claims.

What is claimed is:

1. A condensed cyclic compound represented by Formula 1 below:

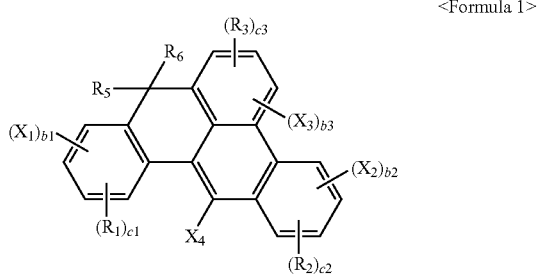

<Formula 1> wherein in Formula 1,
$X_1$ is $-[(L_1)_{a1}-N(Ar_1)(Ar_2)]$;
$X_2$ is $-[(L_2)_{a2}-N(Ar_3)(Ar_4)]$;
$X_3$ is $-[(L_3)_{a3}-N(Ar_5)(Ar_6)]$;
$X_4$ is $-[(L_4)_{a4}-N(Ar_7)(Ar_8)]$ or $R_4$;
$L_1$ to $L_4$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;
a1 to a4 are each independently selected from 0, 1, 2, and 3;
$Ar_1$ to $Ar_8$ are each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group;
b1 and b2 are each independently an integer selected from 0 to 4, b3 is an integer selected from 0 to 3, i) when $X_4$ is $R_4$, b1+b2+b3≥2, and ii) when $X_4$ is $-[(L_4)_{a4}-N(Ar_7)(Ar_5)]$, b1+b2+b3≥1;
$R_1$ to $R_6$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, and $-B(Q_4)(Q_5)$;
c1 and c2 are each independently an integer selected from 0 to 4, and c3 is an integer selected from 0 to 3;
at least one of substituents of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from
a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$);

wherein $Q_1$ to $Q_5$, $Q_{11}$ to $Q_{17}$, $Q_{21}$ to $Q_{27}$, and $Q_{31}$ to $Q_{37}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, or a monovalent non-aromatic condensed heteropolycyclic group.

2. The condensed cyclic compound as claimed in claim 1, wherein $L_1$ to $L_4$ in Formula 1 are each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a phenylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The condensed cyclic compound as claimed in claim 1, wherein
$L_1$ to $L_4$ in Formula 1 are each independently represented by any one of Formulae 3-1 to 3-32:

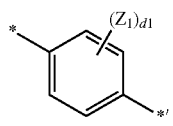

Formula 3-1

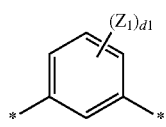

Formula 3-2

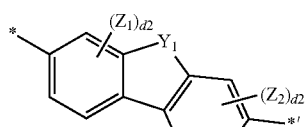

Formula 3-3

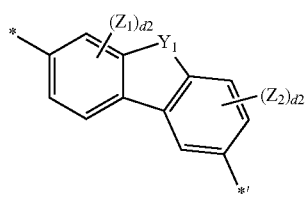

Formula 3-4

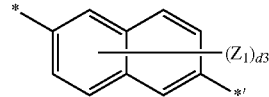

Formula 3-5

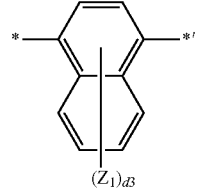

Formula 3-6

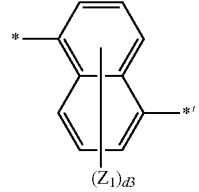

Formula 3-7

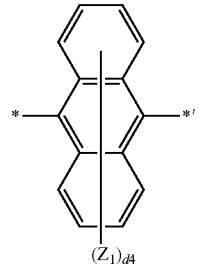

Formula 3-8

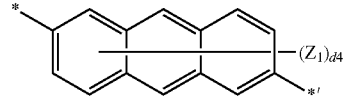

Formula 3-9

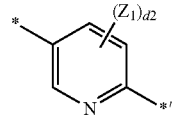

Formula 3-10

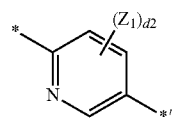

Formula 3-11

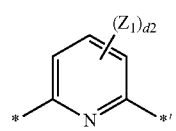

Formula 3-12

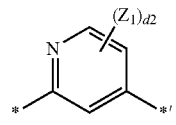

Formula 3-13

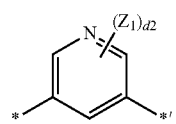

Formula 3-14

-continued

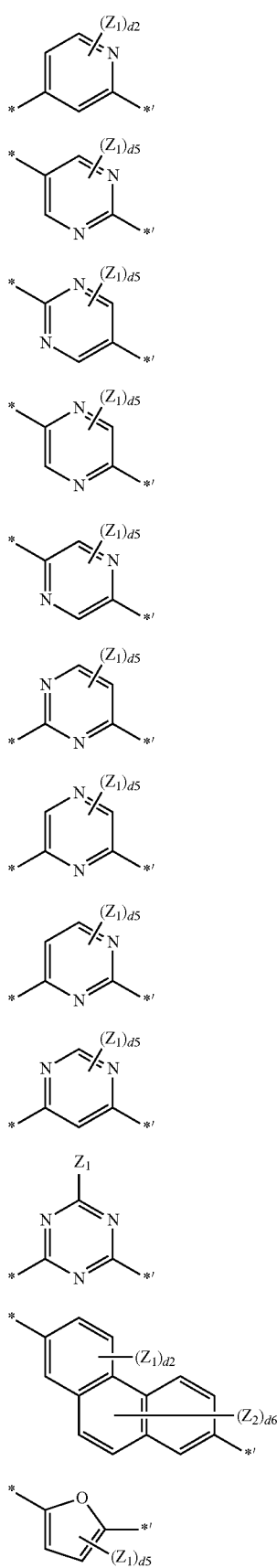

Formula 3-15
Formula 3-16
Formula 3-17
Formula 3-18
Formula 3-19
Formula 3-20
Formula 3-21
Formula 3-22
Formula 3-23
Formula 3-24
Formula 3-25
Formula 3-26

-continued

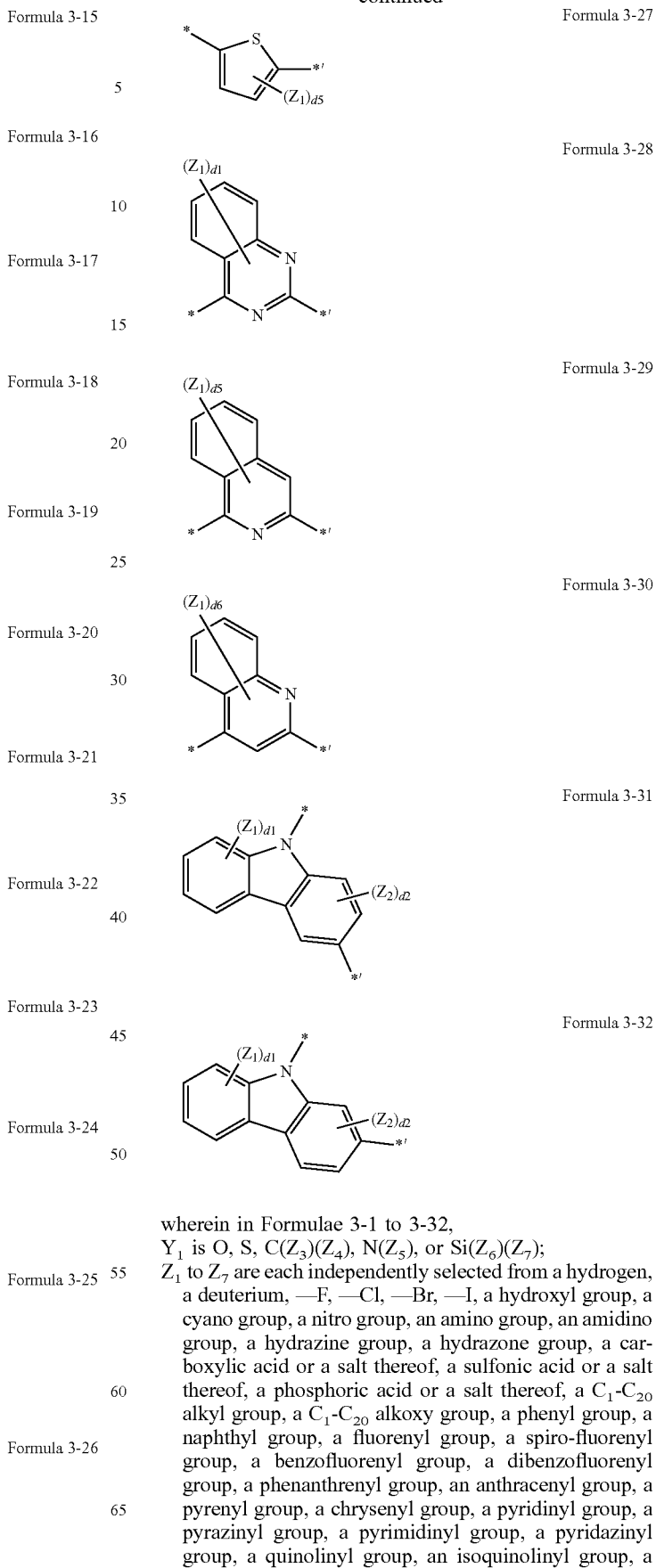

Formula 3-27
Formula 3-28
Formula 3-29
Formula 3-30
Formula 3-31
Formula 3-32 wherein in Formulae 3-1 to 3-32,
$Y_1$ is O, S, $C(Z_3)(Z_4)$, $N(Z_5)$, or $Si(Z_6)(Z_7)$;
$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 is an integer selected from 1 to 4;
d2 is an integer selected from 1 to 3;
d3 is an integer selected from 1 to 6;
d4 is an integer selected from 1 to 8;
d5 is 1 or 2;
d6 is an integer selected from 1 to 5; and
* and *' each indicate a binding site with an adjacent atom.

4. The condensed cyclic compound as claimed in claim 1, wherein $L_1$ to $L_4$ in Formula 1 are each independently represented by any one of Formulae 4-1 to 4-23:

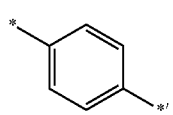

Formula 4-1

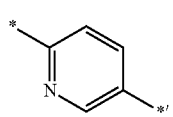

Formula 4-2

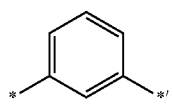

Formula 4-3

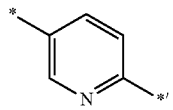

Formula 4-4

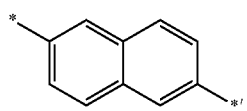

Formula 4-5

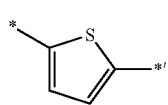

Formula 4-6

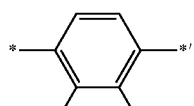

Formula 4-7

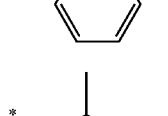

Formula 4-8

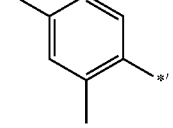

Formula 4-9

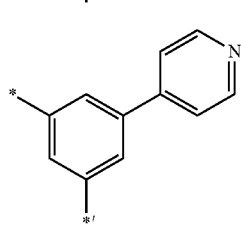

-continued

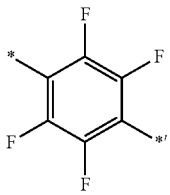

Formula 4-10

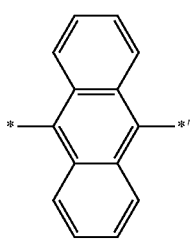

Formula 4-11

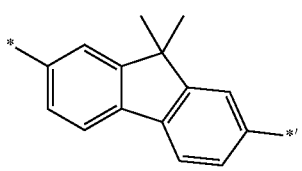

Formula 4-12

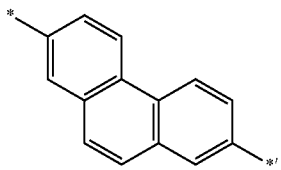

Formula 4-13

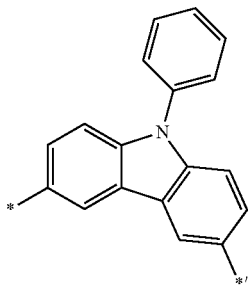

Formula 4-14

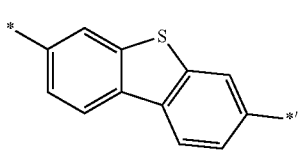

Formula 4-15

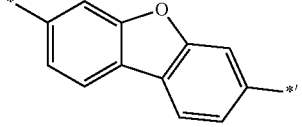

Formula 4-16

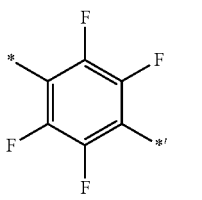

Formula 4-17

-continued

Formula 4-18
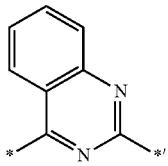

Formula 4-19
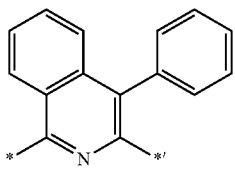

Formula 4-20
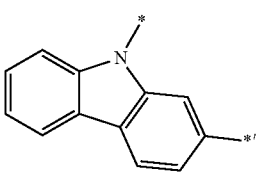

Formula 4-21
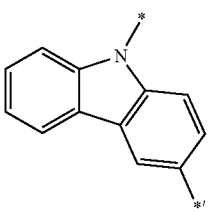

Formula 4-22
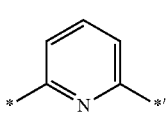

Formula 4-23
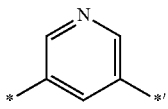

in Formulae 4-1 to 4-23, * and *' each indicate a binding site with an adjacent atom.

5. The condensed cyclic compound as claimed in claim 1, wherein a1 to a4 in Formula 1 are each independently 0 or 1.

6. The condensed cyclic compound as claimed in claim 1, wherein $Ar_1$ to $Ar_8$ in Formula 1 are each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$);

wherein $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

7. The condensed cyclic compound as claimed in claim 1, wherein $Ar_1$ to $Ar_8$ in Formula 1 are each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, a dibenzocarbazolyl group, and —Si($Q_{31}$)($Q_{32}$)($Q_{33}$), wherein $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

8. The condensed cyclic compound as claimed in claim 1, wherein $Ar_1$ to $Ar_8$ in Formula 1 are each independently selected from Formulae 5-1 to 5-14:

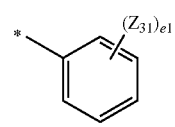

Formula 5-1

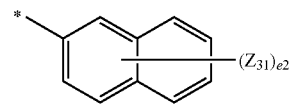

Formula 5-2

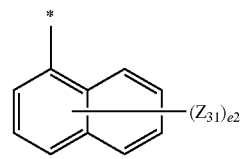

Formula 5-3

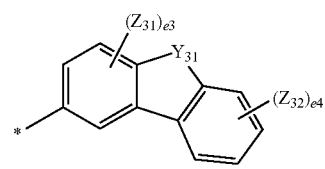

Formula 5-4

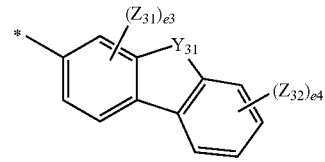

Formula 5-5

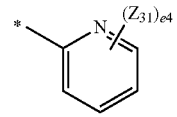

Formula 5-6

-continued

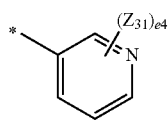
Formula 5-7

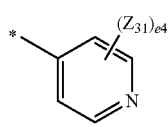
Formula 5-8

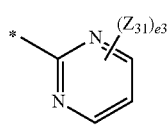
Formula 5-9

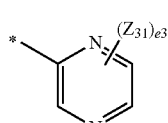
Formula 5-10

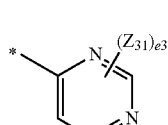
Formula 5-11

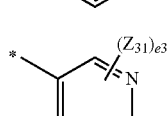
Formula 5-12

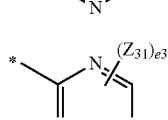
Formula 5-13

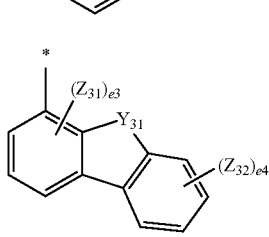
Formula 5-14 wherein Formulae 5-1 to 5-14, $Y_{31}$ is O, S, $C(Z_{33})(Z_{34})$, or $N(Z_{35})$;

$Z_{31}$ to $Z_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, each substituted with at least one selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a naphthyl group; and —$Si(Q_{31})(Q_{32})(Q_{33})$;

wherein $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

e1 is an integer selected from 1 to 5;
e2 is an integer selected from 1 to 7;
e3 is an integer selected from 1 to 3;
e4 is an integer selected from 1 to 4;
e5 is 1 or 2; and
* indicates a binding site with an adjacent atom.

9. The condensed cyclic compound as claimed in claim 1, wherein $Ar_1$ to $Ar_8$ in Formula 1 are each independently selected from Formulae 6-1 to 6-28:

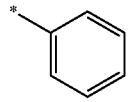
Formula 6-1

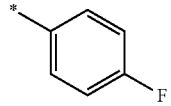
Formula 6-2

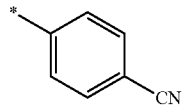
Formula 6-3

-continued
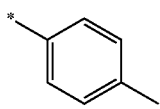
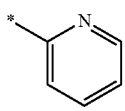
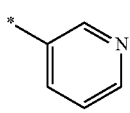
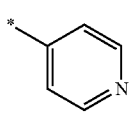
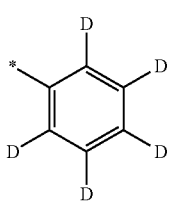
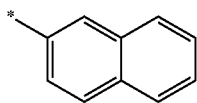
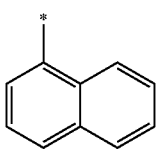
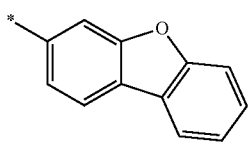
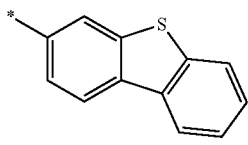
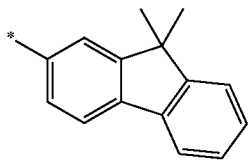
-continued
Formula 6-4
Formula 6-5
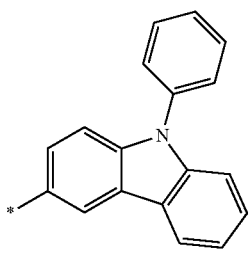
Formula 6-6
Formula 6-7
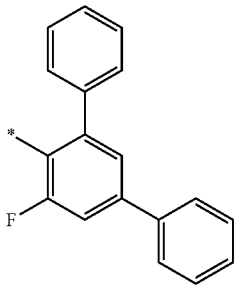
Formula 6-8
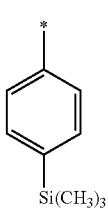
Formula 6-9
Formula 6-10
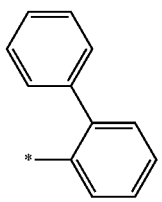
Formula 6-11
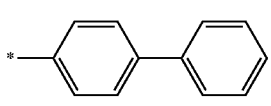
Formula 6-12
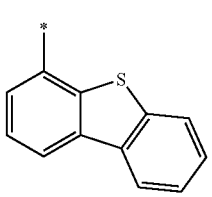
Formula 6-13
Formula 6-14
Formula 6-15
Formula 6-16
Formula 6-17
Formula 6-18
Formula 6-19
Formula 6-20
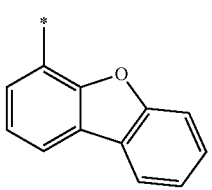

-continued

Formula 6-21
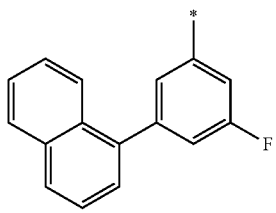

Formula 6-22
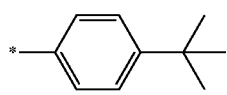

Formula 6-23
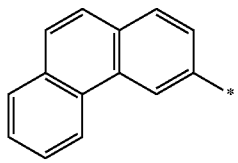

Formula 6-24
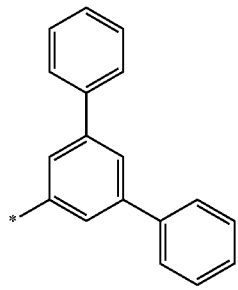

Formula 6-25
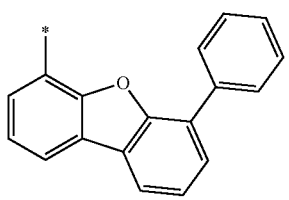

Formula 6-26
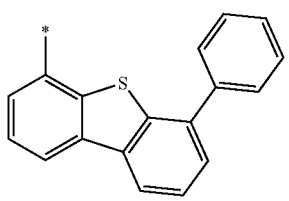

Formula 6-27
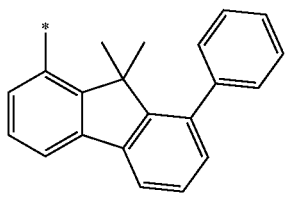

-continued

Formula 6-28
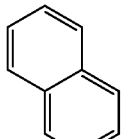
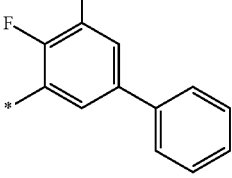

in Formulae 6-1 to 6-28, * indicates a binding site with an adjacent atom.

10. The condensed cyclic compound as claimed in claim 1, wherein $X_4$ is $R_4$, and b1+b2+b3=2.

11. The condensed cyclic compound as claimed in claim 1, wherein $X_4$ is $R_4$, and b1=b2=1, and b3=0;

b1=b3=1, and b2=0; or b2=b3=1, and b1=0.

12. The condensed cyclic compound as claimed in claim 1, wherein $R_1$ to $R_4$ in Formula 1 are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$); and $R_5$ and $R_6$ in Formula 1 are each independently selected from a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, and a substituted or unsubstituted monovalent non-aromatic condensed heteropolycyclic group.

13. The condensed cyclic compound as claimed in claim 1, wherein the condensed cyclic compound is represented by any one selected from Formulae 1-1 to 1-5 below:

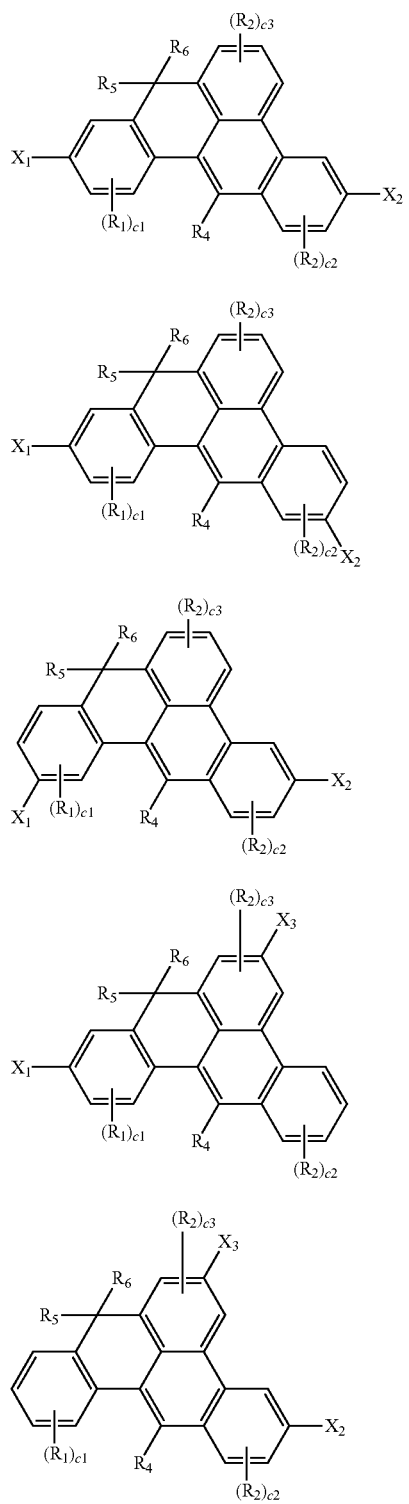

<Formula 1-1>
<Formula 1-2>
<Formula 1-3>
<Formula 1-4>
<Formula 1-5> wherein $X_1$ to $X_3$, $R_1$ to $R_6$, and c1 to c3 in Formulae 1-1 to 1-5 are the same as defined in claim 1.

14. The condensed cyclic compound as claimed in claim 1, wherein the condensed cyclic compound is represented by any one selected from Formulae 1-21 to 1-24:

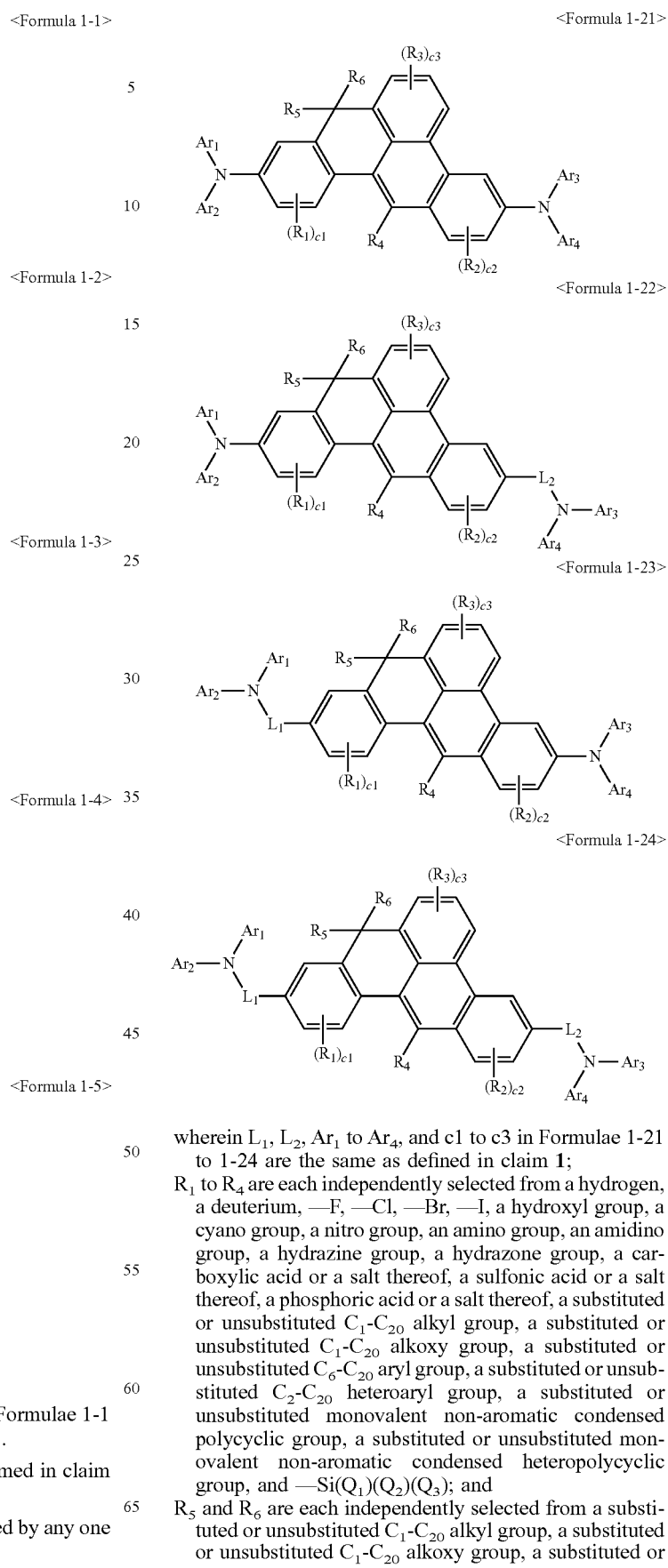

<Formula 1-21>
<Formula 1-22>
<Formula 1-23>
<Formula 1-24> wherein $L_1$, $L_2$, $Ar_1$ to $Ar_4$, and c1 to c3 in Formulae 1-21 to 1-24 are the same as defined in claim 1;

$R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$); and $R_5$ and $R_6$ are each independently selected from a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, and a substituted or unsubstituted monovalent non-aromatic condensed heteropolycyclic group.

15. The condensed cyclic compound as claimed in claim 1, wherein
the condensed cyclic compound is represented by Formula 1-31 or 1-32 below:

<Formula 1-31>

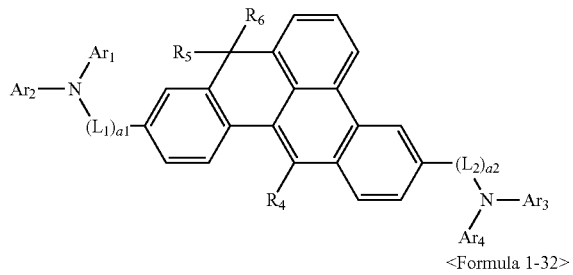

<Formula 1-32>

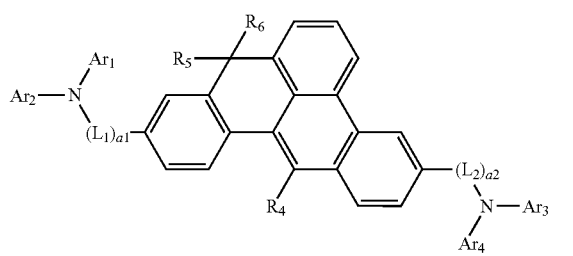

wherein $L_1$, $L_2$, and $Ar_1$ to $Ar_4$ in Formulae 1-31 and 1-32 are the same as defined in claim 1;

$R_4$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

$R_5$ and $R_6$ are each independently selected from a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, and a substituted or unsubstituted monovalent non-aromatic condensed heteropolycyclic group; and a1 and a2 are each independently 0 or 1.

16. The condensed cyclic compound as claimed in claim 1, wherein
the condensed cyclic compound is any one selected from Compounds 1 to 373 below:

1

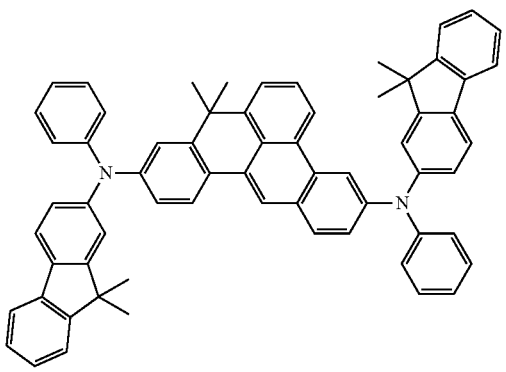

2

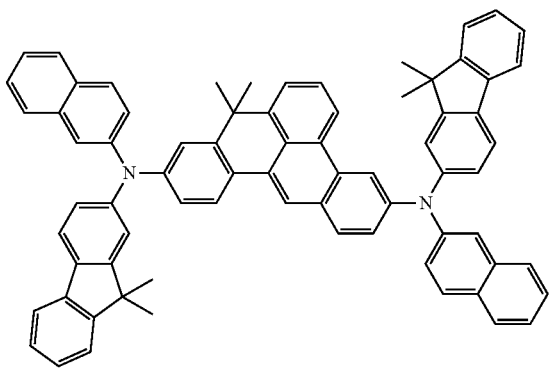

3

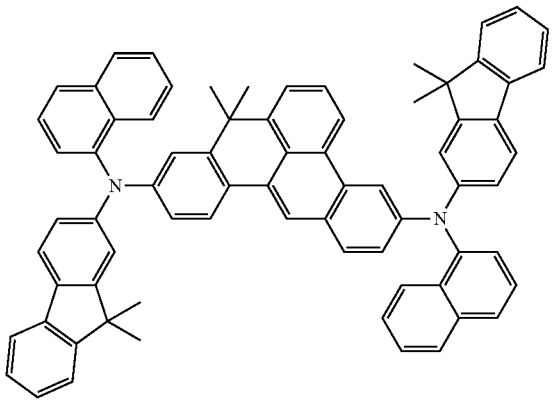

4

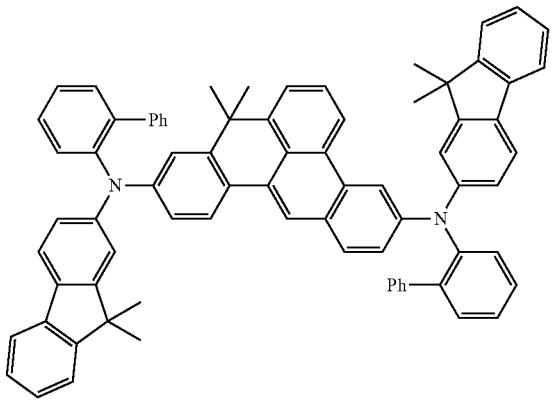

-continued
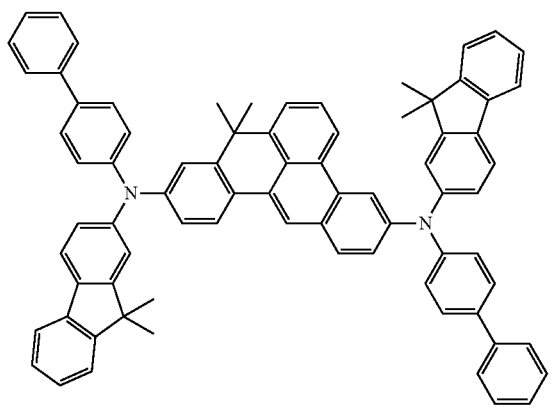
5
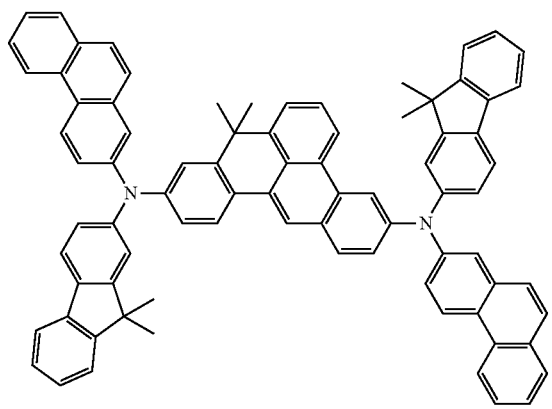
6
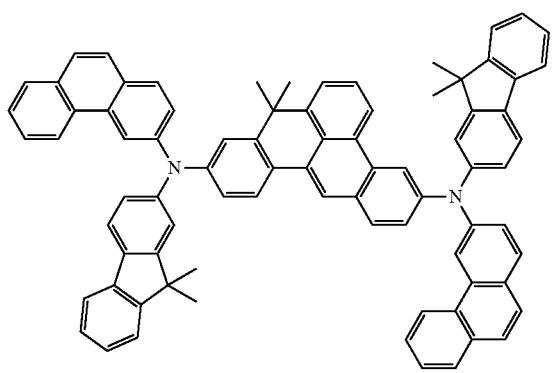
7
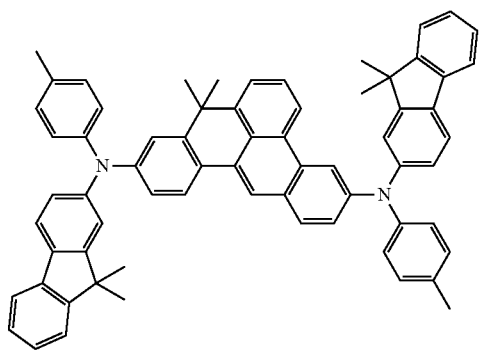
8
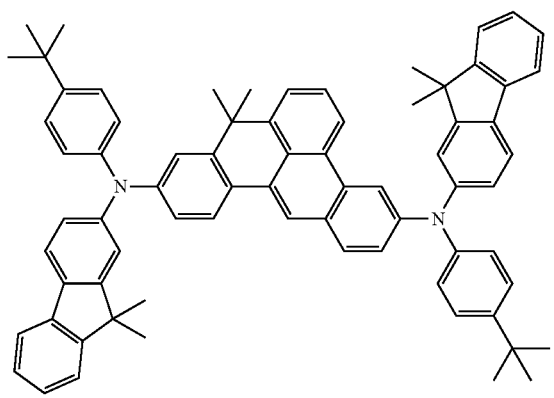
9
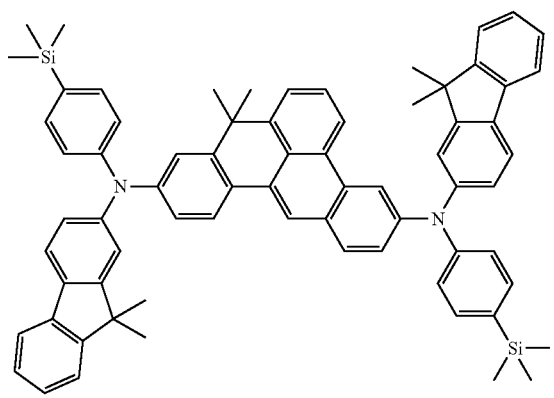
10

-continued
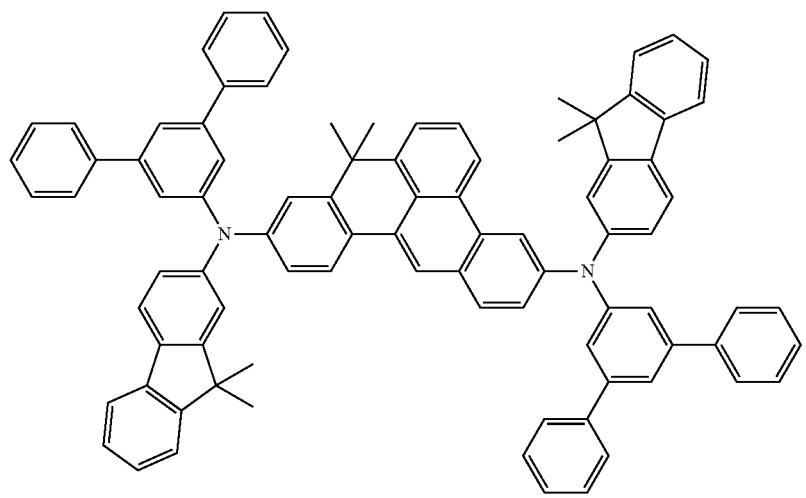
11
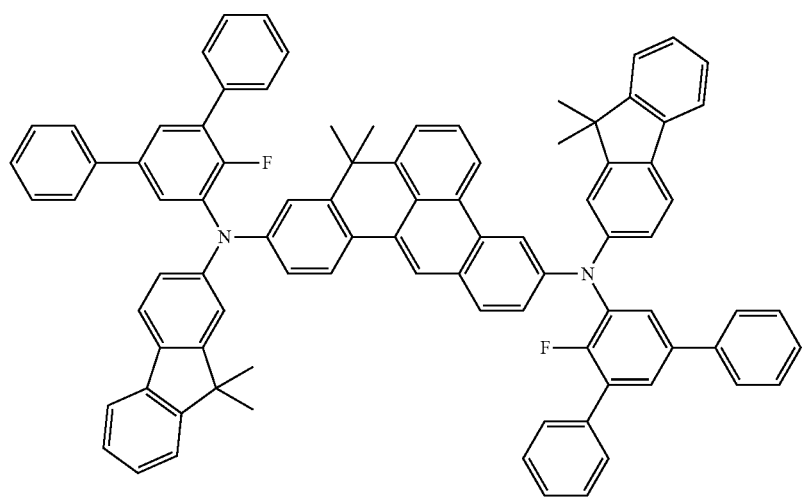
12
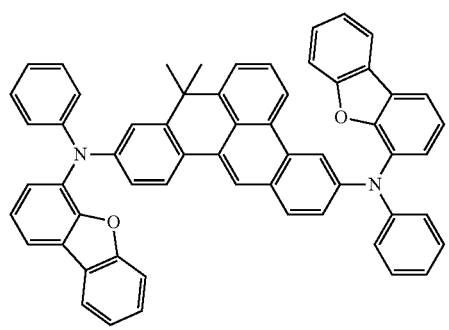
13
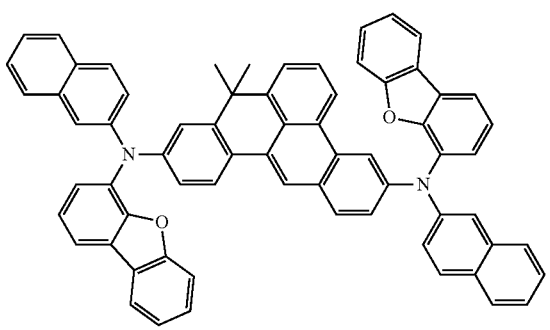
14

-continued
15
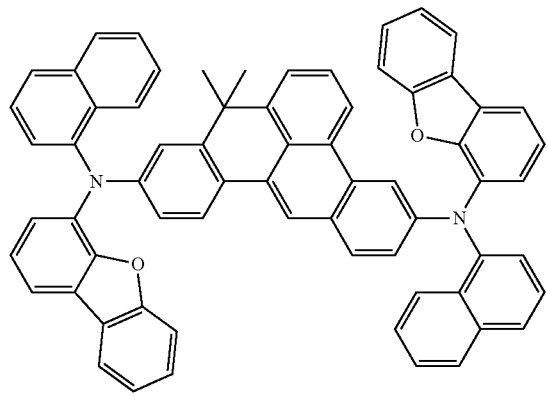
16
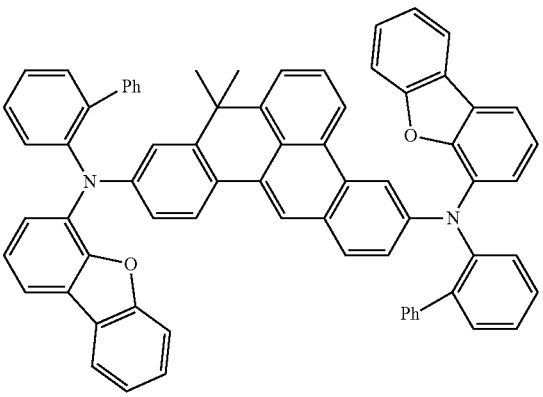
17
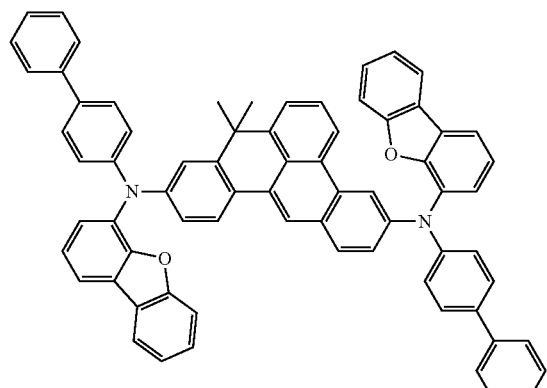
18
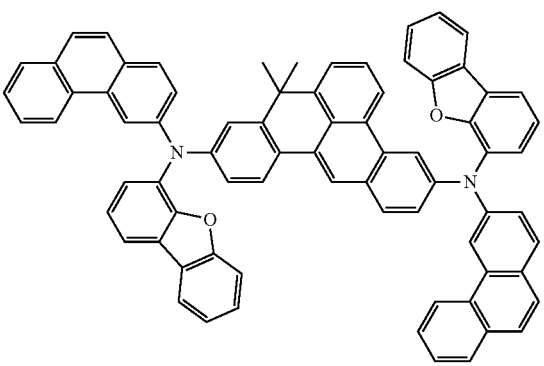
19
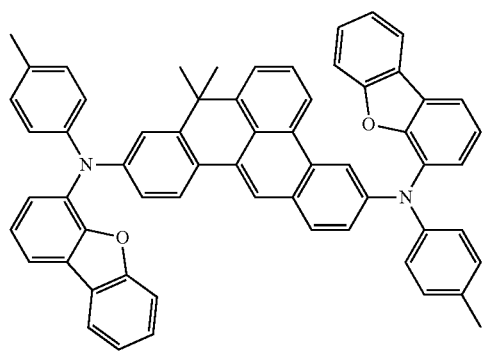
20
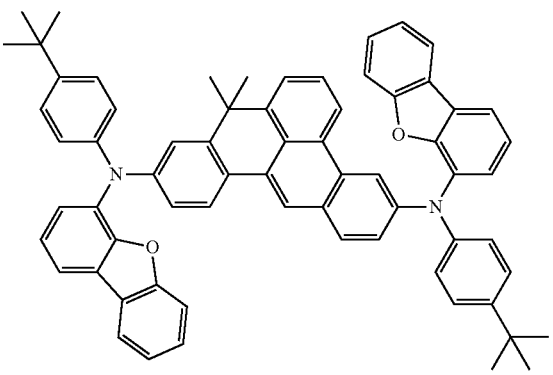
21
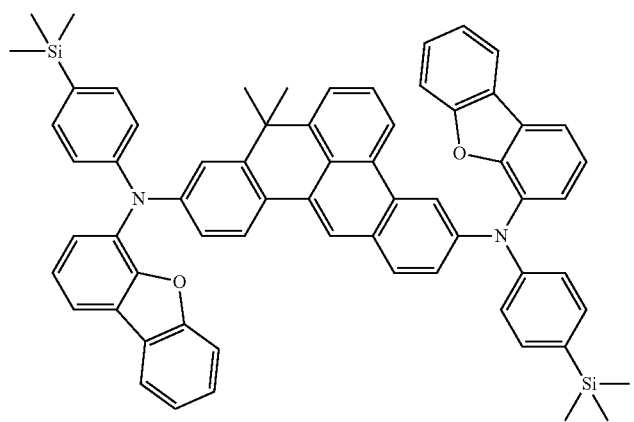

22
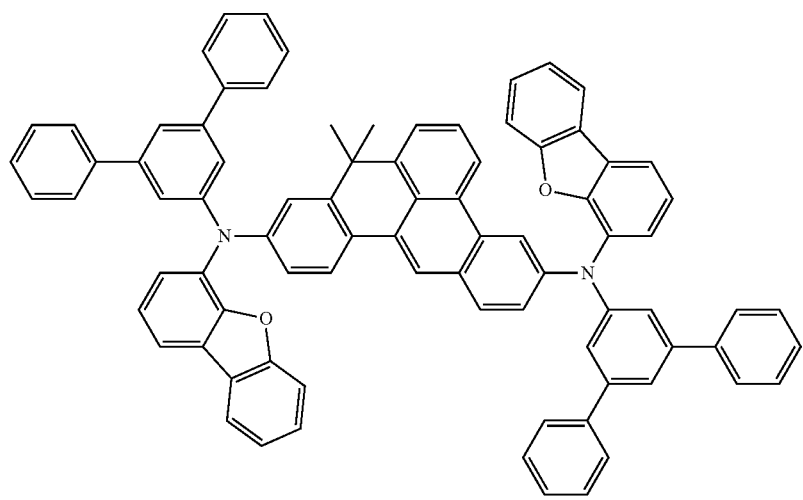
23
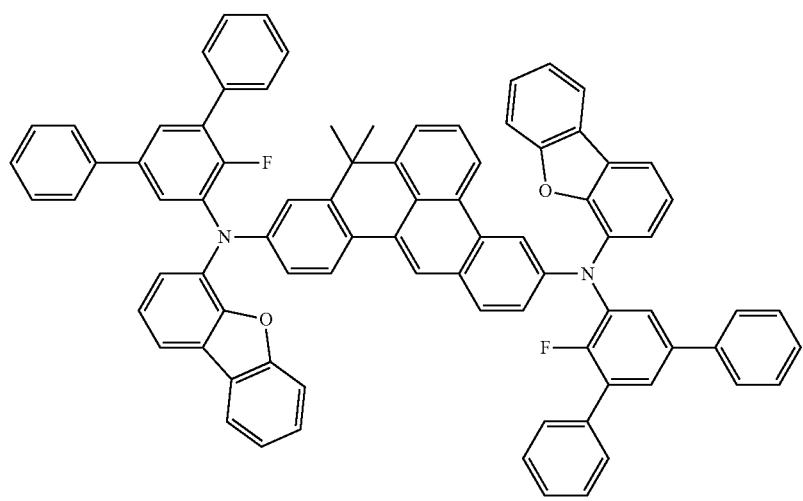
24
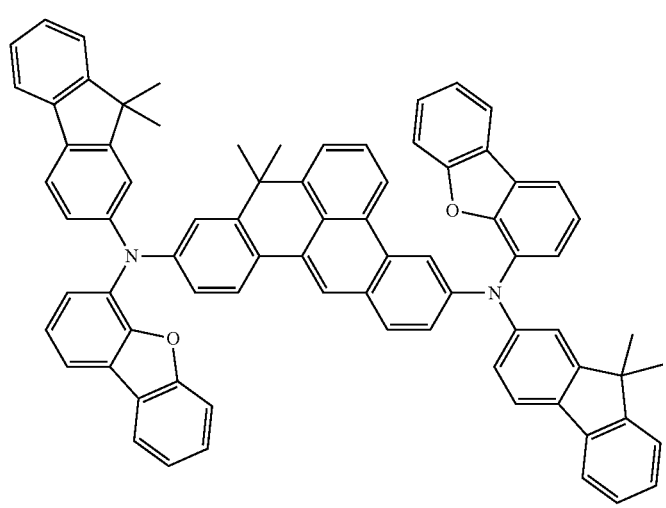

-continued
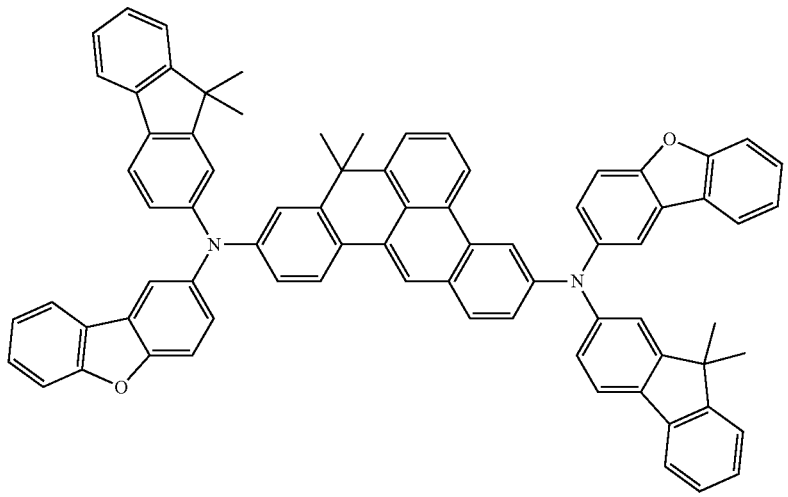
25
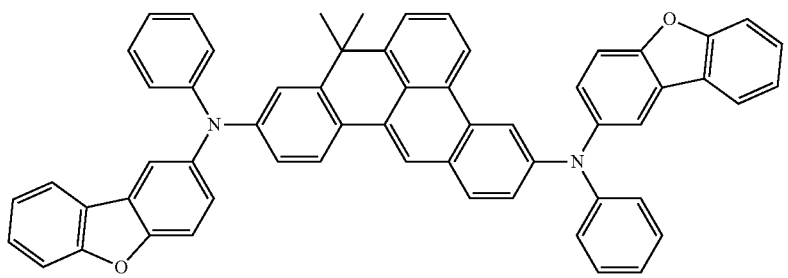
26
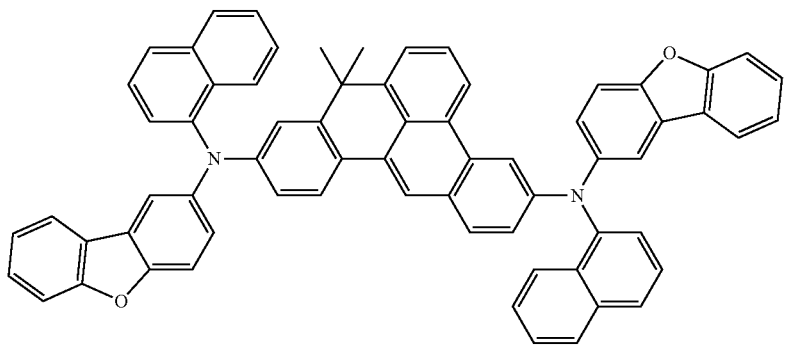
27
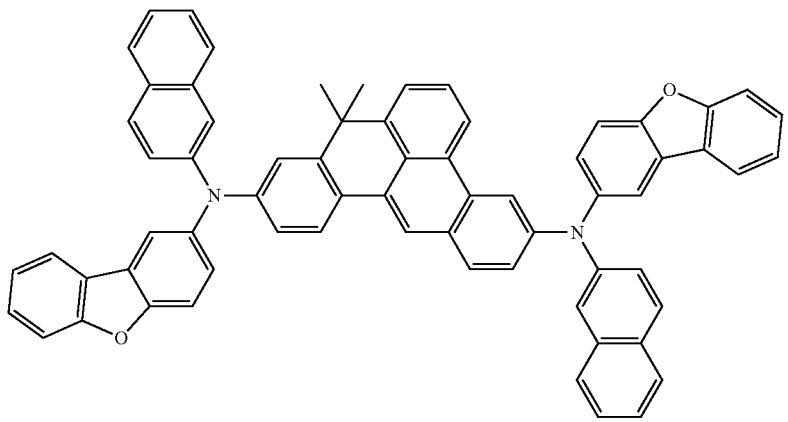
28

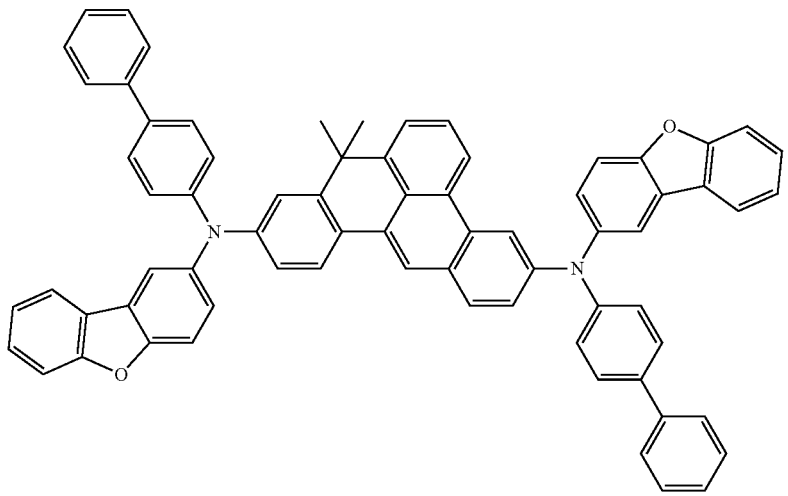
29
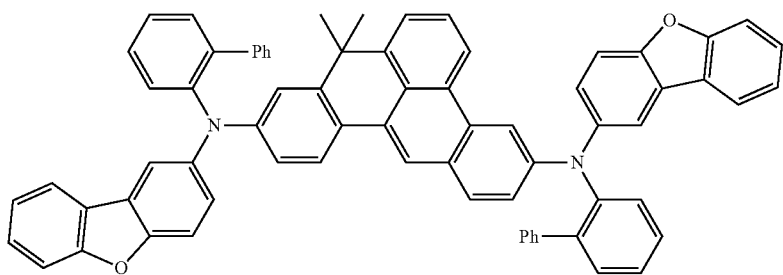
30
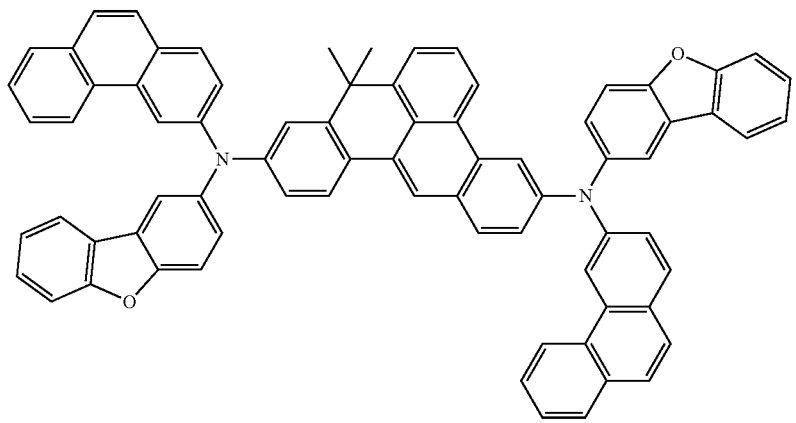
31
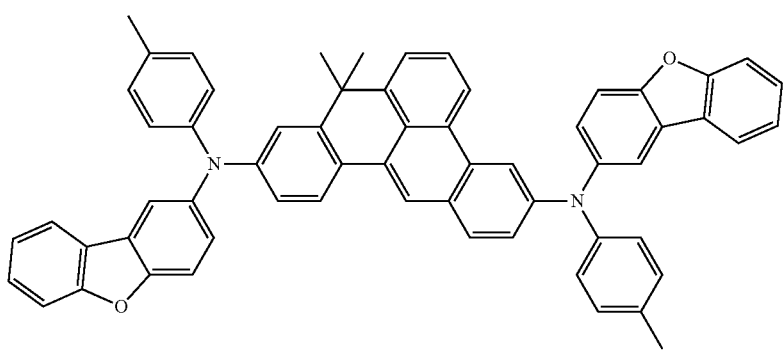
32

33
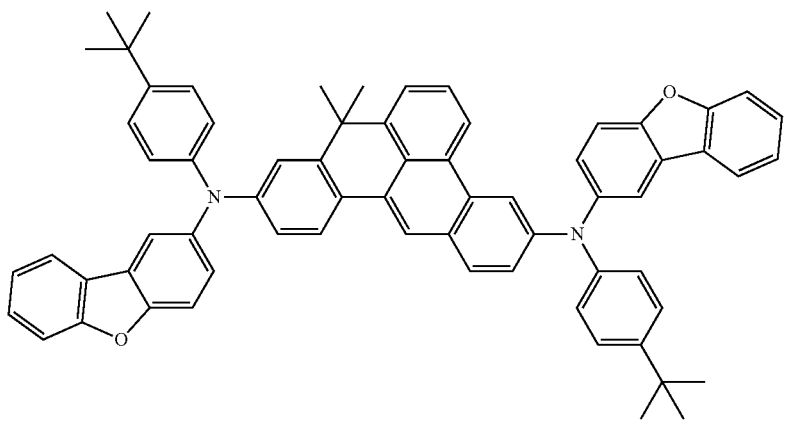
34
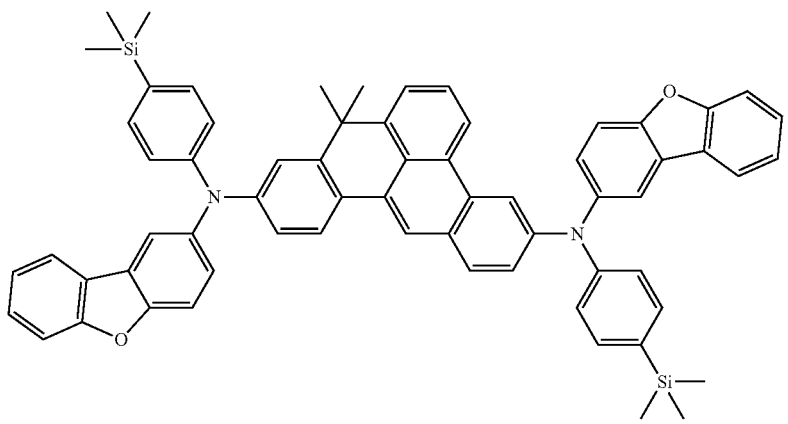
35
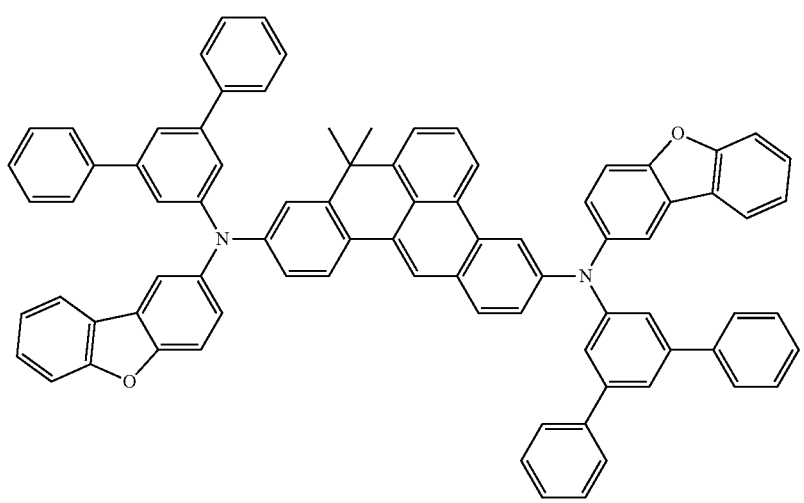

36
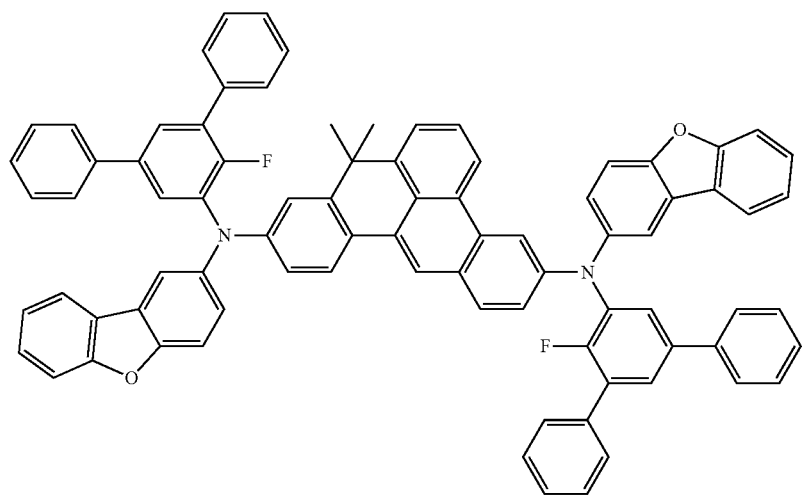
37 38
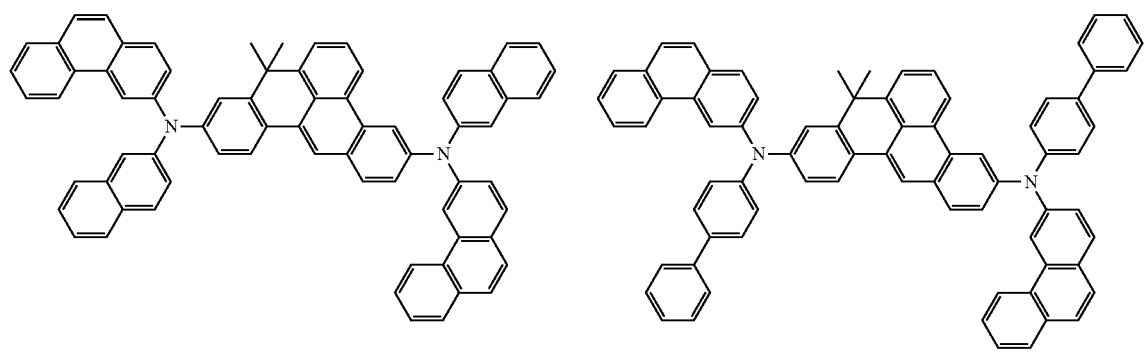
39 40
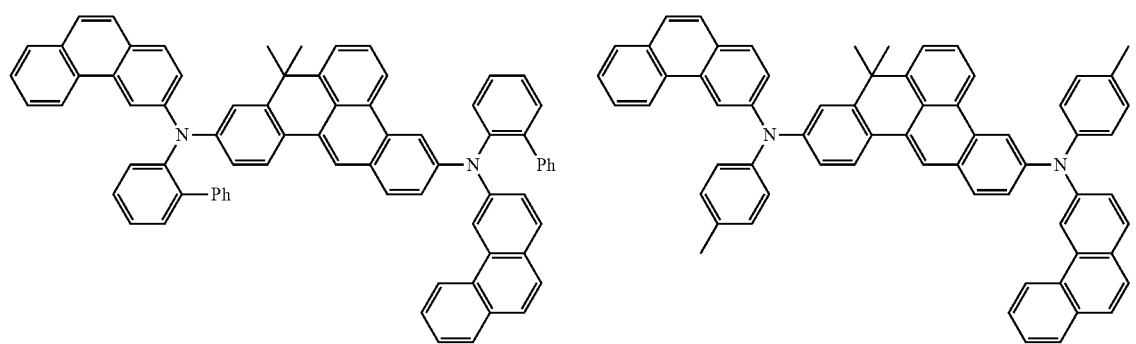
41 42
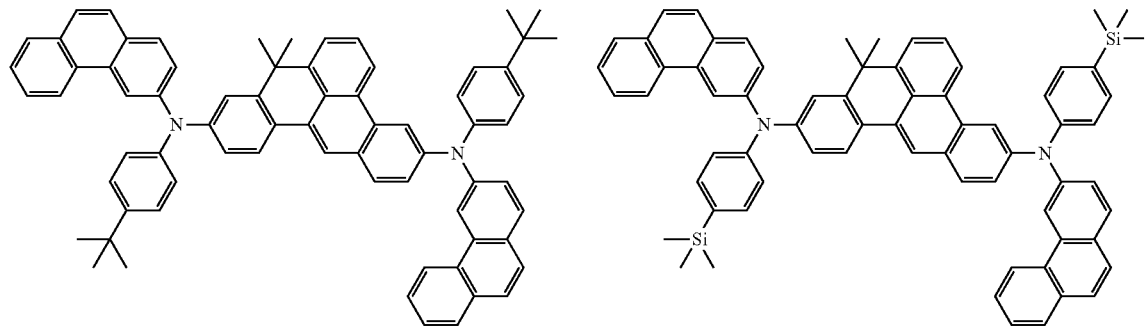

-continued
43
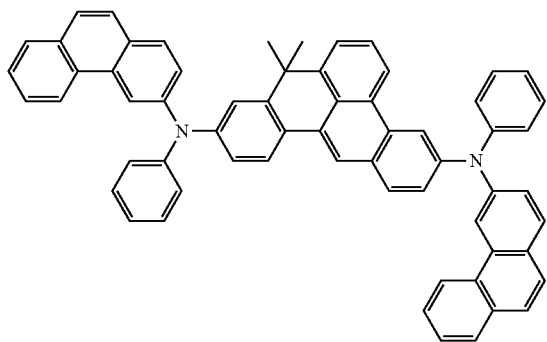
44
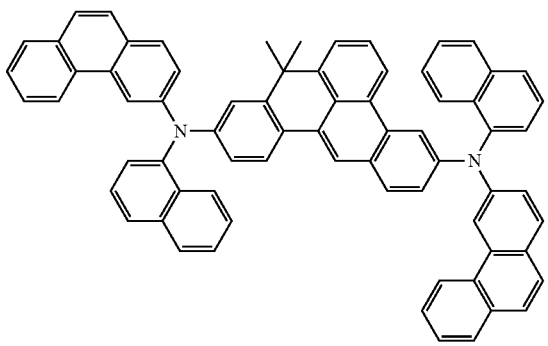
45
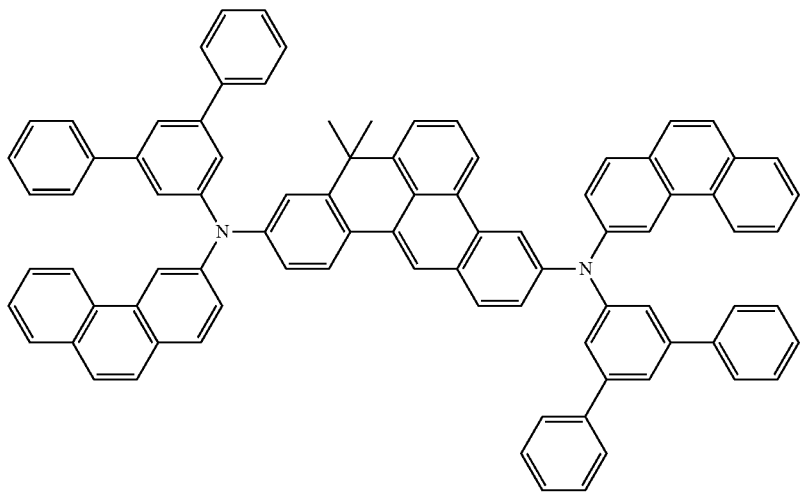
46
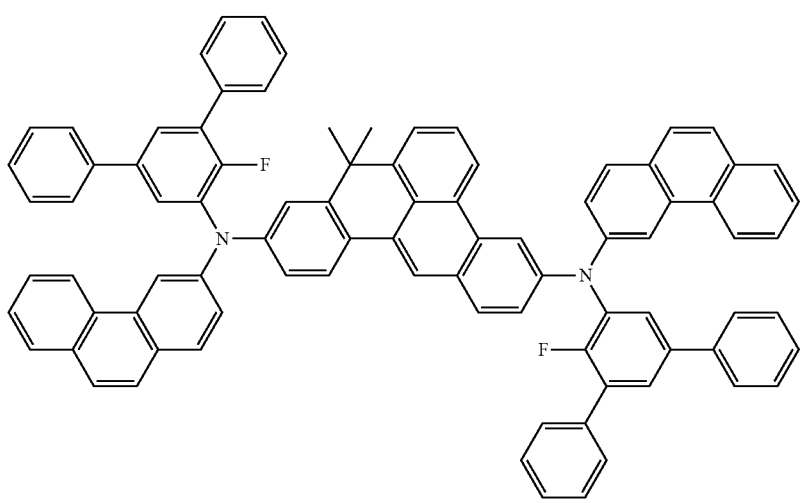

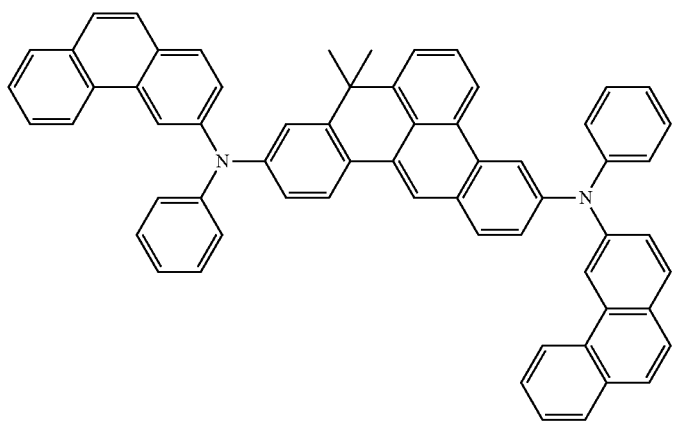
47
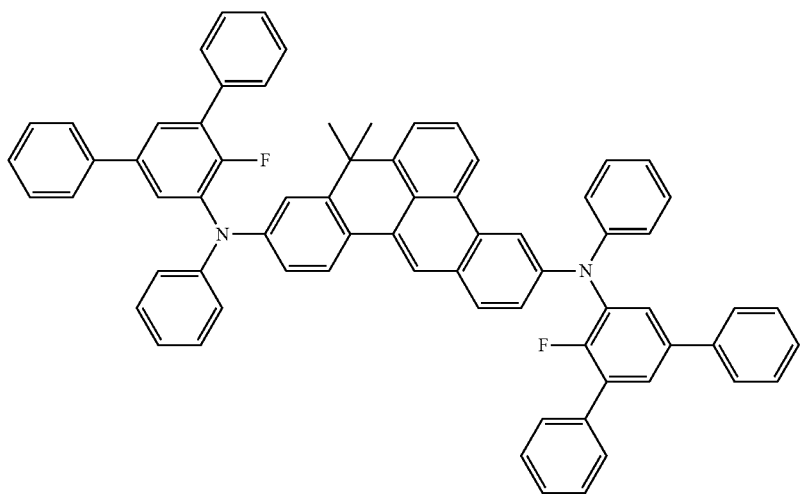
48
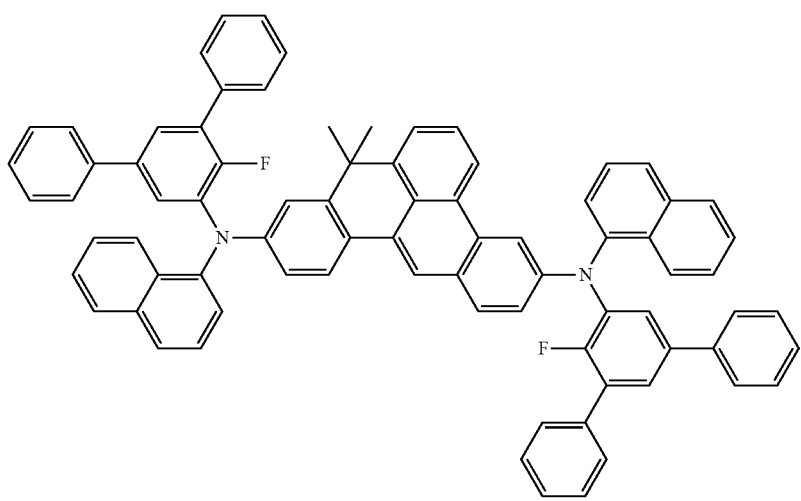
49

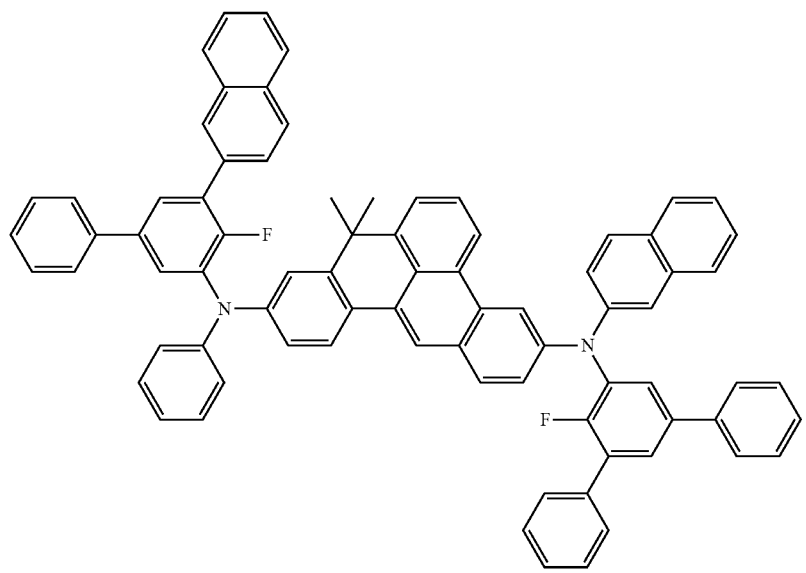
50
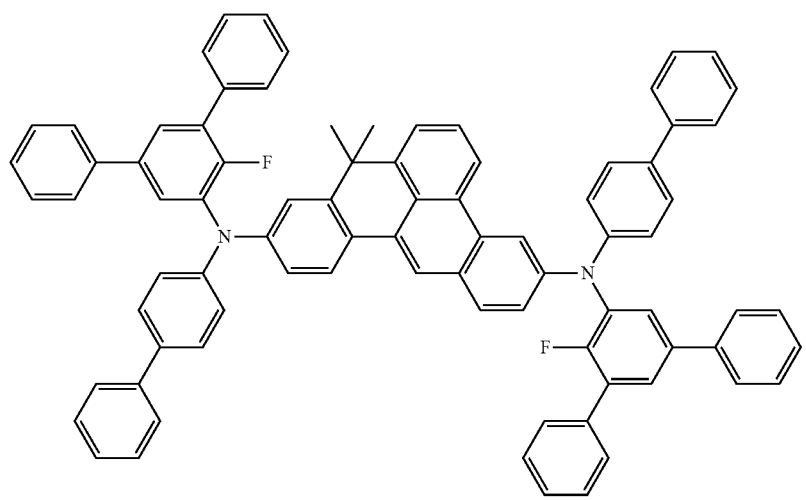
51
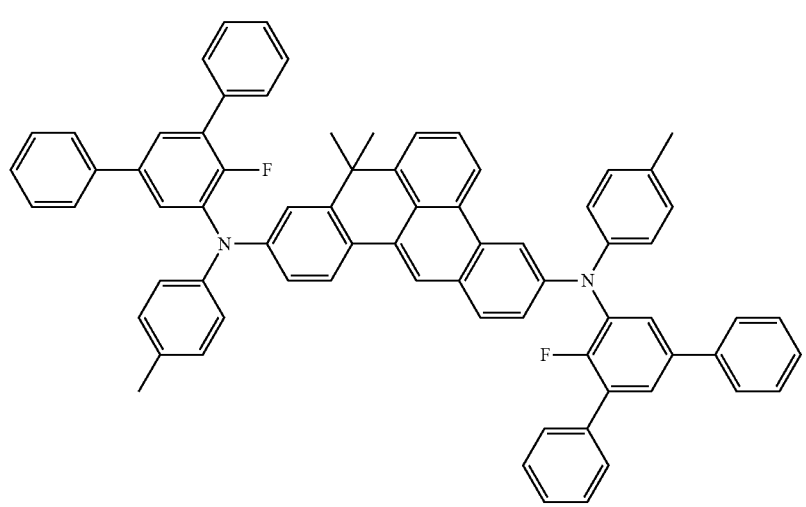
52

-continued
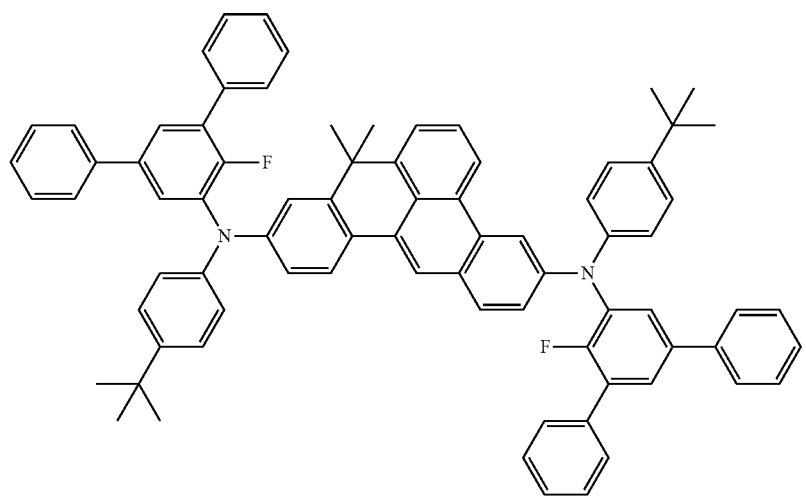
53
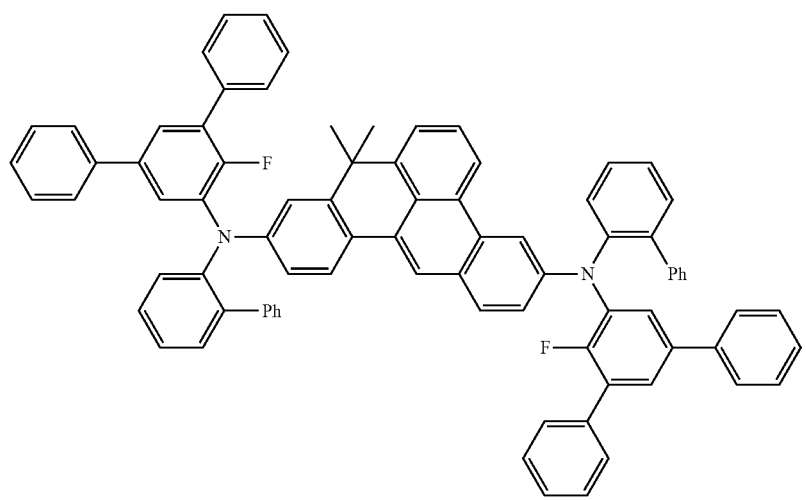
54
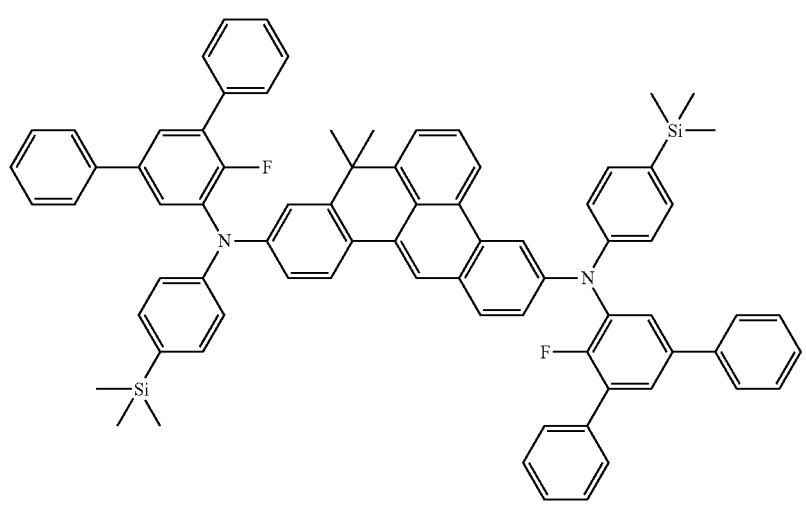
55

-continued
56
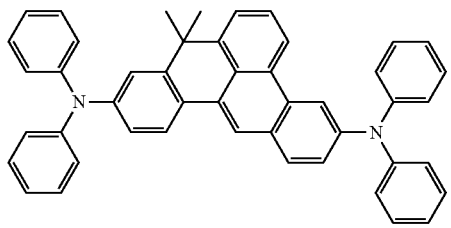
57
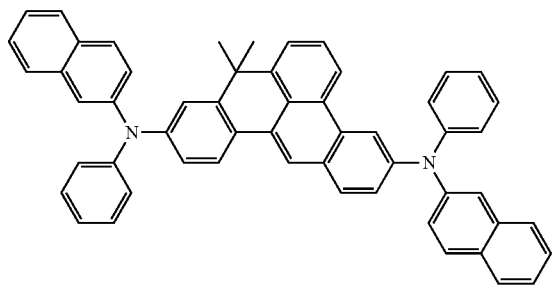
58
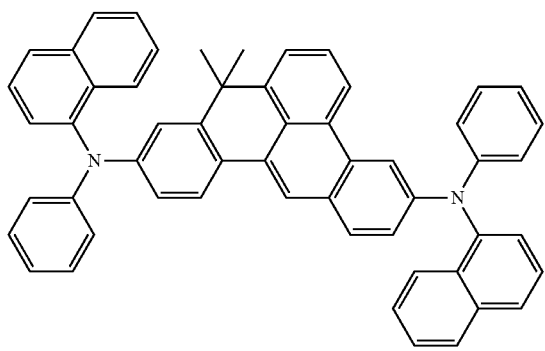
59
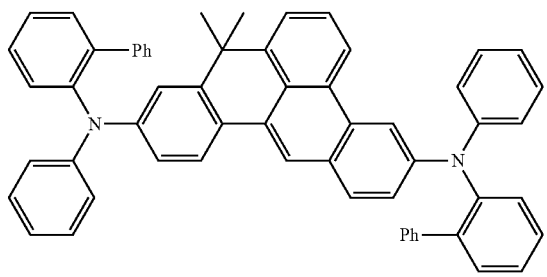
60
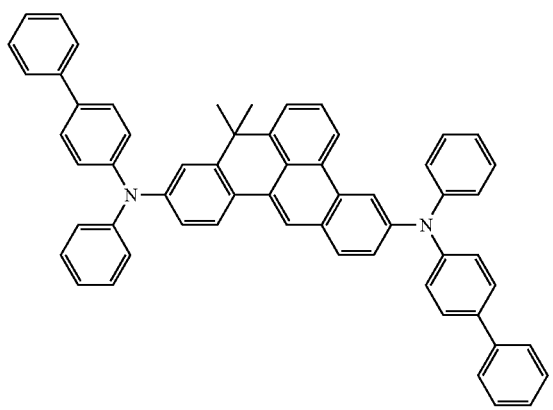
61
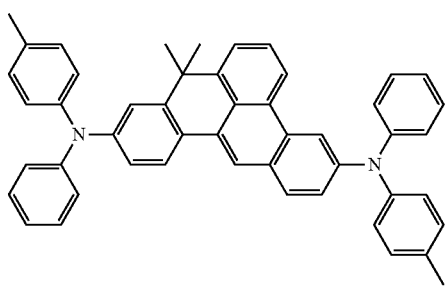
62
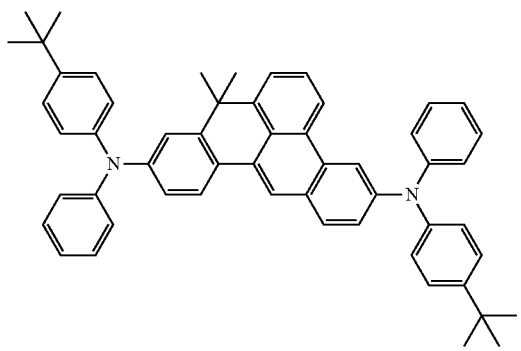
63
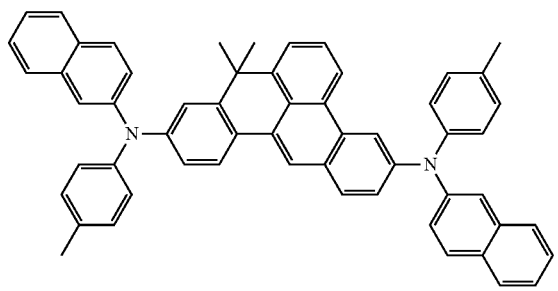

-continued
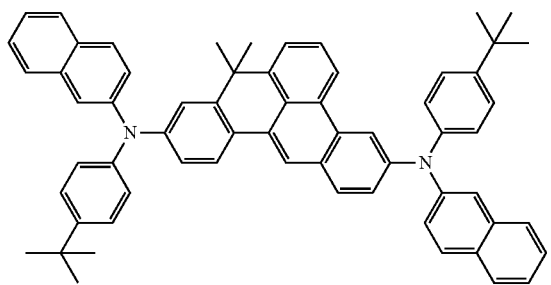
64
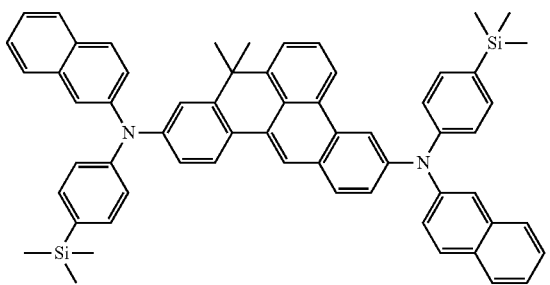
65
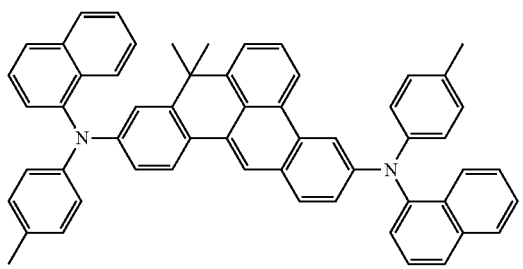
66
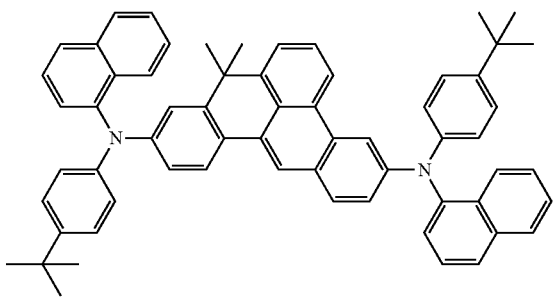
67
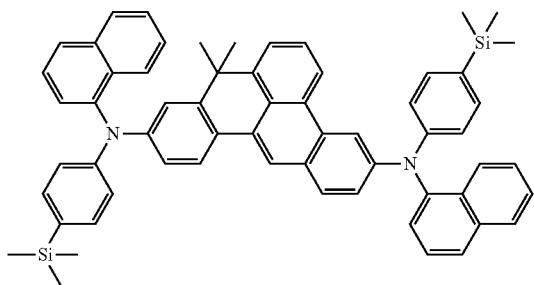
68
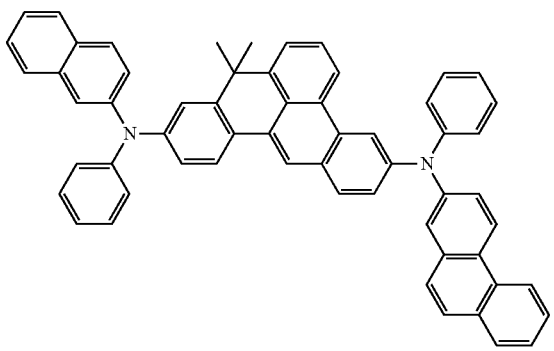
69
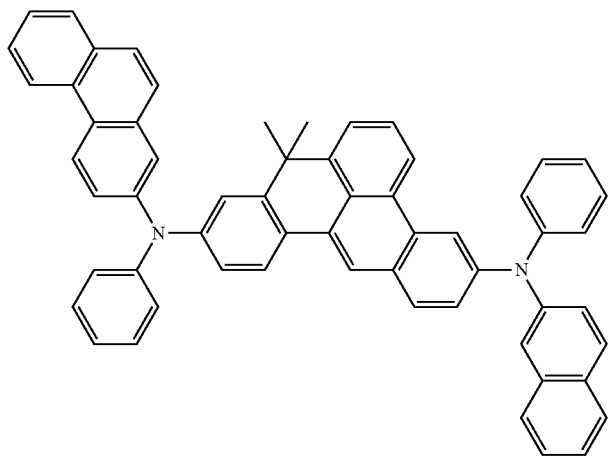
70

71
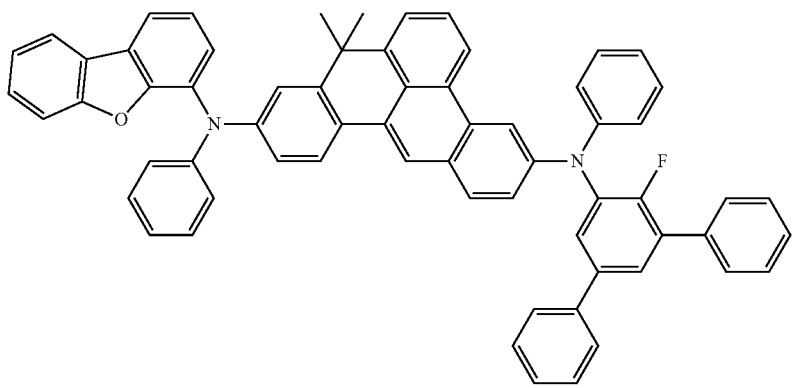
72
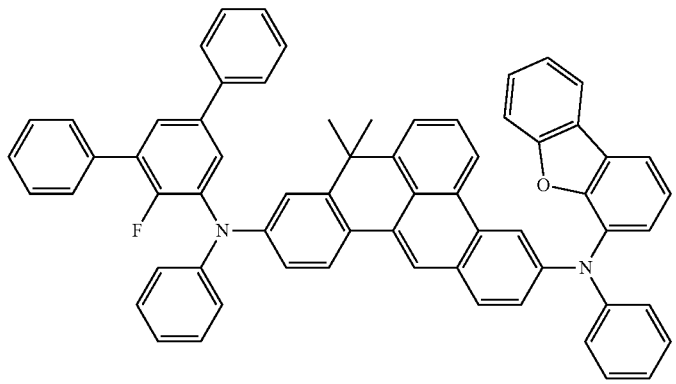
73
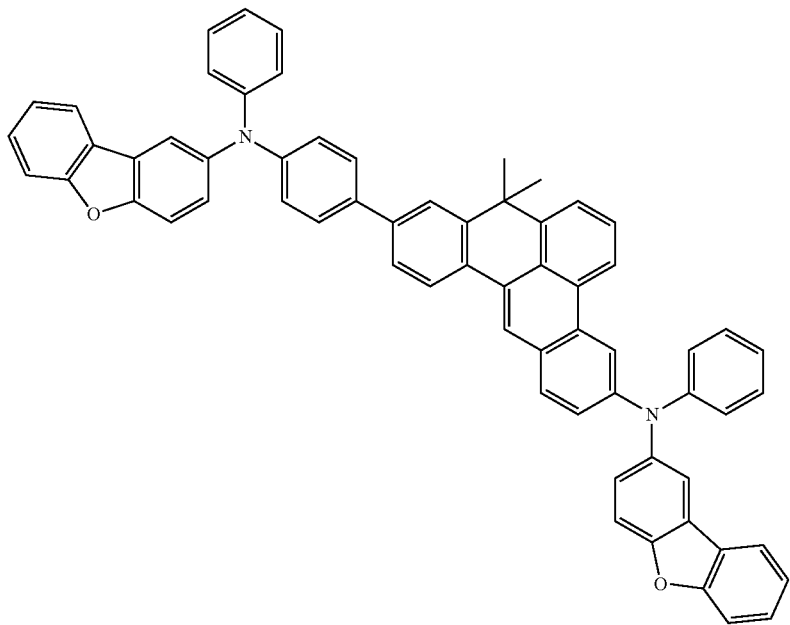

74
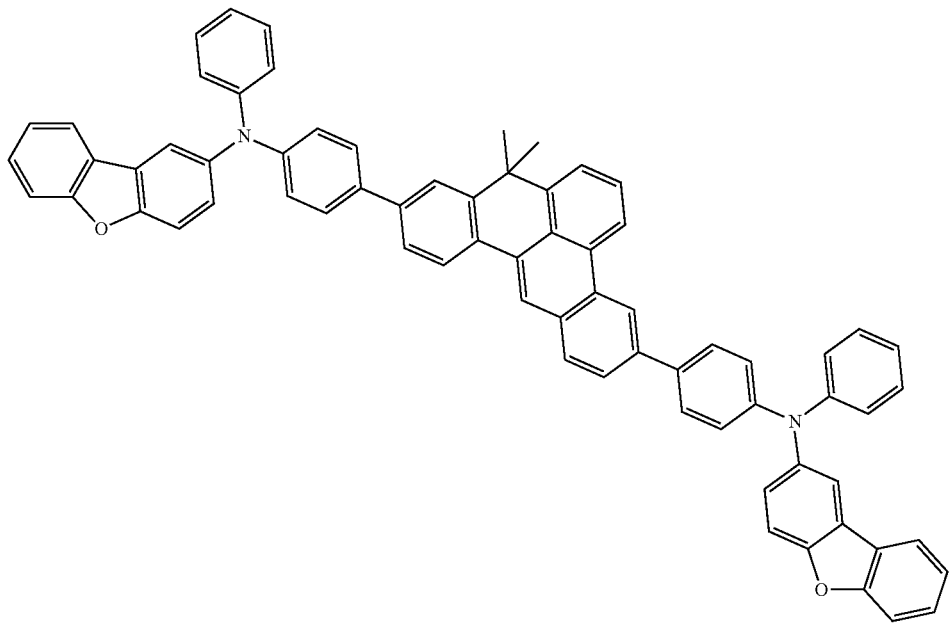
75
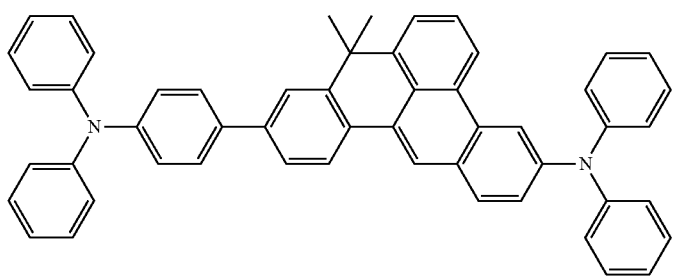
76
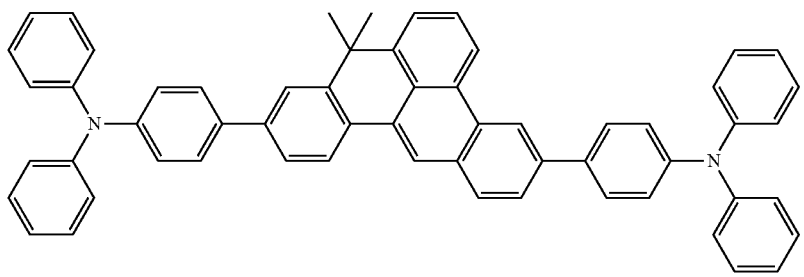
77
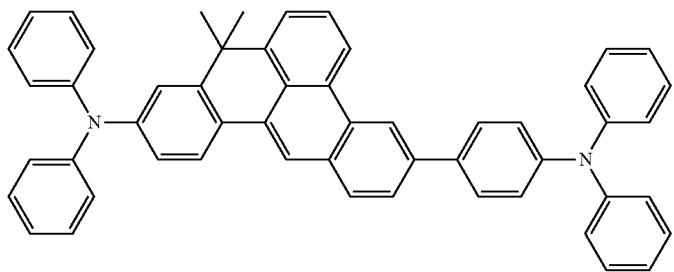

78
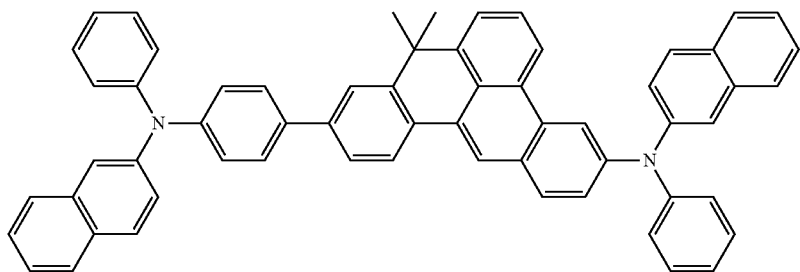
79
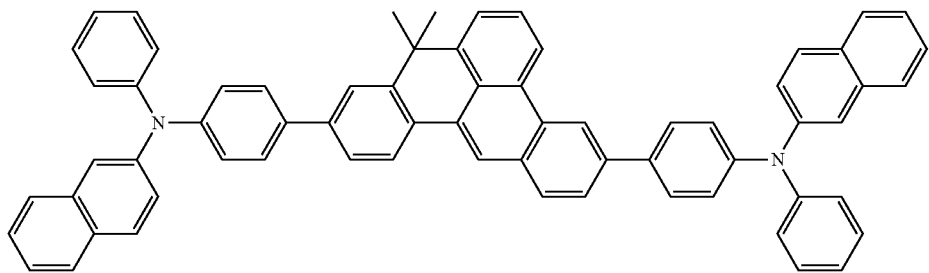
80
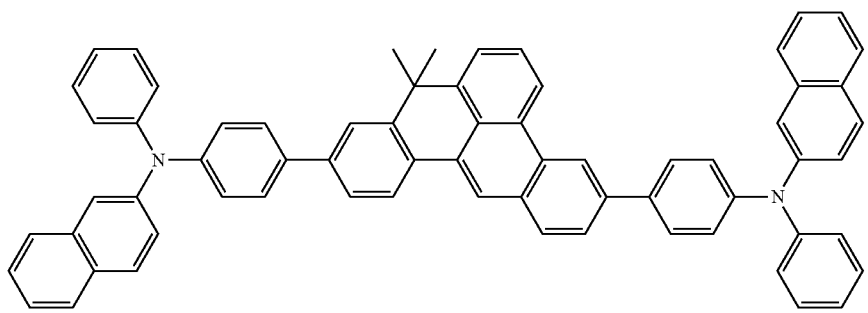
81
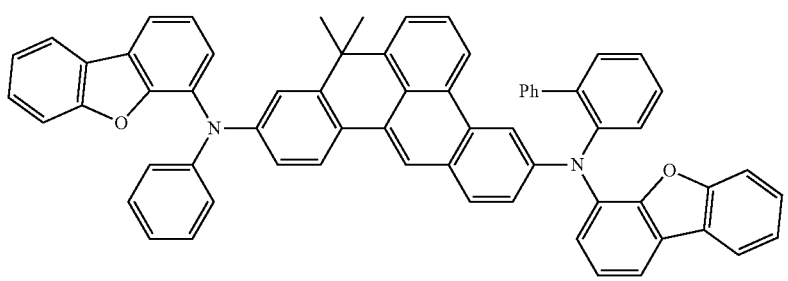
82
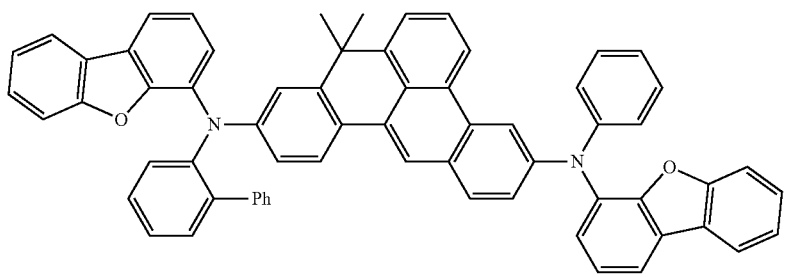

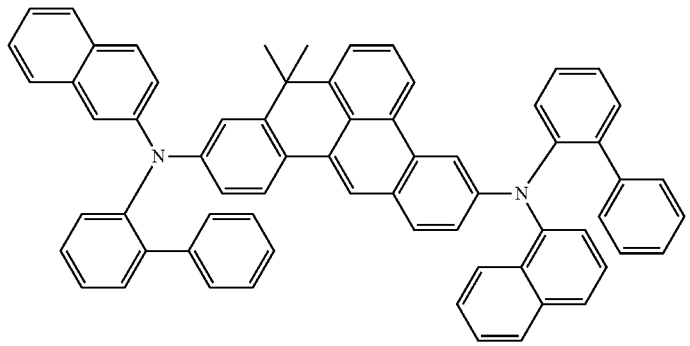
83
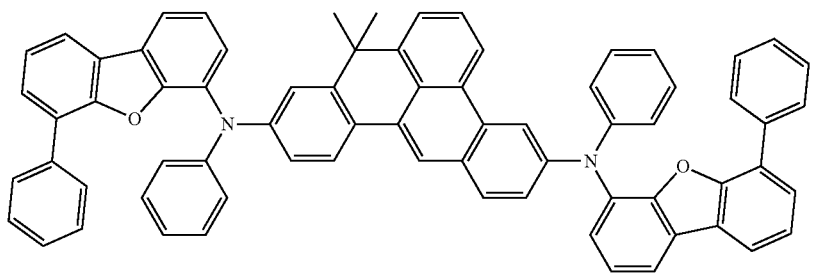
84
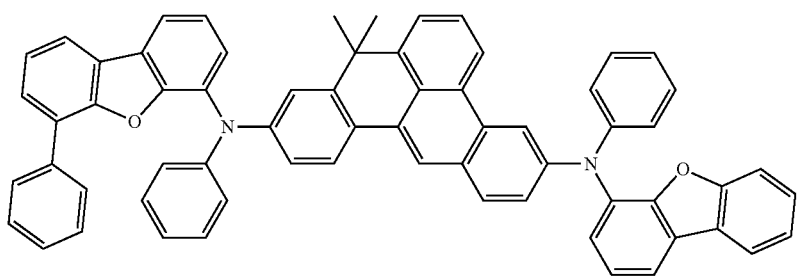
85
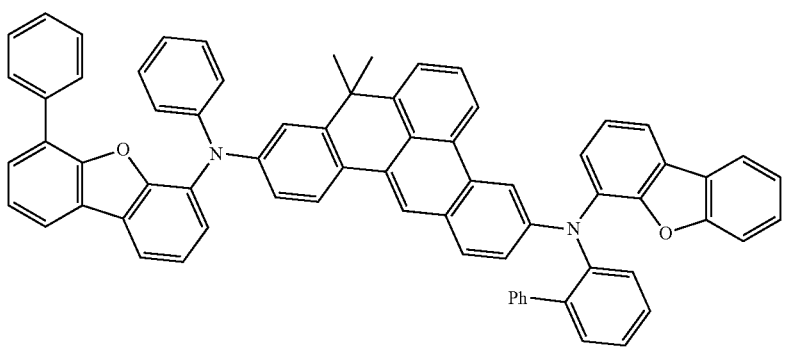
86
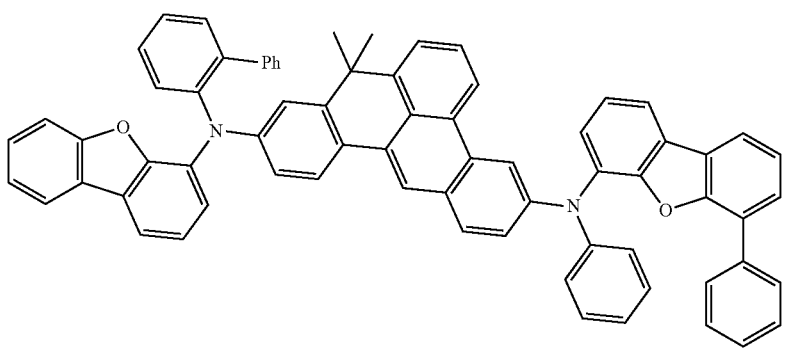
87

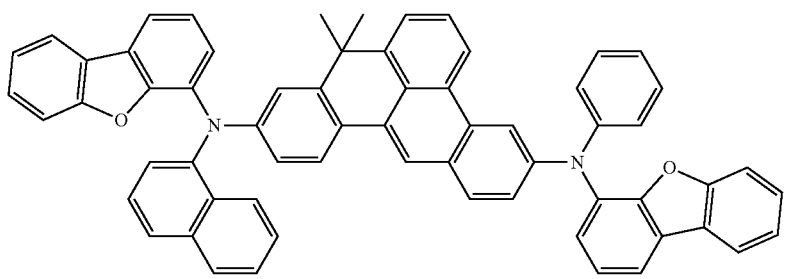
88
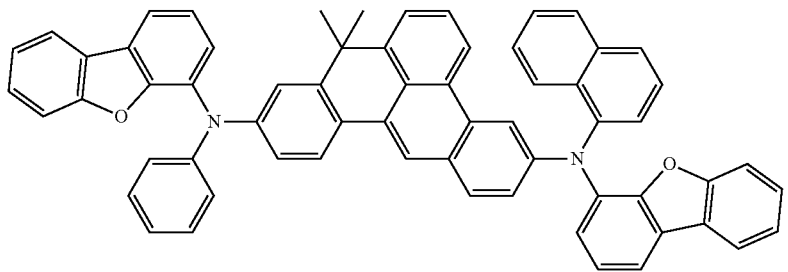
89
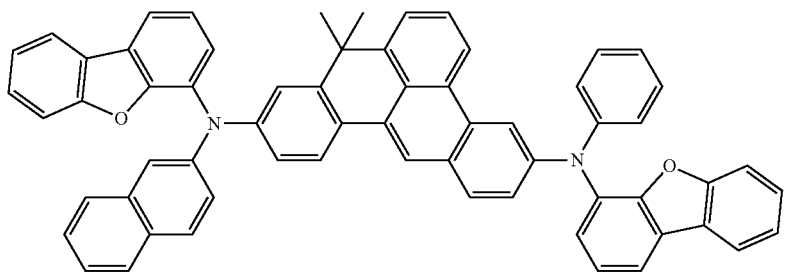
90
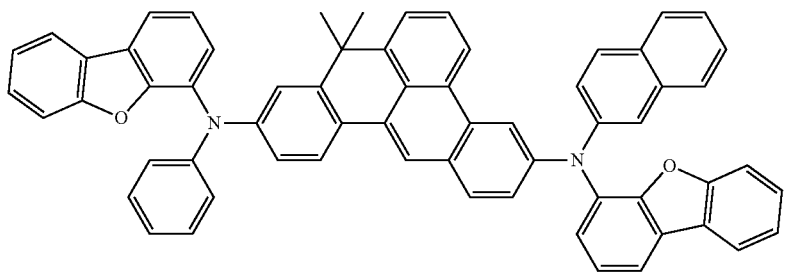
91
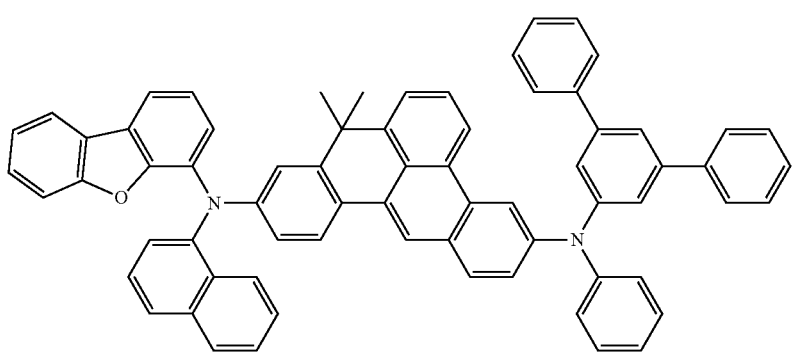
92

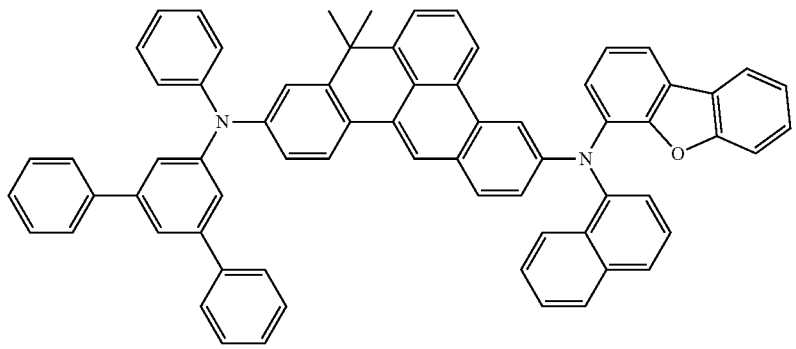
93
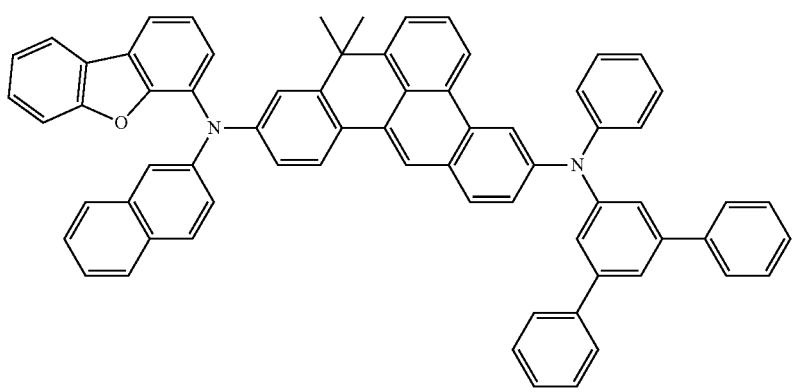
94
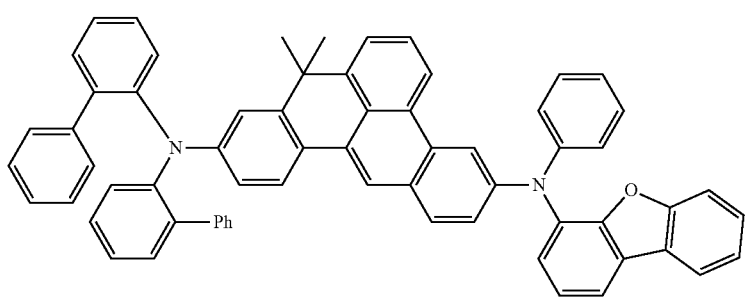
95
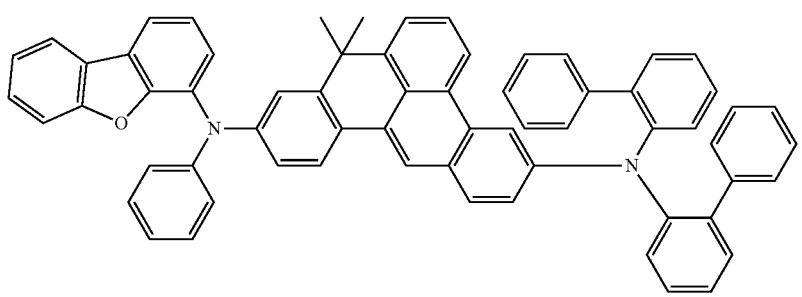
96

-continued
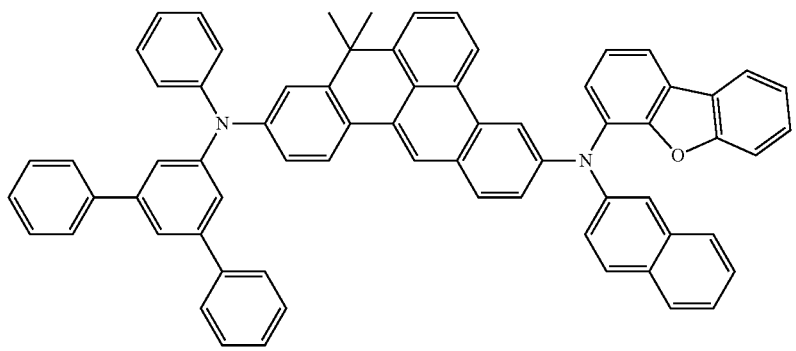
97
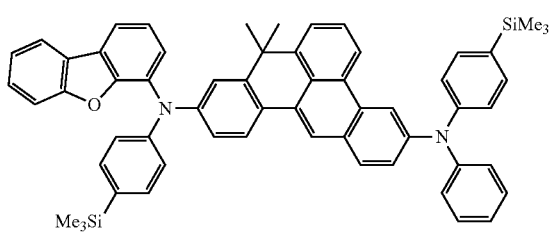
98
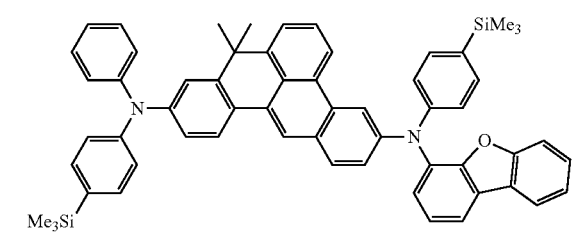
99
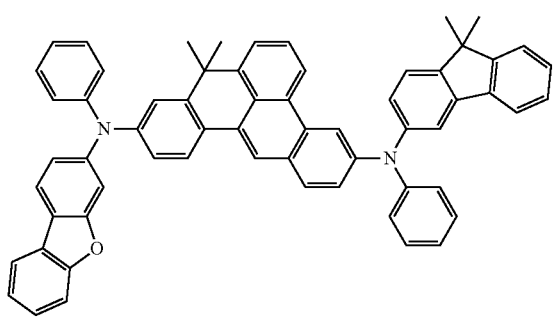
100
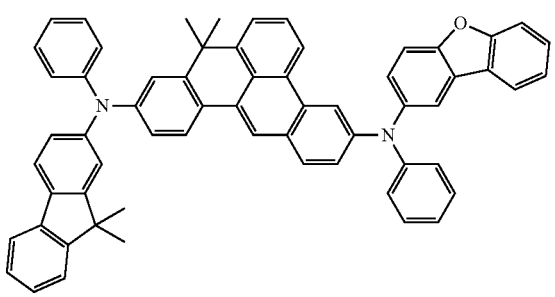
101
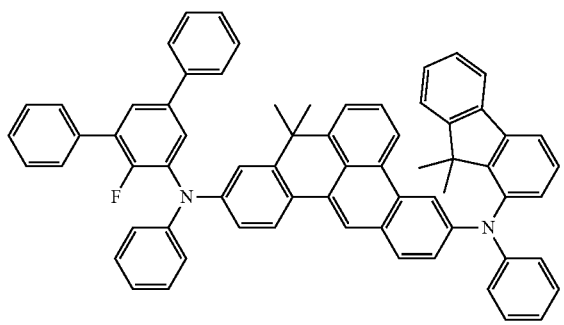
102
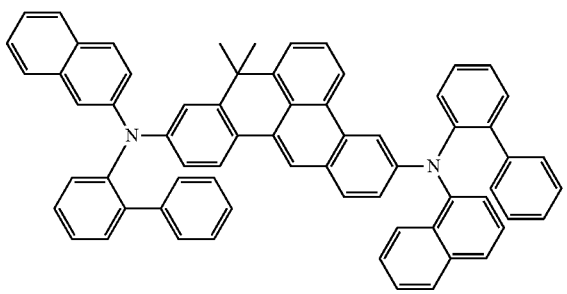
103
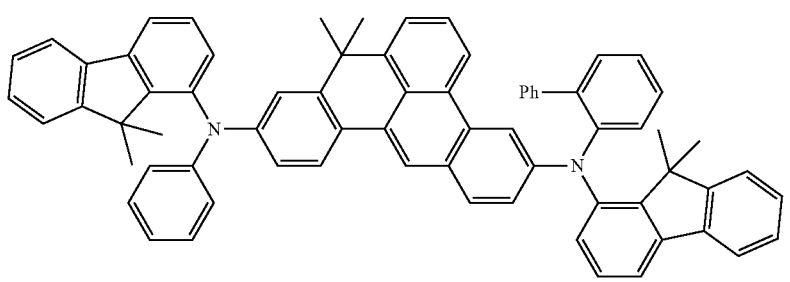
104

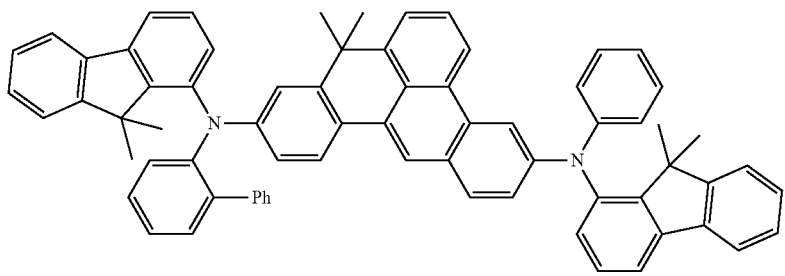
105
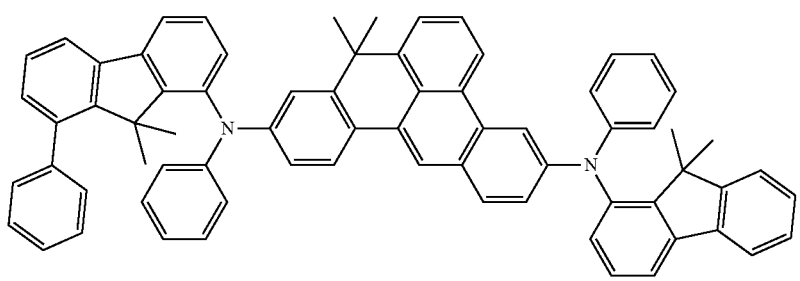
106
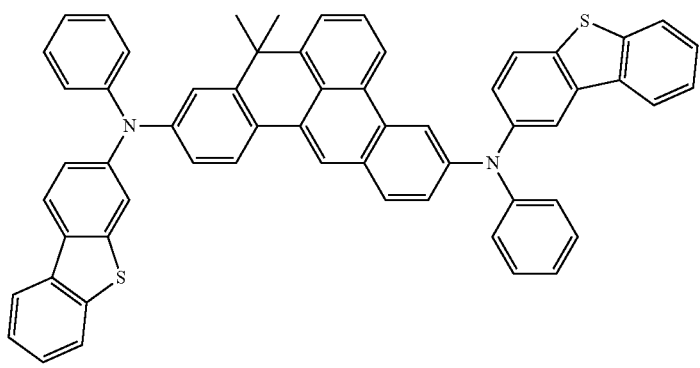
107
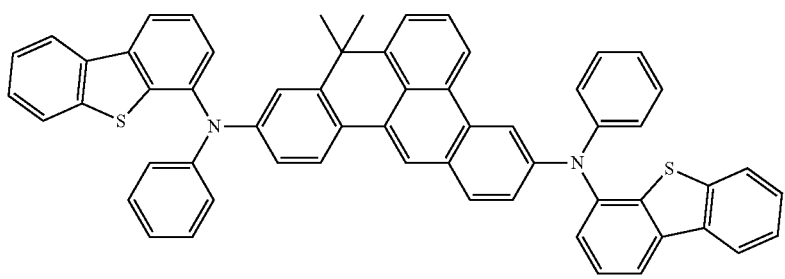
108
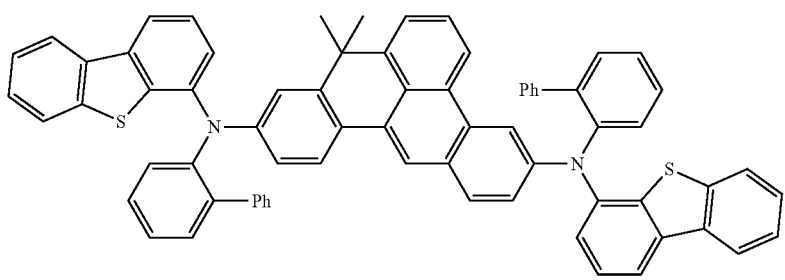
109

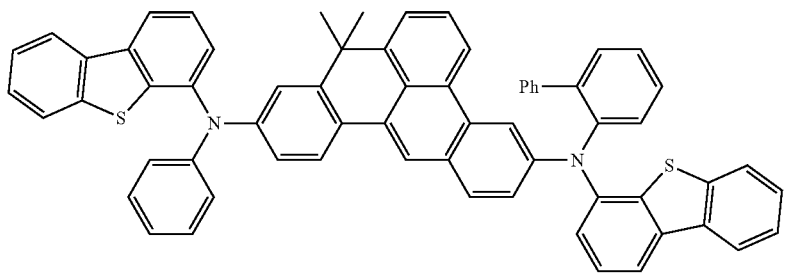
110
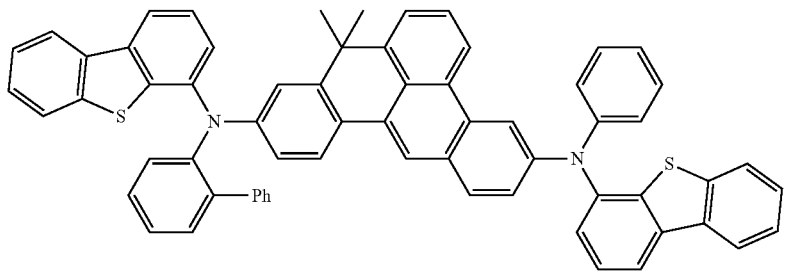
111
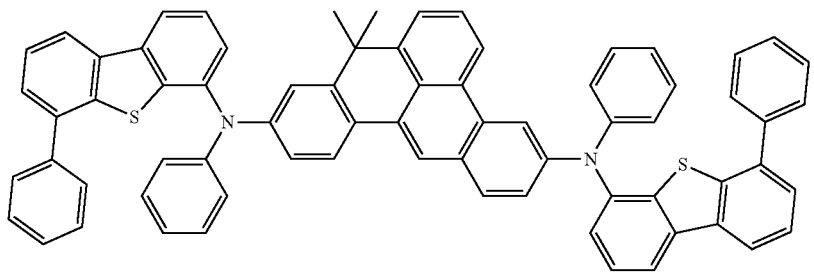
112
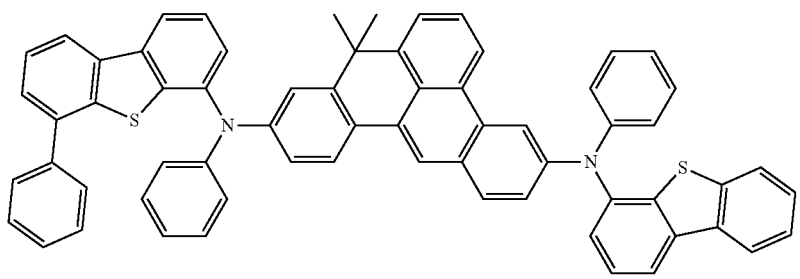
113
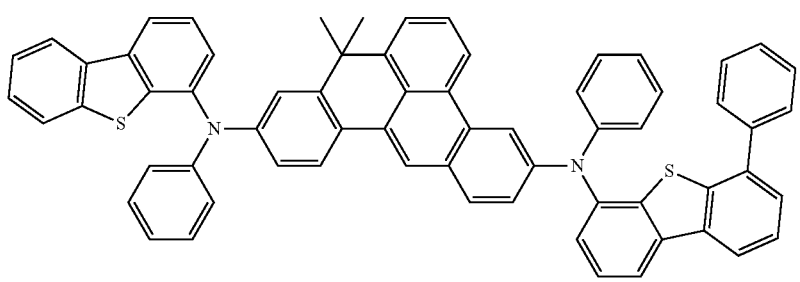
114

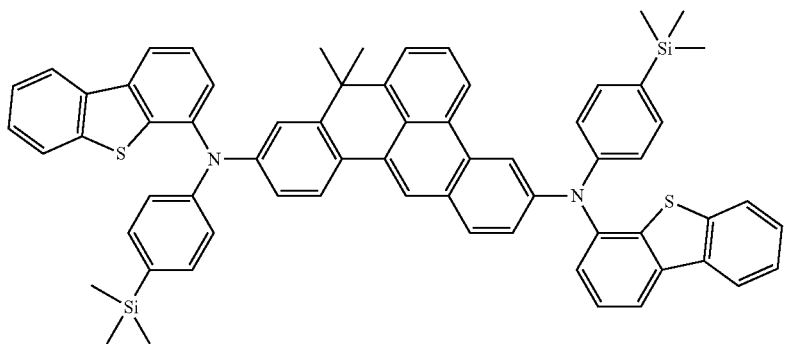
115
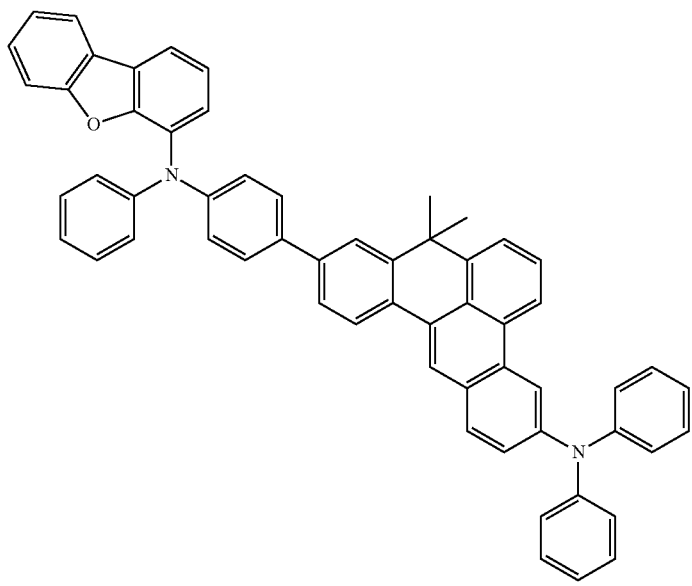
116
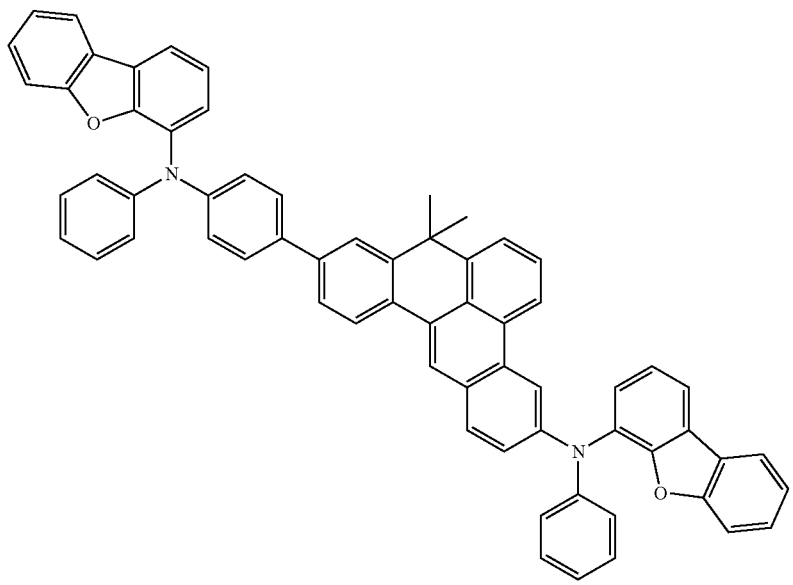
117

118
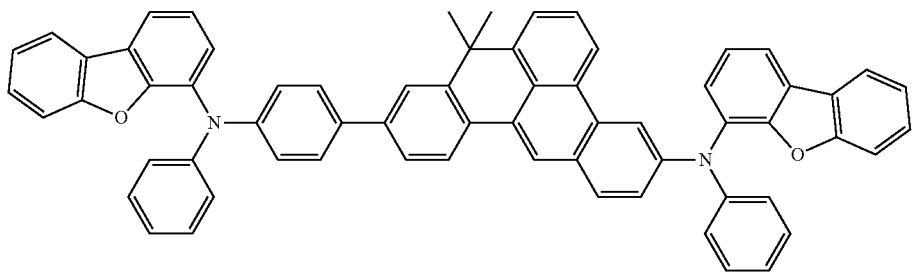
119 120
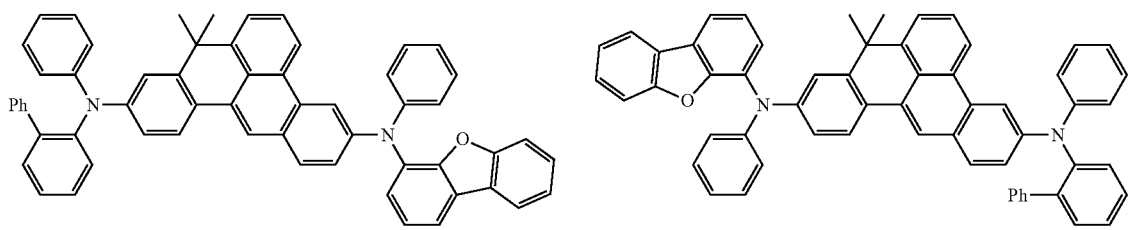
121 122
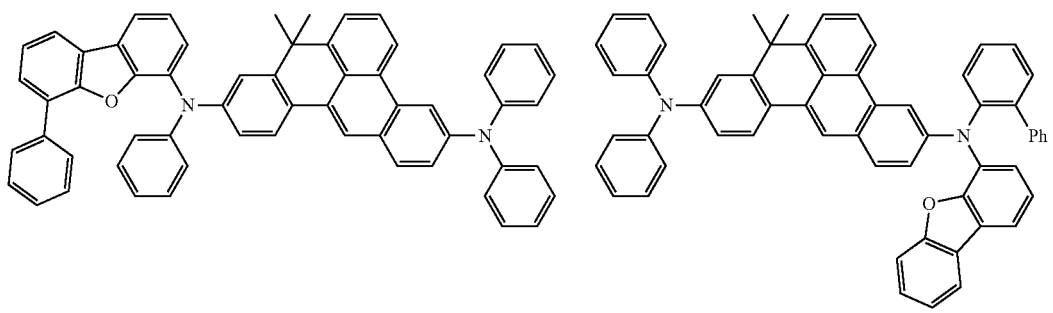
123 124
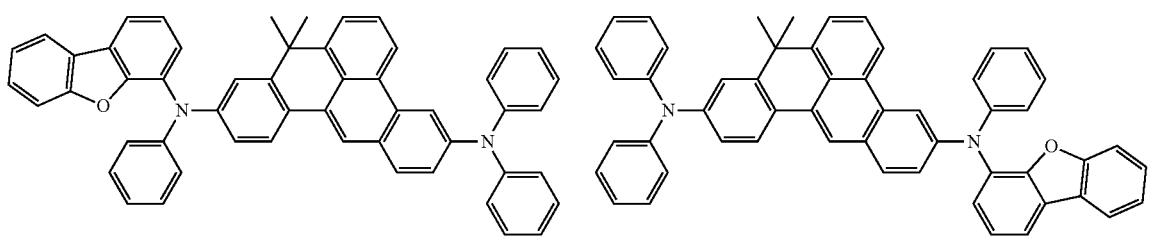
125 126
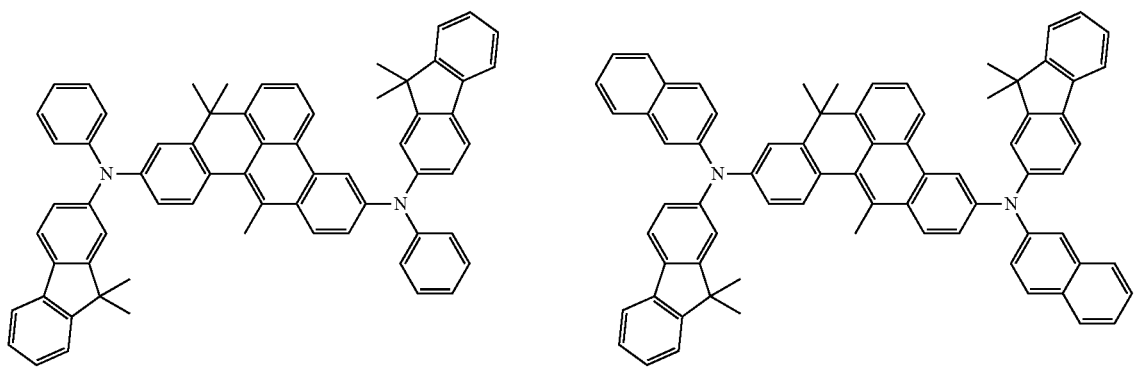

-continued
127
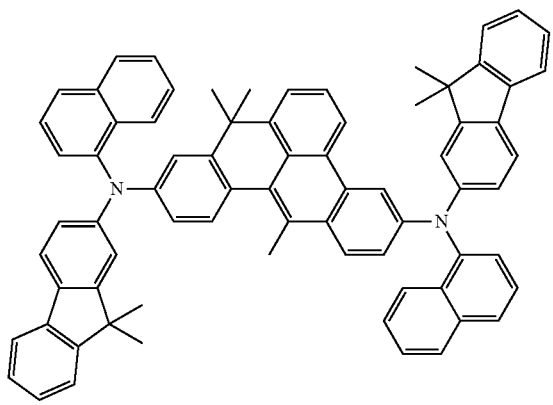
128
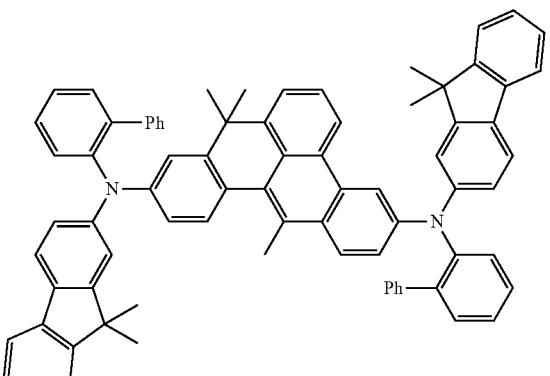
129
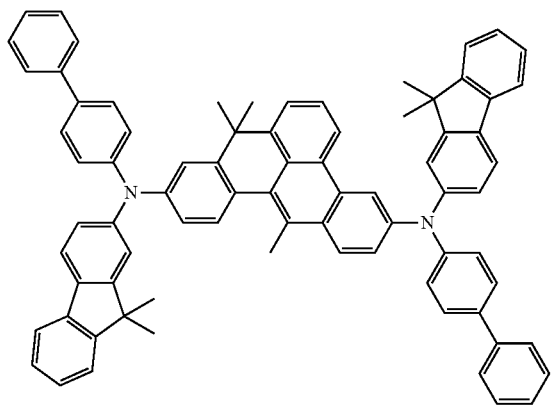
130
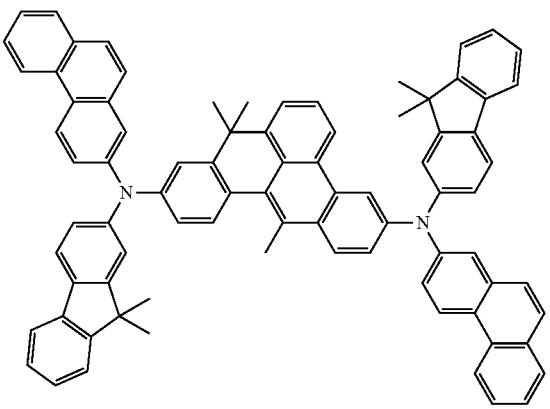
131
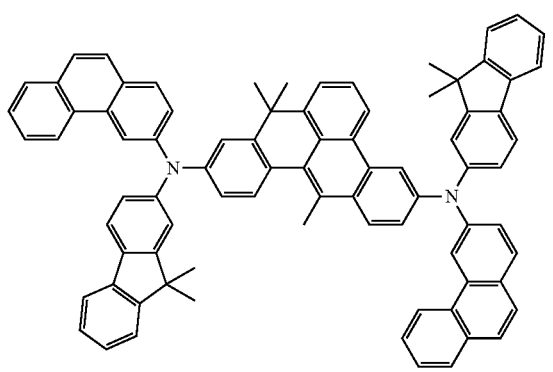
132
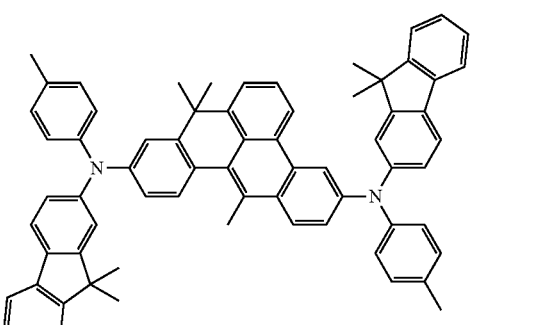
133
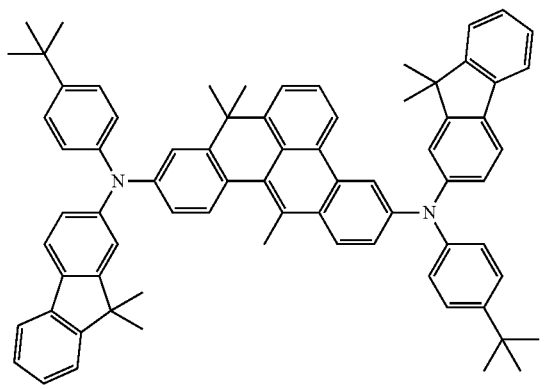
134
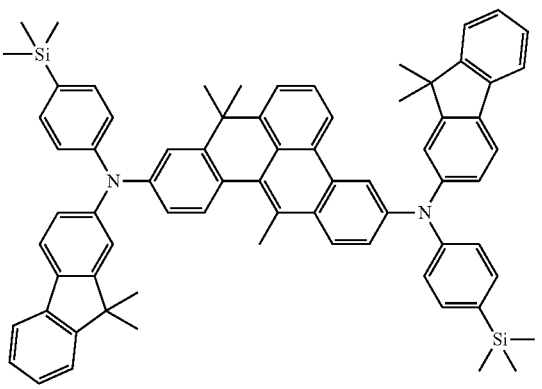

321
322
-continued
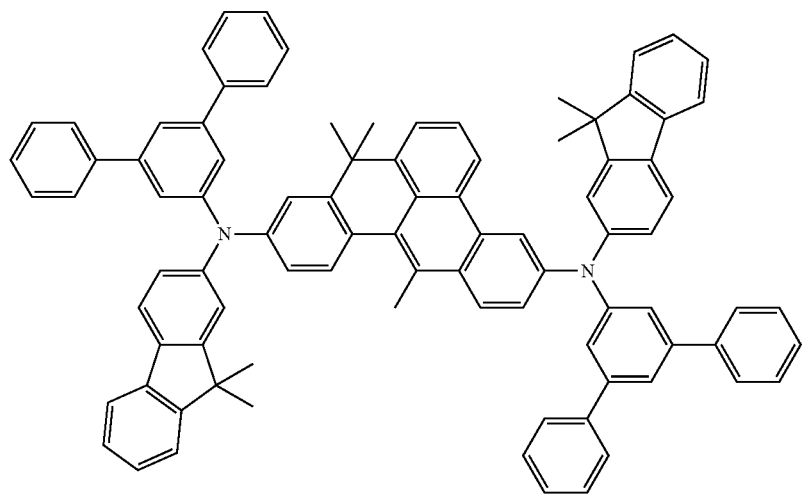
135
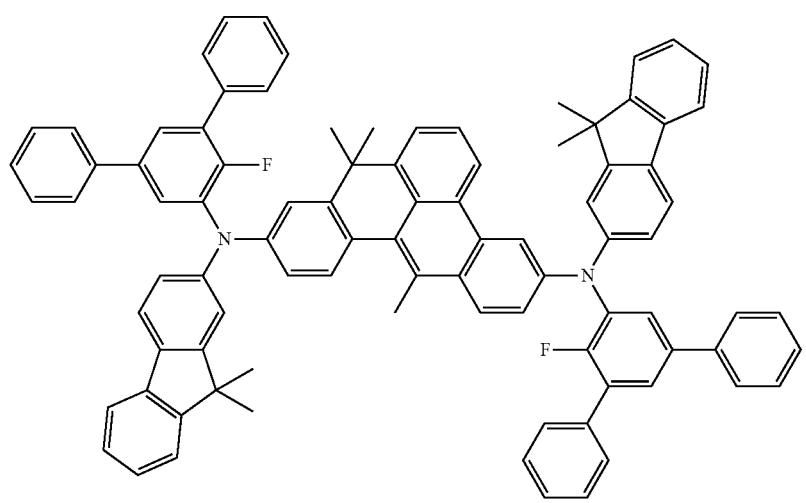
136
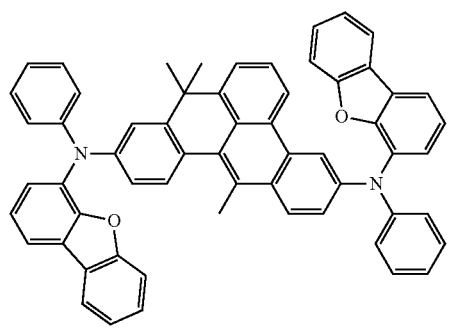
137
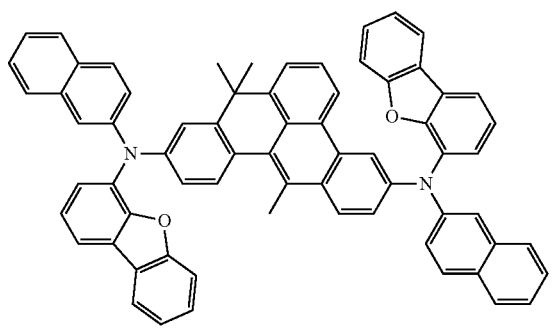
138

-continued
139
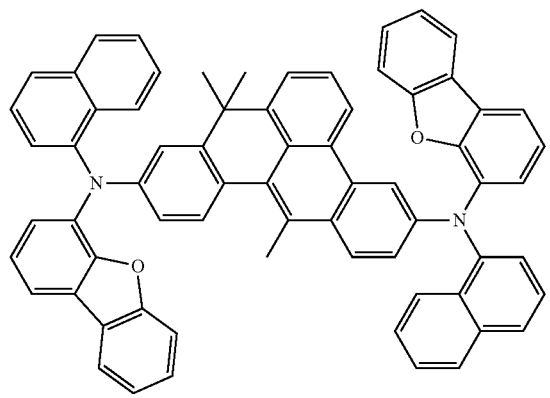
140
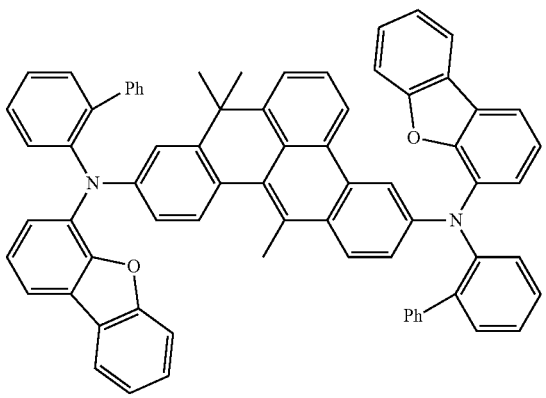
141
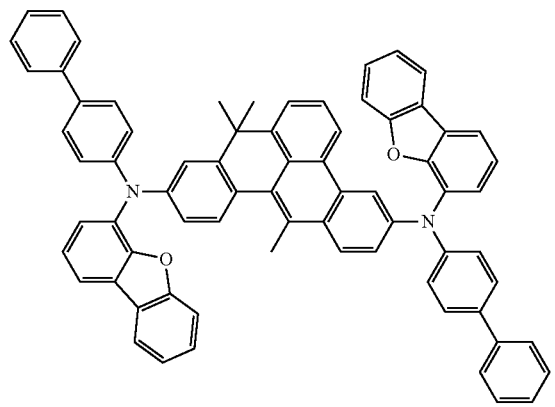
142
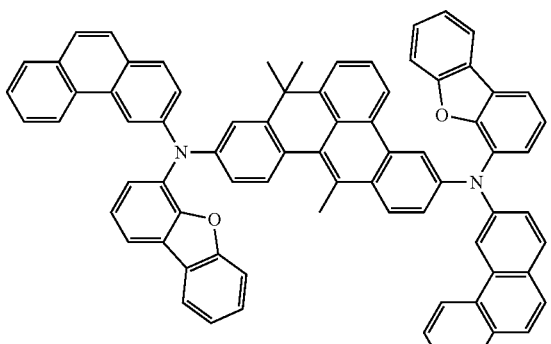
143
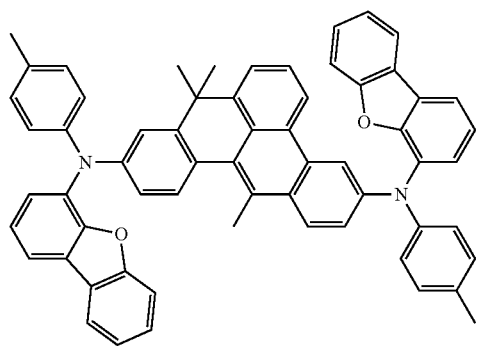
144
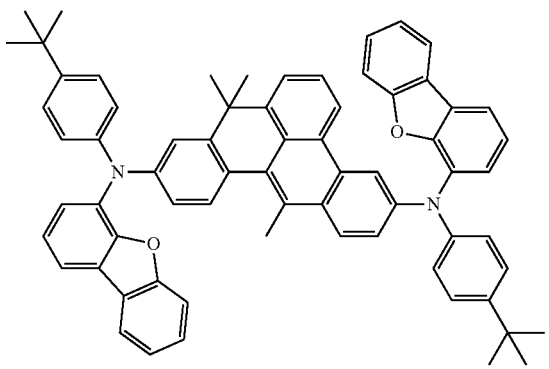
145
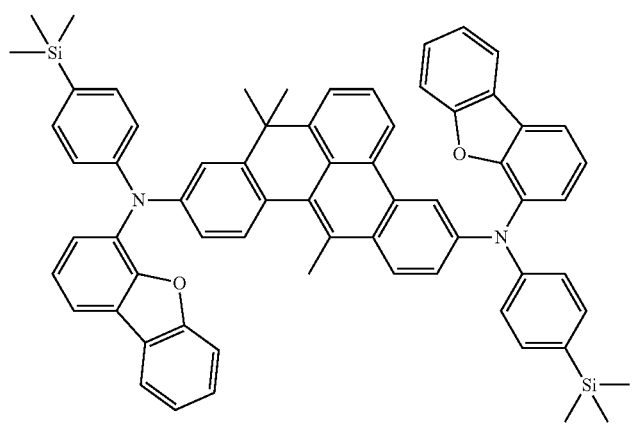

146
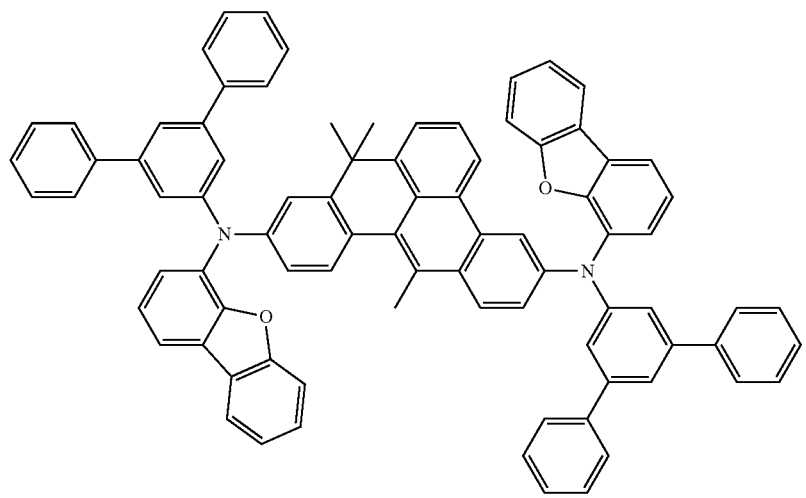
147
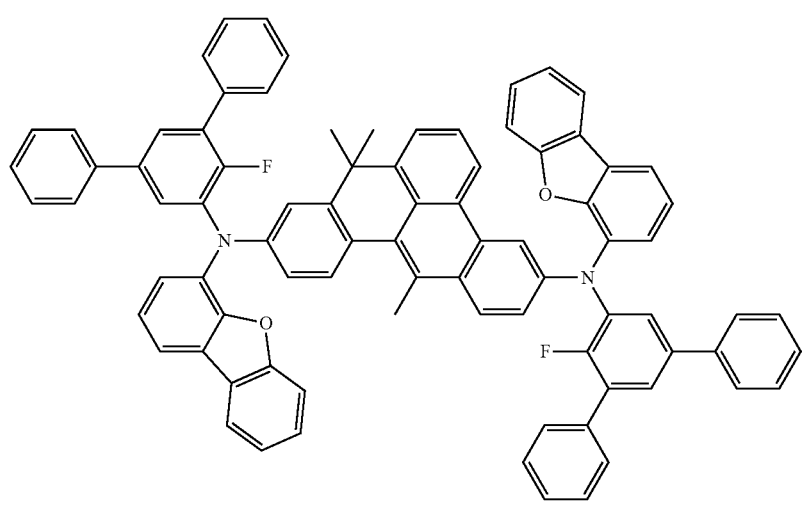
148
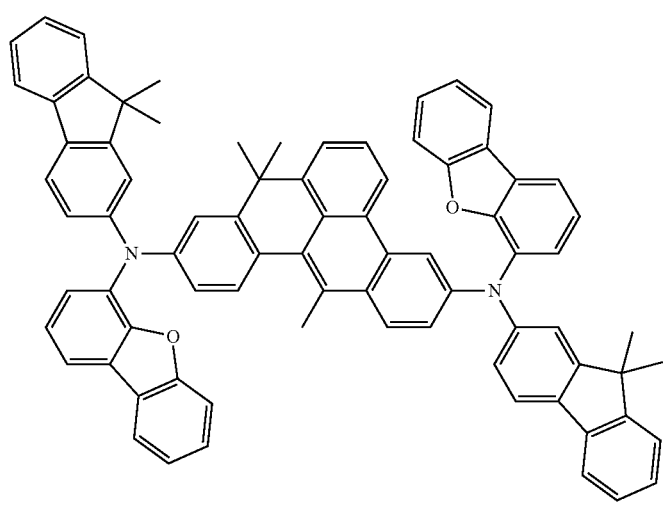

149
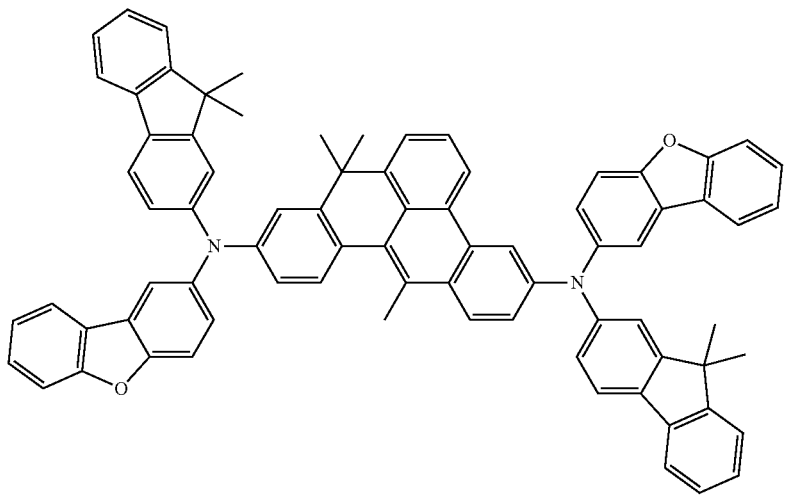
150
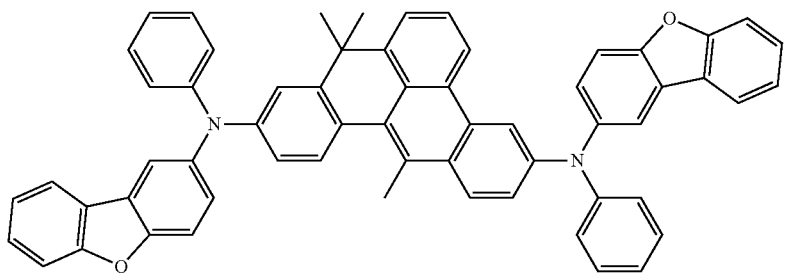
151
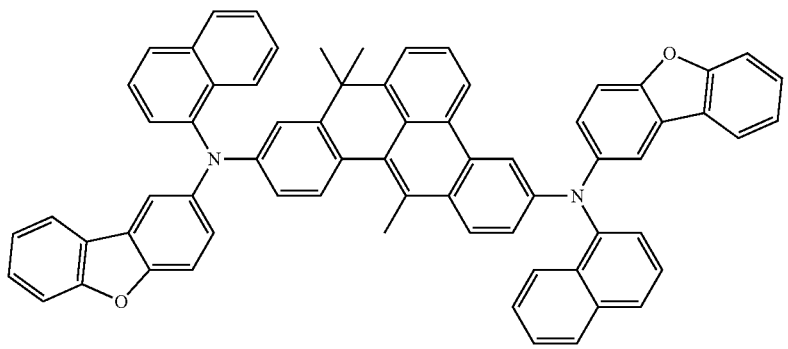
152
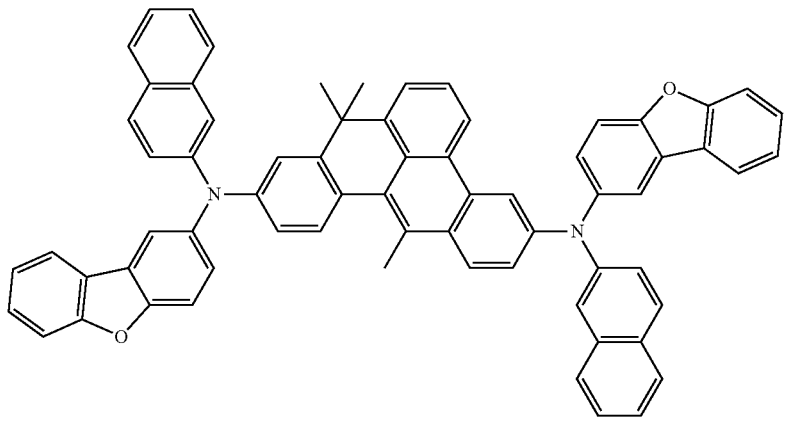

153
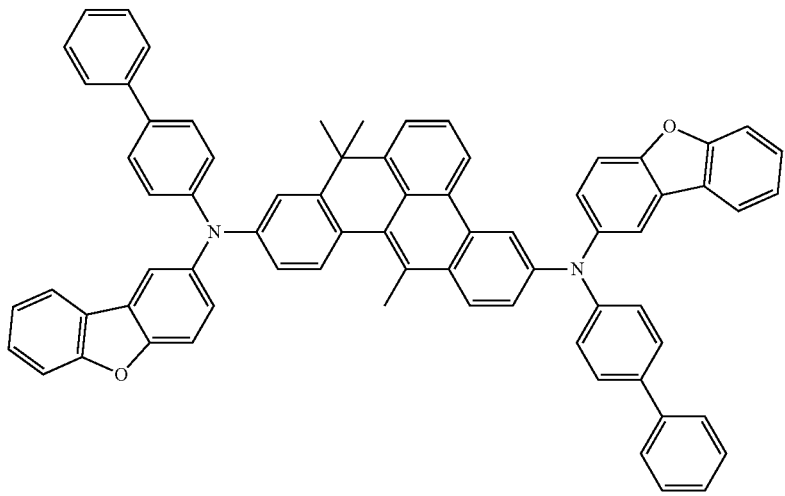
154
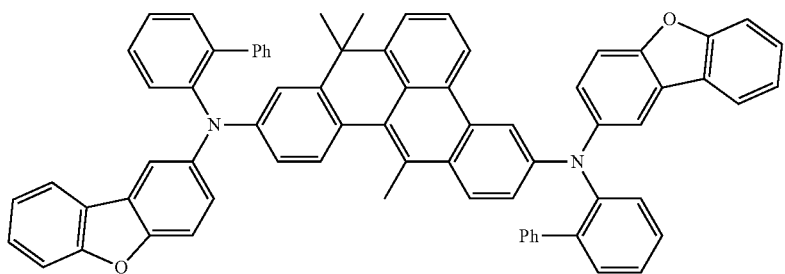
155
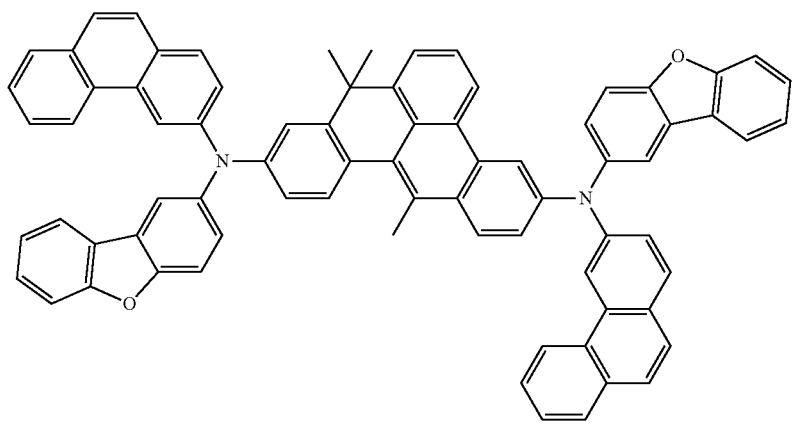
156
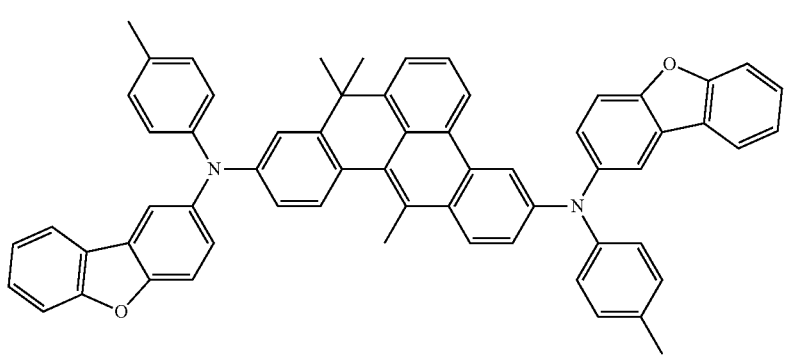

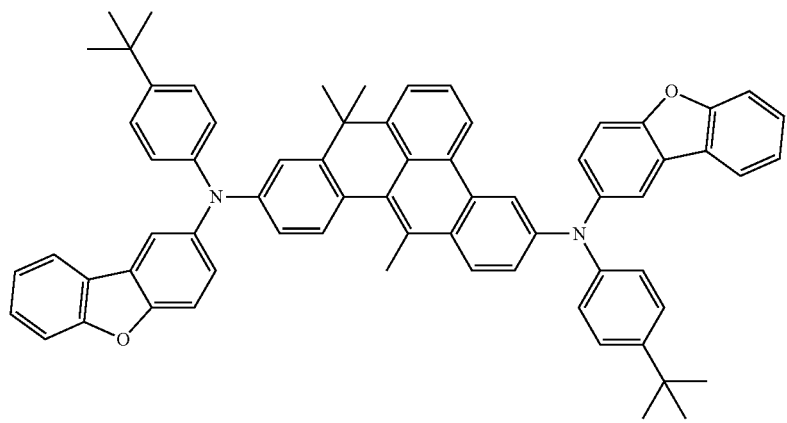
157
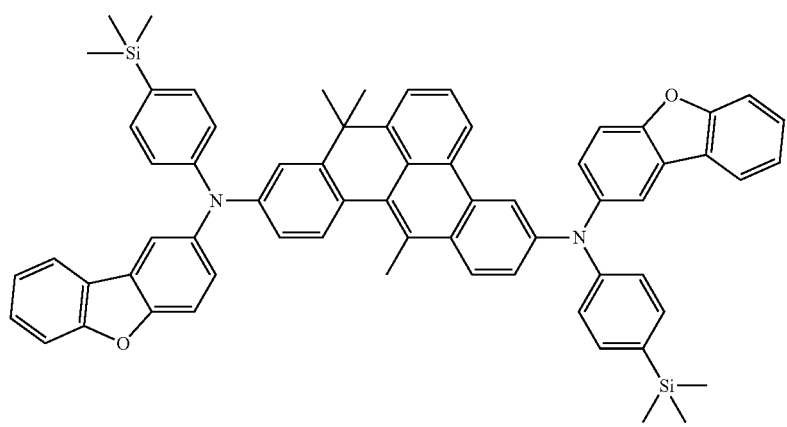
158
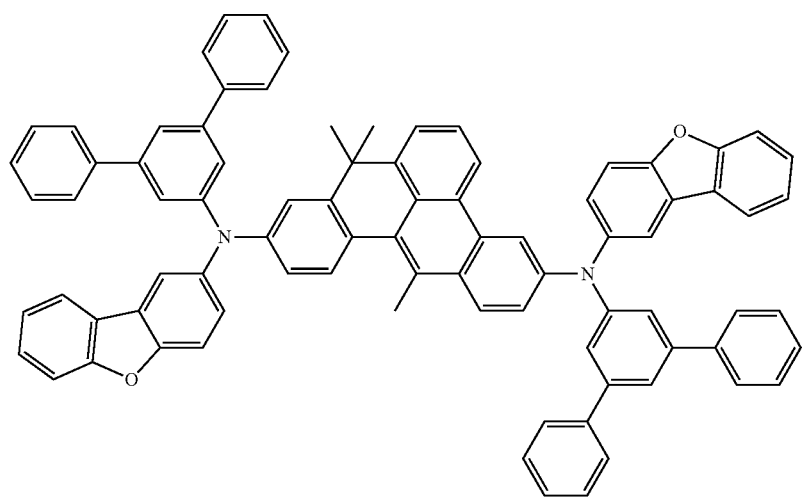
159

160
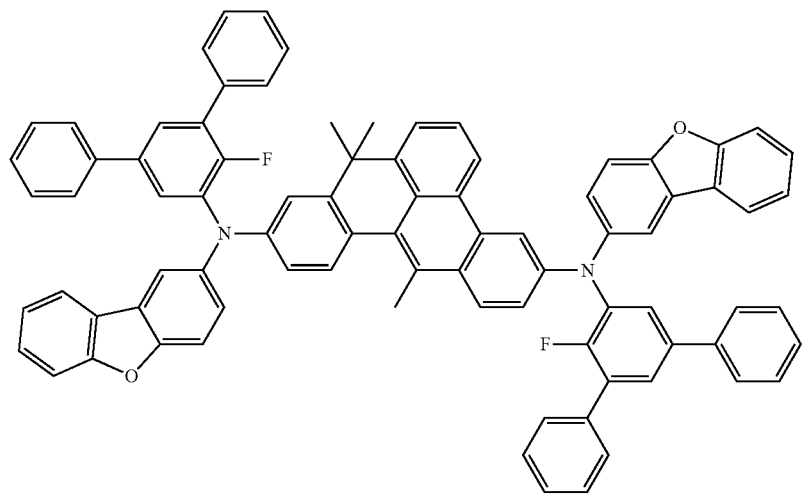
161 162
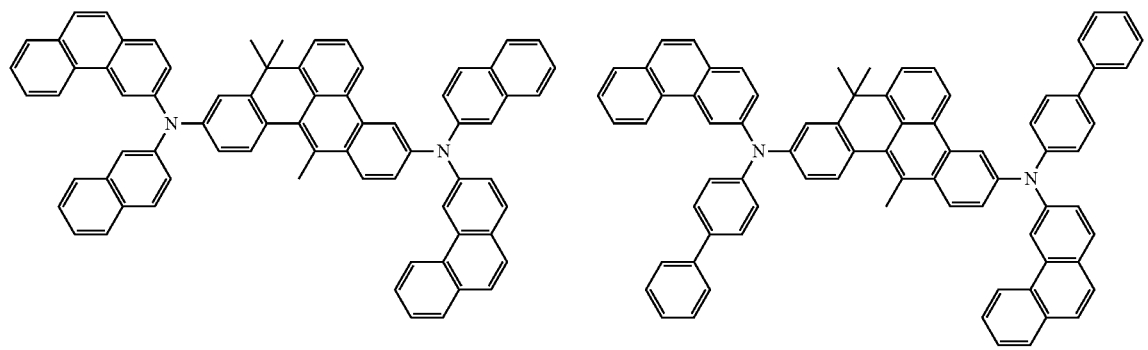
163 164
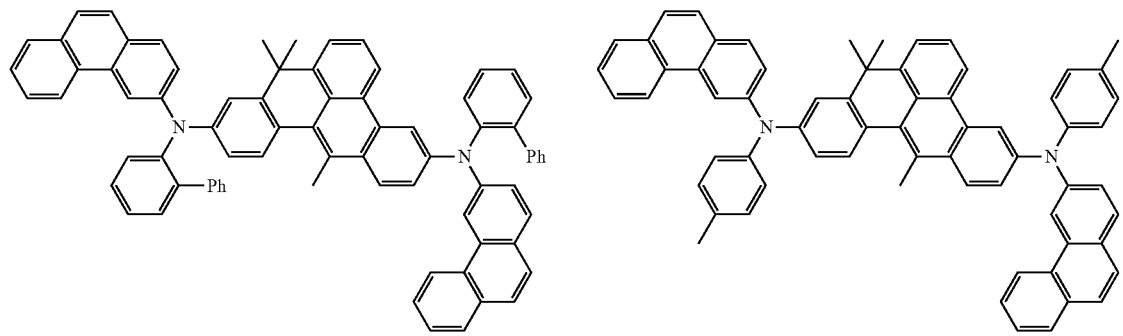
165 166
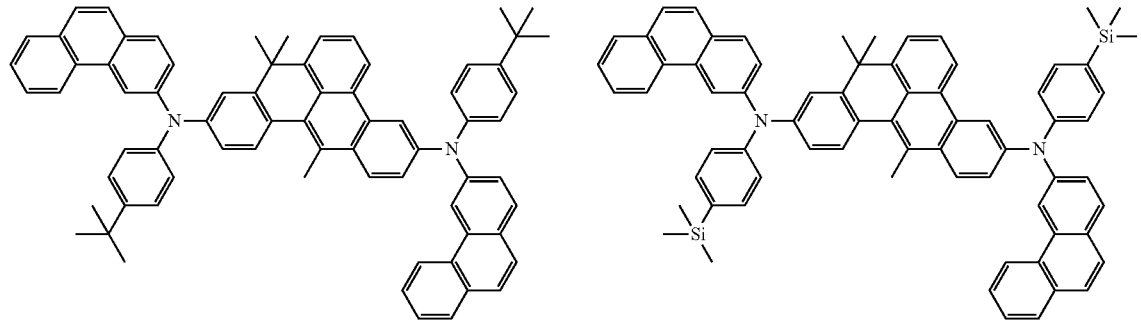

-continued
167
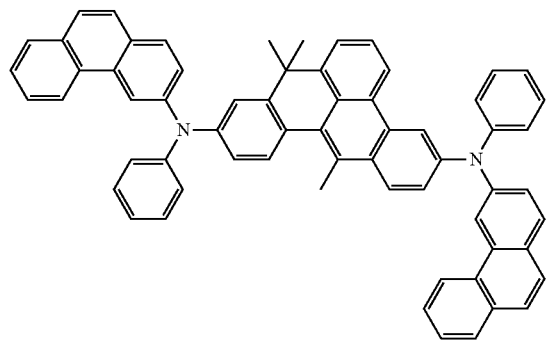
168
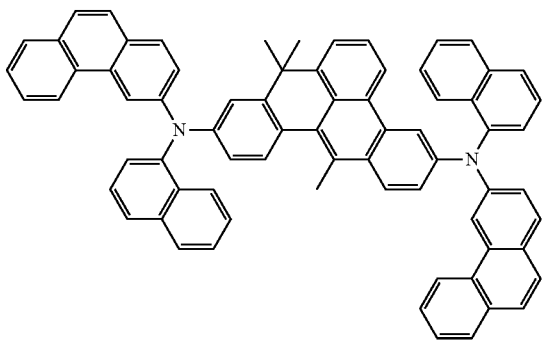
169
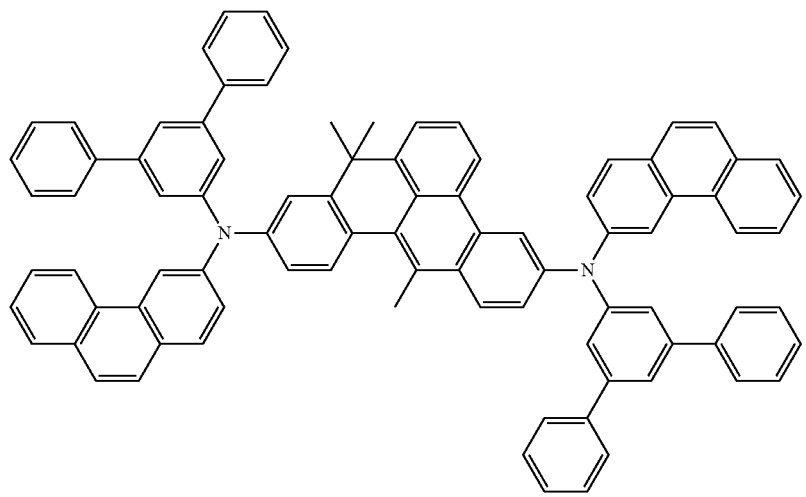
170
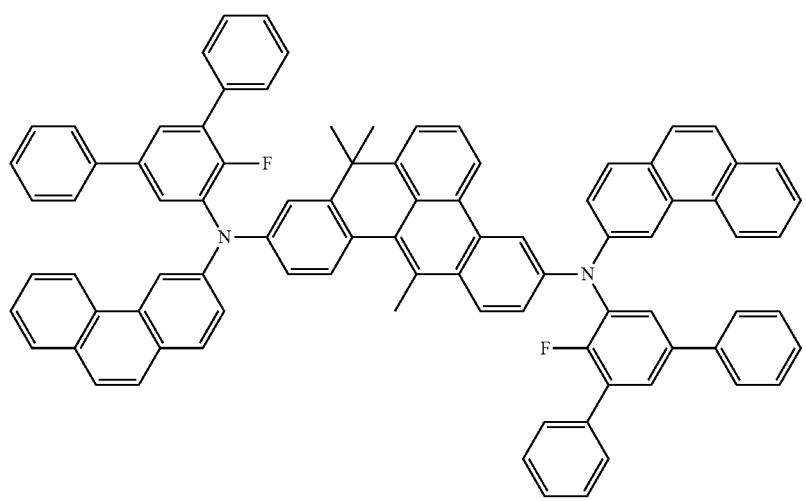

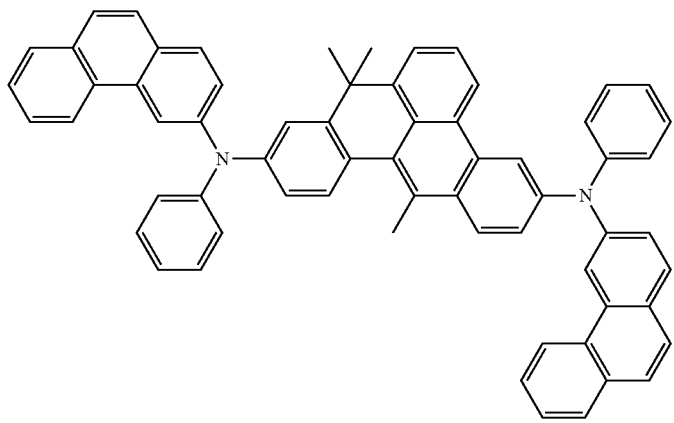
171
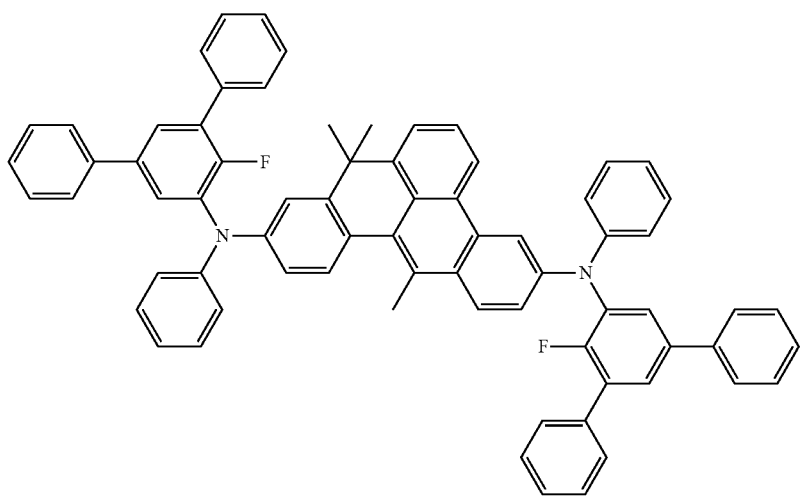
172
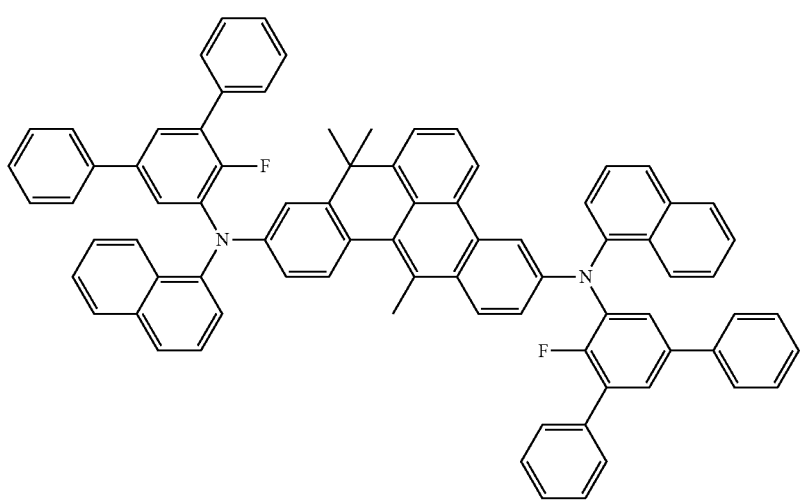
173

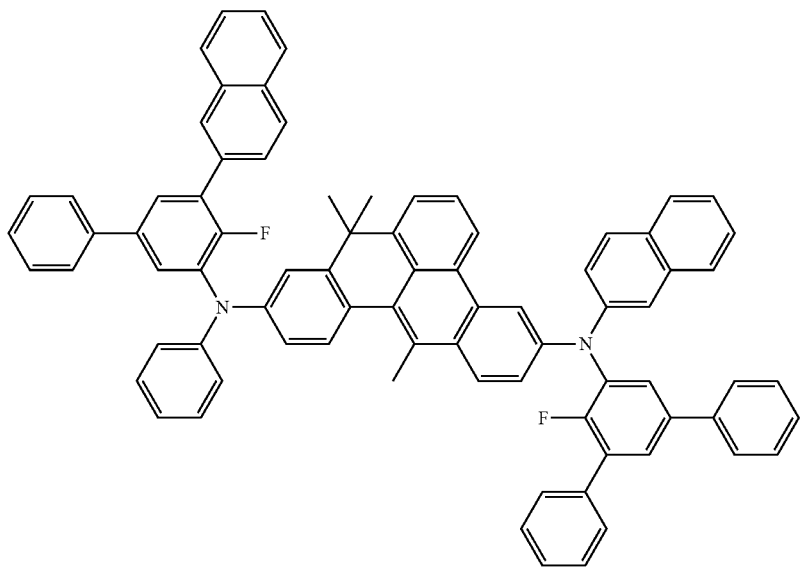
174
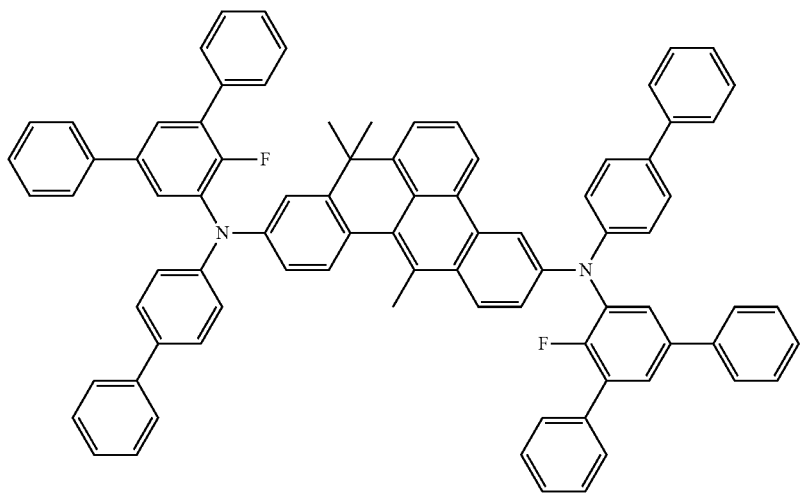
175
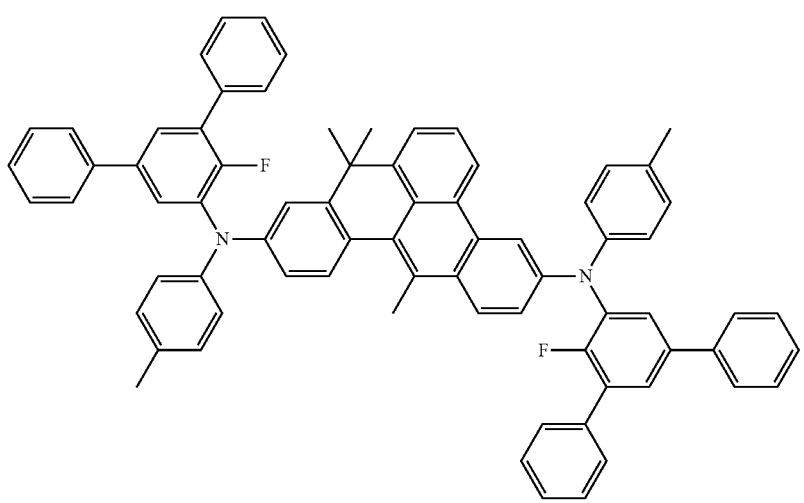
176

177
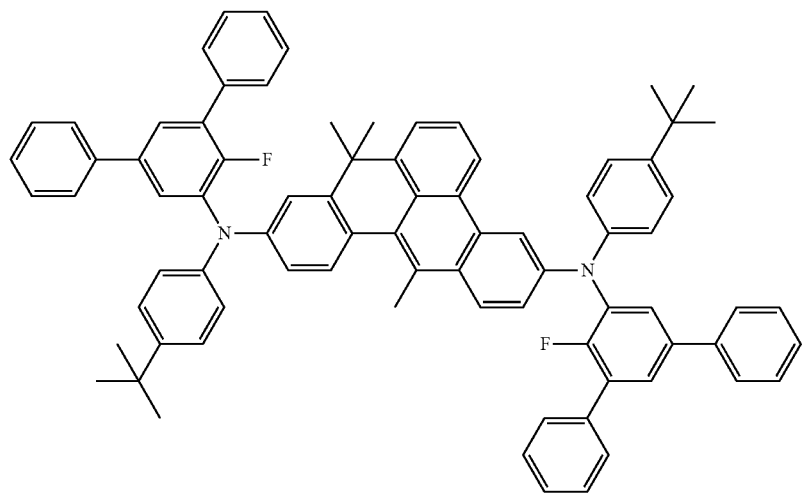
178
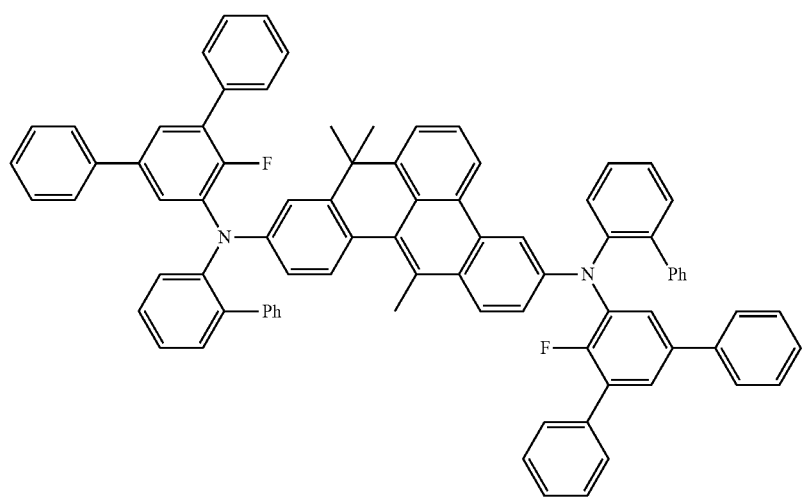
179
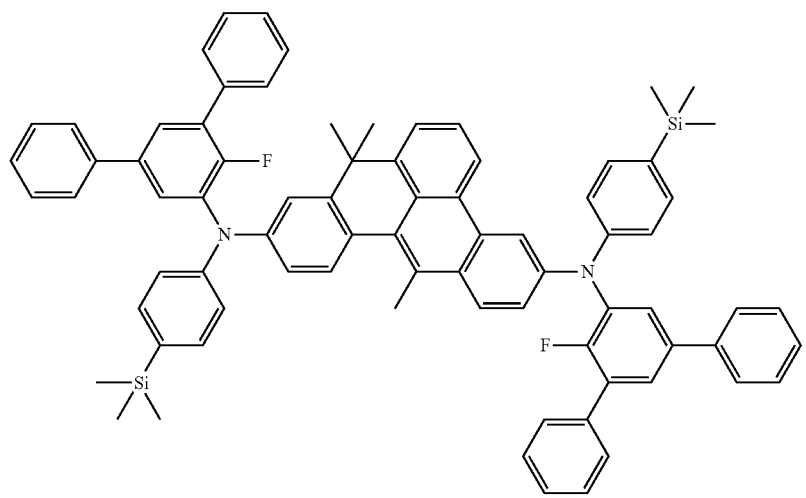

-continued
180
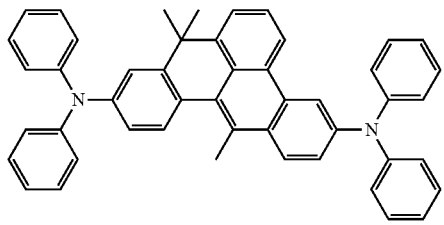
181
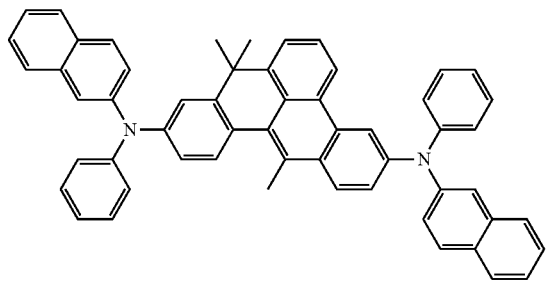
182
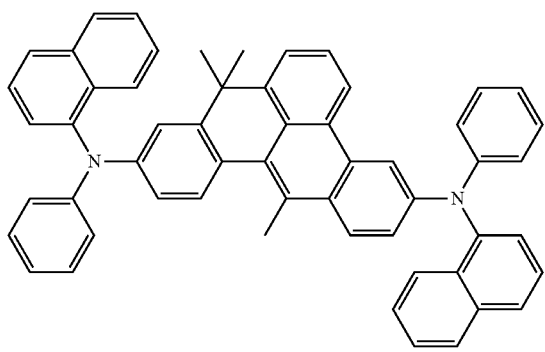
183
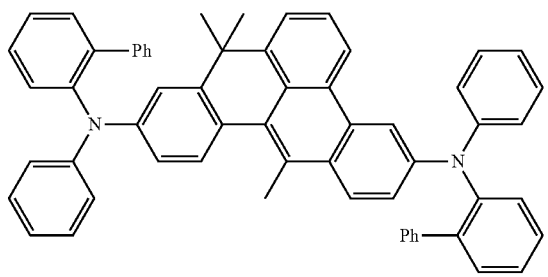
184
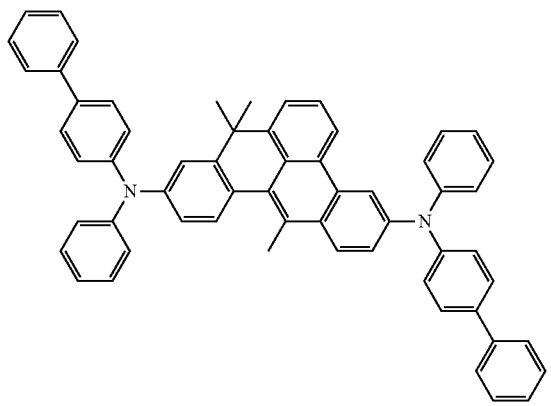
185
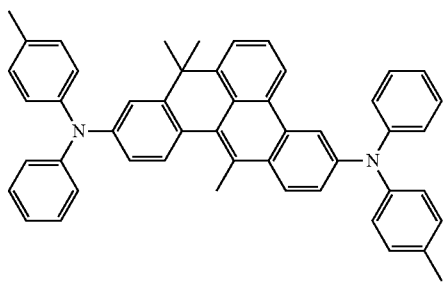
186
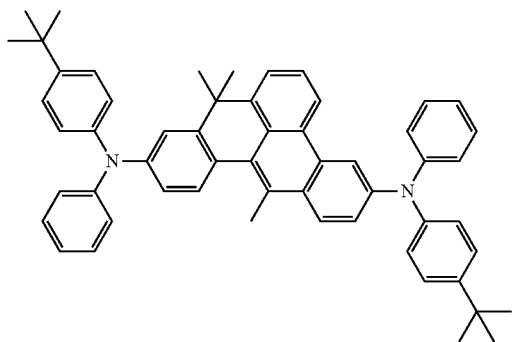
187
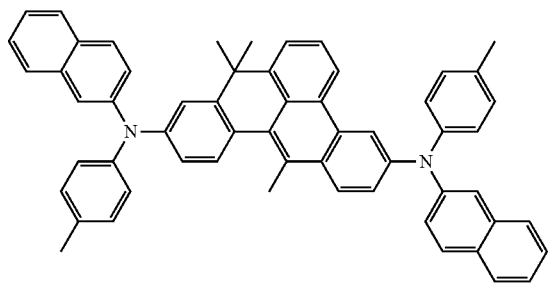

-continued
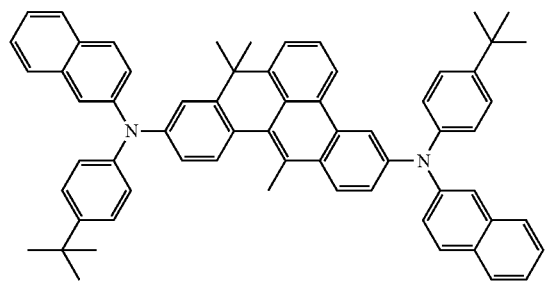
188
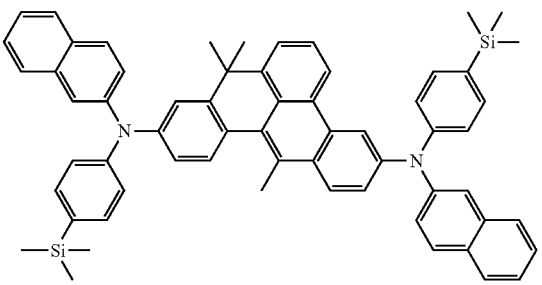
189
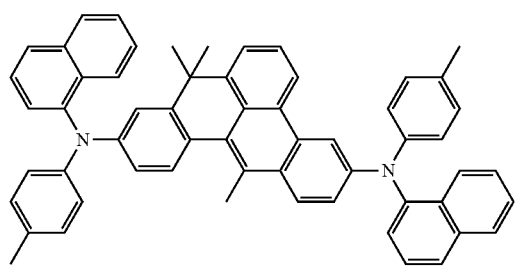
190
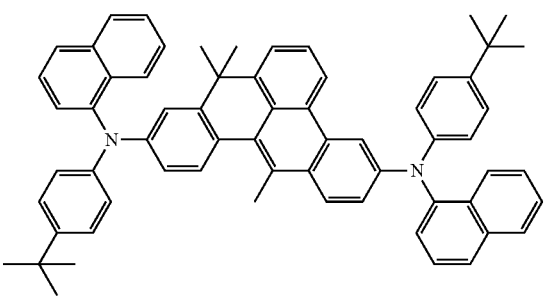
191
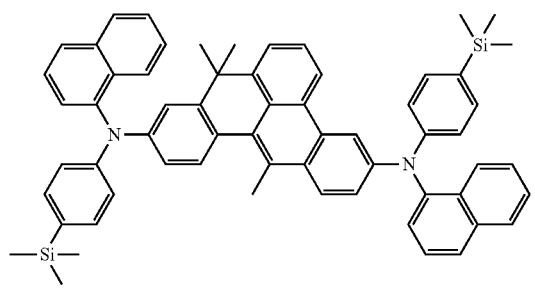
192
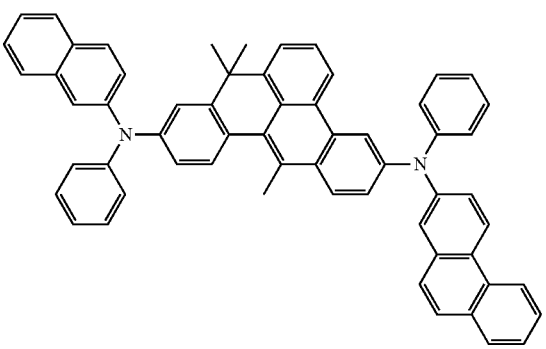
193
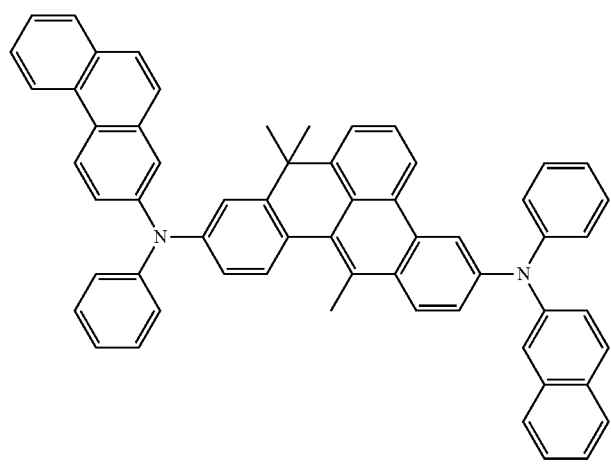
194

-continued
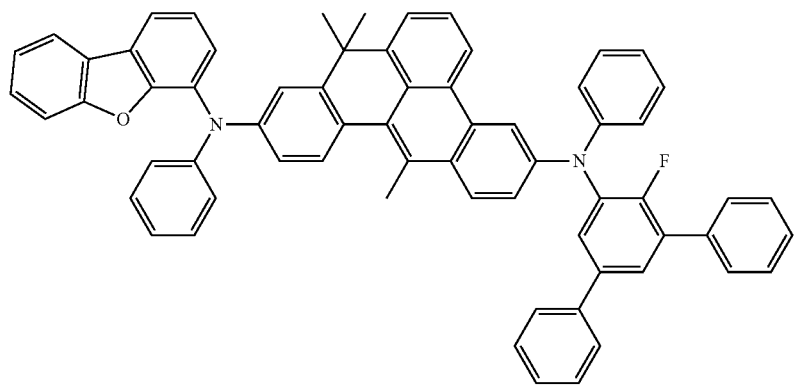
195
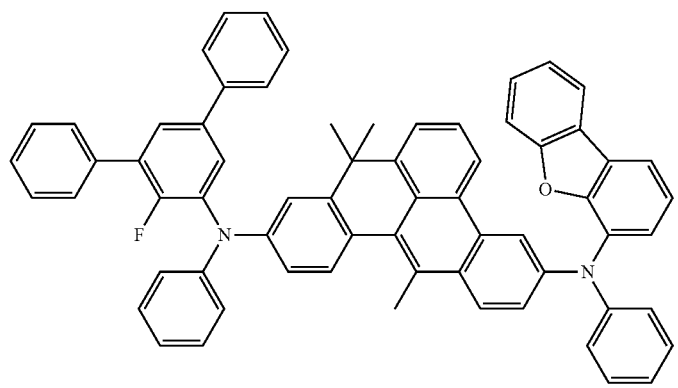
196
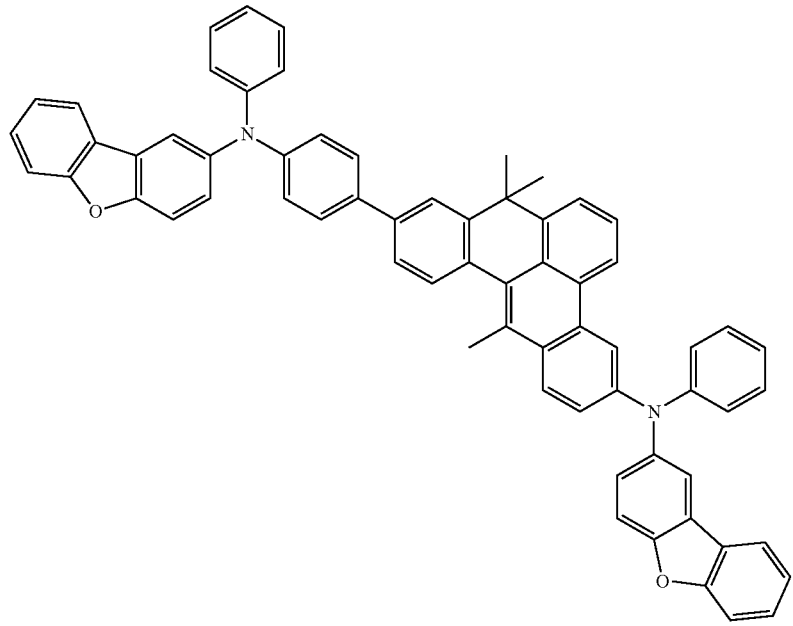
197

198
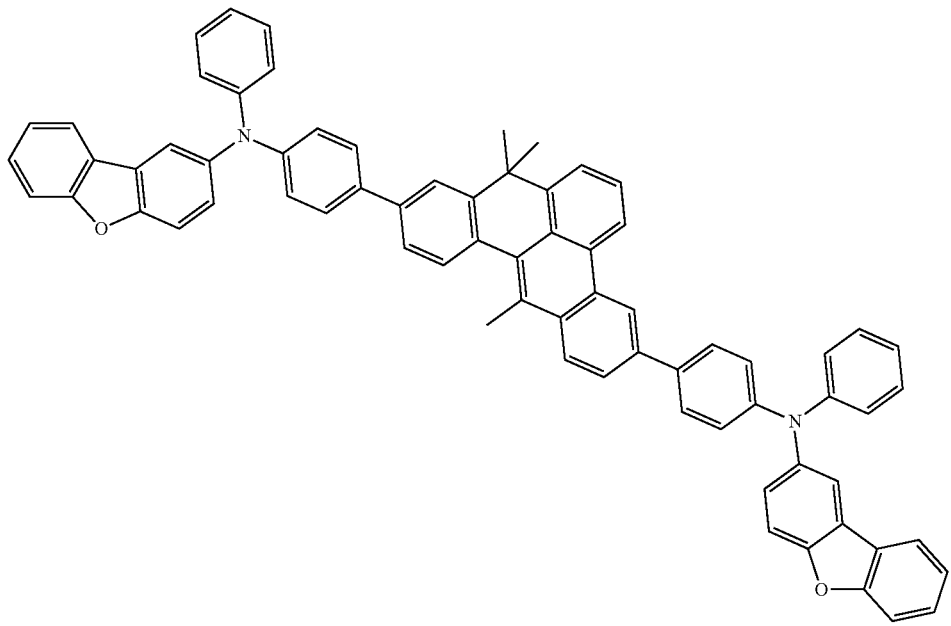
199
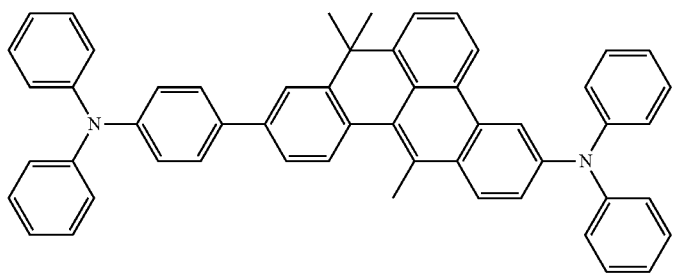
200
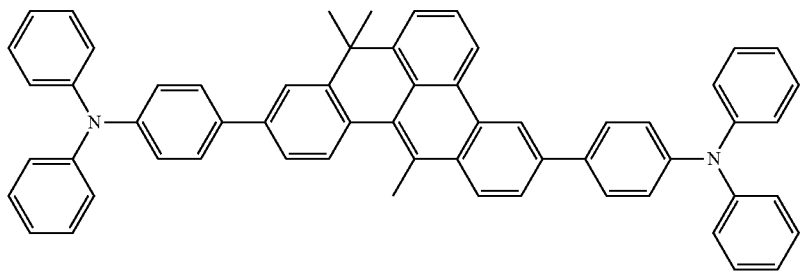
201
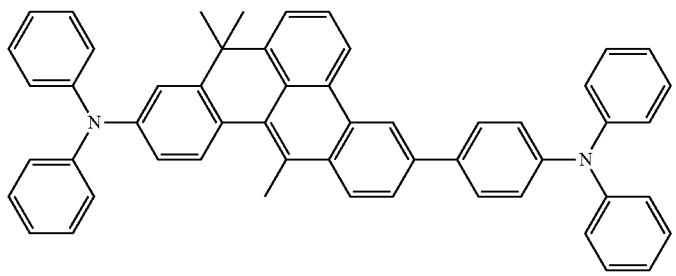

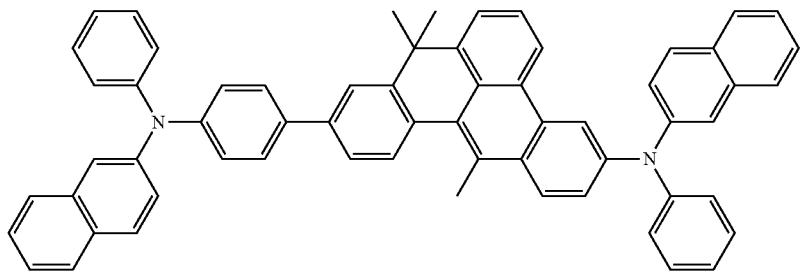
202
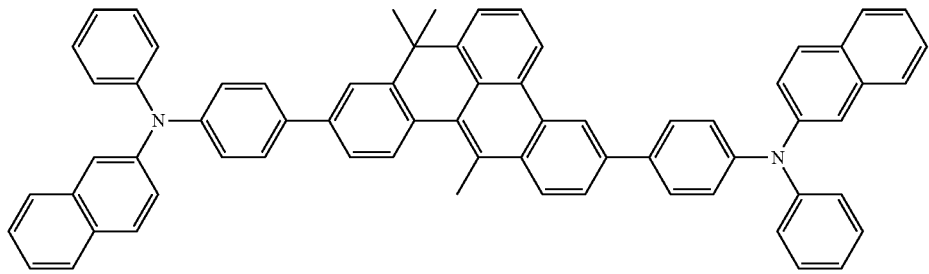
203
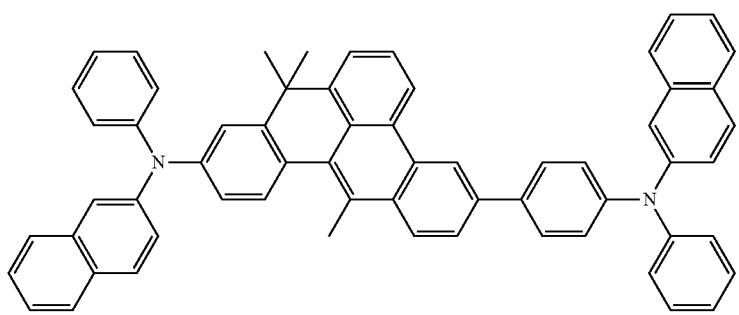
204
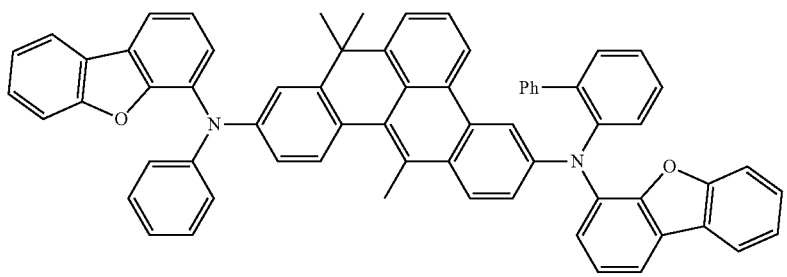
205
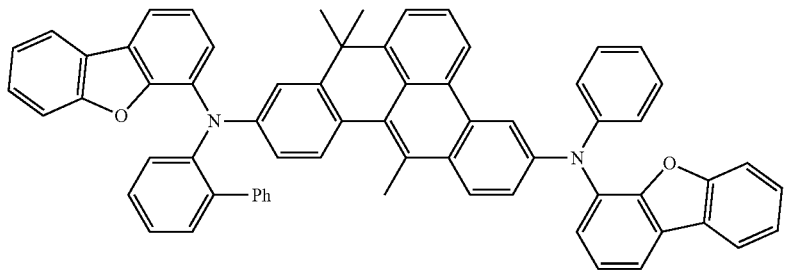
206

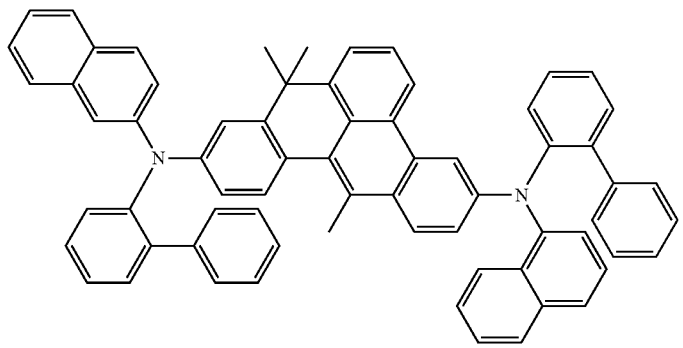
207
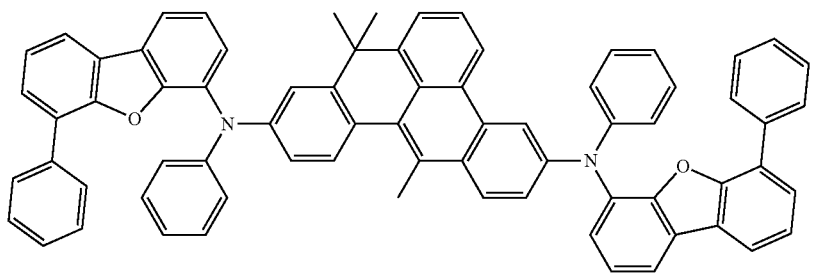
208
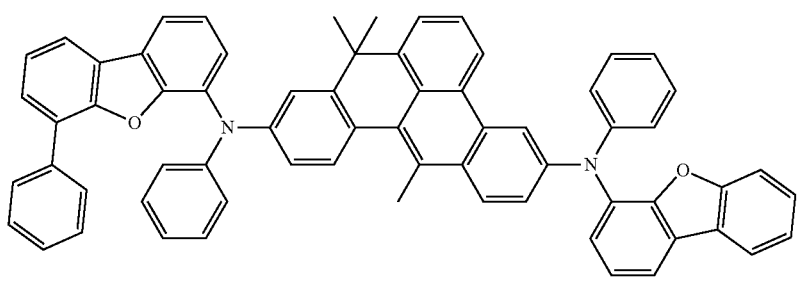
209
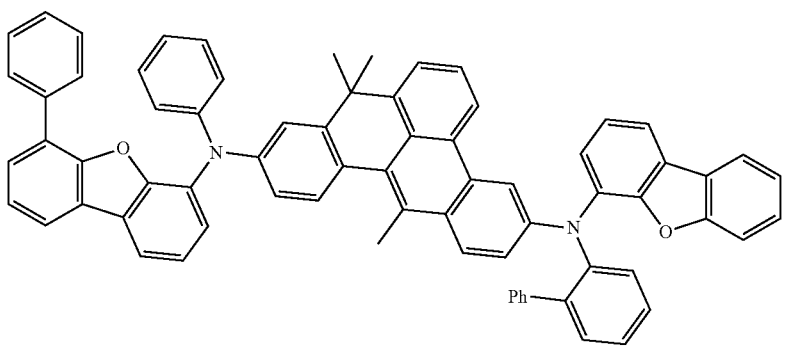
210
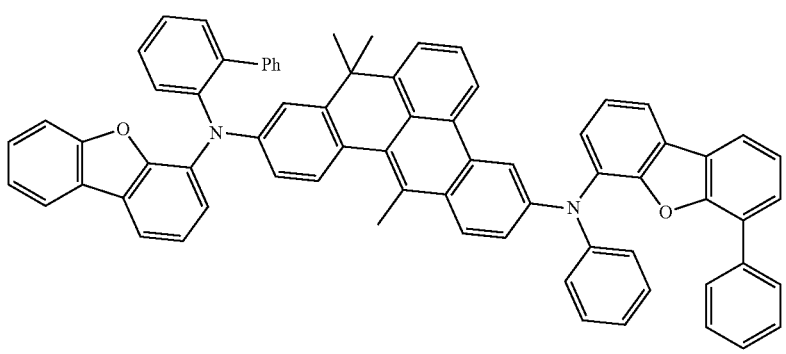
211

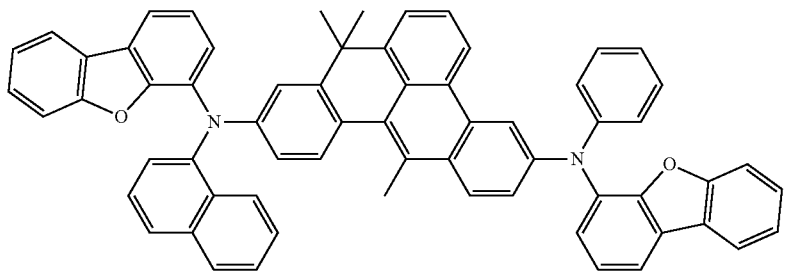
212
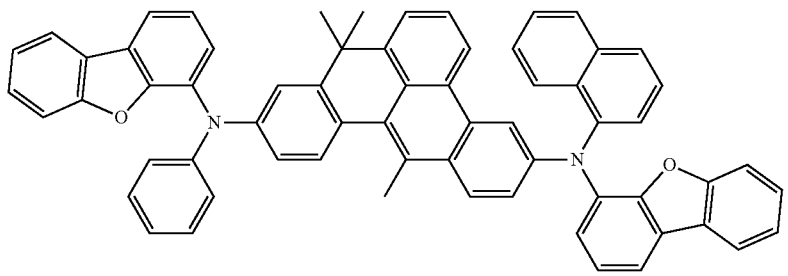
213
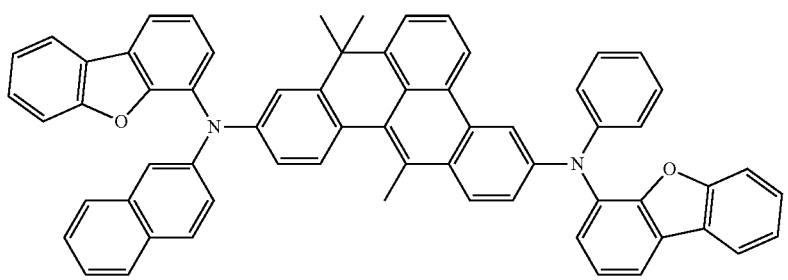
214
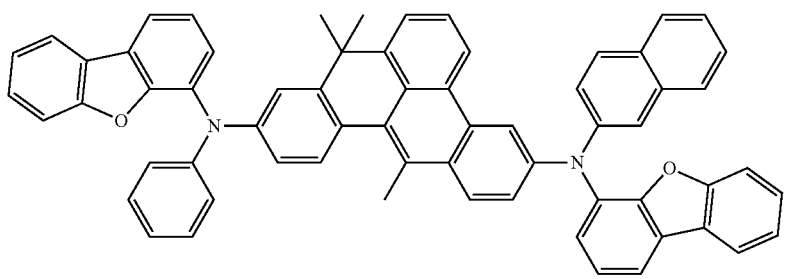
215
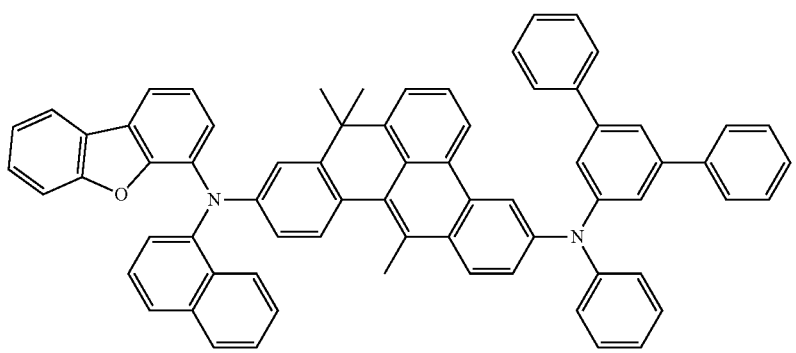
216

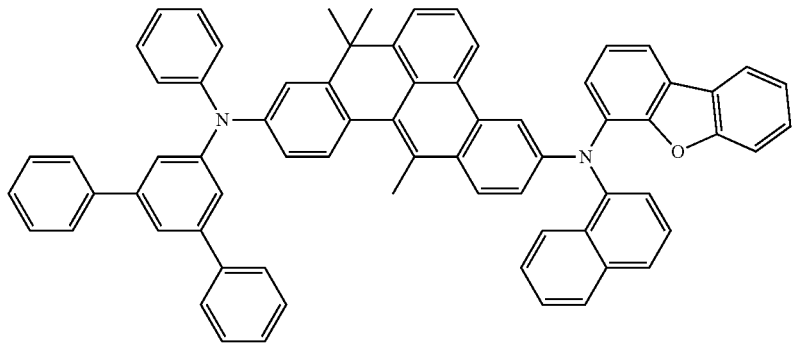
217
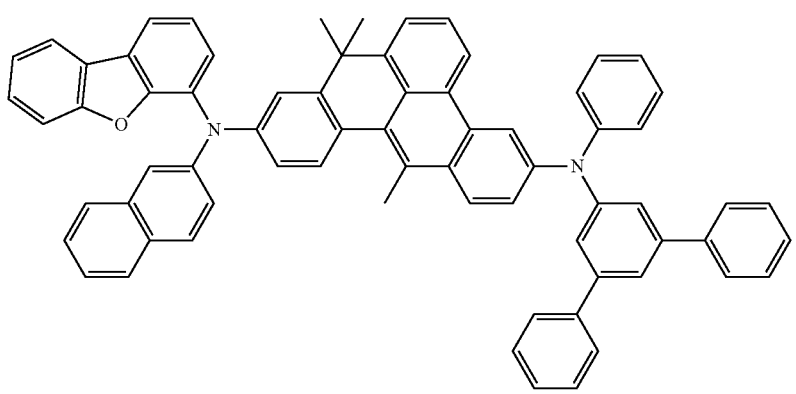
218
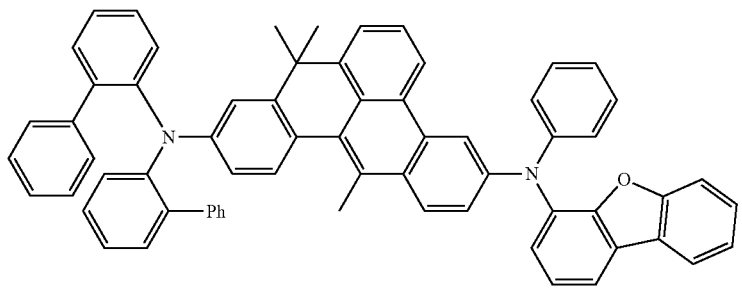
219
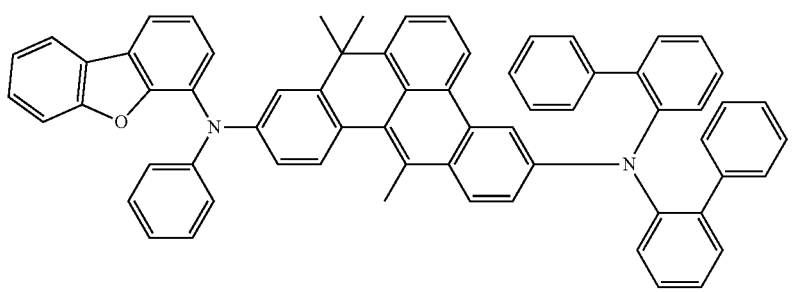
220

-continued
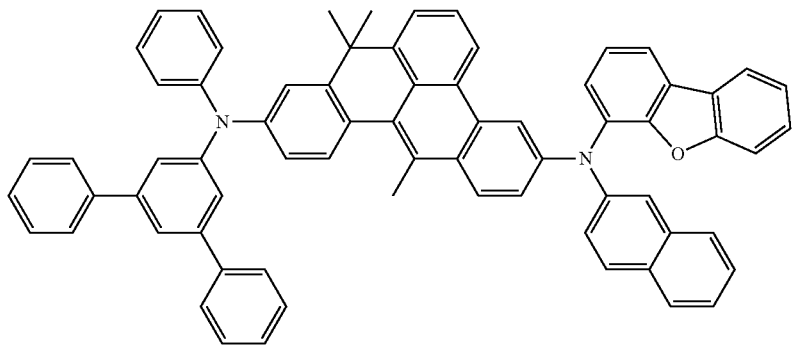
221
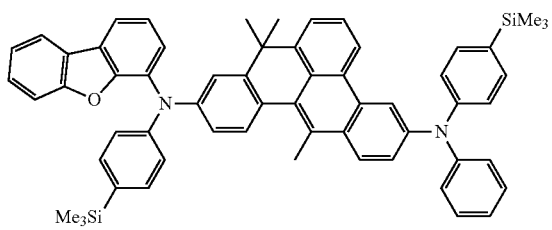
222
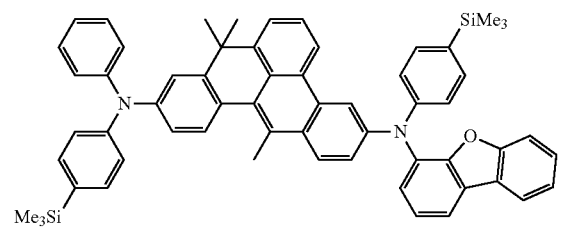
223
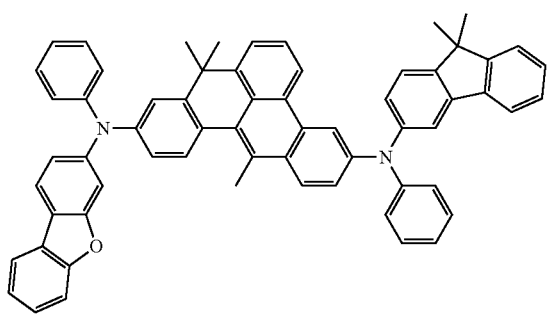
224
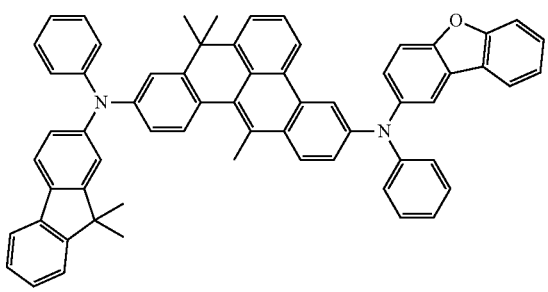
225
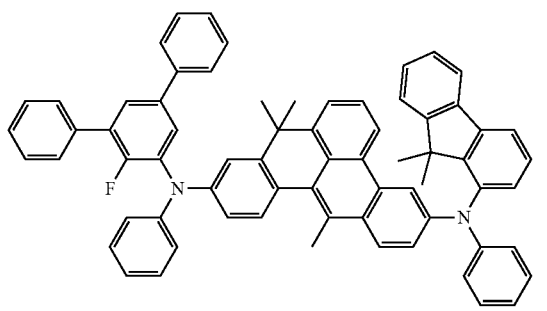
226
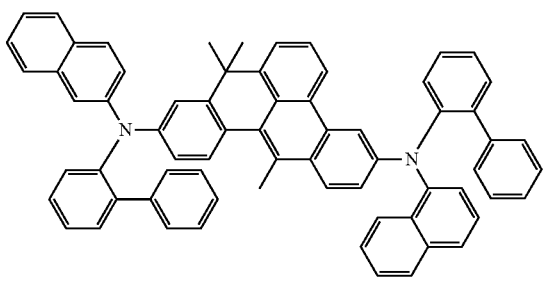
227
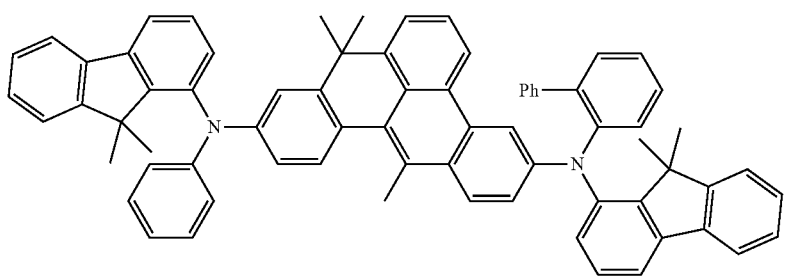
228

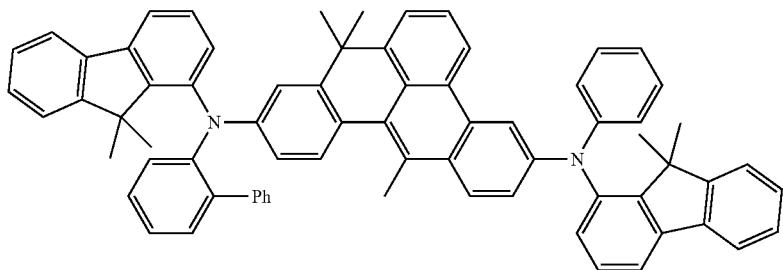
229
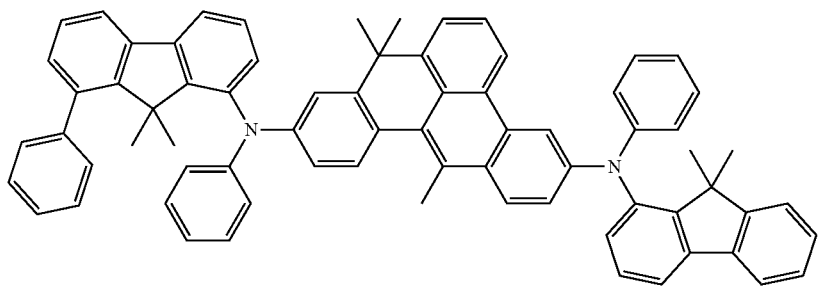
230
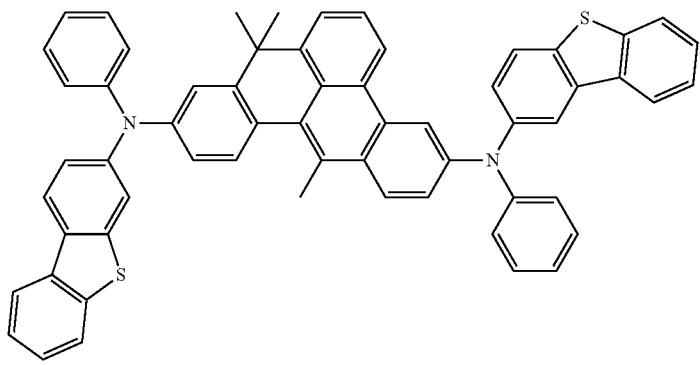
231
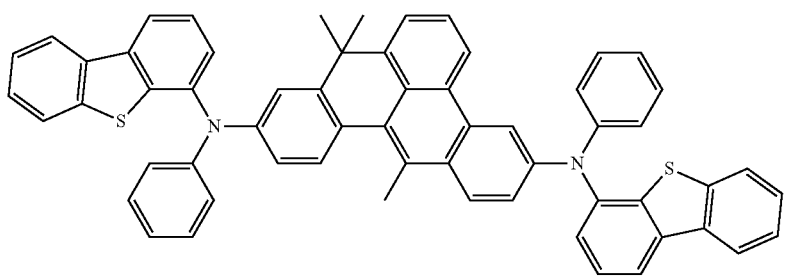
232
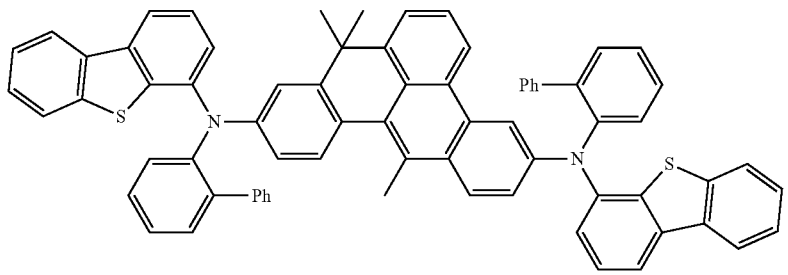
233

234
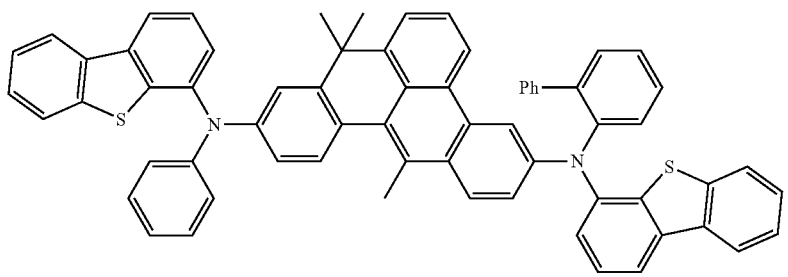
235
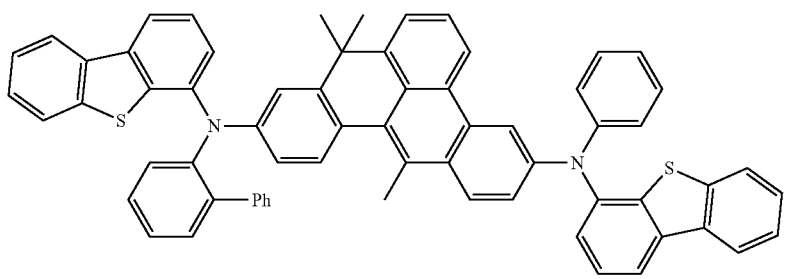
236
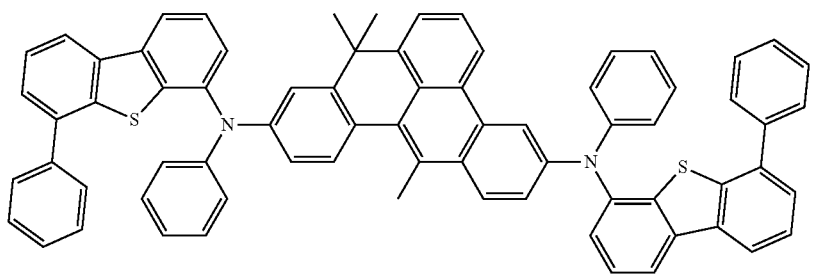
237
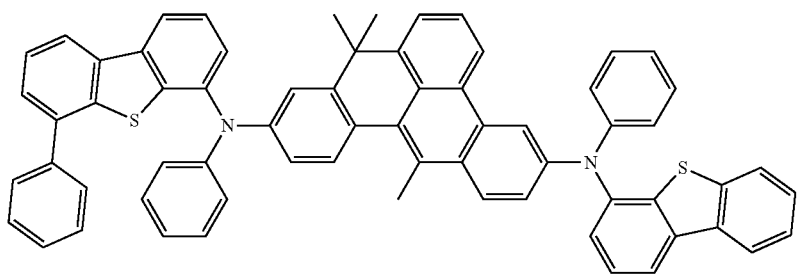
238
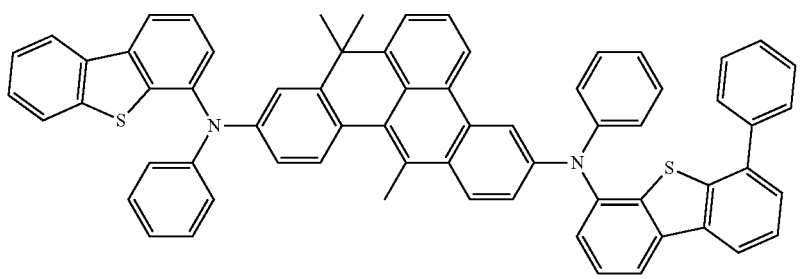

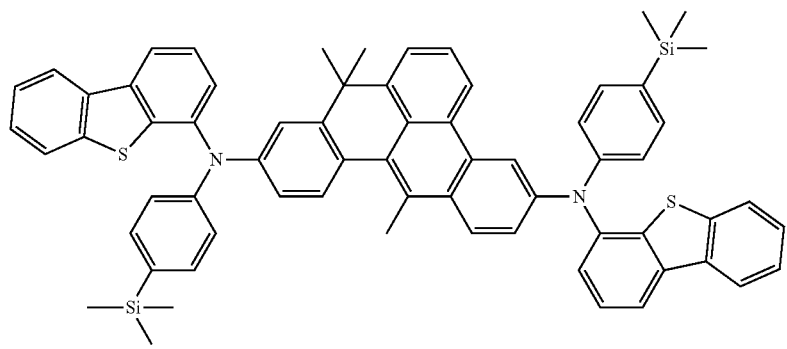
239
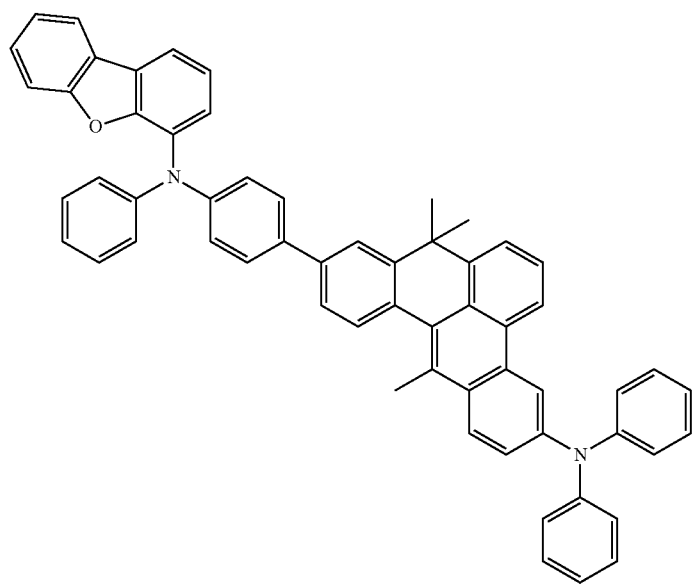
240
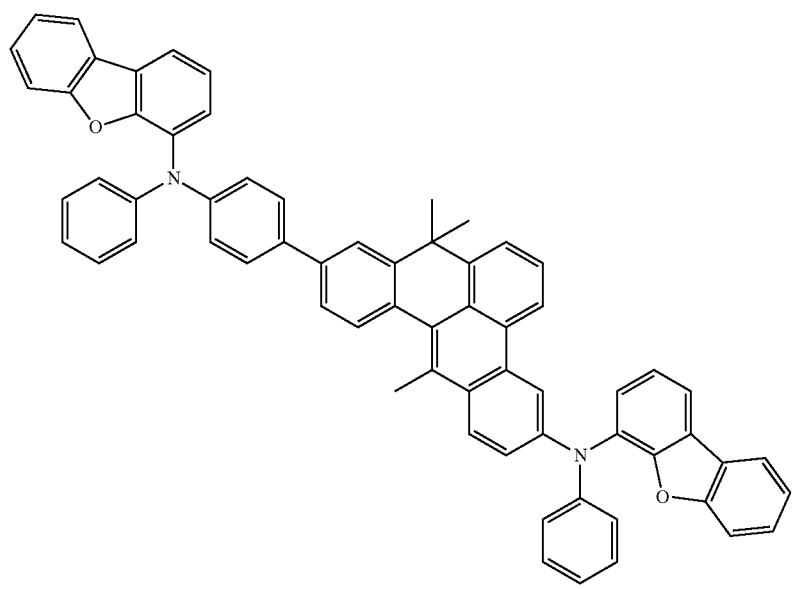
241

-continued
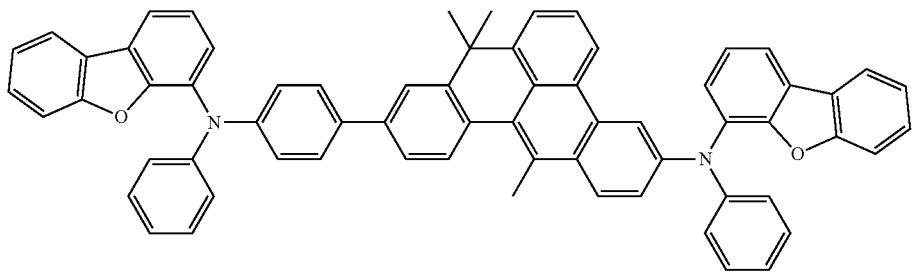
242
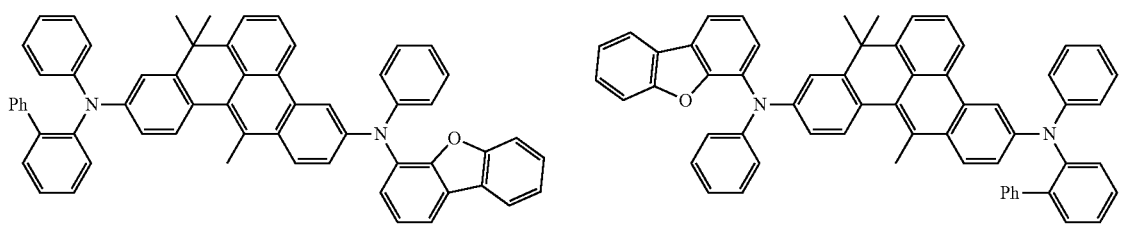
243
244
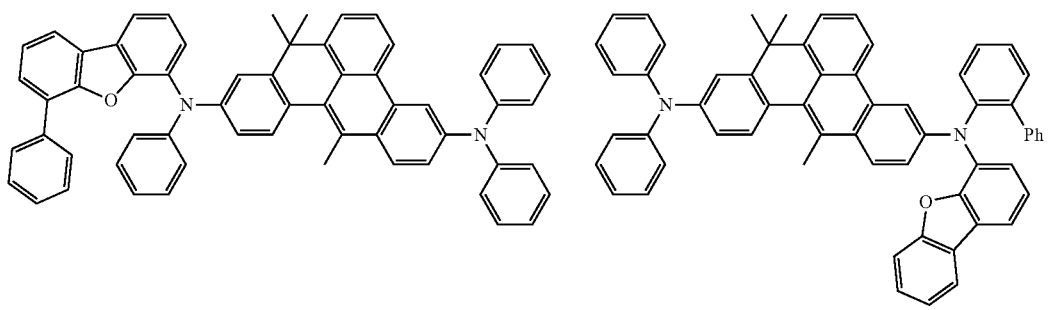
245
246
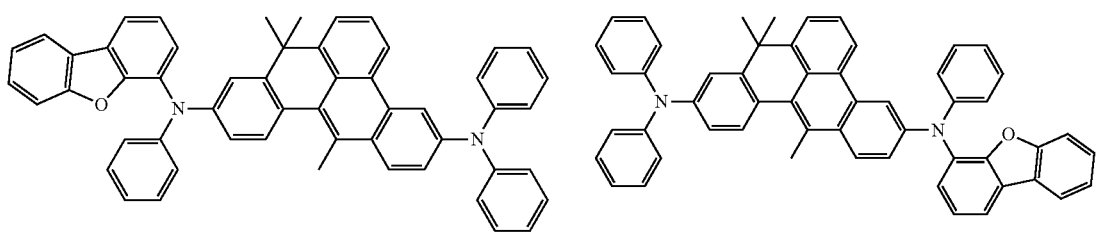
247
248
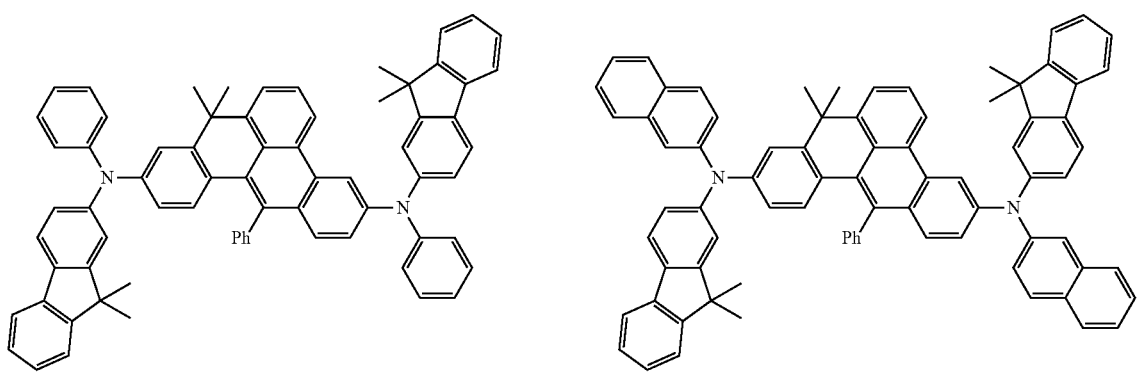
249
250

-continued
251
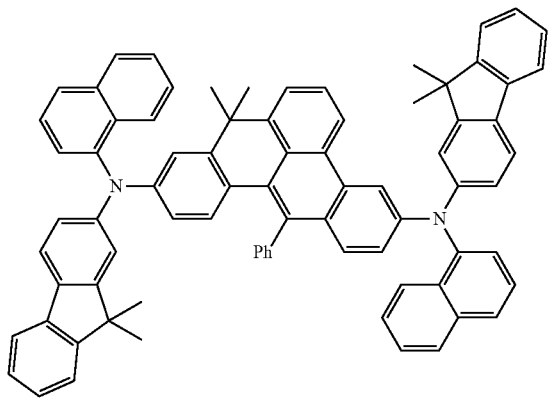
252
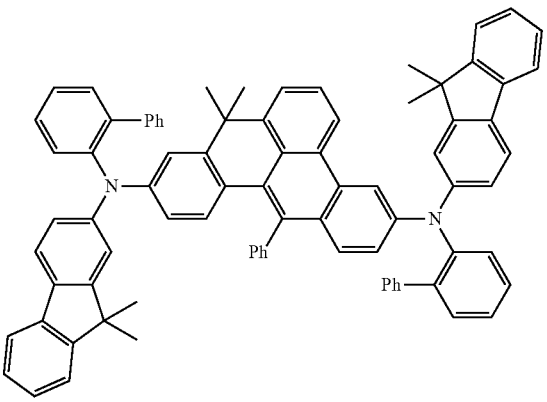
253
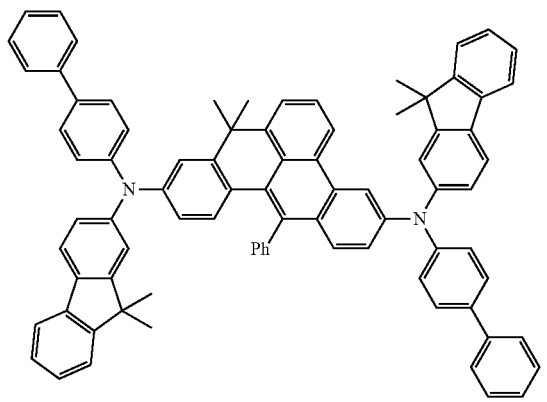
254
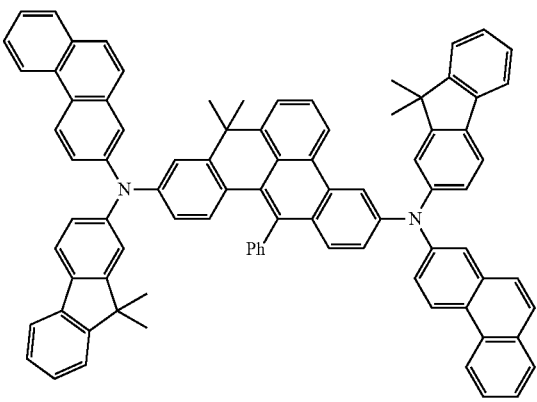
255
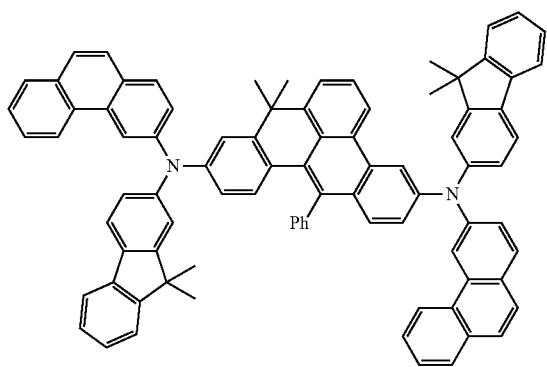
256
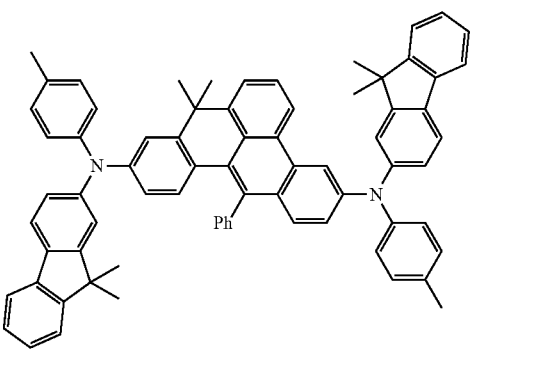
257
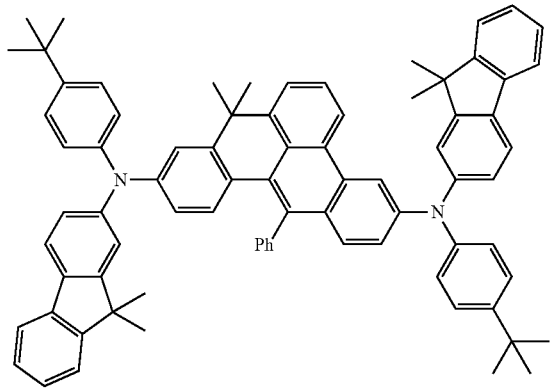
258
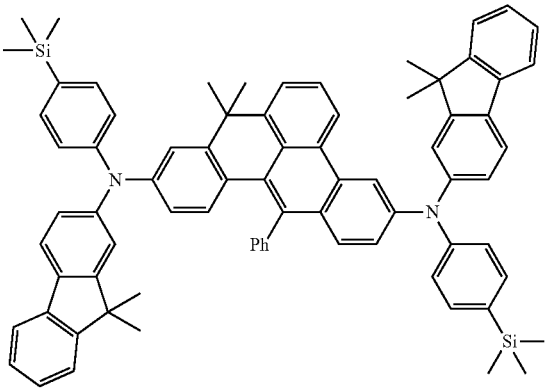

371
372
-continued
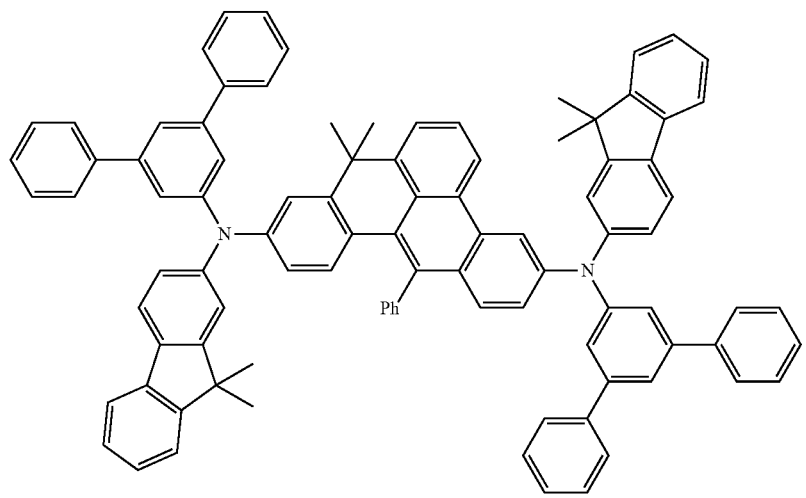
259
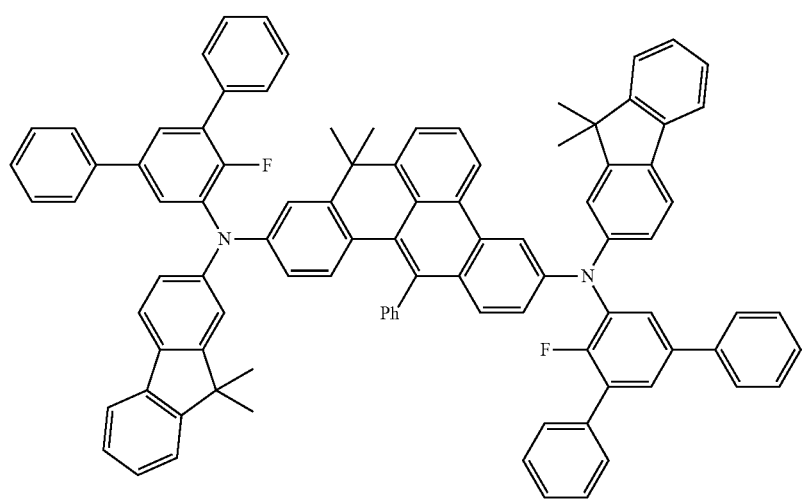
260
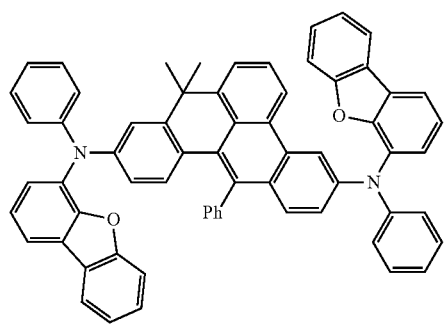
261
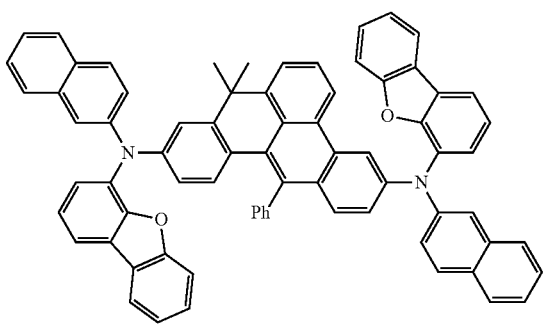
262

-continued
263
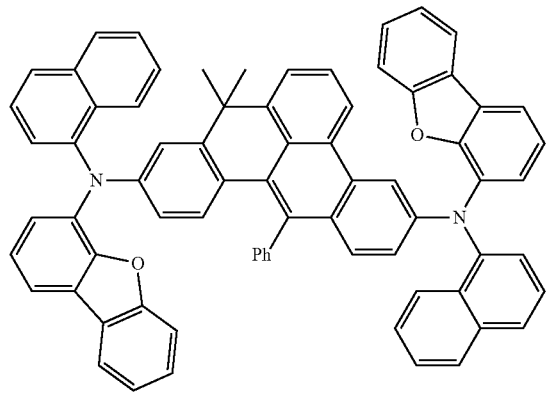
264
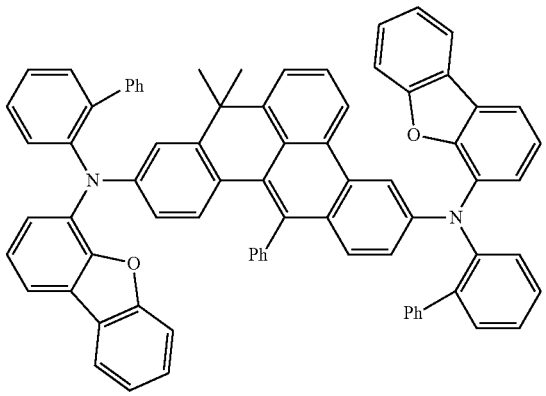
265
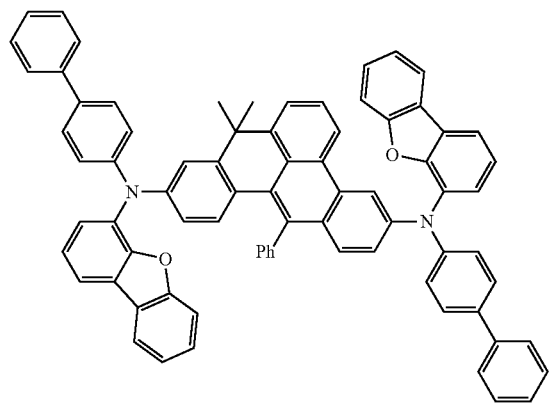
266
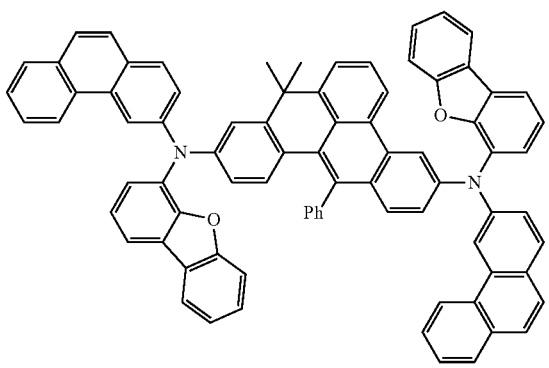
267
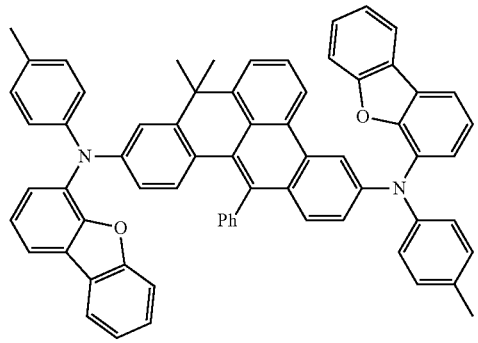
268
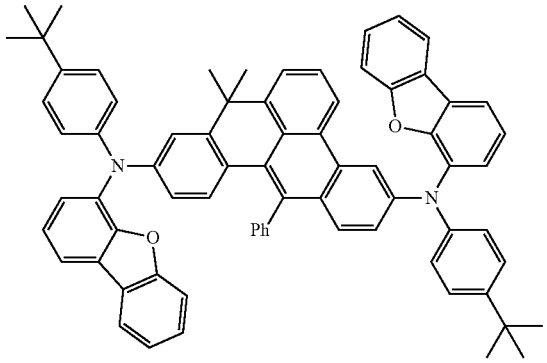
269
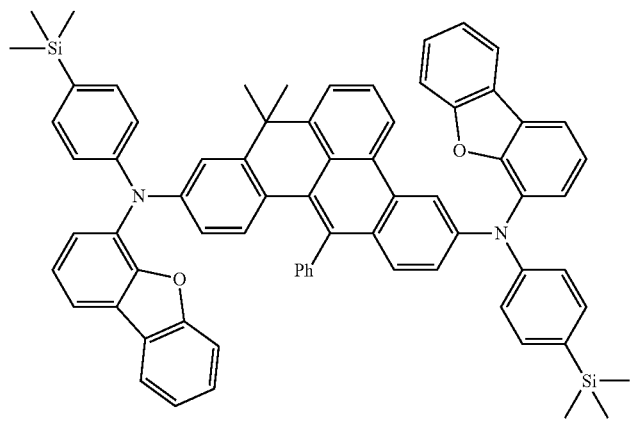

270
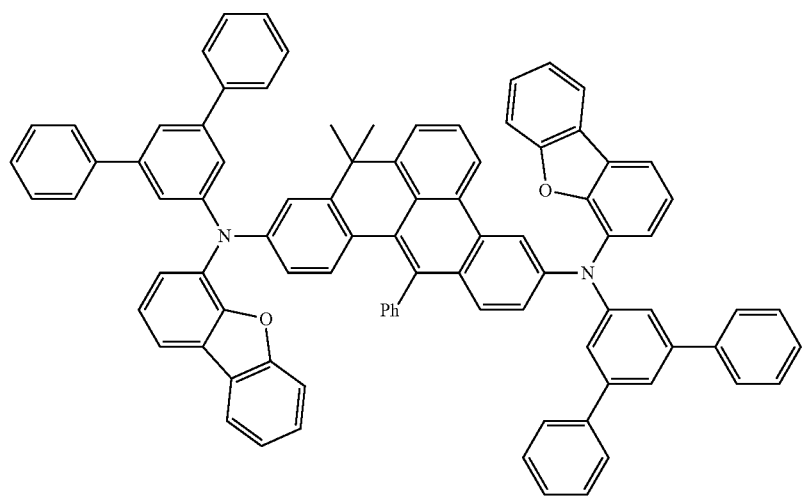
271
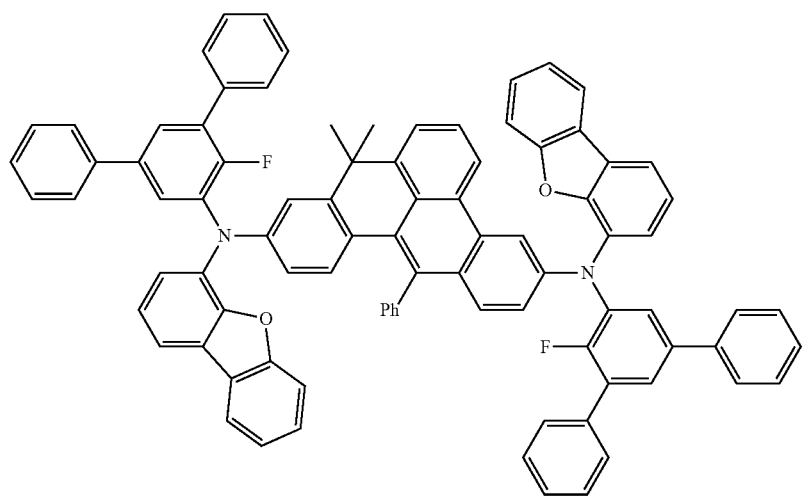
272
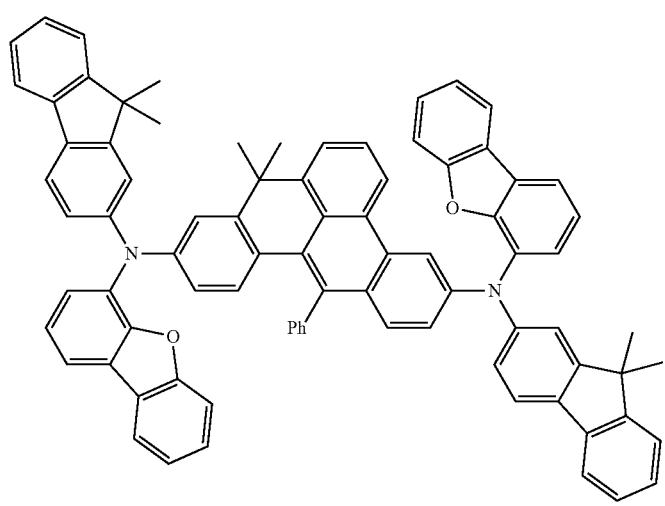

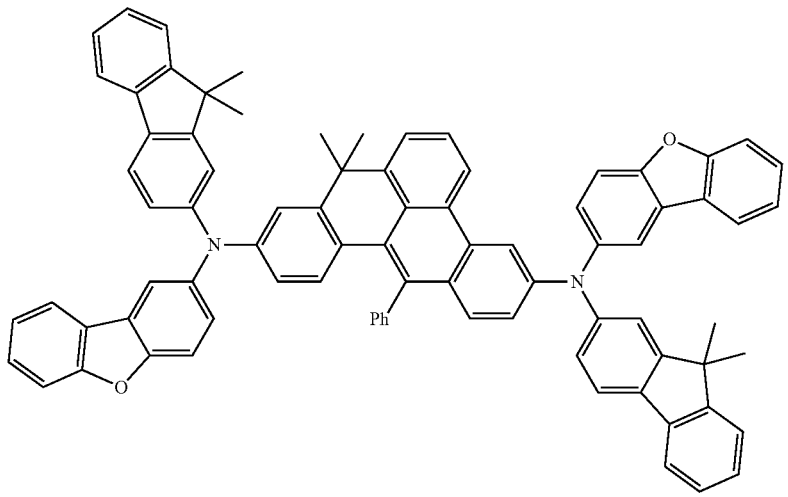
273
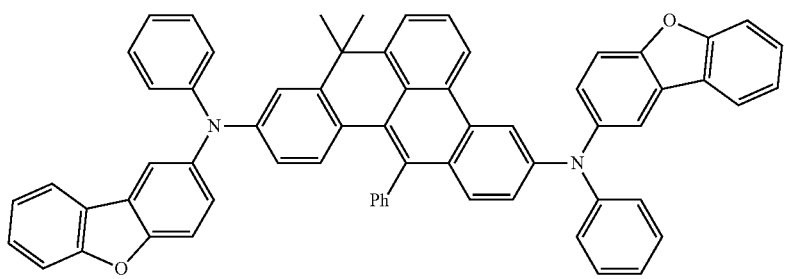
274
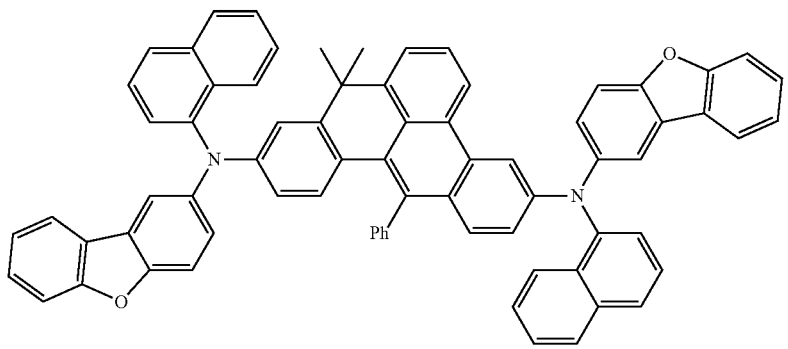
275
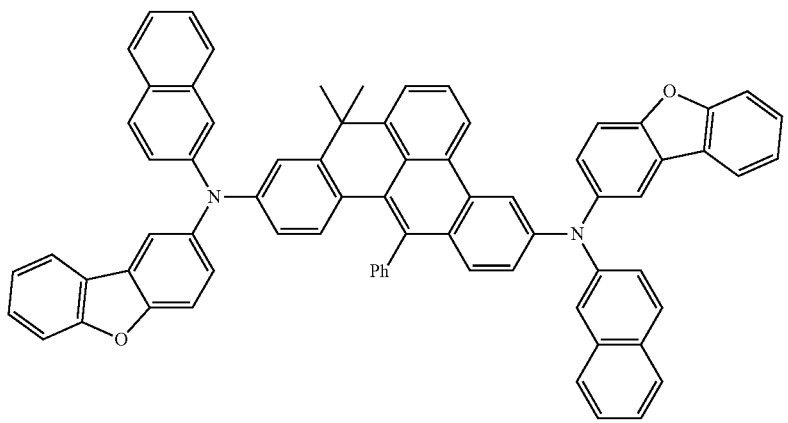
276

-continued
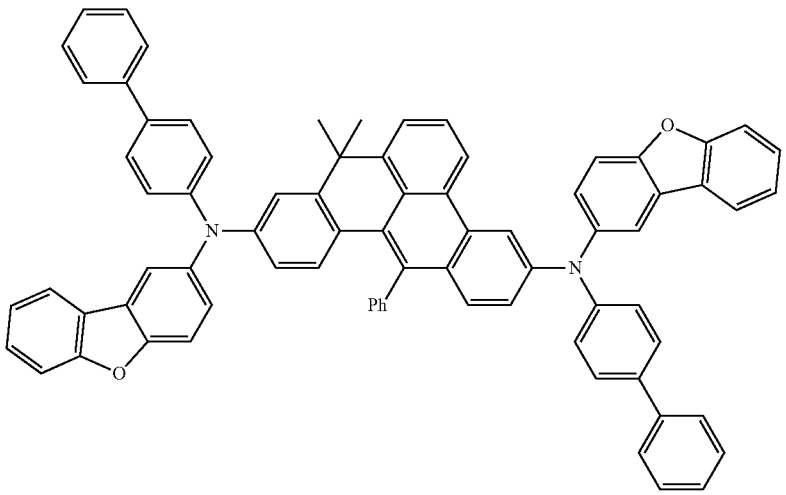
277
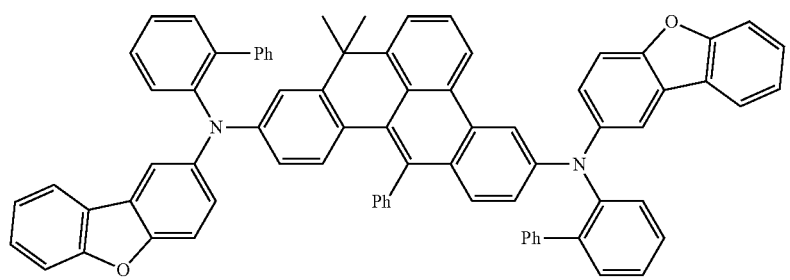
278
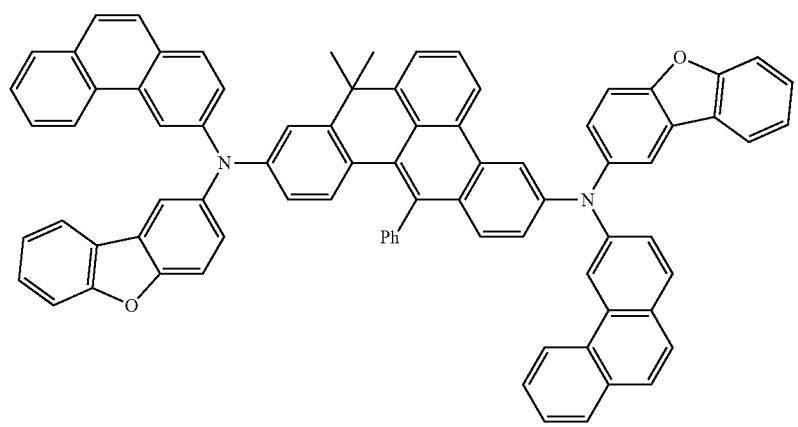
279
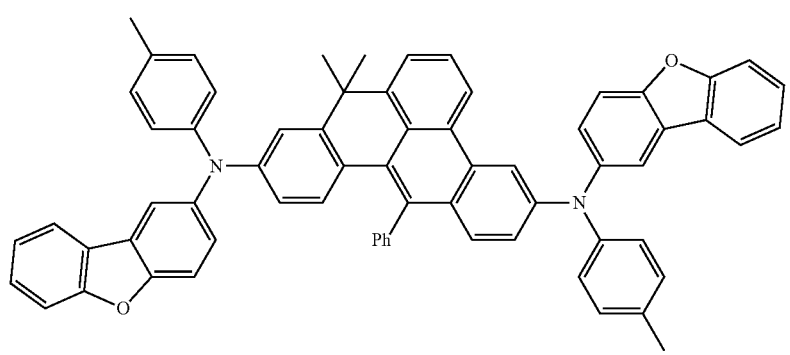
280

281
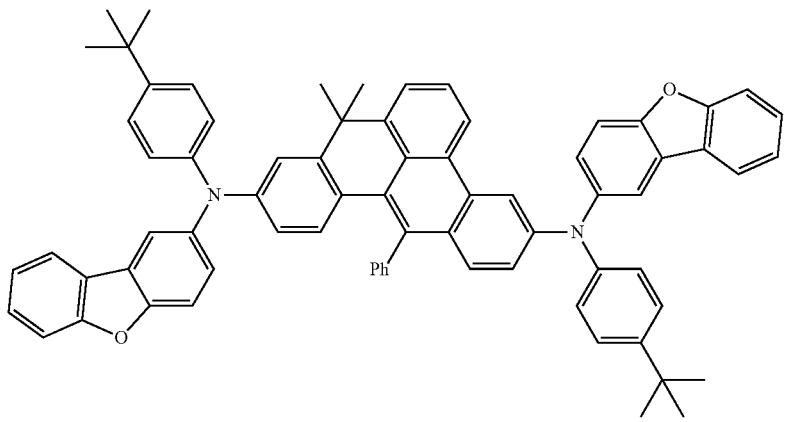
282
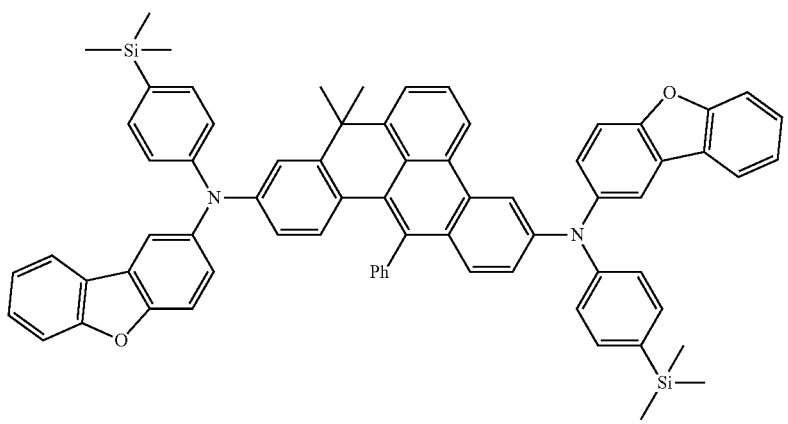
283
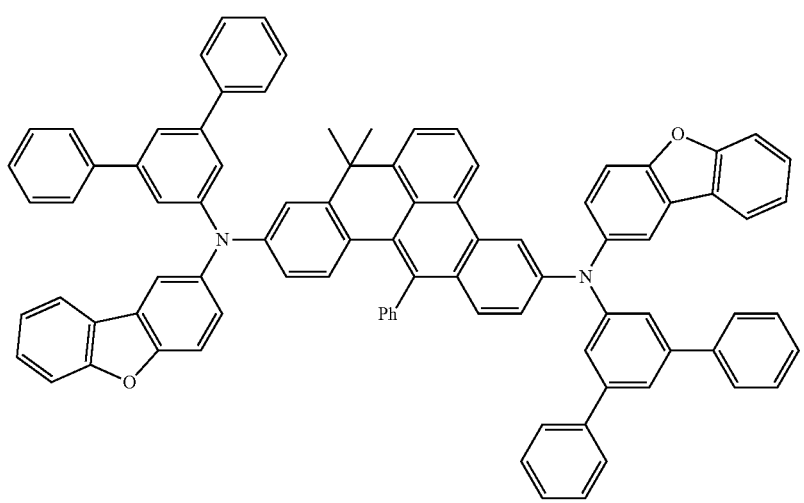

284
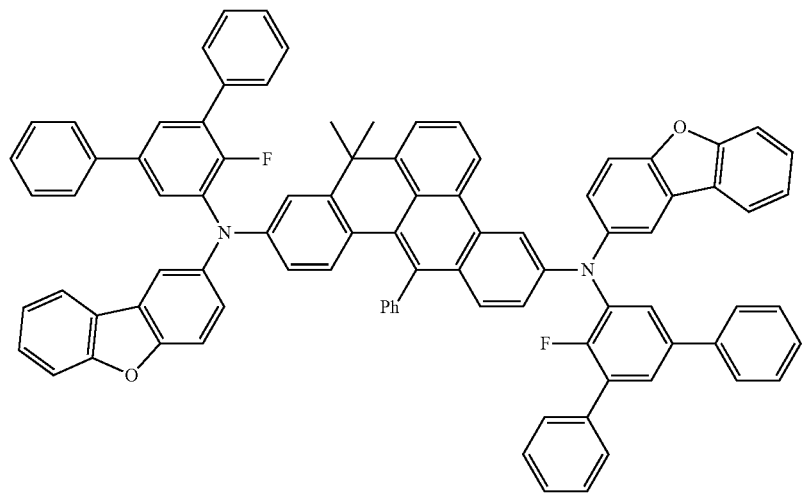
285 286
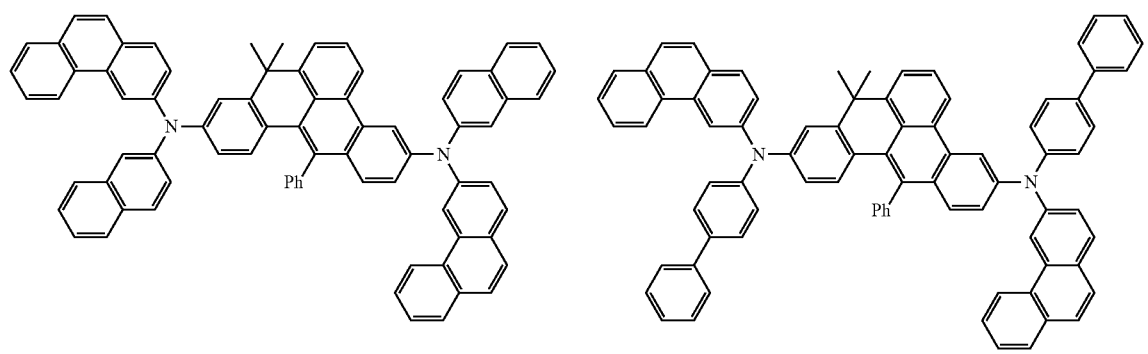
287 288
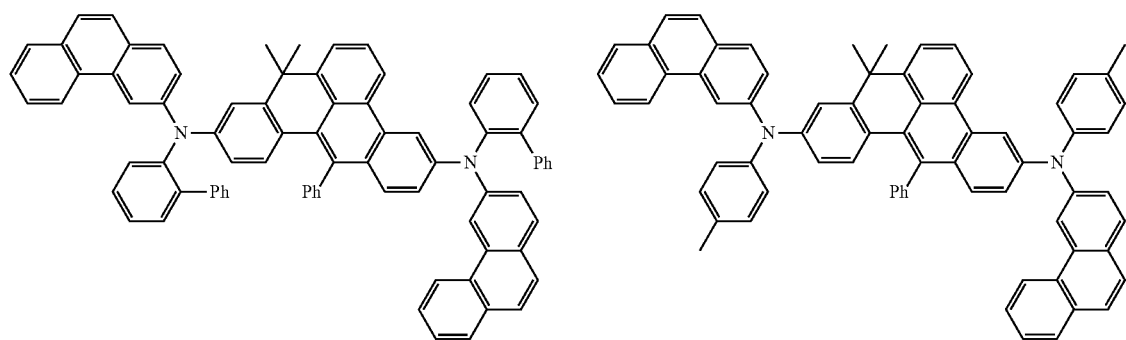
289 290
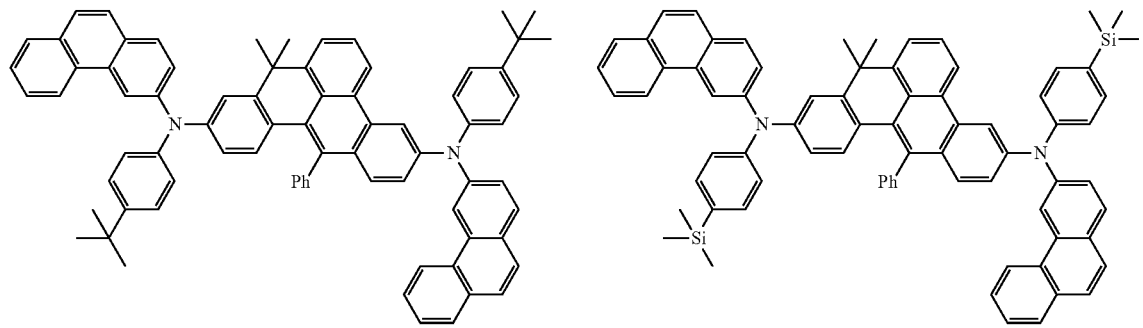

-continued
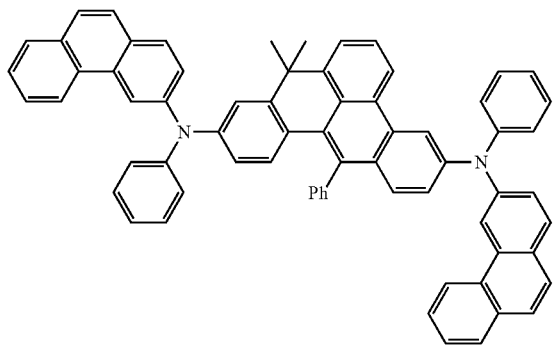
291
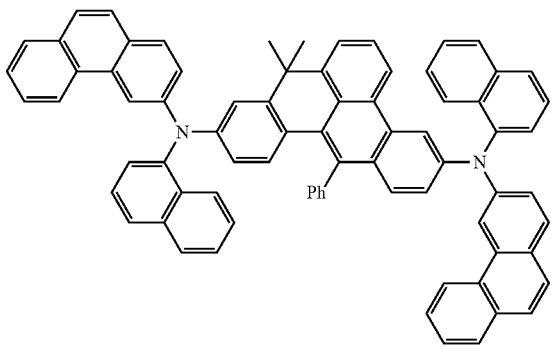
292
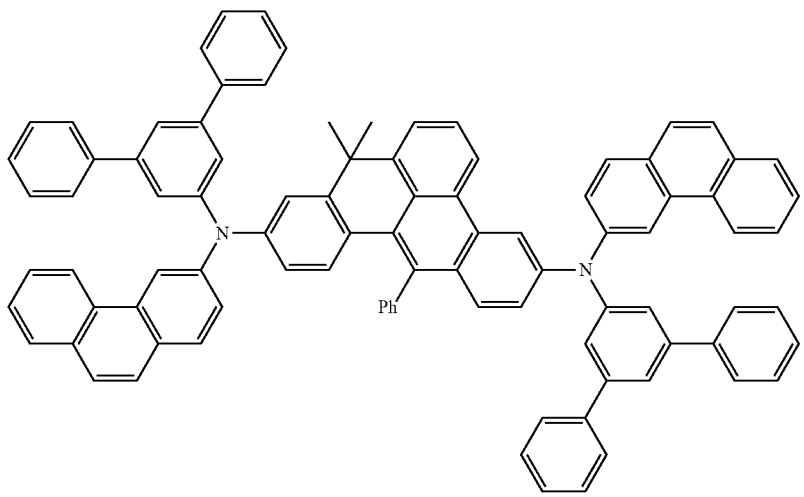
293
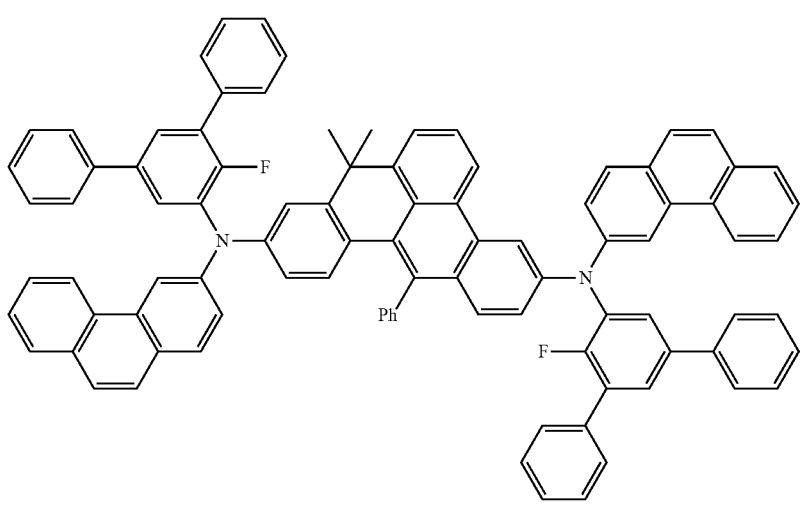
294

-continued
295
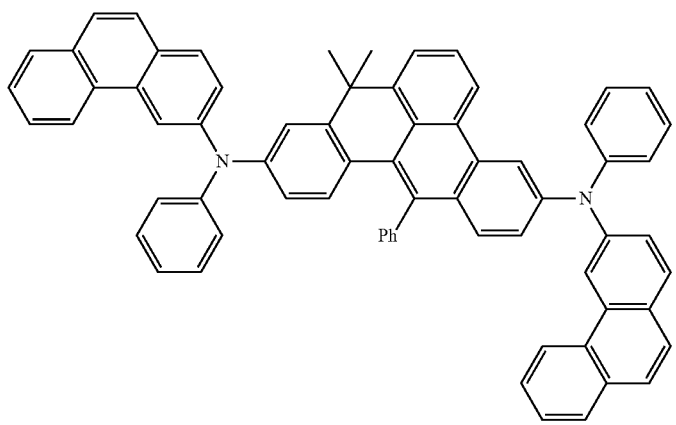
296
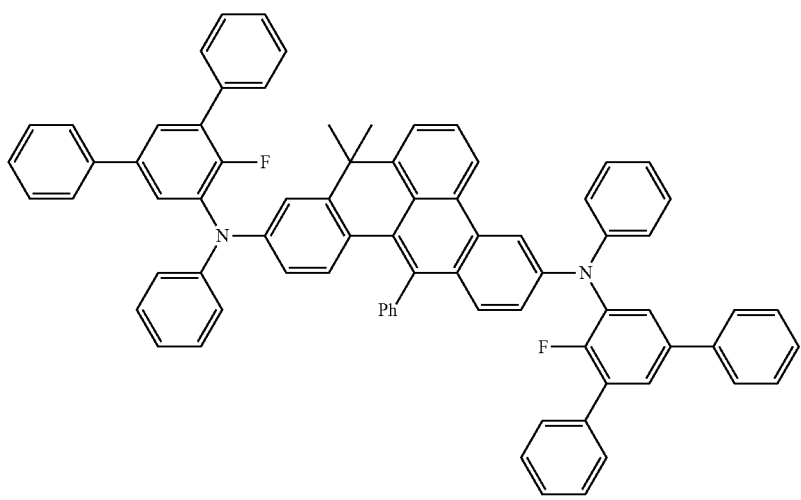
297
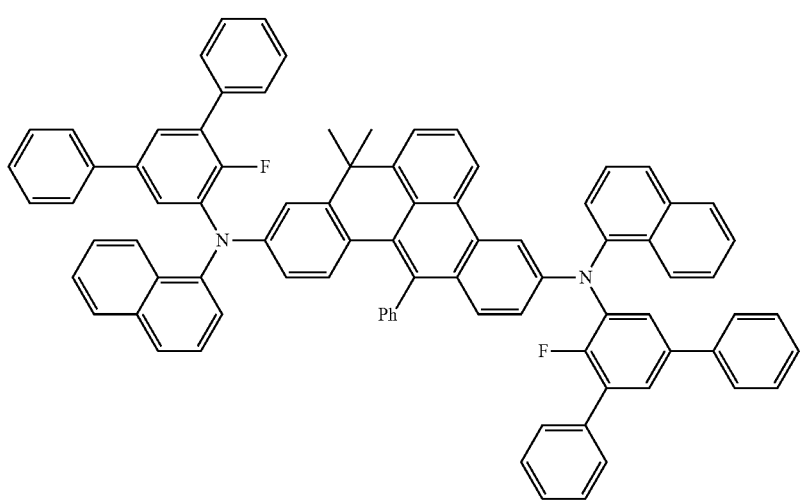

-continued
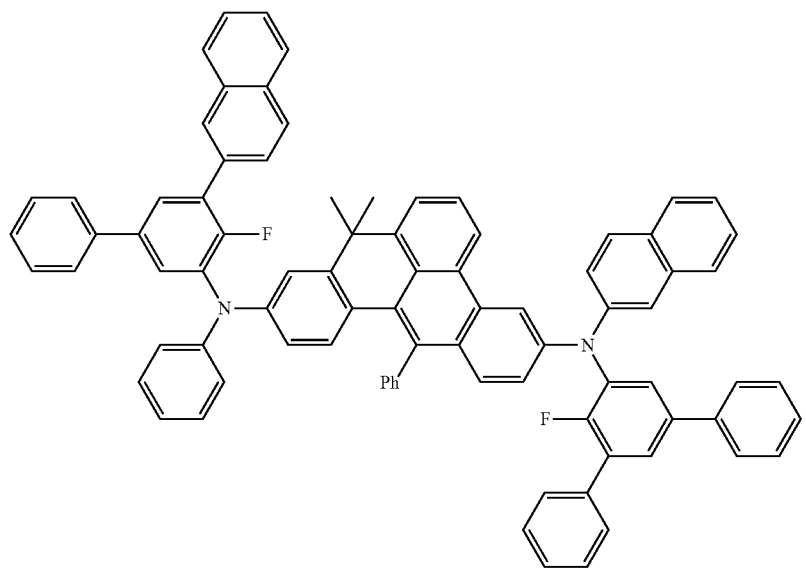
298
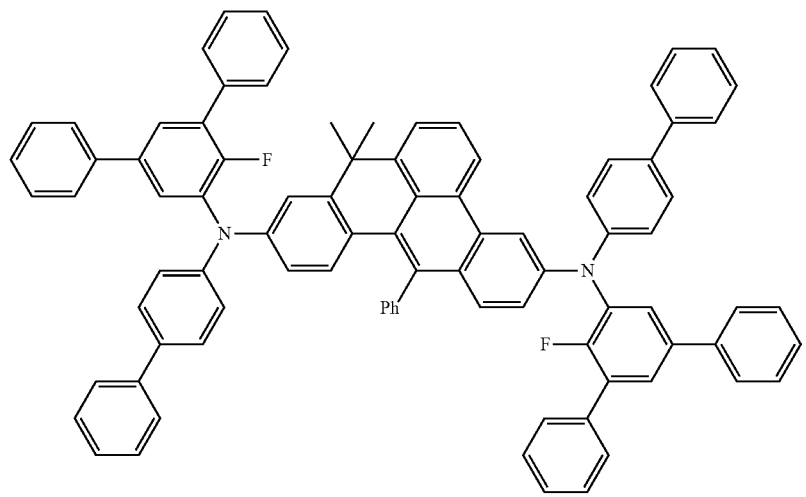
299
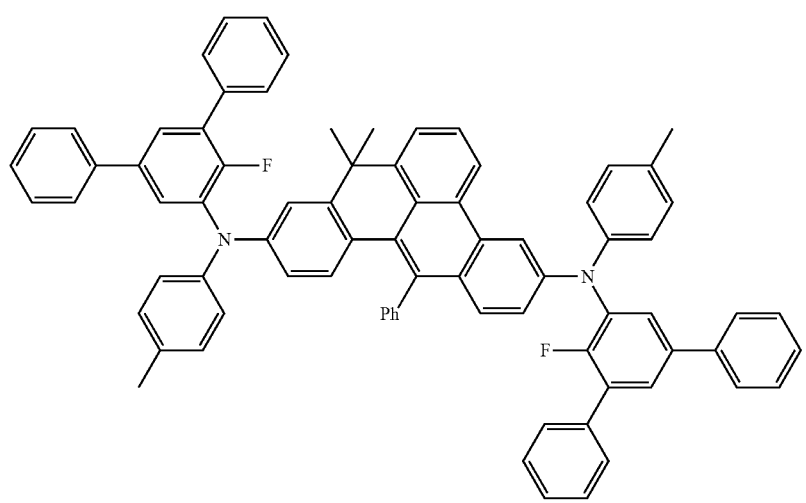
300

-continued
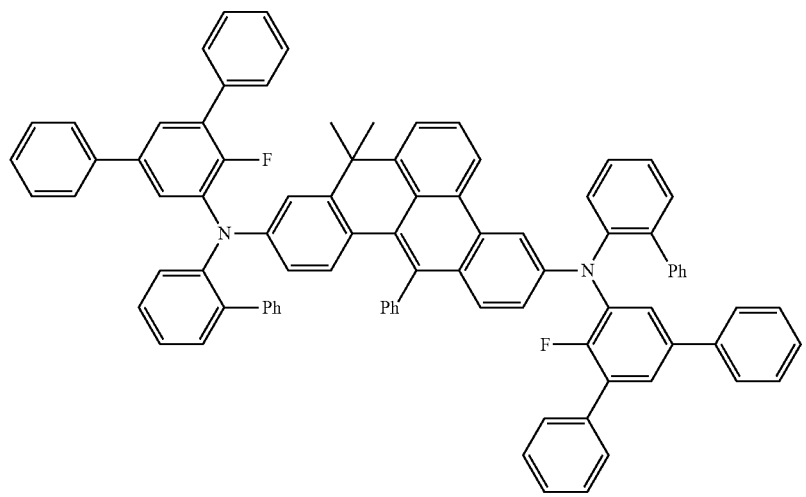
301
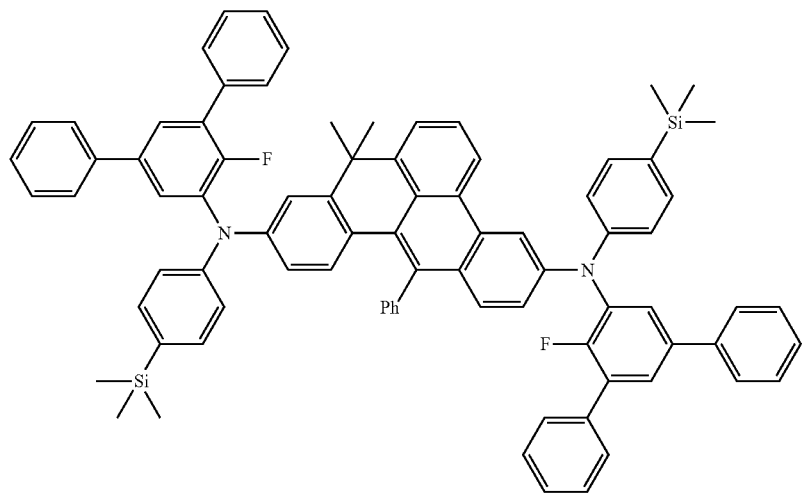
302
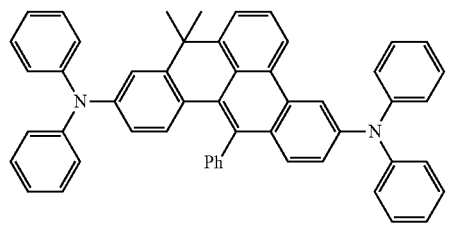
303
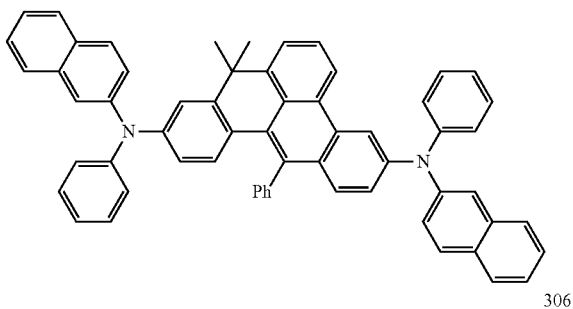
304
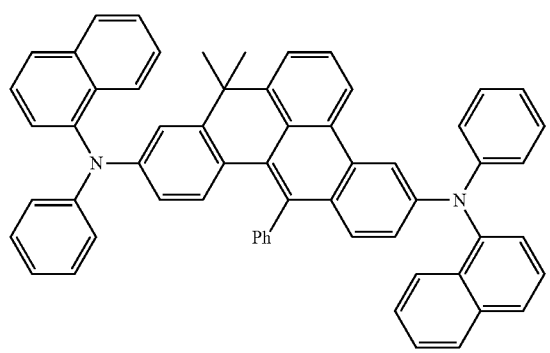
305
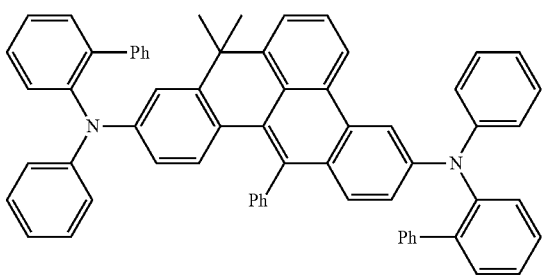
306

307
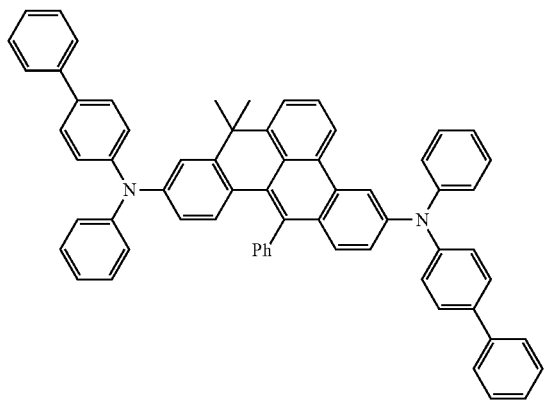
308
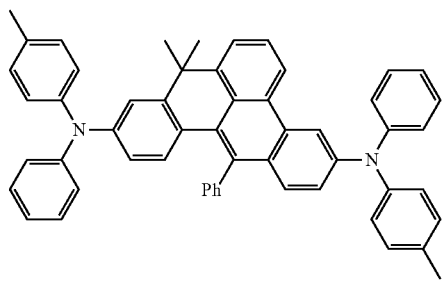
309
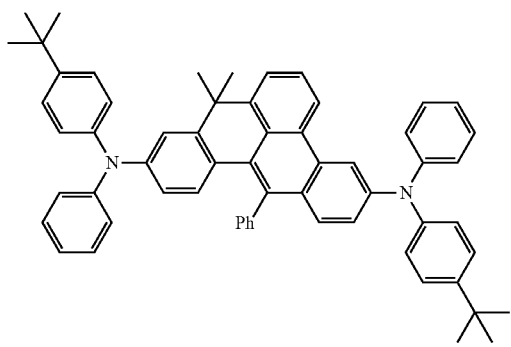
310
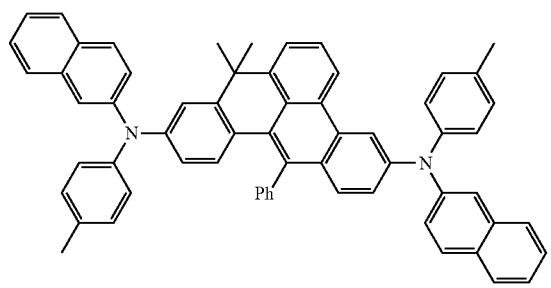
311
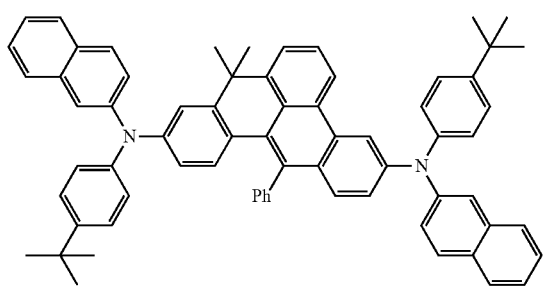
312
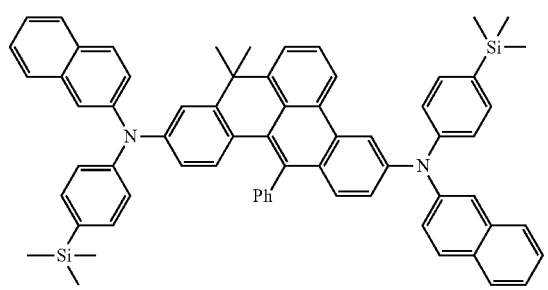
313
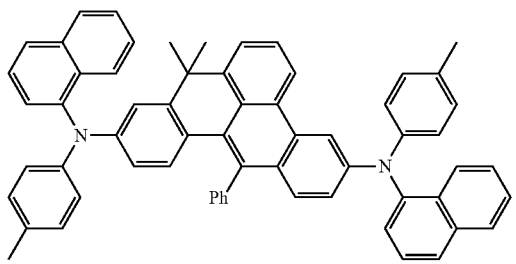
314
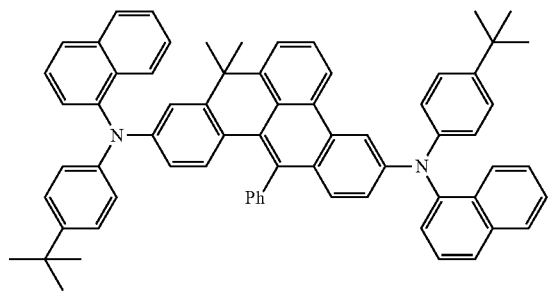

-continued
315
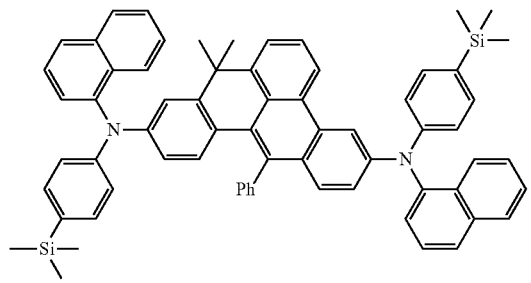
316
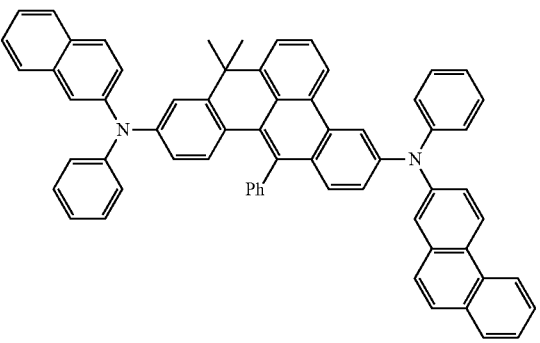
317
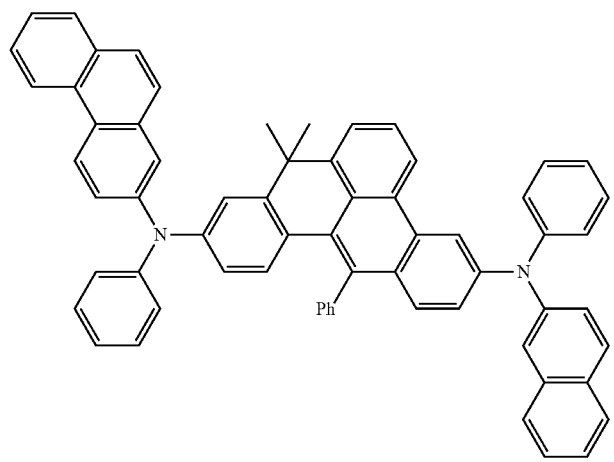
318
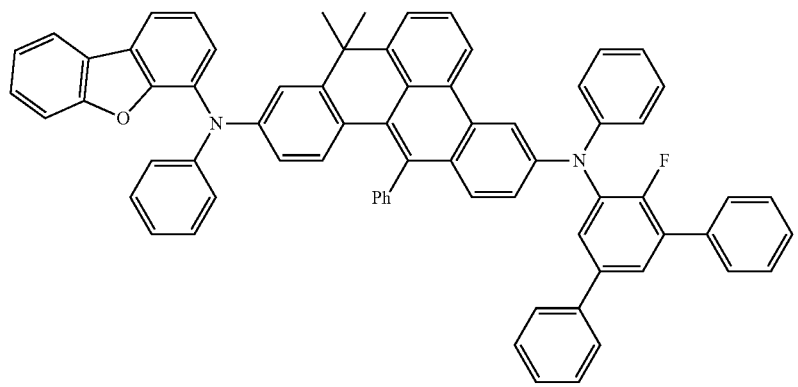
319
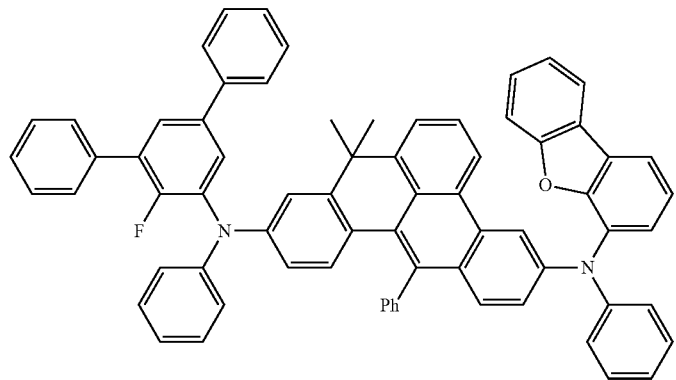

-continued
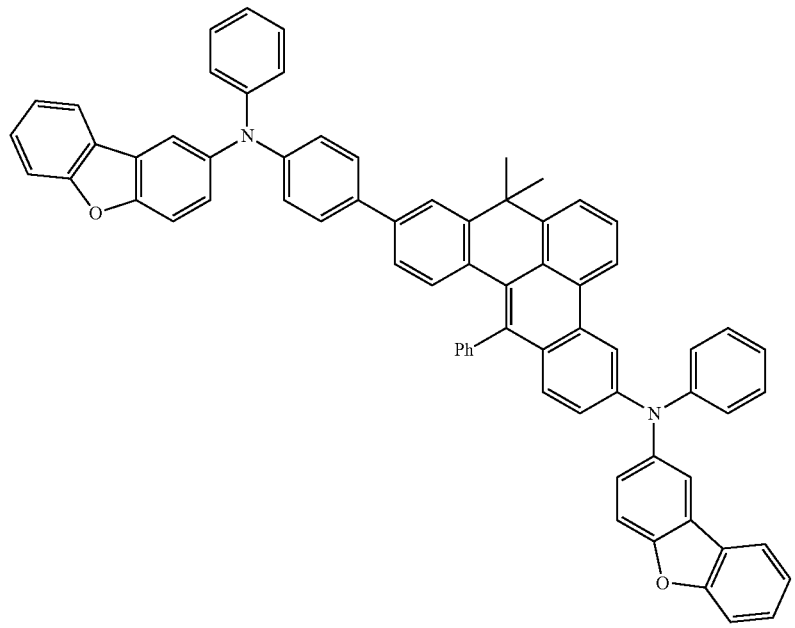
320
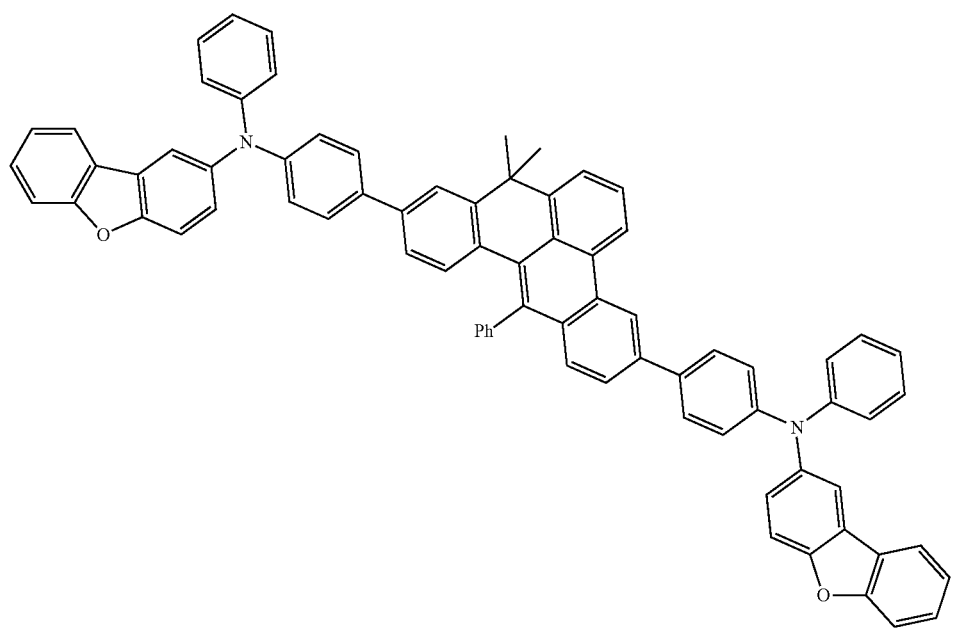
321
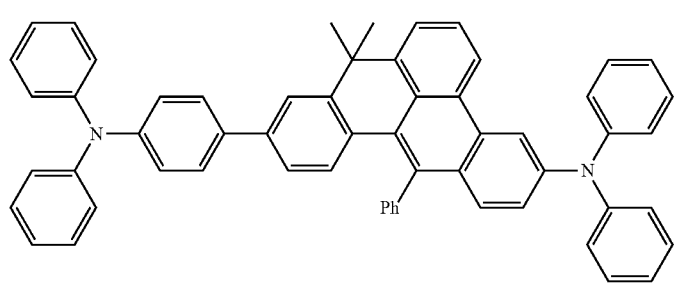
323

-continued
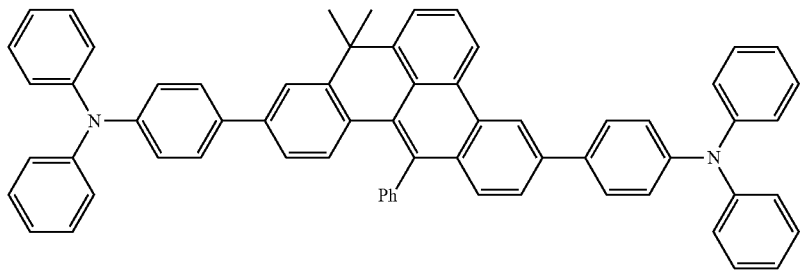
324
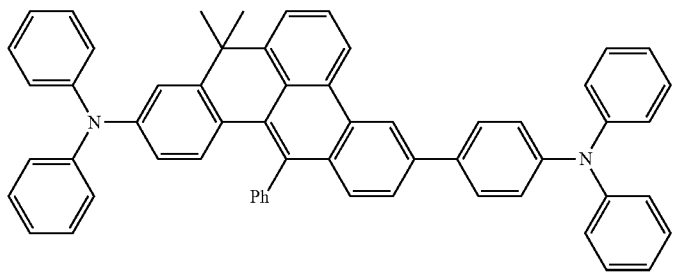
325
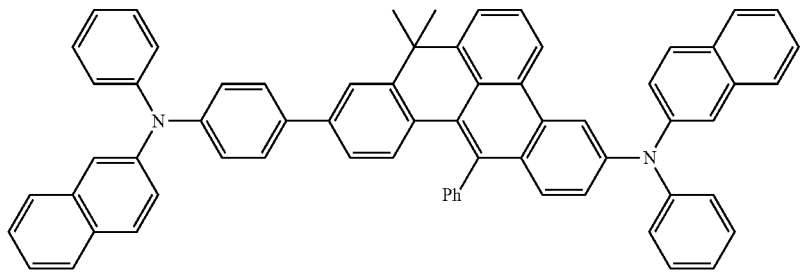
326
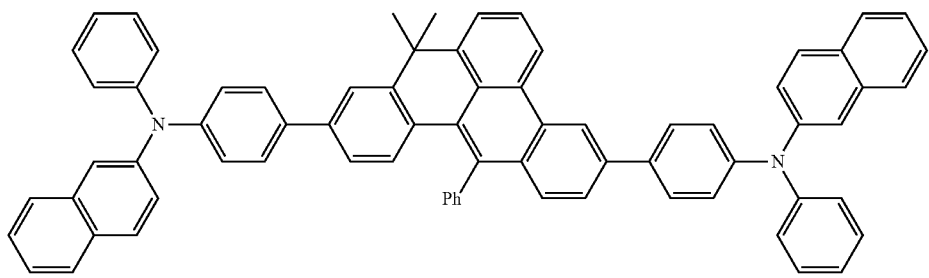
327
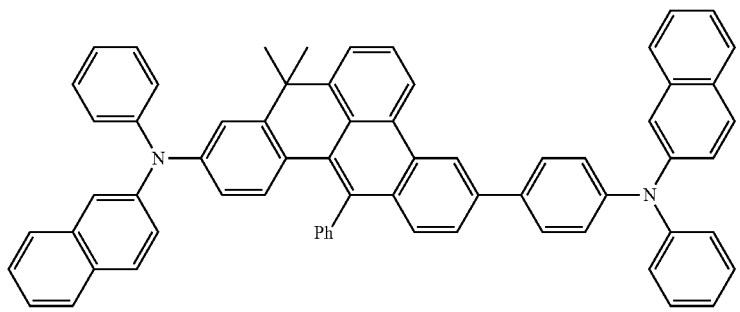
328

-continued
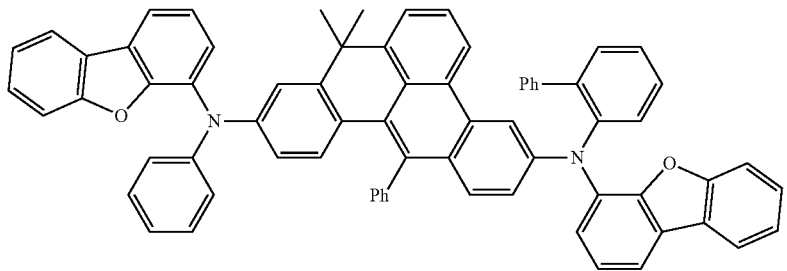
329
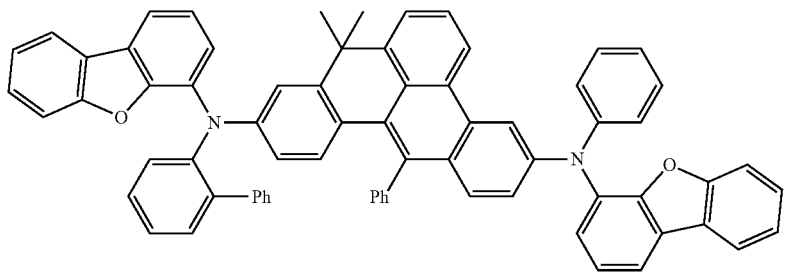
330
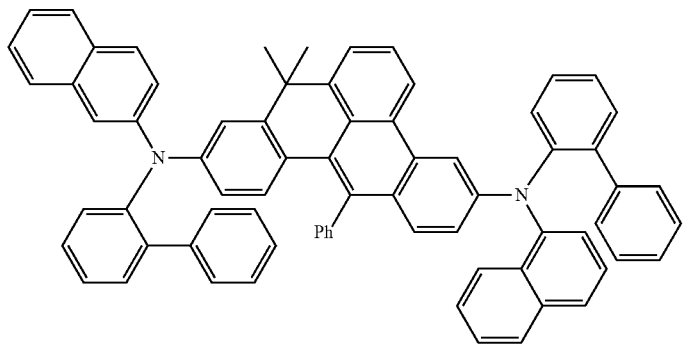
331
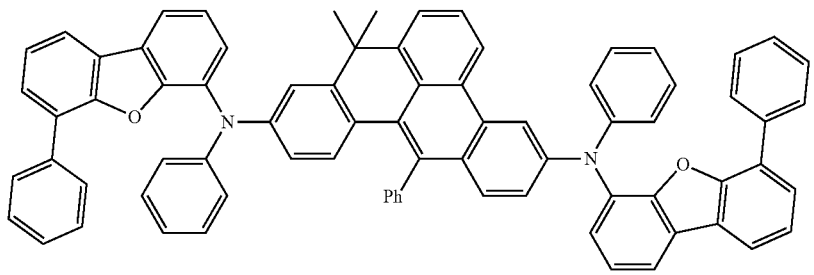
332
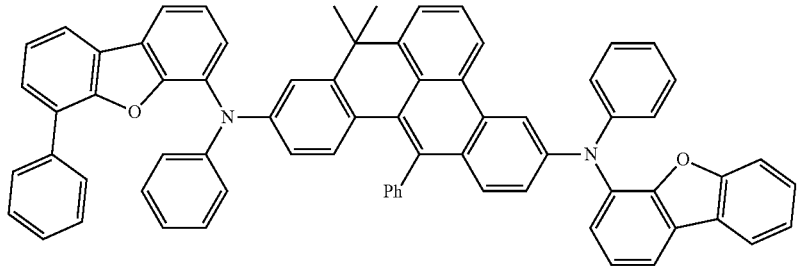
333

-continued
334
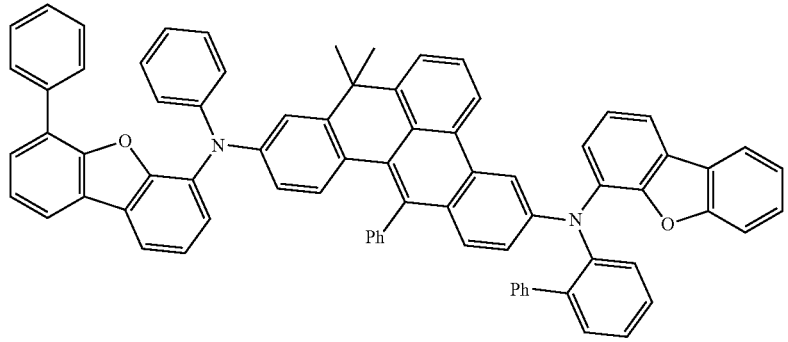
335
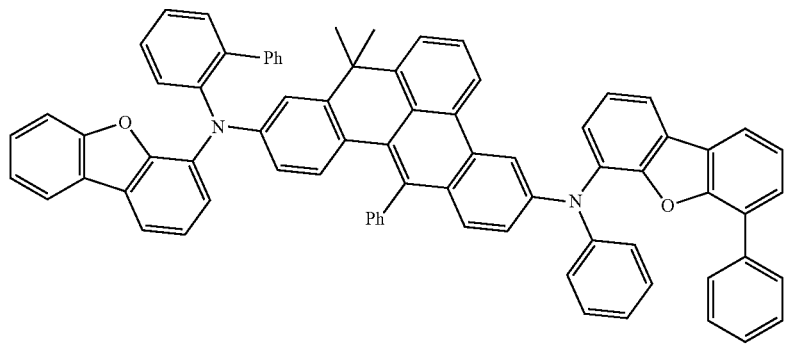
336
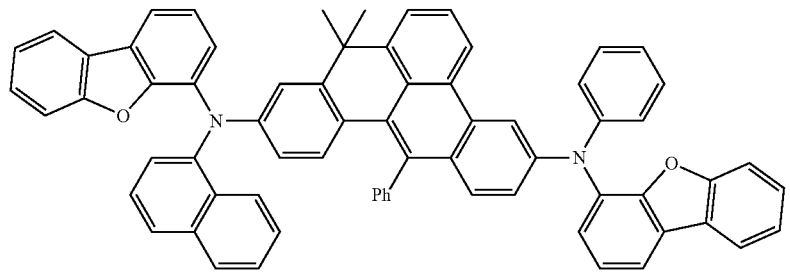
337
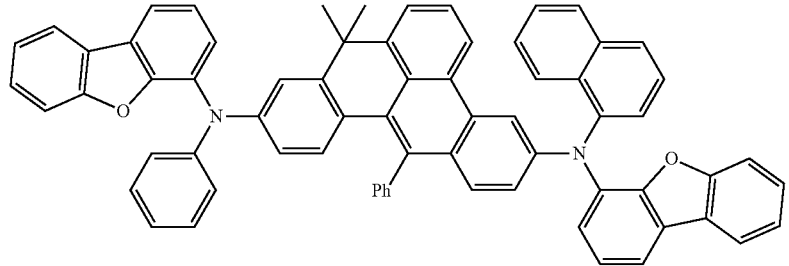
338
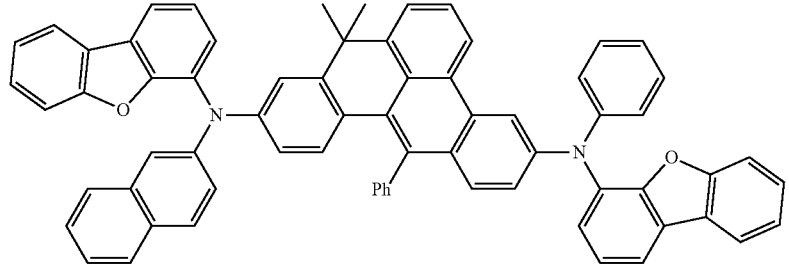

-continued
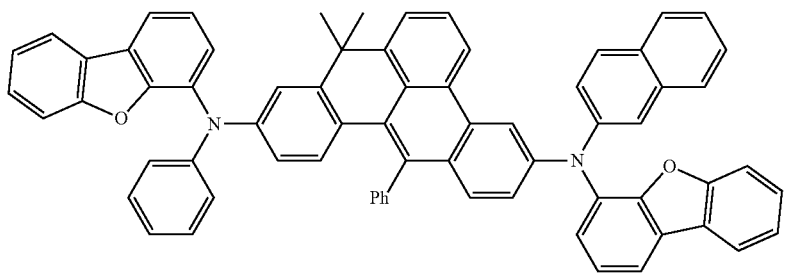
339
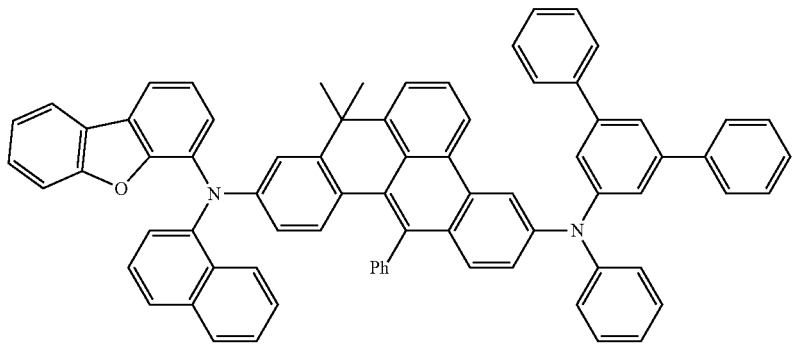
340
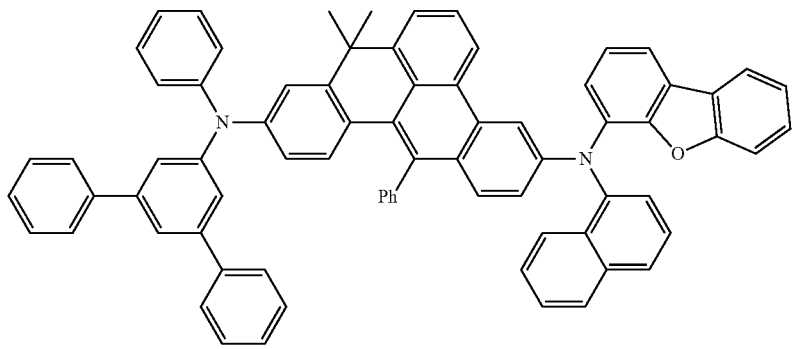
341
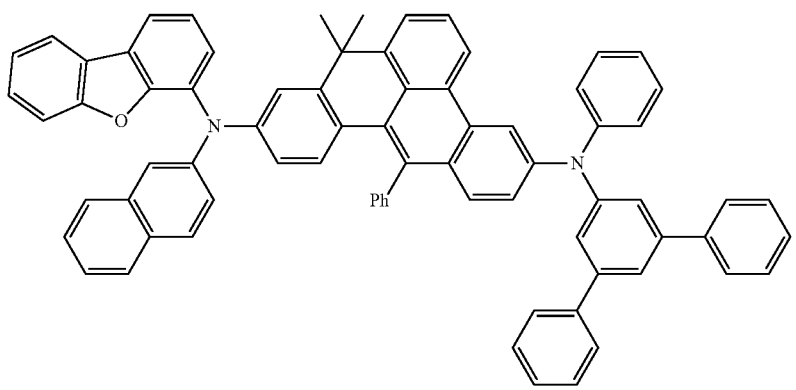
342
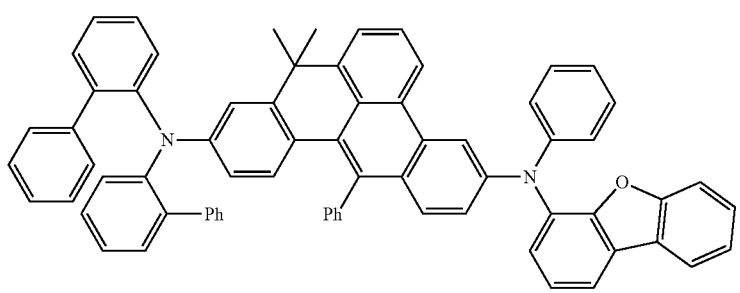
343

-continued
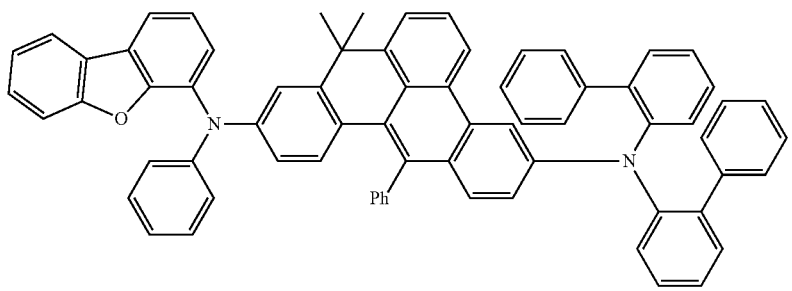
344
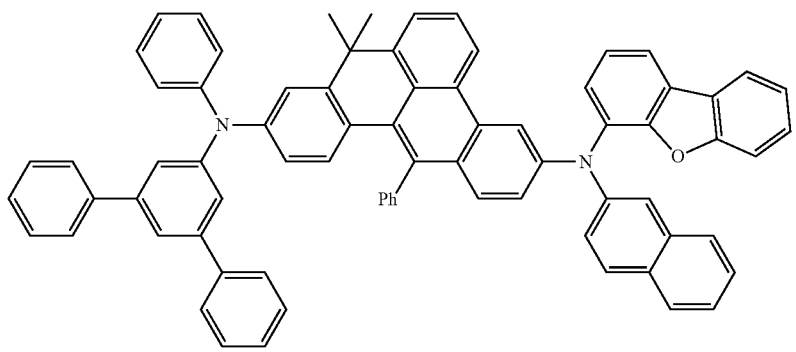
345
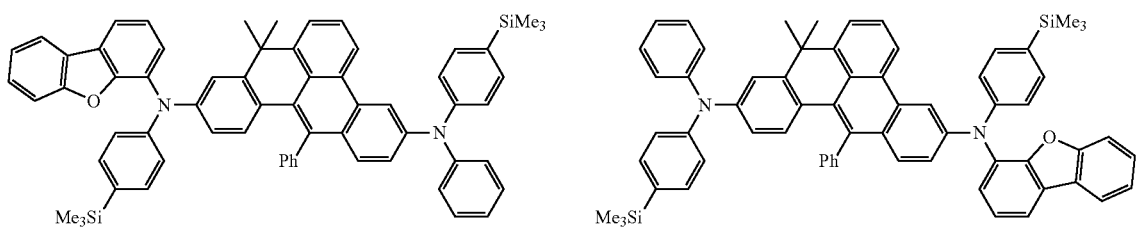
346    347
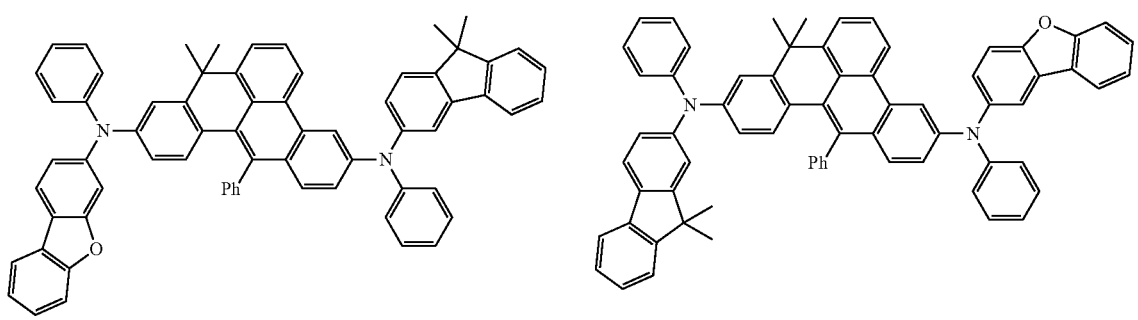
348    349
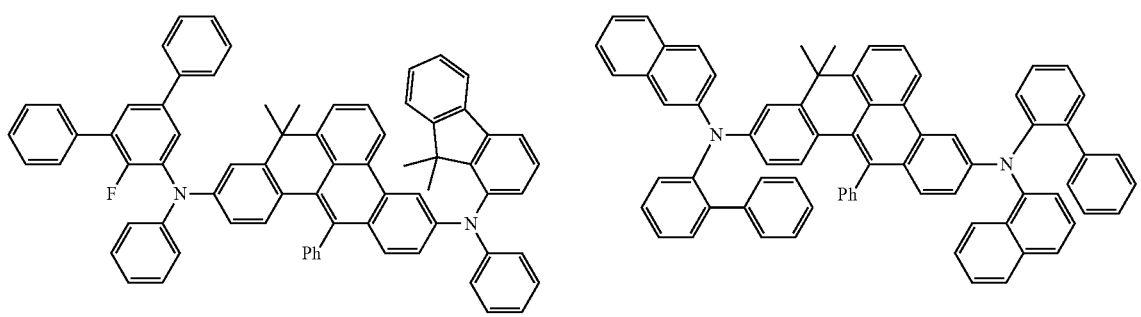
350    351

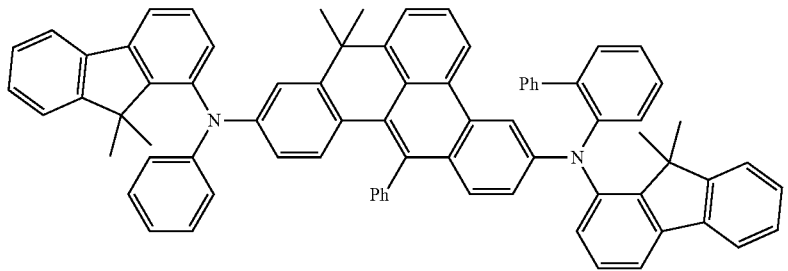
352
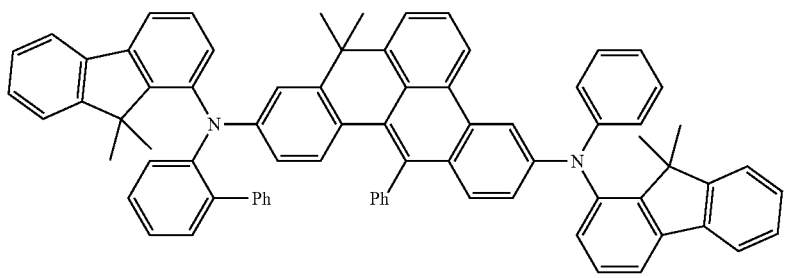
353
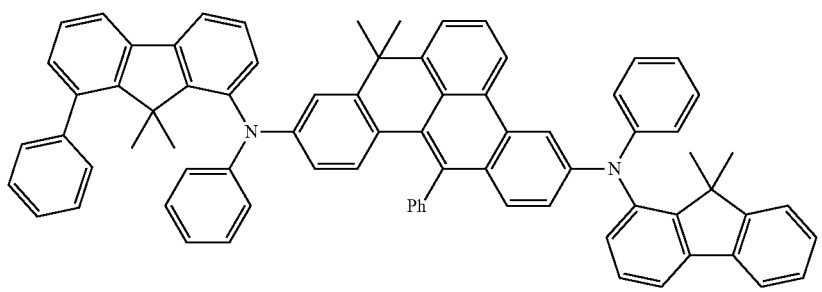
354
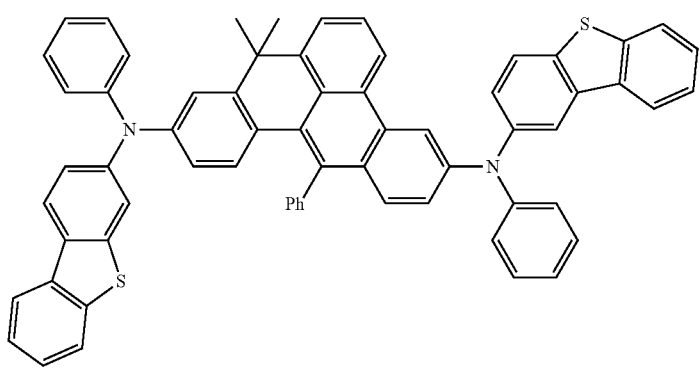
355
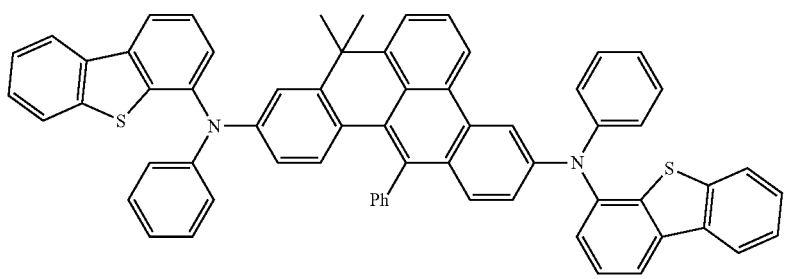
356

-continued
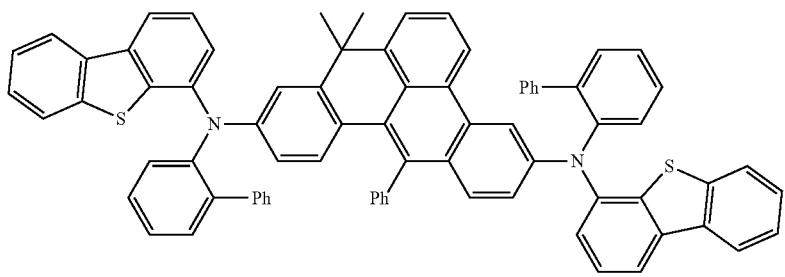
357
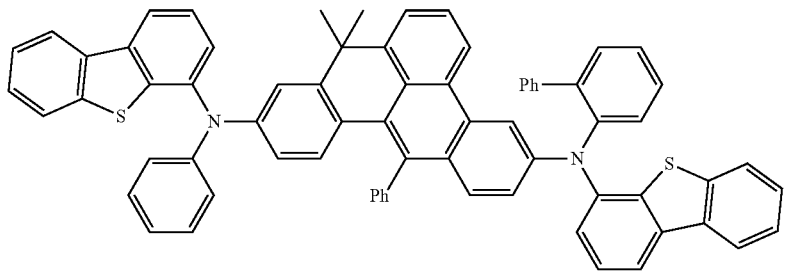
358
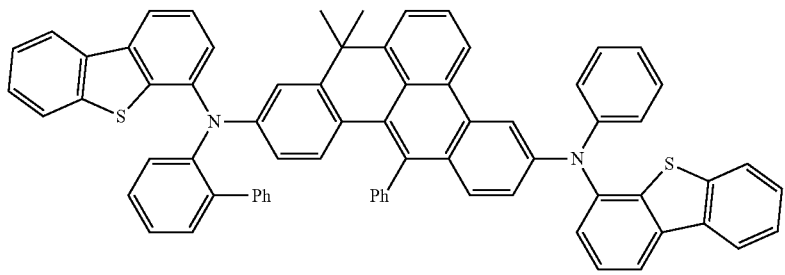
359
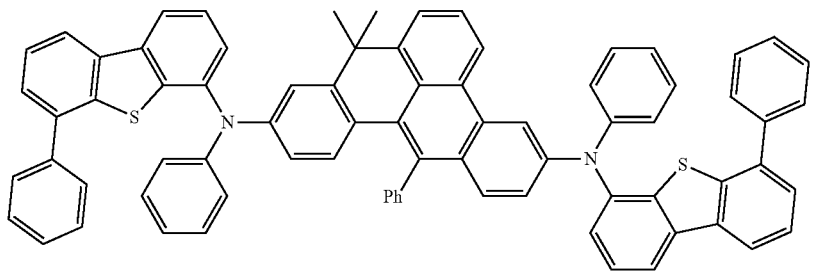
360
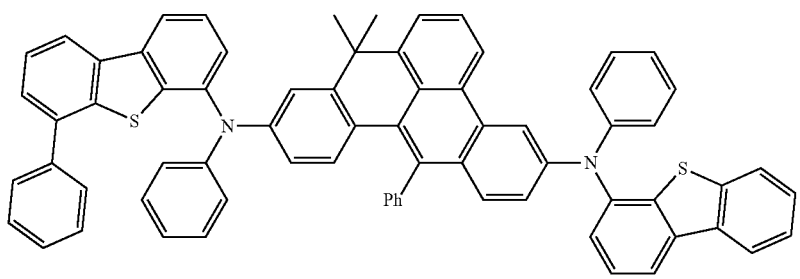
361

362
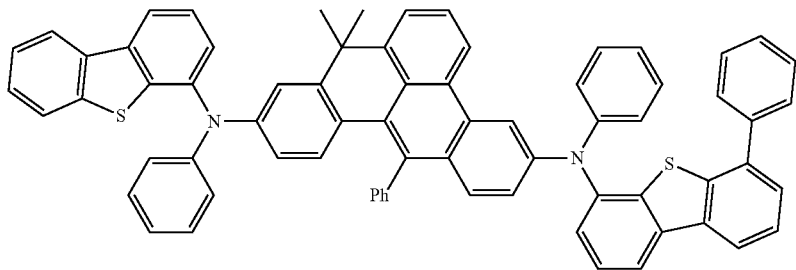
363
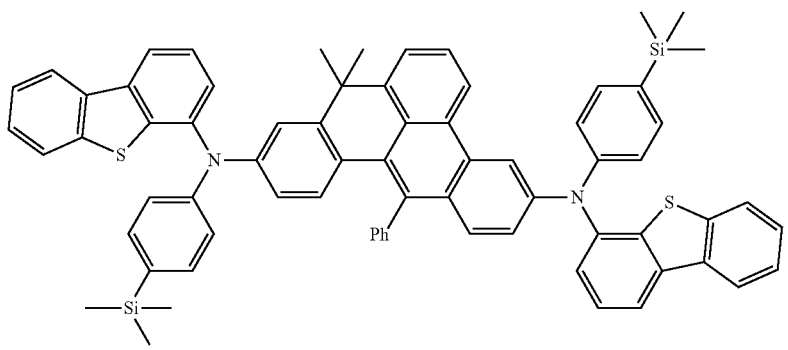
364
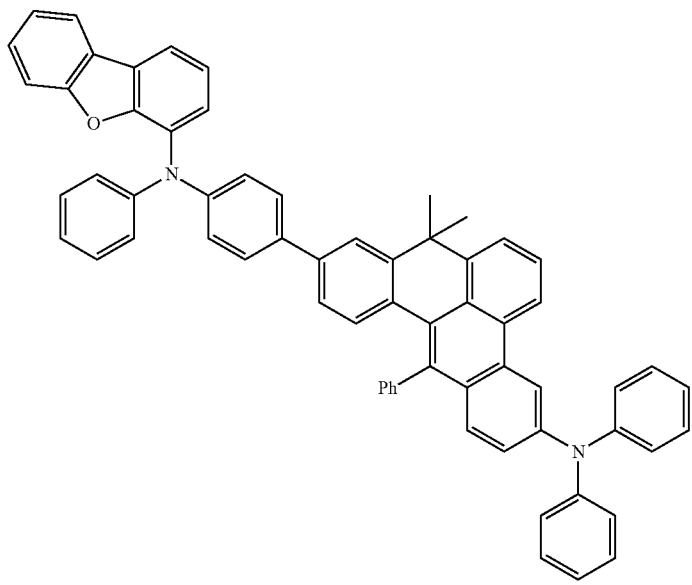

-continued
365
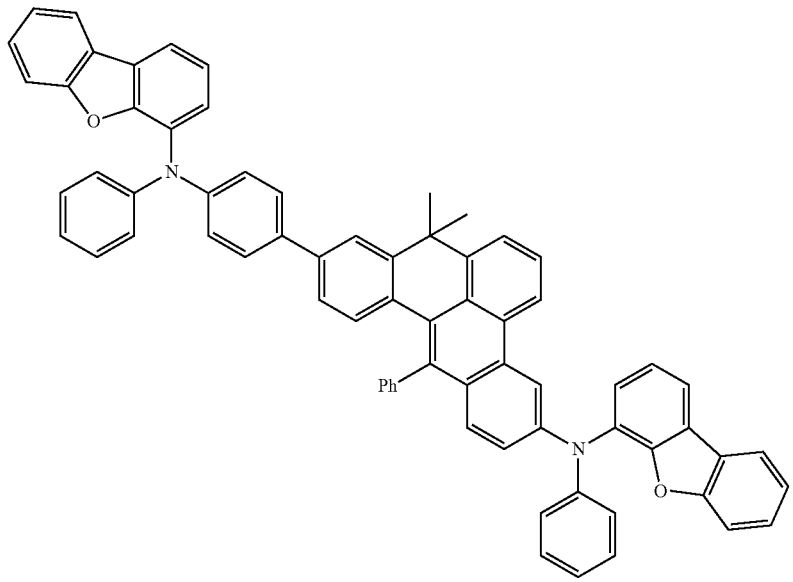
366
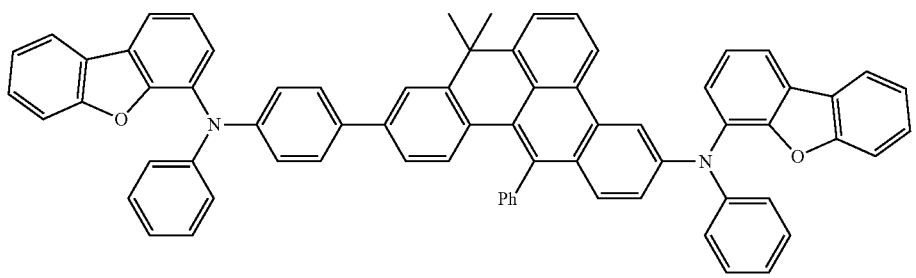
367
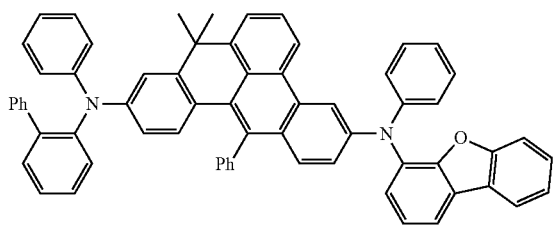
368
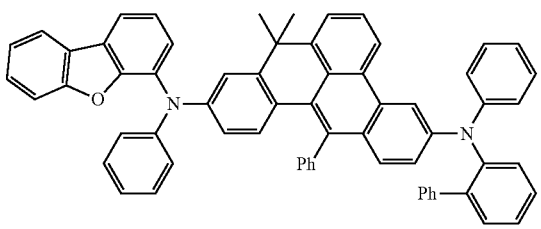
369
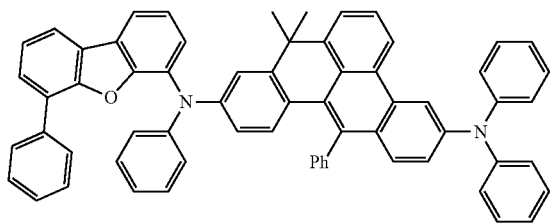
370
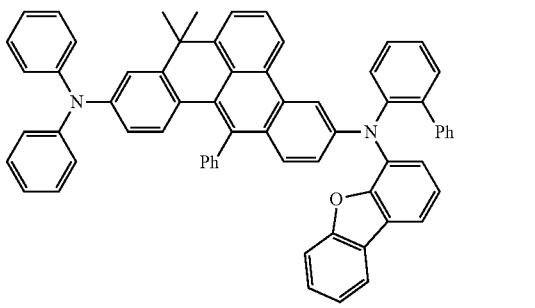

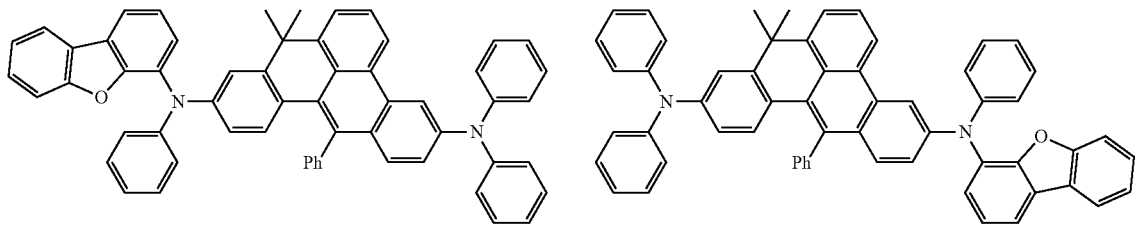

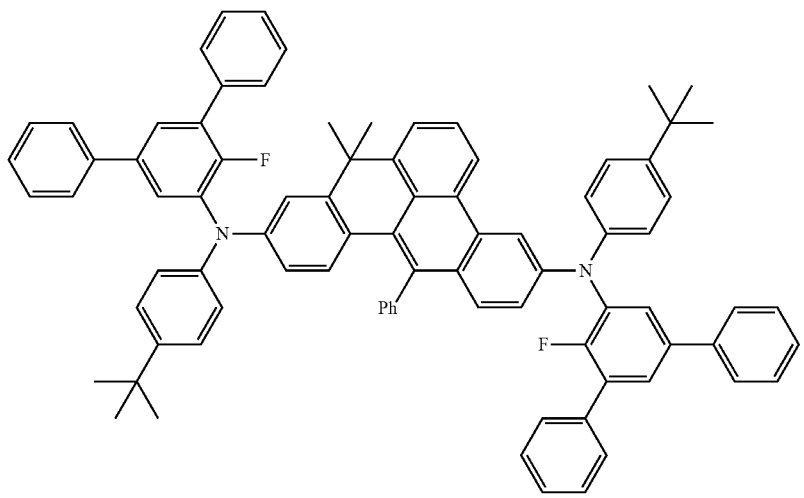

17. An organic light-emitting device, comprising:
a first electrode;
a second electrode facing the first electrode; and
an organic layer between the first electrode and the second electrode, the organic layer including an emission layer;
wherein the organic layer includes at least one condensed cyclic compound as claimed in claim 1.

18. The organic light-emitting device as claimed in claim 17, wherein
the first electrode is an anode,
the second electrode is a cathode,
and the organic layer includes
i) a hole transport region between the first electrode and the emission layer, the hole transport region including at least one selected from a hole injection layer, a hole transport layer, a buffer layer, and an electron blocking layer, and
ii) an electron transport region between the emission layer and the second electrode, the electron transport region including at least one selected from a hole blocking layer, an electron transport layer, and an electron injection layer.

19. The organic light-emitting device as claimed in claim 17, wherein
the emission layer includes the condensed cyclic compound.

20. The organic light-emitting device as claimed in claim 19, wherein
the emission layer further includes a compound represented by Formula 301:

$Ar_{301}$-[($L_{301}$)$_{xb1}$-$R_{301}$]$_{xb2}$ <Formula 301> wherein in Formula 301,
$Ar_{301}$ is selected from
a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and
a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), wherein $Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group;
$L_{301}$ is selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;

$R_{301}$ is selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 is selected from 0, 1, 2, and 3; and xb2 is selected from 1, 2, 3, and 4.

\* \* \* \* \*